US007906710B2

(12) United States Patent
Karunanandaa et al.

(10) Patent No.: US 7,906,710 B2
(45) Date of Patent: *Mar. 15, 2011

(54) TRANSGENIC PLANTS CONTAINING ALTERED LEVELS OF STEROID COMPOUNDS

(75) Inventors: Balasulojini Karunanandaa, St. Louis, MO (US); Martha Post-Beittenmiller, St. Louis, MO (US); Mylavarapu Venkatramesh, St. Louis, MO (US); Ganesh M. Kishore, St. Louis, MO (US); Gregory M. Thorne, St. Louis, MO (US); John R. LeDeaux, St. Louis, MO (US)

(73) Assignee: Monsanto Company, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/477,673

(22) Filed: Jun. 3, 2009

(65) Prior Publication Data

US 2010/0037354 A1    Feb. 11, 2010

Related U.S. Application Data

(62) Division of application No. 10/862,907, filed on Jun. 7, 2004, now Pat. No. 7,544,863, which is a division of application No. 09/885,723, filed on Jun. 20, 2001, now Pat. No. 6,822,142.

(60) Provisional application No. 60/260,114, filed on Jan. 5, 2001.

(51) Int. Cl.
*C12N 15/29* (2006.01)
*C12N 15/52* (2006.01)
*C12N 15/82* (2006.01)
*A01H 5/00* (2006.01)
*A01H 5/10* (2006.01)

(52) U.S. Cl. ........ 800/306; 800/312; 800/314; 800/317; 800/320.1; 536/23.1; 536/23.2; 536/23.6; 435/320.1; 435/419

(58) Field of Classification Search ........................ None
See application file for complete search history.

(56) References Cited

U.S. PATENT DOCUMENTS

| | | | |
|---|---|---|---|
| 5,306,862 A | 4/1994 | Chappell et al. | 800/205 |
| 5,349,126 A | 9/1994 | Chappell et al. | 800/205 |
| 5,365,017 A | 11/1994 | Chappell et al. | 800/205 |
| 5,460,949 A | 10/1995 | Saunders et al. | 435/55 |
| 5,480,805 A | 1/1996 | Wolf et al. | 435/320.1 |
| 5,589,619 A | 12/1996 | Chappell et al. | 800/205 |
| 6,153,815 A | 11/2000 | Covello | 800/306 |
| 6,822,142 B2 | 11/2004 | Karunanandaa et al. | 800/298 |
| 7,544,863 B2 * | 6/2009 | Karunanandaa et al. | 800/306 |

FOREIGN PATENT DOCUMENTS

| | | |
|---|---|---|
| EP | 0486290 | 11/1991 |
| EP | 0480730 | 4/1992 |
| JP | 09121863 | 5/1997 |
| WO | WO 93/02187 | 2/1993 |
| WO | WO 97/03202 | 1/1997 |
| WO | WO 97/34003 | 9/1997 |
| WO | WO 98/45457 | 10/1998 |
| WO | WO 99/04622 | 2/1999 |
| WO | WO 00/61771 | 10/2000 |
| WO | WO 01/31027 | 3/2001 |

OTHER PUBLICATIONS

Bach et al., "Cloning of cDNAs or genes encoding enzymes of sterol biosynthesis from plants and other eukaryotes: heterologous expression and complementation analysis of mutations for functional characterization," *Progress in Lipid Research*, 36(2/3): 197-226, 1997.

Bak et al., "Cloning and expression in *Escherichia coli* of the obtusifoliol 14-alpha-demethylase of Sorghum bicolor (L.) Moench, a cytochrome P450 orthologous to the sterol 14-alpha-demethylases (CYP51) from fungi and mammals," *Plant Journal*, 11(2):191-201, 1997.

Bak et al., "Cloning and expression in *Escherichia coli* of the obtusifoliol 14-alpha-demethylase of Sorghum bicolor (L.) Moench, a cytochrome P450 orthologous to the sterol 14-alpha-demethylases (CYP51) from fungi and mammals," *EMBL Online!*, Database Accession No. U74319, abstract, 1996.

Bard et al., "Genetic and biochemical aspects of yeast sterol regulation involving 3-hydroxy-3-methylglutaryl coenzyme A reductase," *J. General Microbiology*, 125:415-420, 1981.

Basson et al., "Structural and functional conservation between yeast and human 3-hydroxy-3-methylglutaryl coenzyme A reductases, the rate-limiting enzyme of sterol biosynthesis," Molecular Cellular Biology, 8(9):3797-3808, 1998.

Broun et al., "Catalytic plasticity of fatty acid modification enzymes underlying chemical diversity of plant lipids," *Science*, 282:1315-1317, 1998.

(Continued)

*Primary Examiner* — Russell Kallis
(74) *Attorney, Agent, or Firm* — Chunping Li, Esq.; SNR Denton US LLP

(57) ABSTRACT

Disclosed are constructs comprising sequences encoding 3-hydroxy-3methylglutaryl-Coenzyme A reductase and at least one other sterol synthesis pathway enzyme. Also disclosed are methods for using such constructs to alter sterol production and content in cells, plants, seeds and storage organs of plants. Also provided are oils and compositions containing altered sterol levels produced by use of the disclosed constructs. Novel nucleotide sequences useful in the alteration of sterol production are also provided. Also provided are cells, plants, seeds and storage organs of plants comprising sequences encoding 3-hydroxy-3methylglutaryl-Coenzyme A reductase, at least one other sterol synthesis pathway enzyme and at least one tocopherol synthesis enzyme.

12 Claims, 78 Drawing Sheets

OTHER PUBLICATIONS

Cabello-Hurtado et al., "Cloning and functional expression in yeast of a cDNA coding for an obtusifoliol 14-alpha-demethylase (CYP51) in wheat," *Biochemical and Biophysical Research Communications*, 230(2):381-385, 1997.

Cabello-Hurtado et al., "Cloning and functional expression in yeast of a cDNA coding for an obtusifoliol 14-alpha-demethylase (CYP51) in wheat," *EMBL Online!*, Database Accession No. Y09291, abstract, 1996.

Chappell et al., "Is the reaction catalyzed by 3-hydroxy-3-methylglutaryl coenzyme A reductase a rate-limiting step for isoprenoid biosynthesis in plants?" *Plant Physiology*, 109(4):1337-1343, 1995.

Chin et al., "Nucleotide sequence of 3-hydroxy-3-methyl-glutaryl coenzyme A reductase, a glycoprotein of endloplasmic reticulum," *Nature*, 308(5960):613-617, 1984.

Colebatch et al., "*Lotus faponicus* root nodule ESTs: tools for functional genomics," *EMBL Online!*, Database Accession No. AW719774, abstract, 2000.

Covello, "An example of intron junctional sliding in the gene families encoding squalene monooxygenase homologues in *Arabidopsis thaliana* and *Brassica napus*," *EMBL Online!*, Database Accession No. AJ005930, 1998.

Dale et al., "Bacterial expression of the catalytic domain of 3-hydroxy-3-methylglutaryl-CoA reductase (isoform HMGR1) from *Arabidopsis thaliana*, and its inactivation by phosphorylation at Ser577 by *Brassica oleracea* 3-hydroxy-3-methylglutaryl-CoA reductase kinase," *Eur. J. Biochem.*, 233:506-513, 1995.

Deavarenne, "Regulation of squalene synthase, a key enzyme of sterol biosynthesis, in tobacco," *Plant Physiology*, 129:1095-1106, 2002.

Downing et al., "The isolation of two mutants of *Saccharomyces cerevisiae* which demonstrate increased activity of 3-hydroxy-3-methylglutaryl coenzyme a reductase," *Biochemical and Biophysical Research Communications*, 94(3):974-979, 1980.

Fourgoux-Nicol et al., "Isolation of rapeseed genes expressed early and specifically during development of the male gametophyte," *Plant Molecular Biology*, 40:857-872, 1999.

GenBank Accession No. AJ005930, dated Apr. 20, 1999.
GenBank Accession No. AW625933, dated Mar. 28, 2000.
GenBank Accession No. AW719774, dated Apr. 19, 2000.
GenBank Accession No. U74319, dated Mar. 18, 1997.
GenBank Accession No. Y09291, dated Apr. 18, 2005.

Gill et al., "Membrane-bound domain of HMG CoA reductase is required for sterol-enhanced degradation of the enzyme," *Cell*, 41:249-258, 1985.

Gonzalez et al., Abstract of poster at Third Terpnet Meeting of the European Network on Plant Isoprenoids, May 29-30, Poiters, France, 1997.

Jenkins et al., "Plant sterols, health claims and strategies to reduce cardiovascular and strategies to reduce cardiovascular disease risk," *J. of the American College of Nutrition*, 18:559-562, 1999.

Nakamura et al., "A large scale analysis if cDNA in *Aradopsis thalian*: generation of 12,028 non-redundant expressed sequence tags from normalized size-selected cDNA libraries," *EMBL Online!*, Database Accession No. AV440215, 2000.

Nguyen, "The cholesterol-lowering action of plant stanol esters," *J. of Nutrition*, 129:2109-2112, 1999.

Register et al., "Structure and function of selectable and non-selectable transgenes in maize after introduction by particle bombardment," *Plant Mol. Biol.*, 25:951-961, 1994.

Schaeffer et al., "Plant sterol-C24-methyl transferases: different profiles of tobacco transformed with SMT1 or SMT2," *Lipids*, 35:263-269, 2000.

Schafer et al., "An example of intron junctional sliding in the gene families encoding sqalene monooxygenase homologues in *Arabidopsis thaliana* and *Brassica napus*," *Plant Molecular Biology*, 39(4):721-728, 1999.

Schaller et al., "Expression of the *Hevea brasiliensis* (H.B.K.) müll. Arg. 3-hydroxy-3-methylglutaryl-coenzyme A reductase 1 in tobacco results in sterol overproduction," *Plant Physiol.*, 109:761-770, 1995.

Schaller et al., "Overexpression of an arabidopsis cDNA encoding a sterol-C24(1)-methyltransferase in tobacco modifies the ration of 24-methyl cholesterol to sitosterol and is associated with growth reduction," *Plant Physiol.*, 118:461-469, 1998.

Shintani et al., "Elevating the vitamin E content of plants through metabolic engineering," *Science*, 282(5396):2098-2100, 1998.

Tada et al., "Mechanism of photoregulated cartogenesis in *Rhodoturul minuta* v. photoinduction of 3-hydroxy-3-methyl glutaryl coenzyme A reductase," *Plant and Cell Physiol.*, 23(4):615-621, 1982.

Van der Hoeven et al., "Generation of ESTs retrieved from tomato radicule tissue," *EMBL Online!*, Database Accession No. AW625933, abstract, 2000.

Yoder et al., "Transformation systems for generating marker-free transgenic plants," *Bio/Technology*, 12:263-267, 1994.

\* cited by examiner

Construct pMON43800

Construct pMON43818

Construct pMON43052

Construct pMON51850

Construct pMON43057

Construct pMON43058

Construct pMON53734

Construct pMON53735

Construct pMON53736

Construct pMON53737

Construct pMON53738

Construct pMON53740

Construct pMON43843

Construct pMON43844

```
Plurality: 5.00  Threshold: 4  AveWeight 1.00  AveMatch 2.91  AvMisMatch -2.00
                              1
        50
  HMGRclustalW{methanobac}    ..........  ..........  ..........  ..........
..........
  HMGRclustalW{methanococ}    ..........  ..........  ..........  ..........
..........
  HMGRclustalW{halobacter}    ..........  ..........  ..........  ..........
..........
  HMGRclustalW{sulfolobus}    ..........  ..........  ..........  ..........
..........
  HMGRclustalW{    yeast2}    MSLPLKTIVH  LVKPFACTAR  FSARYPIHVI  VVAVLLSAAA
YLSVTQSYLN
  HMGRclustalW{    yeast1}    MPPLFKGLKQ  MAKPIAYVSR  FSAKRPIHII  LFSLIISAFA
YLSVIQYYFN
  HMGRclustalW{phycomyces}    ..........  ..........  ..........  ..........
..........
  HMGRclustalW{   fusarium}   ..........  ..........  ..........  ..........
..........
  HMGRclustalW{    candida}   ..........  ..........  ..........  ..........
..........
  HMGRclustalW{dictyoste2}    ..........  ..........  ..........  ..........
..........
     HMGRclustalW{wheat1}     ..........  ..........  ..........  ..........
..........
  HMGRclustalW{       rice}   ..........  ..........  ..........  ..........
..........
     HMGRclustalW{   corn}    ..........  ..........  ..........  ..........
..........
  HMGRclustalW{wheat3}        ..........  ..........  ..........  ..........
..........
     HMGRclustalW{wheat2}     ..........  ..........  ..........  ..........
..........
HMGRclustalW{     soybean}    ..........  ..........  ..........  ..........
..........
  HMGRclustalW{rubbertre3}    ..........  ..........  ..........  ..........
..........
  HMGRclustalW{rosyperiwi}    ..........  ..........  ..........  ..........
..........
  HMGRclustalW{    tomato}    ..........  ..........  ..........  ..........
..........
  HMGRclustalW{woodtobacc}    ..........  ..........  ..........  ..........
..........
  HMGRclustalW{    potato}    ..........  ..........  ..........  ..........
..........
     HMGRclustalW{radish}     ..........  ..........  ..........  ..........
..........
HMGRclustalW{arabadopsis1}    ..........  ..........  ..........  ..........
..........
  HMGRclustalW{cucumisme1}    ..........  ..........  ..........  ..........
..........
  HMGRclustalW{rubbertre2}    ..........  ..........  ..........  ..........
..........
  HMGRclustalW{rubbertre1}    ..........  ..........  ..........  ..........
..........
  HMGRclustalW{camptothec}    ..........  ..........  ..........  ..........
..........
  HMGRclustalW{arabadops2}    ..........  ..........  ..........  ..........
..........
  HMGRclustalW{chineseham}    ..........  ..........  ..........  ..........
..........
```

FIG. 32A

```
HMGRclustalW{chineseha2}    ..........  ..........  ..........  ..........
..........
HMGRclustalW{syrianhamst}   ..........  ..........  ..........  ..........
..........
    HMGRclustalW{    rat}   ..........  ..........  ..........  ..........
..........
 HMGRclustalW{    rabbit}   ..........  ..........  ..........  ..........
..........
HMGRclustalW{      human}   ..........  ..........  ..........  ..........
..........
HMGRclustalW{      mouse}   ..........  ..........  ..........  ..........
..........
 HMGRclustalW{   xenopus}   ..........  ..........  ..........  ..........
..........
HMGRclustalW{sea urchin}    ..........  ..........  ..........  ..........
..........
 HMGRclustalW{ cockroach}   ..........  ..........  ..........  ..........
..........
HMGRclustalW{drosophila}    ..........  ..........  ..........  ..........
..........
HMGRclustalW{dictyostel}    ..........  ..........  ..........  ..........
..........
HMGRclustalW{schistoscm}    ..........  ..........  ..........  ..........
..........
HMGRclustalW{archaeoglo}    ..........  ..........  ..........  ..........
..........
HMGRclustalW{pseudomonas}   ..........  ..........  ..........  ..........
..........
                Consensus   ----------  ----------  ----------  ----------  ------
----
```

FIG. 32B

```
                                          51
100
   HMGRclustalW{methanobac}      ..........  ..........  ..........  ..........
..........
   HMGRclustalW{methanococ}      ..........  ..........  ..........  ..........
..........
   HMGRclustalW{halobacter}      ..........  ..........  ..........  ..........
..........
   HMGRclustalW{sulfolobus}      ..........  ..........  ..........  ..........
..........
   HMGRclustalW{     yeast2}     EWKLDSN.QY  STYLSIKPDE  LFEKCTHYYR  SPVSDTWKLL
SSKEAADIYT
   HMGRclustalW{     yeast1}     GWQLDSNSVF  ETAPNKDSNT  LFQECSHYYR  DSSLDGWVSI
TAHEASELPA
   HMGRclustalW{phycomyces}      ..........  ..........  ..........  ..........
..........
   HMGRclustalW{   fusarium}     ..........  ..........  .......MCH  EGCQGQHPQQ
CCQWVSNAWS
   HMGRclustalW{    candida}     ..........  ..........  ......MFYH  GASANQHWIA
VDDLSKVPVD
   HMGRclustalW{dictyoste2}      ..........  ..........  ..........  ..........
..........
       HMGRclustalW{wheat1}      ..........  ..........  ..........  ..........
..........
   HMGRclustalW{       rice}     ..........  ..........  ..........  ..........
..........
       HMGRclustalW{   corn}     ..........  ..........  ..........  ..........
..........
       HMGRclustalW{wheat3}      ..........  ..........  ..........  ..........
..........
       HMGRclustalW{wheat2}      ..........  ..........  ..........  ..........
..........
HMGRclustalW{    soybean}        ..........  ..........  ..........  ..........
   HMGRclustalW{rubbertre3}      ..........  ..........  ..........  ..........
..........
   HMGRclustalW{rosyperiwi}      ..........  ..........  ..........  ..........
..........
   HMGRclustalW{     tomato}     ..........  ..........  ..........  ..........
..........
   HMGRclustalW{woodtobacc}      ..........  ..........  ..........  ..........
..........
   HMGRclustalW{     potato}     ..........  ..........  ..........  ..........
..........
       HMGRclustalW{radish}      ..........  ..........  ..........  ..........
HMGRclustalW{arabadopsis1}       ..........  ..........  ..........  ..........
..........
   HMGRclustalW{cucumisme1}      ..........  ..........  ..........  ..........
..........
   HMGRclustalW{rubbertre2}      ..........  ..........  ..........  ..........
..........
   HMGRclustalW{rubbertre1}      ..........  ..........  ..........  ..........
..........
   HMGRclustalW{camptothec}      ..........  ..........  ..........  ..........
..........
   HMGRclustalW{arabadops2}      ..........  ..........  ..........  ..........
..........
   HMGRclustalW{chineseham}      ..........  ..........  ..........  .MLSRLFRMH
GLFVASHPWE
   HMGRclustalW{chineseha2}      ..........  ..........  ..........  .MLSRLFRMH
```

FIG. 32C

```
                              GLFVASHPWE
  HMGRclustalW{syrianhamst}   ..........  ..........  ..........  .MLSRLFRMH
                              GLFVASHPWE
    HMGRclustalW{     rat}    ..........  ..........  ..........  .MLSRLFRMH
                              GLFVASHPWE
  HMGRclustalW{     rabbit}   ..........  ..........  ..........  .MLSRLFRMH
                              GLFVASHPWE
  HMGRclustalW{     human}    ..........  ..........  ..........  .MLSRLFRMH
                              GLFVASHPWE
  HMGRclustalW{     mouse}    ..........  ..........  ..........  ..........
  ..........
    HMGRclustalW{   xenopus}  ..........  ..........  ..........  .MLSRLFRMH
                              GQFVASHPWE
  HMGRclustalW{sea urchin}    ..........  ..........  ..........  .MLSRLFLAQ
                              GRFCSSHPWE
  HMGRclustalW{  cockroach}   ..........  ..........  ..........  .MVGRLFRAH
                              GQFCASHPWE
  HMGRclustalW{drosophila}    ..........  ..........  ..........  .MIGPLFRAT
                              .QFCASHPWE
  HMGRclustalW{dictyostel}    ..........  ..........  ..........  ..........
  ..........
  HMGRclustalW{schistosom}    ..........  ..........  ..........  ..........
  ..........
  HMGRclustalW{archaeoglo}    ..........  ..........  ..........  ..........
  ..........
  HMGRclustalW{pseudomonas}   ..........  ..........  ..........  ..........
  ..........

Consensus   ----------  ----------  ----------  -MLSRLFRMH
GLFVASHPWE
```

FIG. 32D

|  | 101 | | | 150 |
|---|---|---|---|---|
| HMGRclustalW{methanobac} | .......... | .......... | .......... | .......... |
| HMGRclustalW{methanococ} | .......... | .......... | .......... | .......... |
| HMGRclustalW{halobacter} | .......... | .......... | .......... | .......... |
| HMGRclustalW{sulfolobus} | .......... | .......... | .......... | .......... |
| HMGRclustalW{ yeast2} | PFHYYLSTIS | FQSKDNSTTL | PSLDDVIYSV | DHTRYLLSEE PKIPTELVSE |
| HMGRclustalW{ yeast1} | PHHYYLLNLN | FNSPNETDSI | PELANTVFEK | DNTKYILQED LSVSKEISST |
| HMGRclustalW{phycomyces} | .......... | .......... | .......... | .......... |
| HMGRclustalW{ fusarium} | EFLDLLKNAE | TLDIVIMLLG | YIAMHLTFVS | LFLSMRKMGS KFWLGICTLF |
| HMGRclustalW{ candida} | VDHYNVVPFQ | FRRAGEYKEP | VLSGIVELDE | VKFVVSQSDA AEQWQQLTAE |
| HMGRclustalW{dictyoste2} | .......... | .......... | .......... | .......... |
| HMGRclustalW{wheat1} | .......... | .......... | .......... | .......... |
| HMGRclustalW{ rice} | .......... | .......... | .......... | .......... |
| HMGRclustalW{ corn} | .......... | .......... | .......... | .......... |
| HMGRclustalW{wheat3} | .......... | .......... | .......... | .......... |
| HMGRclustalW{wheat2} | .......... | .......... | .......... | .......... |
| HMGRclustalW{ soybean} | .......... | .......... | .......... | .......... |
| HMGRclustalW{rubbertre3} | .......... | .......... | .......... | .......... |
| HMGRclustalW{rosyperiwi} | .......... | .......... | .......... | .......... |
| HMGRclustalW{ tomato} | .......... | .......... | .......... | .......... |
| HMGRclustalW{woodtobacc} | .......... | .......... | .......... | .......... |
| HMGRclustalW{ potato} | .......... | .......... | .......... | .......... |
| HMGRclustalW{radish} | .......... | .......... | .......... | .......... |
| HMGRclustalW{arabadopsis1} | .......... | .......... | .......... | .......... |
| HMGRclustalW{cucumisme1} | .......... | .......... | .......... | .......... |
| HMGRclustalW{rubbertre2} | .......... | .......... | .......... | .......... |
| HMGRclustalW{rubbertre1} | .......... | .......... | .......... | .......... |
| HMGRclustalW{camptothec} | .......... | .......... | .......... | .......... |
| HMGRclustalW{arabadops2} | .......... | .......... | .......... | .......... |
| HMGRclustalW{chineseham} | VIVGTVT..L | TICMMSMN.. | MFTGNNK... | .......... |

FIG. 32E

```
HMGRclustalW(chineseha2)   VIVGTVT..L TICMMSMN.. MFTGNNK... ..........
..........
HMGRclustalW(syrianhamst)  VIVGTVT..L TICMMSMN.. MFTGNNK... ..........
..........
     HMGRclustalW(    rat) VIVGTVT..L TICMMSMN.. MFTGNNK... ..........
   HMGRclustalW(   rabbit) VIVGTVT..L TICMMSMN.. MFTGNDK... ..........
..........
HMGRclustalW(      human)  VIVGTVT..L TICMMSMN.. MFTGNNK... ..........
..........
HMGRclustalW(      mouse)  .......... .......... .......... ..........
..........
HMGRclustalW(    xenopus)  VIVGTVT..L TICMMSMN.. MFTGNDK... ..........
   HMGRclustalW(sea urchin) VIVCTLT..L TICMLSMN.. YFTGLPR... ..........
..........
HMGRclustalW( cockroach)   VIVATLT..L TVCMLTVDQ. RPLGLP.... ..........
..........
HMGRclustalW(drosophila)   VIVALLT..I TACMLNGGQE QYPGCEQRIG HSTASAAAAG
SGSGAGSGAS
HMGRclustalW(dictyostel)   .......... .......... .......... ..........
..........
HMGRclustalW(schistosom)   .......... .......... .......... ..........
..........
HMGRclustalW(archaeoglo)   .......... .......... .......... ..........
..........
HMGRclustalW(pseudomonas)  .......... .......... .......... ..........
..........
          Consensus        VIVGTVT--L TICMMSMN-- MFTGNNK--- ----------
----
```

FIG. 32F

```
                                      151
200
   HMGRclustalW{methanobac}    ..........  ..........  ..........  ..........
..........
   HMGRclustalW{methanococ}    ..........  ..........  ..........  ..........
..........
   HMGRclustalW{halobacter}    ..........  ..........  ..........  ..........
..........
   HMGRclustalW{sulfolobus}    ..........  ..........  ..........  ..........
..........
   HMGRclustalW{     yeast2}   NGTKWRLRNN  SNFILDLHNI  YRNMVKQFSN  KTSEFDQFDL
FIILAAYLTL
   HMGRclustalW{     yeast1}   DGTKWRLRSD  RKSLFDVKTL  AYSLYDVFSE  NVTQADPFDV
LIMVTAYLMM
   HMGRclustalW{phycomyces}    ..........  ..........  ..........  ..........
..........
   HMGRclustalW{   fusarium}   SSVFAFLFGL  VVTTKLGVPI  SVILLSEGLP  FLVVTIGFEK
NIVLTRAVMS
   HMGRclustalW{    candida}   DGTVWRSRAY  HGKLGKYSDM  AVGAFNKVLN  LVRGAETFDI
ALVTCAYIAM
   HMGRclustalW{dictyoste2}    ..........  ..........  ..........  ..........
..........
      HMGRclustalW{    wheat1} ..........  ..........  ..........  ..........
..........
   HMGRclustalW{        rice}  ..........  ..........  ..........  ..........
..........
      HMGRclustalW{      corn} ..........  ..........  ..........  ..........
..........
      HMGRclustalW{    wheat3} ..........  ..........  ..........  ..........
..........
      HMGRclustalW{    wheat2} ..........  ..........  ..........  ..........
..........
HMGRclustalW{       soybean}   ..........  ..........  ..........  ..........
   HMGRclustalW{rubbertre3}    ..........  ..........  ..........  ..........
..........
   HMGRclustalW{rosyperiwi}    ..........  ..........  ..........  ..........
..........
   HMGRclustalW{     tomato}   ..........  ..........  ..........  ..........
..........
   HMGRclustalW{woodtobacc}    ..........  ..........  ..........  ..........
..........
   HMGRclustalW{     potato}   ..........  ..........  ..........  ..........
..........
      HMGRclustalW{    radish} ..........  ..........  ..........  ..........
..........
HMGRclustalW{arabadopsis1}     ..........  ..........  ..........  ..........
..........
   HMGRclustalW{cucumisme1}    ..........  ..........  ..........  ..........
..........
   HMGRclustalW{rubbertre2}    ..........  ..........  ..........  ..........
..........
   HMGRclustalW{rubbertre1}    ..........  ..........  ..........  ..........
..........
   HMGRclustalW{camptothec}    ..........  ..........  ..........  ..........
..........
   HMGRclustalW{ arabadops2}   ..........  ..........  ..........  ..........
..........
   HMGRclustalW{chineseham}    ..........  .........I  CGWNYEC.PK  FEEDVLSSDI
IILTITRCIA
```

FIG. 32G

```
  HMGRclustalW{chineseha2}    ..........  .........I CGWNYEC.PK FEEDVLSSDI
IILTITRCIA
  HMGRclustalW{syrianhamst}   ..........  .........I CGWNYEC.PK FEEDVLSSDI
IILTITRCIA
      HMGRclustalW{    rat}   ..........  .........I CGWNYEC.PK FEEDVLSSDI
IILTITRCIA
  HMGRclustalW{     rabbit}   ..........  .........I CGWNYEC.PK FEEDVLSSDI
IILTITRCIA
  HMGRclustalW{      human}   ..........  .........I CGWNYEC.PK FEEDVLSSDI
IILTITRCIA
  HMGRclustalW{      mouse}   ..........  .......... .......... ..........
..........
  HMGRclustalW{    xenopus}   ..........  .........I CGWNYAC.PK FEEDVLSSDI
IILTITRCIA
  HMGRclustalW{sea urchin}    ..........  .........I CGWNYECAPQ VKESSLSSDV
LVMCIMRTLA
  HMGRclustalW{  cockroach}   ..........  .......... PGWGHNC..I TLEEYNAADM
IVMTLIRCVA
  HMGRclustalW{drosophila}  GTIPPSSMGG SATSSRHRPC HGWSQSC.DG LEAEYNAADV
ILMTIVRCTA
  HMGRclustalW{dictyoste1}    ..........  .......... .......... ..........
..........
  HMGRclustalW{schistosom}    ..........  .........M LKILNTVLLF FDCFSTGTFF
VLLIYLFTRL
  HMGRclustalW{archaeoglo}    ..........  .......... .......... ..........
..........
  HMGRclustalW{pseudomonas}   ..........  .......... .......... ..........
..........

Consensus      ----------  ---------I CGWNYEC-PK FEEDVLSSDI
IILTITRCIA
```

FIG. 32H

```
                                    201
250
   HMGRclustalW{methanobac}    ..........  ..........  ..........  ..........
..........
    HMGRclustalW{methanococ}   ..........  ..........  ..........  ..........
..........
    HMGRclustalW{halobacter}   ..........  ..........  ..........  ..........
..........
    HMGRclustalW{sulfolobus}   ..........  ..........  ..........  ..........
..........
   HMGRclustalW{      yeast2}  FYTLCCLFND  MRKIGSKFWL  SFSALSNSAC  ALYLSLYTTH
SLLKKPASLL
    HMGRclustalW{     yeast1}  FYTIFGLFND  MRKTGSNFWL  SASTVVNSAS  SLFLALYVTQ
CILGKEVSAL
    HMGRclustalW{phycomyces}   ..........  ..........  ..........  ..........
..........
    HMGRclustalW{    fusarium} HAIEHRRIQA  QNSKSGKRSP  DGSTQNMIQY  AVQAAIKEKG
FEIIRDYAIE
    HMGRclustalW{     candida} FYTLFNLFAR  MRAVGSKVWL  GLSTLVSSFF  AFLFALYITT
RVLDLSIPFL
    HMGRclustalW{dictyoste2}   ..........  ..........  ..........  ..........
..........
       HMGRclustalW{wheat1}    ..........  ..........  ..........  ..........
..........
    HMGRclustalW{       rice}  ..........  ..........  ..........  ..........
..........
    HMGRclustalW{       corn}  ..........  ..........  ..........  ..........
..........
       HMGRclustalW{wheat3}    ..........  ..........  ..........  ..........
..........
       HMGRclustalW{wheat2}    ..........  ..........  ..........  ..........
..........
HMGRclustalW{      soybean}    ..........  ..........  ..........  ..........
..........
    HMGRclustalW{rubbertre3}   ..........  ..........  ..........  ..........
..........
    HMGRclustalW{rosyperiwi}   ..........  ..........  ..........  ..........
..........
    HMGRclustalW{     tomato}  ..........  ..........  ..........  ..........
..........
    HMGRclustalW{woodtobacc}   ..........  ..........  ..........  ..........
..........
    HMGRclustalW{     potato}  ..........  ..........  ..........  ..........
..........
       HMGRclustalW{radish}    ..........  ..........  ..........  ..........
..........
HMGRclustalW{arabadopsis1}     ..........  ..........  ..........  ..........
..........
    HMGRclustalW{cucumisme1}   ..........  ..........  ..........  ..........
..........
    HMGRclustalW{rubbertre2}   ..........  ..........  ..........  ..........
..........
    HMGRclustalW{rubbertre1}   ..........  ..........  ..........  ..........
..........
    HMGRclustalW{camptothec}   ..........  ..........  ..........  ..........
..........
    HMGRclustalW{arabadops2}   ..........  ..........  ..........  ..........
..........
    HMGRclustalW{chineseham}   ILYIYFQFQN  LRQLGSKYIL  GIAGLFTIFS  SFVFSTVVIH
..........
```

FIG. 32I

```
HMGRclustalW{chineseha2}    ILYIYFQFQN LRQLGSKYIL GIAGLFTIFS SFVFSTVVIH
..........
HMGRclustalW{syrianhamst}   ILYIYFQFQN LRQLGSKYIL GIAGLFTIFS SFVFSTVVIH
..........
     HMGRclustalW{   rat}   ILYIYFQFQN LRQLGSKYIL GIAGLFTIFS SFVFSTVVIH
..........
  HMGRclustalW{    rabbit}  ILYIYFQFQN LRQLGSKYIL GIAGLFTIFS SFVFSTVVIH
..........
 HMGRclustalW{     human}   ILYIYFQFQN LRQLGSKYIL GIAGLFTIFS SFVFSTVVIH
..........
  HMGRclustalW{     mouse}  .......... .......... .......... ..........
..........
   HMGRclustalW{   xenopus} ILYIYFQFQN LRQLGSKYIL GIAGLFTIFS SFVFSTVVIH
..........
    HMGRclustalW{sea urchin} VAYLYLQFTK LRTTGSKYIL GIAGLFTIFS SFLFSSAVIH
..........
   HMGRclustalW{ cockroach} VLYSYYQFCH LQKLGSKYIL GIAGLFTVFS SFVFSSSVIN
..........
   HMGRclustalW{drosophila} VLYCYYQFCS LHRLGSKYVL GIAGLFTVFS SFIFTTAIIK
..........
   HMGRclustalW{dictyostel} .......... .......... .......... ..........
..........
   HMGRclustalW{schistosom} RTHLLHFSSS NCHLDVIIYQ SRAVIIFLVV FVYFIGVLTC
KINDKILVHT
   HMGRclustalW{archaeoglo} .......... .......... .......... ..........
..........
   HMGRclustalW{pseudomonas} .......... .......... .......... ..........
..........

Consensus      ILYIYFQFQN LRQLGSKYIL GIAGLFTIFS SFVFSTVVIH ------
----
```

FIG. 32J

```
                                    251
300
   HMGRclustalW{methanobac}    ..........  ..........  ..........  ..........
..........
    HMGRclustalW{methanococ}   ..........  ..........  ..........  ..........
..........
    HMGRclustalW{halobacter}   ..........  ..........  ..........  ..........
..........
    HMGRclustalW{sulfolobus}   ..........  ..........  ..........  ..........
..........
    HMGRclustalW{     yeast2}  SLVIGLPFIV  VIIG.FKHKV  RLAAFSLQKF  HRISIDKKIT
VSNIIYEAMF
    HMGRclustalW{     yeast1}  TLFEGLPFIV  VVVG.FKHKI  KIAQYALEKF  ERVGLSKRIT
TDEIVFESVS
    HMGRclustalW{phycomyces}   ..........  ..........  ..........  ..........
..........
    HMGRclustalW{   fusarium}  IVILVIGAAS  GVQGGLQQFC  FLAAWTLF.F  DFILLFTFYT
AILSIKLRST
    HMGRclustalW{    candida}  SLSEGIPFFV  AVVG.FNNKI  LLAEKVLQ.N  QLNAQSSKND
APTVLYQALR
    HMGRclustalW{dictyoste2}   ..........  ..........  ..........  ..........
..........
        HMGRclustalW{wheat1}   ..........  ..........  ..........  ..........
..........
        HMGRclustalW{    rice} ..........  ..........  ..........  ..........
..........
        HMGRclustalW{    corn} ..........  .........M  EVRG......  .GVGQGSAAR
......HPPA
        HMGRclustalW{wheat3}   ..........  ..........  ..........  ..........
..........
        HMGRclustalW{wheat2}   ..........  ..........  ..........  ..........
..........
HMGRclustalW{       soybean}   ..........  ..........  ..........  ..........
..........
    HMGRclustalW{rubbertre3}   ..........  .........M  DEVRRRPP.K  HIVRKDHDGE
VLNSFSHG..
    HMGRclustalW{rosyperiwi}   ..........  .........M  DSRRRSP...  TVTAKAAAGE
LPLAPHEGQ.
    HMGRclustalW{     tomato}  ..........  .........M  DVRRRSEEPV  YPSKVFAAPE
KPLKPHKKQQ
    HMGRclustalW{woodtobacc}   ..........  .........M  DVRRRSEKPA  YPTKEFAAGE
KPLKPHK...
    HMGRclustalW{     potato}  ..........  .........M  DVRRRPVKPL  YTSKDASAG.
EPLKQQE...
        HMGRclustalW{radish}   ..........  .........M  DIRR..RPPK  PPVNSN....
...RFLDNRS
HMGRclustalW{arabadopsis1}     ..........  .........M  DLRR..RPPK  PPVTNNNNSN
GSFRSYQPRT
    HMGRclustalW{cucumismel}   ..........  .........M  DRRRSLRPPR  PNAVQDADAT
CTFRRDEQDA
    HMGRclustalW{rubbertre2}   ..........  ..........  ..........  ..........
..........
    HMGRclustalW{rubbertre1}   ..........  .........M  DTTG..RLH.  ....HR....
......KHAT
    HMGRclustalW{camptothec}   ..........  .........M  DVRRRSINSI  HQIPSVGGTA
PPMLKPKQPT
    HMGRclustalW{arabadops2}   ..........  .........M  EDLRRRFPTK  KNGEEISN..
..........
    HMGRclustalW{chineseham   FLDKELTGLN  EALPFFLLLI  DLSRASALAK  FALSSNSQDE
VRENIARGMA
```

FIG. 32K

| | | | | |
|---|---|---|---|---|
| HMGRclustalW{chineseha2} | FLDKELTGLN | EALPFFLLLI | DLSRASALAK | FALSSNSQDE |
| VRENIARGMA | | | | |
| HMGRclustalW{syrianhamst} | FLDKELTGLN | EALPFFLLLI | DLSRASALAK | FALSSNSQDE |
| VRENIARGMA | | | | |
| HMGRclustalW{ rat} | FLDKELTGLN | EALPFFLLLI | DLSRASALAK | FALSSNSQDE |
| VRENIARGMA | | | | |
| HMGRclustalW{ rabbit} | FLDKELTGLN | EALPFFLLLI | DLSRASALAK | FALSSNSQDE |
| VRENIARGMA | | | | |
| HMGRclustalW{ human} | FLDKELTGLN | EALPFFLLLI | DLSRASTLAK | FALSSNSQDE |
| VRENIARGMA | | | | |
| HMGRclustalW{ mouse} | .......... | .......... | .......... | .......... |
| .......... | | | | |
| HMGRclustalW{ xenopus} | FLDKELTGLN | EALPFFLLLI | DLSKASALAK | FALSSNSQDE |
| VRDNIARGMA | | | | |
| HMGRclustalW{sea urchin} | LFGLELTGLN | EALPFFLLLI | DLTKASALTK | FALSSTTQNE |
| VVDNIARGMA | | | | |
| HMGRclustalW{ cockroach} | FLGSDVSDLK | DALFFFLLLI | DLSKATVLAQ | FALSSRSQDE |
| VKENIARGIA | | | | |
| HMGRclustalW{drosophila} | FLGSDISELK | DALFFLLLVI | DLSNSGRLRS | GAMGSN.QAE |
| VTQNIARGLE | | | | |
| HMGRclustalW{dictyostel} | .......... | .......... | .......... | .......... |
| .......... | | | | |
| HMGRclustalW{schistosom} | MLRNKRQLNT | LFYTLILFTF | ALCSLSSVLF | VPYTSFAIFL |
| LSTSVFLLFS | | | | |
| HMGRclustalW{archaeoglo} | .......... | .......... | .......... | .......... |
| .......... | | | | |
| HMGRclustalW{pseudomonas} | .......... | .......... | .......... | .......... |
| .......... | | | | |
| Consensus | FLDKELTGLN | EALPFFLLL- | DL-RASALAK | FALSSNSQDE |
| VRENIARGMA | | | | |

FIG. 32L

```
                                    301
350
   HMGRclustalW{methanobac}   ..........  ..........  ..........  ..........
..........
    HMGRclustalW{methanococ}  ..........  ..........  ..........  ..........
..........
    HMGRclustalW{halobacter}  ..........  ..........  ..........  ..........
..........
    HMGRclustalW{sulfolobus}  ..........  ..........  ..........  ..........
..........
    HMGRclustalW{    yeast2}  QEGAYLIRDY  LFYISSFIGC  AIYARHLPGL  VNFCILSTFM
LVFDLLLSAT
    HMGRclustalW{    yeast1}  EEGGRLIQDH  LLCIFAFIGC  SMYAHQLKTL  TNFCILSAFI
LIFELILTPT
    HMGRclustalW{phycomyces}  ..........  ..........  ..........  ..........
..........
    HMGRclustalW{   fusarium} VSSVMSICVW  PLRMMASRRV  AENVAKGDDE  LNRVRGDAPL
FGRKSSSIPK
    HMGRclustalW{   candida}  EQGPLLLRDH  LFMITAFLGC  SFYASYLDGL  KNFCILAALI
LAFDILTTST
    HMGRclustalW{dictyoste2}  ..........  ..........  ..........  ..........
..........
       HMGRclustalW{wheat1}   ..........  ..........  ..........  ..........
..........
    HMGRclustalW{      rice}  ..........  ..........  ..........  .MRIT.....
...NGLAMVS
       HMGRclustalW{   corn}  PE....PSRA  ........AA  RVQAGDALPL  PIRHT.....
...NLIFSAL
       HMGRclustalW{wheat3}   ..........  ..........  ..........  ..........
..........
       HMGRclustalW{wheat2}   ..........  ..........  ..........  ..........
..........
HMGRclustalW{     soybean}    ..........  ..........  ..........  ..........
..........
    HMGRclustalW{rubbertre3}  ........HH  L.......PP  LKPSDYSLPL  SLYLA.....
...NALVFSL
    HMGRclustalW{rosyperiwi}  ........NQ  Q.......PS  IPRSSDVLPL  PLYLA.....
...NGVFFTL
    HMGRclustalW{    tomato}  QQ....QEDK  N.......TL  LIDASDALPL  PLYLTT....
...NGLFFTM
    HMGRclustalW{woodtobacc}  QQ....QEQD  N.......SL  LI.ASDALPL  PLYLT.....
...NGLFFTM
    HMGRclustalW{    potato}  ..........  ........VS  SPKASDALPL  PLYLT.....
...NGLFFTM
       HMGRclustalW{radish}   DD....DDRR  K.....TLTS  PPKASDALPL  PLYLT.....
...NAVFFTL
HMGRclustalW{arabadopsis1}    SD....DDHR  RR..ATTIAP  PPKASDALPL  PLYLT.....
...NAVFFTL
    HMGRclustalW{cucumismel}  SA....ADHL  KR.......A  SPKASDALPL  PLYLT.....
...NTIFFTL
    HMGRclustalW{rubbertre2}  ..........  ..........  ..........  ..........
..........
    HMGRclustalW{rubbertre1}  PV....EDRS  P........T  TPKASDALPL  PLYLT.....
...NAVFFTL
    HMGRclustalW{camptothec}  KV....DAVD  L.......PD  SPKASDALPL  PLYIT.....
...NGVFFTL
    HMGRclustalW{arabadops2}  ......VAVD  ........PP  LRKASDALPL  PLYLT.....
...NTFFLSL
    HMGRclustalW{chineseham}  ILGPTFTLDA  LV..ECLVIG  VGTMSGVRQL  EIMCCFGCMS
VLANYFVFMT
```

FIG. 32M

```
  HMGRclustalW{chineseha2}    ILGPTFTLDA LV..ECLVIG VGTMSGVRQL EIMCCFGCMS
VLANYFVFMT
  HMGRclustalW{syrianhamst}   ILGPTFTLDA LV..ECLVIG VGTMSGVRQL EIMCCFGCMS
VLANYFVFMT
      HMGRclustalW{     rat}  ILGPTFTLDA LV..ECLVIG VGTMSGVRQL EIMCCFGCMS
VLANYFVFMT
    HMGRclustalW{   rabbit}   ILGPTFTLDA LV..ECLVIG VGTMSGVRQL EIMCCFGCMS
VLANYFVFMT
    HMGRclustalW{    human}   ILGPTFTLDA LV..ECLVIG VGTMSGVRQL EIMCCFGCMS
VLANYFVFMT
    HMGRclustalW{    mouse}   .......... .......... .......... ..........
..........
    HMGRclustalW{  xenopus}   ILGPTFTLEA LV..ECLVIG VGTMSGVRQL EIMCCFGCMS
VLANYFAFMT
  HMGRclustalW{sea urchin}    ILGPTITLDT VV..TTLVIS IGTMSSIRKM EVFCCFGILS
LIANYFVFMT
  HMGRclustalW{ cockroach}    MLGPTITLDT VV..ETLVIG VGMLSGVRRL EVLCCFACMS
VIVNYVVFMT
  HMGRclustalW{drosophila}    LLGPAISLDT IV..VVLLVG VGTLSGVQRL EVLCMFAVLS
VLVNYVVFMT
  HMGRclustalW{dictyostel}    .......... .........M LFAPPNLETK ELFWIIY.IL
ILIPKVFAKV
  HMGRclustalW{schistosom}    DLSVFFIVLE YYLLEIELVN YEHAKRHCLL SHLFSNQLFV
DHMLGMFLKT
  HMGRclustalW{archaeoglo}    .......... .......... .......... ..........
..........
  HMGRclustalW{pseudomonas}   .......... .......... .......... ..........
..........
                 Consensus    ILGPTFTLDA LV--ECLVIG VGTASD-LPL -LYCTFGCMS
VLANYFFFMT
```

FIG. 32N

```
                              351
400
  HMGRclustalW{methanobac}    .........  .........  .........  .........
.........
  HMGRclustalW{methanococ}    .........  .........  .........  .........
.........
  HMGRclustalW{halobacter}    .........  .........  .........  .........
.........
  HMGRclustalW{sulfolobus}    .........  .........  .........  .........
.........
  HMGRclustalW{      yeast2}  FYSAILSMKL EINIIHRSTV IRQTL..EED GVVPTTADII
YKDETASEPH
  HMGRclustalW{      yeast1}  FYSAILALRL EMNVIHRSTI IKQTL..EED GVVPSTARII
SKAEKKSVSS
  HMGRclustalW{phycomyces}    .........  .........  .........  .........
.........
  HMGRclustalW{    fusarium}  FKVLMILGFI FVNIVNICSI PFRNP..SSM STIRTWASSL
GGVIAPLSVD
  HMGRclustalW{     candida}  FLSAILSLKL EINQIHRSTL LREQL..EDD GLTETTVDDV
LKSNSLAGTK
  HMGRclustalW{dictyoste2}    .........  .........  .........  .........
.........
     HMGRclustalW{wheat1}     .........  .........  .........  .........
.........
  HMGRclustalW{        rice}  LVLSSCDLVR LCSDRER... PL........ ....GGREFA
TVVCQLASVV
  HMGRclustalW{        corn}  FAASLAYLMR RWREKIRSST PLHA...... ...VGLAEML
AIFGLVASLI
  HMGRclustalW{wheat3}        .........  .........  .........  .........
.........
     HMGRclustalW{wheat2}     .........  .........  .........  .........
HMGRclustalW{     soybean}    .........  .........  .........  .........
.........
  HMGRclustalW{rubbertre3}    FFSVAYFLLH RWREKIRKST PLHI...... ...VTFPEIA
ALICLVASVI
  HMGRclustalW{rosyperiwi}    FFSVMYFLLT RWREKIRNAT PLHV...... ...VTLSELA
ALASLIASVI
  HMGRclustalW{      tomato}  FFSVMYFLLS RWREKIRNST PLHV...... ...VTLSELG
AIVSLIASVI
  HMGRclustalW{woodtobacc}    FFSVMYYLLS RWREKIRNST PLHV...... ...VTFSELV
AIASLIASVI
  HMGRclustalW{      potato}  FFSVMYFLLV RWREKIRNSI PLHV...... ...VTLSELL
AMVSLIASVI
     HMGRclustalW{radish}     FFSVAYYLLH RWRDKIRYNT PLHV...... ...VTVTELG
AIVALIASFI
HMGRclustalW{arabadopsis1}    FFSVAYYLLH RWRDKIRYNT PLHV...... ...VTITELG
AIIALIASFI
  HMGRclustalW{cucumismel}    FFSVAYYLLH RWRDKIRNST PLHV...... ...VTLSEIA
AIVSLMASFI
  HMGRclustalW{rubbertre2}    .........  .........  .........  .........
.........
  HMGRclustalW{rubbertre1}    FFSVAYYLLH RWRDKIRNST PLHI...... ...VTLSEIV
AIVSLIASFI
  HMGRclustalW{camptothec}    FFTVVYYLLV RWREKIRNST PLHV...... ...VTLSEIA
AIFTFVASFI
  HMGRclustalW{arabadops2}    FFATVYFLLS RWREKIRNST PLHV...... ...VDLSEIC
ALIGFVASFI
  HMGRclustalW{chineseham}    FFPACVSLVL ELSRESREGR PIWQ...LSH FARVLEEEE.
NKPNPVTQRV
```

FIG. 32O

```
HMGRclustalW{chineseha2}   FFPACVSLVL  ELSRESREGR  PIWQ...LSH  FARVLEEEE.
NKPNPVTQRV
 HMGRclustalW{syrianhamst} FFPACVSLVL  ELSRESREGR  PIWQ...LSH  FARVLEEEE.
NKPNPVTQRV
     HMGRclustalW{   rat}  FFPACVSLVL  ELSRESREGR  PIWQ...LSH  FARVLEEEE.
NKPNPVTQRV
  HMGRclustalW{  rabbit}   FFPACVSLVL  ELSRESREGR  PIWQ...LSH  FARVLEEEE.
NKPNPVTQRV
  HMGRclustalW{   human}   FFPACVSLVL  ELSRESREGR  PIWQ...LSH  FARVLEEEE.
NKPNPVTQRV
  HMGRclustalW{   mouse}   ..........  ..........  ..........  ..........
..........
    HMGRclustalW{ xenopus} FFPACVSLVL  ELSRESREGR  PIWQ...LSQ  FASVLEEEED
NKPNPVTQRV
  HMGRclustalW{sea urchin} FFPACLSLVL  ELSNSNKYGR  PVWH...LGR  FAEVLEEEED
RKPNPVVQRV
  HMGRclustalW{ cockroach} FYPACLSLIL  ELSRSGESGR  PAWHD..KSL  IIKALHEED.
QKPNPVVQRV
  HMGRclustalW{drosophila} FYPACLSLIF  DLSRSGVDMS  VVREKAKGSL  PLKSLTEEE.
QKANPVLQRV
  HMGRclustalW{dictyostel} MSVRELFPFF  KWGFNIRRSN  FLVP......  ...ILSNNVI
VTGEEAVQYE
  HMGRclustalW{schistosom} SLFSISTTSK  YAYLESIFKC  TLMEQIIYIM  IVFVFLPSFM
RIFASYAKRM
   HMGRclustalW{archaeoglo} ..........  ..........  ..........  ..........
..........
    HMGRclustalW{pseudomonas} ..........  ..........  ..........  ..........
..........
             Consensus    FFSACYSLLL  -WRRKIRNST  PLHV---LSH  FARVTLEEEA  AKPN-
VASRI
```

FIG. 32P

```
                                    401
450
  HMGRclustalW{methanobac}       ..........  ..........  ..........  ..........
..........
  HMGRclustalW{methanococ}       ..........  ..........  ..........  ..........
..........
  HMGRclustalW{halobacter}       ..........  ..........  ..........  ..........
..........
  HMGRclustalW{sulfolobus}       ..........  ..........  ..........  ..........
..........
  HMGRclustalW{     yeast2}      FLRSNVAIIL  GKASVIGLLL  LINLYVF...  .TDKLNATIL
NTVYFDSTIY
  HMGRclustalW{     yeast1}      FLNLSVVVII  MKLSVILLFV  FINFYNF...  GANWVN.DAF
NSLYFDKERV
  HMGRclustalW{phycomyces}       ..........  ..........  ..........  ..........
..........
  HMGRclustalW{   fusarium}      PFKVASNGLD  AILPTAKSNN  RPTLVTV...  LTPIKYELEY
PSIHYALGSA
  HMGRclustalW{    candida}      TFTDAPSTLV  TVAKVAGVSV  FFGLHFY...  GFGSAWLSDL
SAGNETNDTF
  HMGRclustalW{dictyoste2}       ..........  ..........  ..........  ..........
..........
      HMGRclustalW{wheat1}       ..........  ..........  ..........  ..........
..........
    HMGRclustalW{      rice}     YLLSLFAHPD  APATTTGDDD  ..........  ..........
..........
      HMGRclustalW{   corn}      YLLSFFGIAF  VQSIVSSGDD  ..........  ..........
..........
      HMGRclustalW{wheat3}       ..........  ..........  ..........  ..........
..........
      HMGRclustalW{wheat2}       ..........  ..........  ..........  ..........
..........
HMGRclustalW{     soybean}       ..........  ..........  ..........  ..........
..........
  HMGRclustalW{rubbertre3}       YLLGFFGIGF  VHSFS.RAST  ..........  ..........
..........
  HMGRclustalW{rosyperiwi}       YLVSFFGLDF  VQSLIYKPNN  ..........  ..........
..........
  HMGRclustalW{     tomato}      YLLGFFGIGF  VQTFVSRGNN  ..........  ..........
..........
  HMGRclustalW{woodtobacc}       YLLGFFGIGF  VQSFVSRDNN  ..........  ..........
..........
  HMGRclustalW{     potato}      YLLGFFGIGF  VQSFVSRSNS  ..........  ..........
..........
      HMGRclustalW{radish}       YLLGFFGIDF  VQSFISRP..  ..........  ..........
..........
HMGRclustalW{arabadopsis1}       YLLGFFGIDF  VQSFISRASG  ..........  ..........
..........
  HMGRclustalW{cucumismel}       YLLGFFGIDF  VQSFIARSSP  ..........  ..........
..........
  HMGRclustalW{rubbertre2}       ..........  ..........  ..........  ..........
..........
  HMGRclustalW{rubbertre1}       YLLGFFGIDF  VQSFIARASH  ..........  ..........
..........
  HMGRclustalW{camptothec}       YLLGFFGIGL  VQPFTSRSSH  ..........  ..........
..........
  HMGRclustalW{arabadops2}       YLLGFCGIDL  IFRSS...SD.  ..........  ..........
..........
  HMGRclustalW{chineseham}       KMIMSLGLVL  VHAHSRWIAD  PSPQNST...  TE.HSKVSLG
LDEDVSKRIE
```

FIG. 32Q

```
HMGRclustalW{chineseha2}   KMIMSLGLVL  VHAHSRWIAD  PSPQNST...  TE.HSKVSLG
LDEDVSKRIE
HMGRclustalW{syrianhamst}  KMIMSLGLVL  VHAHSRWIAD  PSPQNST...  TE.HSKVSLG
LDEDVSKRIE
     HMGRclustalW{    rat} KMIMSLGLVL  VHAHSRWIAD  PSPQNST...  AE.QSKVSLG
LAEDVSKRIE
   HMGRclustalW{  rabbit}  KMIMSLGLVL  VHAHSRWIAD  PSPQNST...  AD.NSKVSLG
LDENVSKRIE
   HMGRclustalW{   human}  KMIMSLGLVL  VHAHSRWIAD  PSPQNST...  AD.TSKVSLG
LDENVSKRIE
   HMGRclustalW{   mouse}  ..........  ..........  ..........  ..........
..........
   HMGRclustalW{  xenopus} KMIMSLGLVL  VHAHSRWISE  PSSQNST...  SISDHEVTTM
LDDMMPKRVE
   HMGRclustalW{sea urchin} KMIMRTGLVL VHAHSYWLAS  ....NDT...  ELMSRDMLYD
GNLLTDKKID
   HMGRclustalW{ cockroach} KVIMSAGLML VHAH.RWVRC  ..........  ........L.
..........
   HMGRclustalW{drosophila} KLIMTTGLMA VHIYSREVSP  ....AAT...  TMVDKTLTPT
LSLNVSNNRT
   HMGRclustalW{dictyostel} KPLPYIPQHN QQQQQKQQPS  ..........  ..........
..........
   HMGRclustalW{schistosom} YGEQKKCLVS NKGVSSSTRK  RRHSYSSGHS  YVEYRRMSVH
NLIGYVVNPN
   HMGRclustalW{archaeoglo} ..........  ..........  ..........  ..........
..........
   HMGRclustalW{pseudomonas} .......... ..........  ..........  ..........
..........
            Consensus      YLL-FFG-VL  V-A-SR-ISD  PSPQNST---  ----SKVSLG LDE-
VSKRIE
```

FIG. 32R

```
                                        451
500
  HMGRclustalW{methanobac}     .......... .......... .......... ..........
..........
  HMGRclustalW{methanococ}     .......... .......... .......... ..........
..........
  HMGRclustalW{halobacter}     .......... .......... .......... ..........
..........
  HMGRclustalW{sulfolobus}     .......... .......... .......... ..........
..........
  HMGRclustalW{       yeast2}  SLPNFINYKD IGNLSNQVII SVLPKQYYTP LKKYHQIEDS
VLLIIDSVSN
  HMGRclustalW{       yeast1}  SLPDFITSNA SENFKEQAIV SVTPLLYYKP IKSYQRIEDM
VLLLLRNVSV
  HMGRclustalW{phycomyces}     .......... .......... .......... ..........
..........
  HMGRclustalW{     fusarium}  ASNPAYN.DA FHHHFQGYGV GGRMVGGILK SLEDPVLSKW
IVIALALSVA
  HMGRclustalW{      candida}  TLYDAVA.DQ IPIGSNGTLV TLFPTRFFLP EKLSTQIEAV
VLSFIGLIST
  HMGRclustalW{dictyoste2}     .......... .......... .......... ..........
..........
  HMGRclustalW{      wheat1}   .......... .......... .......... ..........
..........
  HMGRclustalW{        rice}   ..D....... .......... .......... ..........
..........
  HMGRclustalW{        corn}   ..DEDFLVGS G......... .......... ..........
..........
  HMGRclustalW{      wheat3}   .......... .......... .......... ..........
..........
  HMGRclustalW{      wheat2}   .......... .......... .......... ..........
..........
HMGRclustalW{      soybean}    .......... .......... .......... ..........
..........
  HMGRclustalW{rubbertre3}     ..D.SWDVEE Y......... ..........D DDNIIIKEDT
R.........
  HMGRclustalW{rosyperiwi}     ..E.GWEIEE .......... .......... ..EILMVEDS
RN........
  HMGRclustalW{      tomato}   ..D.SWDE.. .......... ..........N DEEFLLKEDS
RC........
  HMGRclustalW{woodtobacc}     ..DECWDEED E......... ..........N DEQFLLEEDS
RR........
  HMGRclustalW{      potato}   ..D.SWDIED E......... ..........N AEQLIIEEDS
RR........
  HMGRclustalW{      radish}   ..D.SGDSER .......... .......... .....DFDDH
R.........
HMGRclustalW{arabadopsis1}     ..D.AWDLAD T......... ..........I .....DDDDH
R.........
  HMGRclustalW{cucumismel}     ..D.AWDLED .......... .......... .....EIDRT
L.........
  HMGRclustalW{rubbertre2}     .......... .......... .......... ..........
..........
  HMGRclustalW{rubbertre1}     ..D.VWDLED T......... ..........D P.NYLIDEDH
R.........
  HMGRclustalW{camptothec}     ..DDVWGVDD DE........ ..........D VDEIVLKEDT
R.........
  HMGRclustalW{arabadops2}     ..DDVWVNDG .......... .......... ..........
..........
  HMGRclustalW{chineseham}     PSVSLWQFYL SKMISMDIEQ VVTLSLAFLL AVKYIFFEQA
ET..ESTLSL
```

FIG. 32S

| | | | | |
|---|---|---|---|---|
| HMGRclustalW{chineseha2} | PSVSLWQFYL | SKMISMDIEQ | VVTLSLAFLL | AVKYIFFEQA ET..ESTLSL |
| HMGRclustalW{syrianhamst} | PSVSLWQFYL | SKMISMDIEQ | VVTLSLAFLL | AVKYIFFEQA ET..ESTLSL |
| HMGRclustalW{ rat} | PSVSLWQFYL | SKMISMDIEQ | VITLSLALLL | AVKYIFFEQA ET..ESTLSL |
| HMGRclustalW{ rabbit} | PSVSLWQFYL | SKMISMDIEQ | VITLSLALLL | AVKYIFFEQA ET..ESTLSL |
| HMGRclustalW{ human} | PSVSLWQFYL | SKMISMDIEQ | VITLSLALLL | AVKYIFFEQT ET..ESTLSL |
| HMGRclustalW{ mouse} | .......... | .......... | .......... | .......... .......... |
| HMGRclustalW{ xenopus} | PSMPLWQFYL | SRMVTMDVEQ | IITLGLALLL | AVKYIFFEQT ET..ESTFSM |
| HMGRclustalW{sea urchin} | PTMPLWEFYA | TRLWPPTLDY | ILTAILATVL | ASHYIFFSDL ATYPEKRVSI |
| HMGRclustalW{ cockroach} | .SIALWPDLT | S......LRY | FCTHCDTGVS | YSRWSFASEG EE..LPTVKL |
| HMGRclustalW{drosophila} | ESGEIADIII | KWLT.MSADH | IVISIVLIAL | VVKFICFDNR DP...LPDQL |
| HMGRclustalW{dictyostel} | ..QDYIQQPQ | .......... | .......... | ..N....DNN IN........ |
| HMGRclustalW{schistosom} | CHYKCWSTTF | VIFVSLIILH | LNNRYSERIS | SFKHNSSENE VFPVLYHITA |
| HMGRclustalW{archaeoglo} | .......... | .......... | .......... | .......... .......... |
| HMGRclustalW{pseudomonas} | .......... | .......... | .......... | .......... .......... |
| Consensus | PSDSLWDFY- | SKMISMDIEQ | VVTLSLA-LL | AVKYIFFED- RT--ESTLSL |

FIG. 32T

```
                                      501
550
  HMGRclustalW{methanobac}    ..........  ..........  ..........  ..........
..........
  HMGRclustalW{methanococ}    ..........  ..........  ..........  ..........
..........
  HMGRclustalW{halobacter}    ..........  ..........  ..........  ..........
..........
  HMGRclustalW{sulfolobus}    ..........  ..........  ..........  ..........
..........
  HMGRclustalW{     yeast2}   AIRDQFISKL  LFFAFAVSIS  INVYLLNAAK  IHTGYMNFQ.
..PQSNKIDD
  HMGRclustalW{     yeast1}   AIRDRFVSKL  VLSALVCSAV  INVYLLNAAR  IHTSYTADQL
VKTEVTKKSF
  HMGRclustalW{phycomyces}    ..........  ..........  ..........  ..........
..........
  HMGRclustalW{   fusarium}   LNGYLFNVAR  WGIKDPNVPE  HNIDRNELAR  AREFNDTGS.
.........AT
  HMGRclustalW{    candida}   AARDKYISKF  ILFAFAVSAS  INVYLLNVAR  IHTTRLEDA.
.........IE
  HMGRclustalW{dictyoste2}    ..........  ..........  ..........  ..........
..........
     HMGRclustalW{    wheat1} ..........  ..........  ..........  ..........
..........
      HMGRclustalW{     rice} ..........  ..........  ..........  ..........
..........
      HMGRclustalW{     corn} ..........  ..........  ..........  ..........
..........
      HMGRclustalW{   wheat3} ..........  ..........  ..........  ..........
..........
      HMGRclustalW{   wheat2} ..........  ..........  ..........  ..........
..........
HMGRclustalW{      soybean}   ..........  ..........  ..........  ..........
..........
  HMGRclustalW{ rubbertre3}   ..........  ..........  ..........  ..........
..........
  HMGRclustalW{ rosyperiwi}   ..........  ..........  ..........  ....G.....
..........
  HMGRclustalW{     tomato}   ..........  ..........  ..........  ....G.....
..........
  HMGRclustalW{  woodtobacc}  ..........  ..........  ..........  ....G.....
..........
  HMGRclustalW{     potato}   ..........  ..........  ..........  ....G.....
..........
       HMGRclustalW{ radish}  ..........  ..........  ..........  ..........
..........
HMGRclustalW{arabadopsis1}    ..........  ..........  ..........  ..........
..........
  HMGRclustalW{cucumisme1}    ..........  ..........  ..........  ..........
..........
  HMGRclustalW{ rubbertre2}   ..........  ..........  ..........  ..........
..........
  HMGRclustalW{ rubbertre1}   ..........  ..........  ..........  ..........
..........
  HMGRclustalW{  camptothec}  ..........  ..........  ..........  ..........
..........
   HMGRclustalW{ arabadops2}  ..........  ..........  ..........  ..........
..........
    HMGRclustalW{chineseham}  KN..PITSPV  VTPKKAPDNC  CRREPLLVRR  SEKLSSVEEE
PGVSQDRKVE
```

FIG. 32U

```
HMGRclustalW{chineseha2}   KN..PITSPV  VTPKKAPDNC  CRREPLLVRR  SEKLSSVEEE
PGVSQDRKVE
HMGRclustalW{syrianhamst}  KN..PITSPV  ATPKKAPDNC  CRREPVLSRR  NEKLSSVEEE
PGVNQDRKVE
   HMGRclustalW{     rat}  KN..PITSPV  VTPKKAQDNC  CRREPLLVRR  NQKLSSVEED
PGVNQDRKVE
   HMGRclustalW{  rabbit}  KN..PITSPV  VTQKKVPDSC  CREPVVVRN   NQKFCSVEEE
AGMSQDRKVE
   HMGRclustalW{   human}  KN..PITSPV  VTQKKVPDNC  CRREPMLVRN  NQKCDSVEEE
TGINRERKVE
   HMGRclustalW{   mouse}  ..........  ..........  ..........  ..........
..........
   HMGRclustalW{  xenopus} KN..PIISPV  AVQKKQIESC  CRREPEQ.EK  TVHVSTTEEA
S..SKEETEA
   HMGRclustalW{sea urchin} MEGHEVVNPG SDHEDASEVE  TIGTLSSSPS  TSDVRVIESM
TSRTQACQTD
   HMGRclustalW{ cockroach} VTGDSVVNSN STDDAQLHYY  IMRWLTV..S  ADHIVILILL
LALAVKFVFF
   HMGRclustalW{drosophila} RQ....SGPV AIEAKASQTT  PIDEEHVE..  ......QEKD
TENSAAVRTL
   HMGRclustalW{dictyostel} ..........  ..........  ..........  ..........
..........
   HMGRclustalW{schistosom} YEVTSIFHFI YNIFHVINAN  LVVYLFLGLF  LFKRIRLNKP
INSQLRNLNI
   HMGRclustalW{archaecglo} ..........  ..........  ..........  ..........
..........
   HMGRclustalW{pseudomonas} .........  ..........  ..........  ..........
..........

Consensus   KN--PITSPV  VT-KKAPDNC  CRREPLLVRR  --K-SSVEEE -G-
SQDRKVE
```

FIG. 32V

```
                              551
600
  HMGRclustalW{methanobac}    ..........  ..........  ..........  ..........
..........
  HMGRclustalW{methanococ}    ..........  ..........  ..........  ..........
..........
  HMGRclustalW{halobacter}    ..........  ..........  ..........  ..........
..........
  HMGRclustalW{sulfolobus}    ..........  ..........  ..........  ..........
..........
  HMGRclustalW{     yeast2}   LVVQQKSATI  EFSET.....  .....RSMPA  SSGLETPVTA
KDIIISEEIQ
  HMGRclustalW{     yeast1}   TAPVQKASTP  VLTN......  .....KTVIS  GSKVKSLSSA
QSSSSGPSSS
  HMGRclustalW{phycomyces}    ..........  ..........  ..........  ..........
..........
  HMGRclustalW{   fusarium}   LPLGEYVPPT  PMRTQ.....  .....PSTPA  ITDDEAEG..
..LHMTKARP
  HMGRclustalW{    candida}   LKKPKKKASK  TAVSV.....  .....PKAVV  VKDSETTKSS
EILHSSSESE
  HMGRclustalW{dictyoste2}    ..KGKSVNVE  DLKDQ.....  .....EIIAL  VDKGEIQP..
...HNLETRL
       HMGRclustalW{wheat1}   ..........  ..........  ..........  ..........
..........
  HMGRclustalW{       rice}   .......GQG  GSR.......  ..........  ..RA.....A
PPEPAPMHGH
  HMGRclustalW{       corn}   ......SSGS  AAA.......  ..........  ...PSRQHAQA
PAPCELLGSP
       HMGRclustalW{wheat3}   ..........  ..........  ..........  ..........
..........
       HMGRclustalW{wheat2}   ..........  ..........  ..........  ..........
..........
HMGRclustalW{     soybean}    ..........  ..........  ..........  ..........
..........
  HMGRclustalW{rubbertre3}    .......PTG  AC........  ..........  ...AAPSLDCS
LSLPTKIHAP
  HMGRclustalW{rosyperiwi}    ..T..NCTTL  GC........  ..........  ...AVPPPSVP
KIAPVVPQQP
  HMGRclustalW{     tomato}   ..P...ATTL  GC........  ..........  ...AVPAPPAR
QIAPMAPPQP
  HMGRclustalW{woodtobacc}    ..P...ATTL  GCT.......  ..........  ...AVPPPPAL
QIVPMVPPQP
  HMGRclustalW{     potato}   ..PCAAATTL  GC........  ..........  ...VVPPPPVR
KIAPMVPQQP
       HMGRclustalW{radish}   ......LVTC  PPP.......  ..........  ...PPP....S
QIVAAKLPNP
HMGRclustalW{arabadopsis1}    ......LVTC  SPP.......  ..........  ...TP......
IVSVAKLPNP
  HMGRclustalW{cucumismel}    ......LIDN  NRY.......  ..........  ...AAPRSASA
VALPSKVVDA
  HMGRclustalW{rubbertre2}    ..........  ..........  ..........  ..........
..........
  HMGRclustalW{rubbertre1}    ......LVTC  PPA.......  ..........  ...NISTKTTI
IAAPTKLPTS
  HMGRclustalW{camptothec}    .......TVP  CAA.......  ..........  ...APVDCPLP
PIKPKVVDPV
  HMGRclustalW{arabadops2}    ......MIPC  NQ........  ..........  ...SLDCREVL
PIKPNSVDPP
  HMGRclustalW{chineseham}    VIKPLVVETE  SAS.......  .RATFVLG.A  .SGTSPPVAA
RTQELEIELP
```

FIG. 32W

```
HMGRclustalW{chineseha2}   VIKPLVVETE .SAS....... .RATFVLG.A .SGTSPPVAA
RTQELEIELP
HMGRclustalW{syrianhamst}  VIKPLVAETE STS....... .RATFVLG.A .SGGCSPVAL
GTQEPEIELP
  HMGRclustalW{      rat}  VIKPLVAEAE TSG....... .RATFVLG.A .SAASPPLAL
GAQEPGIELP
  HMGRclustalW{   rabbit}  VIKPLVAETD SPH....... .RAAFVVGGS .SFPDTSLVL
ETKEPEIELP
  HMGRclustalW{    human}  VIKPLVAETD TPN....... .RATFVVGNS .SLLDTSSVL
VTQEPEIELP
  HMGRclustalW{    mouse}  .......... .......... .......... ..........
..........
  HMGRclustalW{  xenopus}  VIKPLPLETS P......... .KAKFIVG.. .DSSPLELSP
EDKNTMFDLP
HMGRclustalW{sea urchin}   PVTASPRNSR SSSPVSSHSV KPARFTIGSS GSGSEDEEEE
VIKEEEVEWV
HMGRclustalW{ cockroach}   ETRDELTTTR GMDG.....W VEVSSPVEHK YVQTEQPSCS
APEQPLEEPP
HMGRclustalW{drosophila}   LFTIEDQSSA N......... .......... ..ASTQTDLL
PLRHRLVGPI
HMGRclustalW{dictyostel}   .....SGKEQ EQ........ .......... ..QQQQQQQQ
QQTPDITNQP
HMGRclustalW{schistosom}   PKIKETLISD QVKQSPVLPK FSKKLNDIPL QSRKRIYCLH
KDDDYIDRND
HMGRclustalW{archaeoglo}   .......... .......... .......... ..........
..........
 HMGRclustalW{pseudomonas} .......... .......... .......... ..........
..........
            Consensus      VIKPLVAETE --S------- -RATFV-G-A -SA-PPPPA- -I-
PPEIELP
```

FIG. 32X

```
                                  601
650
    HMGRclustalW{methanobac}   ..........  ..........  ..........  .......MS.
...IMDDLME
    HMGRclustalW{methanococ}   ..........  ..........  ..........  .......MEN
YNDILEKMLN
    HMGRclustalW{halobacter}   ..........  ..........  ..........  .......MTD
AASLADRVRE
    HMGRclustalW{sulfolobus}   ..........  ..........  ..........  .......MK.
IDEVVEKLVK
    HMGRclustalW{    yeast2}   NNE.CVYALS  SQDEPIRP.L  SNLVELME..  ...KEQLKNMN
NTEVSNLVVN
    HMGRclustalW{    yeast1}   SEEDDSRDIE  SLDKKIRP.L  EELEALLS..  ...SGNTKQLK
NKEVAALVIH
    HMGRclustalW{phycomyces}   ..........  ..........  ..........  ..........
..........
    HMGRclustalW{   fusarium}  ANL.......  ....PNRS.N  EELEKLLS..  ...ENALREMT
DEEVISLSMR
    HMGRclustalW{    candida}  SEQ.......  ....SSRP.L  EQVIELYK..  ...DGKVKTLV
DDEVVSLVTA
    HMGRclustalW{dictyoste2}   PNN.......  ..........F QRAVHIRR..  ...KLLARDLQ
KEHQRALHAQ
        HMGRclustalW{wheat1}   ..........  ..........  ..........  ..........
..........
    HMGRclustalW{      rice}   G.........  ..........  ..........  ...GGMMEGD
DEEIVAAVAS
        HMGRclustalW{   corn}  AA........  ..........  .......A..  ...PEKMPED
DEEIVASVVA
        HMGRclustalW{wheat3}   ..........  ..........  ..........  ..........
..........
        HMGRclustalW{wheat2}   ..........  ..........  ..........  ..........
..........
HMGRclustalW{      soybean}    ..........  ..........  ..........  ..........
..........
    HMGRclustalW{rubbertre3}   ..........  ..........I VSTTT.....  ...TSTLSDD
DEQIIKSVVS
    HMGRclustalW{rosyperiwi}   SK........  ......MV.I  IEKPAPLI..  ...TPQNSEE
DEDIIKAVVA
    HMGRclustalW{     tomato}  S.........  ......MS.M  VEKPAPLI..  ...TSASSGE
DEEIIKSVVQ
    HMGRclustalW{woodtobacc}   SKV.......  ......AA.M  SEKPAPLV..  ...TPAASEE
DEEIIKSVVQ
    HMGRclustalW{     potato}  AKV.......  .....ALS.Q  TEKPSPII..  ...MPALSED
DEEIIQSVVQ
        HMGRclustalW{radish}   E.........  ..........  ..........  ...QPPLPKE
DEEIVKSVLD
HMGRclustalW{arabadopsis1}     EP........  ..........  .......IV..  ...TESLPEE
DEEIVKSVID
    HMGRclustalW{cucumismel}   EA........  ..........  .......LN..  ...TIPLPEE
DEEVVKMVVD
    HMGRclustalW{rubbertre2}   ..........  ..........  ..........  ..........
..........
    HMGRclustalW{rubbertre1}   EP........  ..........  .......LI..  ...APLVSEE
DEMIVNSVVD
    HMGRclustalW{camptothec}   P.........  ..........  ..........I..  ...SPPSSEE
DEEIIKSVVE
    HMGRclustalW{arabadops2}   RE........  ..........  ..........  ...SELDSVE
DEEIVKLVID
    HMGRclustalW{chineseham}   SE........  .....PRP.N  EECLQILE..  SAEKGAKFLS
DAEIIQLVNA
```

FIG. 32Y

```
HMGRclustalW{chineseha2}   SE........ .....PRP.N EECLQILE.. SAEKGAKFLS
DAEIIQLVNA
  HMGRclustalW{syrianhamst} SE........ .....PRP.N EECLQILE.. SAEKGAKFLS
DAEIIQLVNA
    HMGRclustalW{      rat} SE........ .....PRP.N EECLQILE.. SAEKGAKFLS
DAEIIQLVNA
   HMGRclustalW{    rabbit} KE........ .....PRP.N EECLQILG.. NAEKGAKFLS
DAEIIQLVNA
   HMGRclustalW{     human} RE........ .....PRP.N EECLQILG.. NAEKGAKFLS
DAEIIQLVNA
   HMGRclustalW{     mouse} .......... .......... .......... ..........
..........
   HMGRclustalW{   xenopus} EE........ .....PRP.L DECVRILK.. NPDKGAQYLT
DAEVISLVNA
   HMGRclustalW{sea urchin} LET....... .ELKAPRP.M PELLEIL... NVGKGPNALT
DDEVQLLVGA
   HMGRclustalW{ cockroach} AS........ .....NRS.I DECLSVC... KSDVGAQALS
DCEVMALVTS
   HMGRclustalW{drosophila} KP........ .....PRP.V QECLDILNST EEGSGPAALS
DEEIVSIVHA
   HMGRclustalW{dictyostel} TKTN...... .......... .......... .KKIPIKELS
NEEILIKLEK
   HMGRclustalW{schistosom} SSSVSTFSNT CKNSNERPSN VLDLDMLTEK IKQGLGHELS
DTEILQLLSH
   HMGRclustalW{archaeoglo} .......... .......... .......... ..........
.MQVLRLDRR
   HMGRclustalW{pseudomonas} .......... .......... .......... ..........
..........
              Consensus    SE-------- -----PRP-N EECLQIL--- -AEKGAKSLS
DEEIKLVVA
```

FIG. 32Z

```
                                        651
700
    HMGRclustalW{methanobac}    GR..IKLYEI  E.RHVPVDEA  VRIRREFIE.  ....RTCGVK
..LEHVSNYS
    HMGRclustalW{methanococ}    GE..IKPYQL  D.KMFGSKIA  TEIRRKFIE.  ....KKVGIE
..FKHICNYS
    HMGRclustalW{halobacter}    GD..LRLHEL  E.AHADADTA  AEARRLLVE.  ....SQSGAS
..LDAVGNYG
    HMGRclustalW{sulfolobus}    GE..ISFHEV  D.NLLEANAA  MVARRLALE.  ....KIVGVG
..LPSIGSTV
    HMGRclustalW{    yeast2}    G..KLPLYSL  EKKLEDTTRA  VLVRRKALST  LAESPILVS.
...EKLPFRN
    HMGRclustalW{    yeast1}    G..KLPLYAL  EKKLGDTTRA  VAVRRKALSI  LAEAPVLAS.
...DRLPYKN
    HMGRclustalW{phycomyces}    ..........  ..........  ..........  ..........
..........
    HMGRclustalW{  fusarium}    G..KIPGYAL  EKTLGDFTRA  VKIRRSIIAR  NKAAADITHS
LDRSKLPYEN
    HMGRclustalW{   candida}    G..KLPLYAL  EKQLGDNLRA  VAIRRKAISD  LADAPVLRS.
...NKLPYLH
    HMGRclustalW{dictyoste2}    A..VVAAAEK  AATSGEDPSS  IQPVVPPTSN  LDFEGSLTN.
.....LPVDH
        HMGRclustalW{wheat1}    ..........  ..........  ..........  ..........
..........
       HMGRclustalW{    rice}   G..ALPSHRL  ESRLGDCRRA  ARLRREALR.  ....RVTGRG
..VEGLPFDG
       HMGRclustalW{    corn}   G..KVPSYAL  EARLGDCRRA  AGIRREALR.  ....RITGRD
..IEGLPLDG
        HMGRclustalW{wheat3}    ..........  ..........  ..........  ..........
..........
        HMGRclustalW{wheat2}    ..........  ..........  ..........  ..........
..........
HMGRclustalW{       soybean}    ..........  ..........  ..........  ..........
..........
    HMGRclustalW{rubbertre3}    G..SIPSYSL  ESKLGNCKRA  ALIRRETLQ.  ....RMSGRS
..LEGLPLDG
    HMGRclustalW{rosyperiwi}    G..KIPSYSL  ESKLGDCKRA  AGIRREALQ.  ....RITGKS
..LEGLPLEG
    HMGRclustalW{    tomato}    G..KIPSYSL  ESKLGDCKRA  ASIRKEVMQ.  ....RITGKS
..LEGLPLEG
    HMGRclustalW{woodtobacc}    G..KMPSYSL  ESKLGDCKRA  ASIRKEALQ.  ....RITGKS
..LEGLPLEG
    HMGRclustalW{    potato}    G..KTPSYSL  ESKLGDCMRA  ASIRKEALQ.  ....RITGKS
..LEGLPLEG
        HMGRclustalW{radish}    G..VVPSYSL  ESRLGDCKRA  ASIRREALQ.  ....RLTGRS
..IEGLPLDG
HMGRclustalW{arabadopsis1}      G..VIPSYSL  ESRLGDCKRA  ASIRREALQ.  ....RVTGRS
..IEGLPLDG
    HMGRclustalW{cucumismel}    G..SVPSYSL  ESKLGDPKRA  ASIRREALQ.  ....RTTGRS
..IHGLPFEG
    HMGRclustalW{rubbertre2}    ..........  ..........  ..........  ..........
..........
    HMGRclustalW{rubbertre1}    G..KIPSYSL  ESKLGDCKRA  AAIRREALQ.  ....RMTRRS
..LEGLPVEG
    HMGRclustalW{camptothec}    G..TTPSYAL  ESKLGDSHRA  AAIRREALQ.  ....RMTKKS
..LAGLPLDG
    HMGRclustalW{arabadops2}    G..TIPSYSL  ETKLGDCKRA  AAIRREAVQ.  ....RITGKS
..LTGLPLEG
    HMGRclustalW{chineseham}    K..HIPAYKL  ETLMETHERG  VSIRRQLLST  K..LPEPSS.
..LQYLPYRD
```

FIG. 32AA

```
HMGRclustalW{chineseha2}  K..HIPAYKL  ETLMETHERG  VSIRRQLLST  K..LPEPSS.
..LQYLPYRD
HMGRclustalW{syrianhamst} K..HIPAYKL  ETLMETHERG  VSIRRQLLST  K..LPEPSS.
..LQYLPYRD
    HMGRclustalW{    rat} K..HIPAYKL  ETLMETHERG  VSIRRQLLSA  K..LAEPSS.
..LQYLPYRD
    HMGRclustalW{ rabbit} K..HIPAYKL  ETLMETHERG  VSIRRQLLSK  K..LPEPSS.
..LQYLPYRD
HMGRclustalW{      human} K..HIPAYKL  ETLMETHERG  VSIRRQLLSK  K..LSEPSS.
..LQYLPYRD
HMGRclustalW{      mouse} ..........  ..........  ..........  ..........
..........
    HMGRclustalW{xenopus} K..HIPAYKL  ETMMESPREG  VAIRRQMLSD  K..LPQRSA.
..LQSLPYKN
HMGRclustalW{sea urchin}  K..HIPAYKL  ENILDNPERG  VAVRRQIISK  L..LPITDA.
..LEKLPYAS
HMGRclustalW{ cockroach}  G..HIAGYQL  EKVVRNPERG  VGIRRQILTK  T..ADLKDA.
..LDNLPYKN
HMGRclustalW{drosophila}  GGTHCPLHKI  ESVLDDPERG  VRIRRQIIGS  R..AKMPVGR
..LDVLPYEH
HMGRclustalW{dictyostel}  G..EVLAYRL  ENELGDCSRA  VEIRRMLLEK  ....QLSKK.
..IEPIPHEG
HMGRclustalW{schistosom}  G..RLKTREL  ESVVRNPFRA  VELRRLDLS.  ....TFLNNP
HIIERIPYKD
HMGRclustalW{archaeoglo}  HYKSGKIRRA  MSSRIPGFYK  LSVEERLKKV  AEFAGLSDEE
..VKAVLSQG
HMGRclustalW{pseudomonas} ........MS  LDSRLPAFRN  LSPAARLDHI  GQLLGLSHDD
..VSLLANAG Consensus     G---IPSYSL  ESKLGDCKRA  VSIRREALSK  K--LRITGSS
LEGLPYEG
```

FIG. 32BB

```
                                            701
750
  HMGRclustalW{methanobac}   IDMERASRRN  IENPIGVVQI  PLGVAGPLRV  RGEHADGEYY
VPLATSEGAL
  HMGRclustalW{methanococ}   IDEEMAMKKN  IENMIGAIQI  PLGFAGPLKI  NGEYAKGEFY
IPLATTEGAL
  HMGRclustalW{halobacter}   FPAEAAES.A  IENMVGSIQV  PMGVAGPVSV  DGGSVAGEKY
LPLATTEGAL
  HMGRclustalW{sulfolobus}   IDYSEIKNKN  AENVIGAIQI  PLGIVGPIRV  NGDYAKGDFY
VPMATTEGAL
  HMGRclustalW{     yeast2}  YDYDRVFGAC  CENVIGYMPI  PVGVIGPLII  DGT....SYH
IPMATTEGCL
  HMGRclustalW{     yeast1}  YDYDRVFGAC  CENVIGYMPL  PVGVIGPLVI  DGT....SYH
```

FIG. 32CC

```
IPMATTEGCL
    HMGRclustalW{phycomyces}    .........  ........  ........  ........
PMATTEGCL
    HMGRclustalW{  fusarium}    YNWERFFGAC CENVIGYMPL PVGVAGPLVI DGQ....SYF
IPMATTEGVL
    HMGRclustalW{   candida}    YDYDRVFGAC CENVIGYMPL PVGVAGPLII DGK....PYH
IPMATTEGCL
    HMGRclustalW{dictyoste2}    FDYTKVLGAC CENVIGYIPI PVGVAGPILL DGK....LVS
IPMATTEGCL
        HMGRclustalW{wheat1}    .........  ........  ........  ........
..........
    HMGRclustalW{      rice}    MDYQAILGQC CEMPVGYVQL PVGVAGPLLL DGR....EYH
VPMATTEGCL
    HMGRclustalW{      corn}    FDYASILGQC CELPVGYVQL PVGVAGPLLL DGR....RFY
LPMATTEGCL
        HMGRclustalW{wheat3}    .........  ........  ........  ........
..........
        HMGRclustalW{wheat2}    .........  ........  ........  ........
..........
    HMGRclustalW{   soybean}    .........  ........  ........  ........
..........
    HMGRclustalW{rubbertre3}    FDYESILGQC CEMAIGYVQI PVGIAGPLLL DGK....EYT
VPMATTEGCL
    HMGRclustalW{rosyperiwi}    FDYASILGQC CEMPVGYVQL PVGIAGPLLL DGR....EYM
LPMATTEGCL
    HMGRclustalW{    tomato}    FNYESILGQC CEMPIGYVQI PVGIAGPLLL NGK....EFS
VPMATTEGCL
    HMGRclustalW{woodtobacc}    FDYESILGQC CEMPIGYVQI PVGIAGPLLL DGR....EYS
VPMATTEGCL
    HMGRclustalW{    potato}    FDYSSILGQC CEMPVGYVQI PVGIAGPLLL DGR....EYS
VPMATTEGCL
        HMGRclustalW{radish}    FDYDSILGQC CEMPVGYIQI PVGIAGPLLL DGY....EYS
VPMATTEGCL
HMGRclustalW{arabadopsis1}      FDYESILGQC CEMPVGYIQI PVGIAGPLLL DGY....EYS
VPMATTEGCL
    HMGRclustalW{cucumismel}    FDYESILGQC CEMPVGYVQI PVGIAGPLLL DGF....EYT
VPMATTEGCL
    HMGRclustalW{rubbertre2}    .........  ........  ........  ........
..........
    HMGRclustalW{rubbertre1}    FDYESILGQC CEMPVGYVQI PVGIAGPLLL NGR....EYS
VPMATTEGCL
    HMGRclustalW{camptothec}    FDYDSILGQC CEMPVGYVQI PVGIAGPLLL DGR....EYS
VPMATTEGCL
    HMGRclustalW{arabadops2}    FDYNSILGQC CEMPVGYVQI PVGIAGPLLL DGV....EYS
VPMATTEGCL
    HMGRclustalW{chineseham}    YNYSLVMGAC CENVIGYMPI PVGVAGPLCL DGK....EYQ
VPMATTEGCL
    HMGRclustalW{chineseha2}    YNYSLVMGAC CENVIGYMPI PVGVAGPLCL DGK....EYQ
VPMATTEGCL
    HMGRclustalW{syrianhamst}   YNYSLVMGAC CENVIGYMPI PVGVAGPLCL DGK....EYQ
VPMATTEGCL
        HMGRclustalW{   rat}    YNYSLVMGAC CENVIGYMPI PVGVAGPLCL DGK....EYQ
VPMATTEGCL
    HMGRclustalW{    rabbit}    YNYSLVLGAC CENVIGYMPI PVGVVGPLCL DGK....EFQ
VPMATTEGCL
    HMGRclustalW{     human}    YNYSLVMGAC CENVIGYMPI PVGVAGPLCL DEK....EFQ
VPMATTEGCL
    HMGRclustalW{     mouse}    .........  ........  ........  ........
..........
    HMGRclustalW{   xenopus}    YNYSLVMGAC CENVIGYMPI PVGVAGPLLL NNK....EYQ
```

FIG. 32DD

```
                              VPMATTEGCL
  HMGRclustalW{sea urchin}    YDYSFVSGAC  CENVIGYMPV  PVGVAGPLLL  DGQ....EFQ
                              VPMATTEGCL
  HMGRclustalW{ cockroach}    YDYLKVMGAC  CENVIGYMPV  PVGVAGPLNL  DGR....LVH
                              VPLATTEGCL
  HMGRclustalW{drosophila}    FDYRKVLNAC  CENVLGYVPI  PVGYAGPLLL  DGE....TYY
                              VPMATTEGAL
  HMGRclustalW{dictyostel}    FDFAKVQGQC  CENVIGYVPI  PVGTAGPIQL  NGQ....LVT
                              IPMATTEGCL
  HMGRclustalW{schistosom}    YDYRLVYGQC  CEEVIGYMPI  PVGKIGPLLL  DGR....SHY
                              IPLATTEGCL
  HMGRclustalW{archaeoglo}    .LPLDVADRM  IENVIGTFEL  PLGIATNFLI  DGK....DYL
                              IPMAIEEPSV
  HMGRclustalW{pseudomonas}   ALPMDIANGM  IENVIGTFEL  PYAVASNFQI  NGR....DVL
                              VPLVVEEPSI
               Consensus      FDY-SVLG-C  CENVIGY--I  PVGVAGPLLL  DGK----EYS
VPMATTEGCL
                                          HMGCoA binding
E
```

FIG. 32EE

```
                                    751
800
   HMGRclustalW{methanobac}   VASVNRGCSV  ITRAGGATVR  VTGDSMT.RA  PVIRTGSVVE
ALQLREWIYE
   HMGRclustalW{methanococ}   VASVNRGCSI  ITKCGGATVR  VIDDKMT.RA  PCLKTKSVVD
AIKVRDWIRE
   HMGRclustalW{halobacter}   LASVNRGCSV  INSAGGATAR  VLKSGMT.RA  PVFRVADVAE
AEALVSWTRD
   HMGRclustalW{sulfolobus}   IASVNRGIKA  VTLSGGVRAK  VLKDEMT.RA  PVFKFDSIEQ
IPNFLKFIEE
   HMGRclustalW{    yeast2}   VASAMRGCKA  INAGGGATTV  LTKDGMT.RG  PVVRFPTLIR
SGACKIWLDS
   HMGRclustalW{    yeast1}   VASAMRGCKA  INAGGGATTV  LTKDGMT.RG  PVVRFPTLKR
SGACKIWLDS
   HMGRclustalW{phycomyces}   VASTARGCKA  INAGGGASTI  VIADGMT.RG  PCVEFPTILR
AAACKLWIEN
   HMGRclustalW{   fusarium}  VASASRGCKA  INSGGGAITV  LTADGMT.RG  PCVAFETLER
AGAAKLWLDS
   HMGRclustalW{    candida}  VASAMRGCKA  INLGGGVTTV  LTKDGMT.RG  PCVKFPSLKR
AGQCKLWLDS
   HMGRclustalW{dictyoste2}   VASTHRGAKA  ITKSGGAKTV  LLQSGMT.RA  PVCRLPSSIR
AGELKQWIEN
         HMGRclustalW{wheat1}  ..........  ..........  ..........  ..........
..........
   HMGRclustalW{       rice}  VASVNRRVQG  HLVSGGAFSV  LLRDAMS.RA  PAVKLPCPMR
AAELKAFAEA
      HMGRclustalW{    corn}  VASTNRGCKA  IAESGGATSV  VLRDAMT.RA  PVARFPTARR
AAELKAFLED
         HMGRclustalW{wheat3}  ..........  ..........  ..........  ..........
..........
         HMGRclustalW{wheat2}  ..........  ..........  ..........  ..........
..........
HMGRclustalW{     soybean}    ..........  ..........  ..........  ..........
..........
    HMGRclustalW{rubbertre3}  VASANRGCKA  IYASGGATSV  LLRDGMT.RA  PVVRFPTAKR
AADLKFFMED
    HMGRclustalW{rosyperiwi}  VASTNRGCKA  ILASGGANSV  LLRDGMT.RA  PVVRFGTAKR
AAELKFYMED
   HMGRclustalW{     tomato}  VASTNRGCKA  IYASGGATCI  LLRDGMT.RA  PCVRFGTAKR
AAELKFFVED
   HMGRclustalW{woodtobacc}   VASTNRGCKA  IYASGGATSV  LLRDGMT.RA  PCVRFGTAKR
AAELKFFVED
   HMGRclustalW{     potato}  VASTNRGCKA  IFVSGGADSV  LLRDGMT.RA  PVVRFTTAKR
AAELKFFVED
         HMGRclustalW{radish}  VASTNRGCKA  MYVSGGATST  VLKDGMT.RA  PVVRFASARR
ASELKFFLES
HMGRclustalW{arabadopsis1}    VASTNRGCKA  MFISGGATST  VLKDGMT.RA  PVVRFASARR
ASELKFFLEN
   HMGRclustalW{cucumismel}   VASTNRGCKA  IYASGGATSM  LLKDGMT.RA  PVVRFGSAKR
ASELKFFLED
    HMGRclustalW{rubbertre2}  ..........  ..........  ..........  ..........
..........
    HMGRclustalW{rubbertre1}  VASTNRGCKA  IYLSGGATSV  LLKDGMT.RA  PVVRFASATR
AAELKFFLED
   .HMGRclustalW{camptothec}  VASTNRGCKA  IFACGGATSV  LLRDAMT.RA  PVVRFGSAKR
AADLKFFLEN
   HMGRclustalW{arabadops2}   VASTNRGFKA  IHLSGGAFSV  LVKDAMT.RA  PVVRFPSARR
AALVMFYLQD
   HMGRclustalW{chineseham}   VASTNRGCRA  IGLGGGASSR  VLADGMT.RG  PVVRLPRACD
SAEVKAWLET
```

FIG. 32FF

```
HMGRclustalW{chineseha2}    VASTNRGCRA  IGLGGGASSR  VLADGMT.RG  PVVRLPRACD
SAEVKAWLET
HMGRclustalW{syrianhamst}   VASTNRGCRA  IGLGGGASSR  VLADGMT.RG  PVVRLPRACD
SAEVKAWLET
    HMGRclustalW{     rat}  VASTNRGCRA  ISLGGGASSR  VLADGMS.RG  PVVRLPRACD
SAEVKSWLET
HMGRclustalW{     rabbit}   VASTNRGCRA  ICLGGGASSR  VLADGMT.RG  PVVRLPRACD
SAEVKAWLET
HMGRclustalW{      human}   VASTNRGCRA  IGLGGGASSR  VLADGMT.RG  PVVRLPRACD
SAEVKAWLET
HMGRclustalW{      mouse}   ..........  ..........  ..........  ..........
..........
    HMGRclustalW{ xenopus}  VASTNRGCRA  IMLGGGAKSR  VLADGMT.RG  PVVRLPTACD
AAEVKAWLDS
HMGRclustalW{sea urchin}    VASTNRGCRA  LRSAGGIHSV  LIGDGMT.RG  PLVRLPSAQE
AGAIKQWLEV
HMGRclustalW{ cockroach}    VASTNRGMRA  LMRCG.VTSR  IVADGMT.RG  PVVRFPNIDR
ASEAMLWMQV
HMGRclustalW{drosophila}    VASTNRGCKA  LSVRG.VRSV  VEDVGMT.RA  PCVRFPSVAR
AAEAKSWIEN
HMGRclustalW{dictyostel}    VASTHRGCKA  ITESGGAKCT  ITSRGMT.RA  PVVRFSDIVK
ASEFVSWIND
HMGRclustalW{schistosom}    VASTNRGCRA  IFLAGGIKSV  VYRDQMT.RA  PVVWFPSIID
SVKCIAWIDS
HMGRclustalW{archaeoglo}    VAAASNAARM  ARESGGFTTD  YTGSLMIGQI  QVTKLLNPNA
AKFEVLRQKD
HMGRclustalW{pseudomonas}   VAAASYMAKL  ARANGGFTTS  SSAPLMHAQV  QIVGIQDPLN
ARLSLLRRKD Consensus     VASTNRGCKA  I-LSGGATSV  VLADGMT-RA  PVVRFPSAKR
AAELKFWLED
```

FIG. 32GG

```
                                          801
850
    HMGRclustalW{methanobac}   NM..DALREE AESTTRHGKL VKIDPI..... IVAGSYVYPR
FVYTTGDSMG
    HMGRclustalW{methanococ}   NF..ERIKEV AESTTRHGKL IKIEPI.... LIVGRNLYPR
FVFKTGDAMG
    HMGRclustalW{halobacter}   NF..AALKEA AEETTNHGEL LDVTP..... YVVGNSVYLR
FRYDTKDAMG
    HMGRclustalW{sulfolobus}   NL..EKIRNI ANSTSHHGKL KSITP..... FVLGNNVWLR
FSFETGDAMG
    HMGRclustalW{    yeast2}   EEGQNSIKKA FNSTSRFARL QHIQT..... CLAGDLLFMR
FRTTTGDAMG
    HMGRclustalW{    yeast1}   EEGQNAIKKA FNSTSRFARL QHIQT..... CLAGDLLFMR
FRTTTGDAMG
    HMGRclustalW{phycomyces}   EG.NDIVTNA FNSTSRFARL RKLKI..... ALAGKLVFIR
FSTTTGDAMG
    HMGRclustalW{   fusarium}  EAGQDMMKKA FNSTSRFARL QSMKT..... ALAGTNLYIR
FKTTTGDAMG
    HMGRclustalW{    candida}  DEGQEEMKKA FNSTSRFARL QHLQT..... ALAGDLLFIR
FRTVTGDAMG
    HMGRclustalW{dictyoste2}   QENFYQVASA FNSTSRFARL KSIKV..... VIAGRLVYLR
FKSSTGDAMG
        HMGRclustalW{wheat1}   .......... .......... .......... ..........
.....GDAMG
    HMGRclustalW{      rice}   PANFELLAAV FNRSSRFGRL QDIRC..... ALAGRNLYMR
FSCITGDAMG
    HMGRclustalW{      corn}   PANFDTLSVV FNRSSRFARL QGVQC..... AMAGRNLYMR
FSCSTGDAMG
        HMGRclustalW{wheat3}   .......... .......... .......... ..........
.....GDAMG
        HMGRclustalW{wheat2}   .......... .......... .......... ..........
.....GDAMG
HMGRclustalW{      soybean}   .......... .......... .......... ..........
..........
    HMGRclustalW{rubbertre3}   PDNFDTIAVV FNKSSRFARL QSVQC..... AIAGKNLYMR
FSCSTGDAMG
    HMGRclustalW{rosyperiwi}   TQNFETISVV FNKSSRFAKL QSVQC..... AIAGKNLYIR
FSCSTGDAMG
    HMGRclustalW{    tomato}   PIKFESLANV FNQSSRFARL QRIQC..... AIAGKNLYMR
LCCSTGDAMG
    HMGRclustalW{woodtobacc}   PVKFETLAAV FNQSSRFARL QRIQC..... AIAGKNLYMR
FVCSTGDAMG
    HMGRclustalW{    potato}   PLNFETLSLM FNKSSRFARL QGIQC..... AIAGKNLYIT
FSCSTGDAMG
        HMGRclustalW{radish}   PENFETLAVV FNRSSRFARL QSVMC..... TLAGKNAYVR
FSCSTGDAMG
HMGRclustalW{arabadopsis1}    PENFDTLAVV FNRSSRFARL QSVKC..... TIAGKNAYVR
FCCSTGDAMG
    HMGRclustalW{cucumismel}   PSNFDTLAVV FNRSSRFARL QSIRC..... SIAGKNLYVR
FCCSTGDAMG
    HMGRclustalW{rubbertre2}   .......... .......... .......... ..........
..........
    HMGRclustalW{rubbertre1}   PDNFDTLAVV FNKSSRFARL QGIKC..... SIAGKNLYIR
FSCSTGDAMG
    HMGRclustalW{ camptothec}  PLNFETLAAV FNSSSRFGKL QNIKC..... AIAGKNLYMR
YSCSTGDAMG
    HMGRclustalW{arabadops2}   PSNFERLSLI FNKSSRFARL QSITC..... TIAGRNLYPR
FACSTGDAMG
    HMGRclustalW{chineseham}   PEGFAVIKDA FDSTSRFARL QKLHV..... TMAGRNLYIR
FQSKTGDAMG
```

FIG. 32HH

```
HMGRclustalW{chineseha2}   PEGFAVIKDA  FDSTSRFARL  QKLHV.....  TMAGRNLYIR
FQSKTGDAMG
HMGRclustalW{syrianhamst}  PEGFAVIKDA  FDSTSRFARL  QKLHV.....  TMAGRNLYIR
FQSKTGDAMG
     HMGRclustalW{    rat} PEGFAVVKEA  FDSTSRFARL  QKLHV.....  TLAGRNLYIR
LQSKTGDAMG
HMGRclustalW{     rabbit}  PEGFAVIKEA  FDSTSRFARL  QKLHI.....  SMAGRNLYIR
FQSRTGDAMG
HMGRclustalW{      human}  SEGFAVIKEA  FDSTSRFARL  QKLHT.....  SIAGRNLYIR
FQSRSGDAMG
HMGRclustalW{      mouse}  ..........  ..........  ..........  ..........
..........
HMGRclustalW{    xenopus}  AEGFKVIKDA  FDSTSRFARL  GRLQN.....  CVAGRNLYIR
FQSKTGDAMG
HMGRclustalW{sea urchin}   PENFAAIKER  FESTSRFAKL  KSIQT.....  ALAGRYMFLR
FKALTGDAMG
HMGRclustalW{  cockroach}  PYNFEQIKKN  FDSTSRFARL  SKIHI.....  RVAGRHLFIR
FIATTGDAMG
HMGRclustalW{drosophila}   DENYRVVKTE  FDSTSRFGRL  KDCHI.....  AMDGPQLYIR
FVAITGDRMG
HMGRclustalW{dictyostel}   TDNYQALKAV  FDSTSRFARL  SAIKC.....  TIAGRSVYIR
FKCDTGDAMG
HMGRclustalW{schistosom}   EEGFQTLKSA  FDKTSAHVNL  LSVFA.....  CPAGRYIHIR
FAARTGDAMG
HMGRclustalW{archaeoglo}   EIIERANECD  PMLVNLGGGC  KDIEAR.VID  TIMGKMLIVH
LIVDVKDAMG
HMGRclustalW{pseudomonas}  EIIELANRKD  QLLNSLGGGC  RDIEVHTFAD  TPRGPMLVAH
LIVDVRDAMG Consensus      PENFETLK-A  FNSTSRFARL  QSIQC-----  AIAGRNLYIR
FSCSTGDAMG
                                                              NADH binding domain 1
(continued)
```

FIG. 32II

```
                                      851
900
   HMGRclustalW{methanobac}  MNMVTIATER ALELLT...R ETGAHV..IA LSGNLCTDKK
PAAVNLIEGR
   HMGRclustalW{methanococ}  MNMVTIATEK ACNFIEGELK KEGIFVKTVA VSGNACVDKK
PSGMNLINGR
   HMGRclustalW{halobacter}  MNMATIATEA VCGVVE...A ETAASL..VA LSGNLCSDKK
PAAINAVEGR
   HMGRclustalW{sulfolobus}  MNMVTIAVEK VCEFIE.... ENFPSADCLA VSGNMCSDKK
QTNVNSLFGR
   HMGRclustalW{    yeast2}  MNMISKGVEY SLKQMVEEY. .GWEDMEVVS VSGNYCTDKK
PAAINWIEGR
   HMGRclustalW{    yeast1}  MNMISKGVEY SLKQMVEEY. .GWEDMEVVS VSGNYCTDKK
PAAINWIEGR
    HMGRclustalW{phycomyces} MNM...... .......... .......... ..........
..........
   HMGRclustalW{   fusarium} MNMISKGVEH ALSVMANDG. .GFDDMQIIS VSGNYCTDKK
AAALNWIDGR
   HMGRclustalW{    candida} MNMISKGVEY ALKQMTEVF. .GWDDMMVVS VSGNYCTDKK
PAAVNWINGR
   HMGRclustalW{dictyoste2}  MNMVSKGVEK ALEVITEY.. ..FPEMEVLS LSGNVCTDKK
PSSINWLEGR
    HMGRclustalW{wheat1}     MNMVSKGVEN VLGYIRNN.. ..FPDMDVIS ISGNYCSDKK
ATAVNWIDGR
   HMGRclustalW{      rice}  MNMVSKGVEN VLGYLQNV.. ..FPDMDVIS VSGNYCSDKK
PTAVNWIEGR
       HMGRclustalW{  corn}  MNMVSKGVQN VLDFLQDD.. ..FHDMDVIS ISGNFCSDKK
PSAVNWIEGR
       HMGRclustalW{wheat3}  MNMISKGVQN VLDYLQDD.. ..FPDMDVIS ISGNFCSDKK
PAAVNWIEGR
       HMGRclustalW{wheat2}  MNMISKGVQH VLDYLEED.. ..FPDMDVVS ISGNFCSDKK
SAAVNWIEGR
HMGRclustalW{     soybean}   .......... .......... .......... ..........
..........
   HMGRclustalW{rubbertre3}  MNMVSKAVQN VIDYLQND.. ..FPDMDVIG LTGNFCADKK
AAAVNWIEGR
   HMGRclustalW{rosyperiwi}  MNMVSKGVQN VLEFLQTD.. ..YPDMDVLG ISGNFCADKK
PAAVNWIEGR
   HMGRclustalW{    tomato}  MNMVSKGVQN VLDYLQNE.. ..YPDMDVIG ISGNFCSDKK
PAAVNWIEGR
   HMGRclustalW{woodtobacc}  MNMVSKGVQN VLDYLQNE.. ..YPDMDVIG ISGNFCSDKK
PAAVNWIEGR
   HMGRclustalW{    potato}  MNMVSKGVQN VLDYLQSE.. ..YPDMDVIG ISGNFCSDKK
PAAVNWIEGR
       HMGRclustalW{radish}  MNMVSKGVQN VLEFLTED.. ..FPDMDVIG ISGNFCSDKK
PAAVNWIEGR
HMGRclustalW{arabadopsis1}   MNMVSKGVQN VLEYLTDD.. ..FPDMDVIG ISGNFCSDKK
PAAVNWIEGR
   HMGRclustalW{cucumismel}  MNMVSKGVQN VLEFLQHD.. ..FSDMEVIG ISGNFCADKK
PAAVNWIEGR
   HMGRclustalW{rubbertre2}  .......... ....LESD.. ..FADMDVIG ISGNFCSDKK
PAAVNWIEGR
   HMGRclustalW{rubbertre1}  MNMVSKGVQN VLEFLQSD.. ..FSDMDVIG ISGNFCSDKK
PAAVNWIEGR
   HMGRclustalW{camptothec}  MNMISKGVQN VLDFLQDD.. ..FPDMDVIG ISGNYCSDKK
PAAVNWIEGR
   HMGRclustalW{arabadops2}  MNMVSKGVQN VLDFVKSE.. ..FPDMDVIG ISGNYCSDKK
ASAVNWIEGR
   HMGRclustalW{chineseham}  MNMISKGTEK ALLKLQEF.. ..FPEMQILA VSGNYCTDKK
PAAINWIEGR
```

FIG. 32JJ

```
    HMGRclustalW{chineseha2}   MNMISKGTEK ALLKLQEF..  ..FPEMQILA VSGNYCTDKK
PAAINWIEGR
    HMGRclustalW{syrianhamst}  MNMISKGTEK ALVKLQEF..  ..FPEMQILA VSGNYCTDKK
PAAVNWIEGR
       HMGRclustalW{     rat}  MNMISKGTEK ALLKLQEG..  ..VPELQILA VSGNYCTDKK
PAAINWIEGR
       HMGRclustalW{  rabbit}  MNMISKGTEK ALSKLHEY..  ..FPEMQILA VSGNYCTDKK
PAAVNWIEGR
       HMGRclustalW{   human}  MNMISKGTEK ALSKLHEY..  ..FPEMQILA VSGNYCTDKK
PAAINWIEGR
       HMGRclustalW{   mouse}  ........EK ALLKLQEF..  ..FPDMQILA VSGNYCTDKK
PAAINWIEGR
       HMGRclustalW{ xenopus}  MNMISKVTEQ ALARLQEE..  ..FPDLHVLA VSGNYCTDKK
PAAINWIEGR
    HMGRclustalW{sea urchin}   MNMISKGTEQ ALHALQTM..  ..FPNIEIMS LSGNYCTDKK
VAAINWIEGR
    HMGRclustalW{ cockroach}   MNMLSKGTEV ALAYVQQV..  ..YPDMEILS LSGNFCTDKK
PAAVNWIEGR
    HMGRclustalW{drosophila}   MNMVSKALRW PFAEFTLH..  ..FPDMQIIS LSGNFCCDKK
PAAINWIKGR
    HMGRclustalW{dictyostel}   MNMVSKGVEA VLEHLKII..  ..FDDMTLLS ISGNMCTDKK
PSSINWTEGR
    HMGRclustalW{schistosom}   MNMVSKATDS ALHCLKKY..  ..FSNMQVIS LSGNMCTDKK
PATINTILGR
    HMGRclustalW{archaeoglo}   ANAVNTMCEK VAPFIERITG .GKVYLRIIS NLAAYRLARA
KAVFDKDVIG
    HMGRclustalW{pseudomonas}  ANTVNTMAEA VAPLMEAITG .GQVRLRILS NLADLRLARA
QVRITPQQLE Consensus        MNMVSKGVEN VL--LQED-- -GFPDMDVIS ISGNYCTDKK
PAAVNWIEGR
                NADH binding domain 1 (concluded)
```

FIG. 32KK

```
                                901
950
   HMGRclustalW{methanobac}   GKSITAEITV  PGEMVESVLK  TTPEAVVEVN  TAKVLIGSAA
AG..SMG.FN
   HMGRclustalW{methanococ}   GKSIVAEVFL  TEKEVNKYLK  TTSQAIAEVN  RLKVYIGSAI
SN..SMG.FN
   HMGRclustalW{halobacter}   GRSVTADVRI  PREVVEERLH  TTPERGRELN  TRKVLVGSAK
AA..SLG.FN
   HMGRclustalW{sulfolobus}   GKTVLAEALI  KCDVIRNILH  SNAQLIHDIN  LRKVWLGTAR
AG..SLSQFN
   HMGRclustalW{    yeast2}   GKSVVAEATI  PGDVVKSVLK  SDVSALVELN  ISKVLVGSAM
AG..SVGGFN
   HMGRclustalW{    yeast1}   GKSVVAEATI  PGDVVRKVLK  SDVSALVELN  IAKVLVGSAM
AG..SVGGFN
   HMGRclustalW{phycomyces}   ..........  ..........  ..........  ..........
..........
   HMGRclustalW{   fusarium}  GKGVVAEAII  PGEVVRSVLK  SDVDSLVELN  VAKVLIGSAM
AG..SVGGFN
   HMGRclustalW{    candida}  GKSVVAEASI  PKDAVVKVLK  SSVKAVVDVN  VNKVLIGSAM
AG..SVGGFN
   HMGRclustalW{dictyoste2}   GKSVVAEAVI  SGDIVRDVLK  TTVEALVSLN  IDKVLIGSAM
AG..SIGGFN
       HMGRclustalW{wheat1}   GKSVVCEATI  KGRVVQSVID  TTVEKLVELN  IIKVLAGSAV
AG..ALGGFN
   HMGRclustalW{      rice}   GKSVVCEAII  KGDVVQKVLK  TTVEKLVELN  IIKVLAGSAV
AG..ALGGFN
       HMGRclustalW{  corn}   GKSVVCEAVI  GEEVVKKVLK  TDVQSLVELN  TIKVLAGSAV
AG..ALGGFN
       HMGRclustalW{wheat3}   GKSVVCEAVI  REELLKKVLK  TNVQSLVELN  VIKVLAGSAV
AG..ALGGFN
       HMGRclustalW{wheat2}   GKSVVCEAII  REEVVEKVLD  TNVQSLVELN  VIKVLAGSAV
AG..ALGGFN
HMGRclustalW{     soybean}    ..........  ........LK  TNVSALVELN  MLKVLAGSAV
AG..ALGGFN
   HMGRclustalW{rubbertre3}   GKSVVCEAII  KEEVVKKVLK  TNVAALVELN  MIKVLTGSAV
AG..SLGGFN
   HMGRclustalW{rosyperiwi}   GKSVVCEAII  KEEIVKTVLK  TEVAALIELN  MVKVLAGSAI
AG..ALGGFN
   HMGRclustalW{    tomato}   GKSVVCEAII  TEEVVKKVLK  TEVAALVELN  MLKVLTGSAM
AG..ALGGFN
   HMGRclustalW{woodtobacc}   GKSVVCEAII  TEEVVKKVLK  TEVAALVELN  MLKVLTGSAM
AG..ALGGFN
   HMGRclustalW{    potato}   GKSVVCEAII  KEEVVKKVLK  TEVAALVELN  MLKVLTGSAM
AG..ALGGFN
       HMGRclustalW{radish}   GKSVVCEAVI  RGETVNKVLK  TSVASLVELN  MLKVLTGSAI
AG..SLGGFN
HMGRclustalW{arabadopsis1}    GKSVVCEAVI  RGEIVNKVLK  TSVAALVELN  MLKVLAGSAV
AG..SLGGFN
   HMGRclustalW{cucumismel}   GKSVVCEAVI  KDEVVRKVLK  TSVASLVELN  MLKVLTGSAM
AG..ALGGFN
   HMGRclustalW{rubbertre2}   GKSVVCEAII  KEEVVKKVLK  TDVALLVELN  MLKVLAGSAV
AG..ALGGFN
   HMGRclustalW{rubbertre1}   GKSVVCEAII  KEEVVKKVLK  TNVASLVELN  MLKVLAGSAV
AG..ALGGFN
   HMGRclustalW{ camptothec}  GKSVVCEAVI  KEEVVKKVLK  TNVASLVELN  MLKVLTGSAM
AG..ALGGFN
   HMGRclustalW{arabadops2}   GKHVVCEAFI  KAEIVEKVLK  TSVEALVELN  TLKVLVGSAM
AG..SLGGFN
   HMGRclustalW{chineseham}   GKTVVCEAVI  PAKVVREVLK  TTTEAMIDVN  INKVLVGSAM
```

FIG. 32LL

```
AG..SIGGYN
  HMGRclustalW{chineseha2}   GKTVVCEAVI PAKVVREVLK TTTEAMIDVN INKVLVGSAM
AG..SIGGYN
  HMGRclustalW{syrianhamst}  GKTVVCEAVI PARVVREVLK TTTEAMIDVN INKVLVGSAM
AG..SIGGYN
   HMGRclustalW{      rat}   GKTVVCEAVI PAKVVREVLK TTTEAMVDVN INKVLVGSAM
AG..SIGGYN
   HMGRclustalW{   rabbit}   GKTVVCEAVI PAKVVREVLK TTTEAMIDVN INKVLVGSAM
AG..SIGGYN
   HMGRclustalW{    human}   GKSVVCEAVI PAKVVREVLK TTTEAMIEVN INKVLVGSAM
AG..SIGGYN
   HMGRclustalW{    mouse}   GKTVVCEAVI PAKVVREVLK TTTEAMVDVN INKVLVGSAM
AG..SIGGYN
    HMGRclustalW{  xenopus}  GKSVVCEAII PAKVVREVLK SSTEALVEVN INKNFIGSAM
AG..SIGGYN
    HMGRclustalW{sea urchin} GKSVVCEATV PAHIVQQVLK TSASALVDLN IHKNLVGSAM
AG..SIGGFN
    HMGRclustalW{ cockroach} GKSVVCEAIV PADIIKSVLK TSVQALMDVN ITKVLIGSAV
AG..SIGGFN
    HMGRclustalW{drosophila} GKRVVTECTI SAATLRSVLK TDAKTLVECN KLKVMGGSAM
AG..SIGGNN
    HMGRclustalW{dictyostel} GRSVVCEAMI TGDVVQRVLK TNVQALVDLN IAKVLIGSAM
AG..SIGGFN
    HMGRclustalW{schistosom} GKSVIAEAHL SADVLAQVLH TNAQRLARLT HSKVWIGSAM
AGCPGMMGCN
    HMGRclustalW{archaeoglo} .....GEEVV EGIMLAYAFA AADPFRCATH NKGIMNGISA
LM........
    HMGRclustalW{pseudomonas} TAEFSGEAVI EGILDAYAFA AVDPYRAATH NKGIMNGIDP
LI........
           Consensus         GKSVVCEAVI PAEVVRKVLK TTVEALVELN ILKNLVGSAM AG--
SLGGFN
                                                                     K
```

FIG. 32MM

```
                                    951
1000
   HMGRclustalW{methanobac}   AHYANIIGAI FLATGQDEAH IVEGSLGVTI AEERK.....
.....GDLYF
   HMGRclustalW{methanococ}   AHYANIIGAI FLATGQDEAH IVEGSLGITM AEVED.....
.....DGLYF
   HMGRclustalW{halobacter}   AHVANVVAAM FLATGQDEAQ VVEGANAITT AEVQD.....
.....GDLYV
   HMGRclustalW{sulfolobus}   AHFANIVTAI FIATGQDVAQ IVESSSGYTW TEVRG.....
.....EDLYI
  HMGRclustalW{      yeast2}  AHAANLVTAL FLALGQDPAQ NVESSNCITL MKEVD.....
.....GDLRI
  HMGRclustalW{      yeast1}  AHAANLVTAV FLALGQDPAQ NVESSNCITL MKEVD.....
.....GDLRI
    HMGRclustalW{phycomyces}  .......... .......... .......... ..........
..........
   HMGRclustalW{    fusarium} AHAANIVAAI FLATGQDPAQ VVESANCITI MKNLN.....
.....GALQI
   HMGRclustalW{     candida} AQAANMVTAV YLALGQDPAQ NVESSNCITL MTETED....
.....GDLKV
   HMGRclustalW{  dictyoste2} AHASNIVTAL YIATGQDPAQ NVESSNCITL MESINCG...
.....KDLYI
       HMGRclustalW{  wheat1} AHASNIATAL FIATGQDPAQ NVESSQCITM LEAVNEG...
.....KDLHI
    HMGRclustalW{        rice} AHASNIVTAL FIATGQDPAQ NVESSQCITM LEEVNDG...
.....DDLHI
       HMGRclustalW{    corn} AHASNIVTAI FIATGQDPAQ NVESSHCITM LEPVNAG...
.....RDLHI
       HMGRclustalW{  wheat3} AHASNIVTAI FIATGQDPAQ NVESSQCIAM LEAVNDG...
.....KDLHI
       HMGRclustalW{  wheat2} AHASNIVSAI FIATGQDPAQ NVESSQCITM LEAVNGG...
.....RDLHI
HMGRclustalW{        soybean} AHASNIVSAI FIATGQDPAQ NVESSHCITM MEAINDG...
.....RDLHI
   HMGRclustalW{  rubbertre3} AHASNMVTAV YIATGQDPAQ NVESSHCITM MEAVNDG...
.....KDLHI
   HMGRclustalW{  rosyperiwi} AHASNIVSAI FIATGQDPAQ NVESSQCITM MEAVNDG...
.....KDLHI
    HMGRclustalW{      tomato} AHASNIVSAV FIATGQDPAQ NIESSHCITM MEAVNDG...
.....KDLHI
   HMGRclustalW{  woodtobacc} AHASNIVSAV YIATGQDPAQ NIESSHCITM MEAVNDG...
.....KDLHV
    HMGRclustalW{      potato} AHASNIVSAV YLATGQDPAQ NVESSHCITM MEAVNDG...
.....KDLHV
       HMGRclustalW{  radish} RHASNIVSAV FLATGQDPAQ NVESSQCITM MEAINDG...
.....KDIHI
HMGRclustalW{arabadopsis1}    AHASNIVSAV FIATGQDPAQ NVESSQCITM MEAINDG...
.....KDIHI
   HMGRclustalW{  cucumismel} AHSSNIVSAI FLATGQDPAQ NVESSHCITM MEPVNNG...
.....RDLHI
   HMGRclustalW{  rubbertre2} AHAGNIVSAI FIATGQDPAQ NVESSHCITM MEAVNDG...
.....KDLHI
   HMGRclustalW{  rubbertre1} AHAGNIVSAI FIATGQDPAQ NVESSHCITM MEAVNDG...
.....KDLHI
   HMGRclustalW{   camptothec} AHASNIVSAV YLATGQDPAQ NVESSHCITM MEAINDG...
.....KDLHV
   HMGRclustalW{  arabadops2} AHSSNIVSAV FIATGQDPAQ NVESSHCMTM ILPDGD....
......DLHI
    HMGRclustalW{  chineseham} AHAANIVTAI YIACGQDAAQ NVGSSNCITL MEASGPTN..
```

FIG. 32NN

```
                              .....EDLYI
  HMGRclustalW{chineseha2}  AHAANIVTAI YIACGQDAAQ NVGSSNCITL MEASGPTN..
.....EDLYI
 HMGRclustalW{syrianhamst}  AHAANIVTAI YIACGQDAAQ NVGSSNCITL MEASGPTN..
.....EDLYI
     HMGRclustalW{     rat} LHAANIVTAI YIACGQDAAQ NVGSSNCITL MEASGPTN..
.....EDLYI
  HMGRclustalW{     rabbit} AHAANYVTAI YIACGQDAAQ NVGSSNCITL MEASGPPN..
.....EDLYI
 HMGRclustalW{       human} AHAANIVTAI YIACGQDAAQ NVGSSNCITL MEASGPTN..
.....EDLYI
 HMGRclustalW{       mouse} AHAANIVTAI YIACGQDAAQ NVGSSNCITL MEASGPTN..
.....EDLYI
  HMGRclustalW{    xenopus} AHAANIVTAI YIACGQDAAQ NVGSSNCITI MEATGPTY..
.....EDLYI
  HMGRclustalW{sea urchin}  AHAANIVTAI YIATGQDAAQ NIASSNCMTL METRGPKG..
.....GDLYL
  HMGRclustalW{ cockroach}  AHAANIVTAI FIATGQDPAQ NVGSSNCMTL MEPWGEDG..
.....KDLYV
 HMGRclustalW{drosophila}   AHAANMVTAV FLATGQDPAQ NVTSSNCSTA MECWAENS..
.....EDLYM
  HMGRclustalW{dictyostel}  AHASNIVTAI FLATGQDCAQ NVESSNCITQ MEACNDG...
.....QDLYI
  HMGRclustalW{schistosom}  AHAANIIAGM FAATGQDLAQ VVDSSSCLTQ LEVDLSD...
.....DSLVA
   HMGRclustalW{archaeoglo} .......... .IATGNDFRA IEAGAHSYAA IGG.YKPLTT
YEVDRKGNLV
 HMGRclustalW{pseudomonas}  .......... .VATGNDWRA VEAGAHAYAC RSGHYGSLTT
WEKDNNGHLV Consensus    AHAANIVTAI FIATGQDPAQ NVESSNCITM MEAVNDGN-- -----
KDLHI
```

```
                              1001
1050
    HMGRclustalW{methanobac}  AVNLPDVPLA TVGGGTGLET ASECLDIMGV RGGG......
RVHAFAEIVG
    HMGRclustalW{methanococ}  SVTLPDVPIG TVGGGTRVET QKECLEMLGC YGDN......
KALKFAEIVG
    HMGRclustalW{halobacter}  SVSIASLEVG TVGGGTKLPT QSEGLDILGV SGGGDP.AGS
NADALAECIA
    HMGRclustalW{sulfolobus}  SVTLPSLEVG TVGGGTRLPT QKEALSIMGV YGSGNP.PGS
NAKKLAEIIA
    HMGRclustalW{     yeast2} SVSMPSIEVG TIGGGTVLEP QGAMLDLLGV RGPHPTEPGA
NARQLARIIA
    HMGRclustalW{     yeast1} SVSMPSIEVG TIGGGTVLEP QGAMLDLLGV RGPHATAPGT
NARQLARIVA
    HMGRclustalW{phycomyces}  .......... .......... .......... ..........
..........
    HMGRclustalW{   fusarium} SVSMPSLEVG TLGGGTILEP QGAMLDILGV RGSHPTNPGD
NARRLARIIG
    HMGRclustalW{    candida} SVSMPSIEVG TIGGGTILDP QGSMLELLGV RG.PADVPGE
NARQLAKIVA
    HMGRclustalW{dictyoste2}  SVTMPSIEVG TVGGGTHLPA QSACLDLLKI RGANLERPGA
NSEQLARVVA
        HMGRclustalW{wheat1}  SVTMPPIEV. .......... .......... ..........
..........
    HMGRclustalW{      rice} SVTMPSIEVG TIGGGTCLAS QAACLNLLGV KGSNHGSPGA
NAGRLATIVA
    HMGRclustalW{       corn} SVTMPSIEVG TVGGGTQLAS QSACLDLLGV RGASRDRPGS
NARLLATVVA
        HMGRclustalW{wheat3}  SVTMPPIEV. .......... .......... ..........
..........
        HMGRclustalW{wheat2}  SVTMPPIEV. .......... .......... ..........
..........
HMGRclustalW{     soybean}   SVTMPSIEVG TVGGGTQLAS QSACLNLLGV KGASKESPGS
NSRLLATIVA
    HMGRclustalW{rubbertre3}  SVSMPSIELG TVGGGTQLAS QSACLNLLGV KGASKDSPGS
NSRLLATIVA
    HMGRclustalW{rosyperiwi}  SVTMPSIEVG TVGGGTQLAS QSACLNLLGV KGASKDSPGA
NSRLLATIVA
    HMGRclustalW{     tomato} SVTMPSIEVG TVGGGTQLAS QSACLNLLGV KGANREAPGS
NARLLATVVA
    HMGRclustalW{woodtobacc}  SVTMPSIEVG TVGGGTQLAS QSACLNLLGV KGANREVPGS
NARLLATIVA
    HMGRclustalW{     potato} SVTMPSIEVG TVGGGTQLAS QSACLNLLGV KGANRDAPGS
NARLLATIVA
    HMGRclustalW{    radish}  SVTMPSIEVG TVGGGTQLAS QSACLNLLGV KGASKESPGM
NSRRLATIVA
HMGRclustalW{arabadopsis1}   SVTMPSIEVG TVGGGTQLAS QSACLNLLGV KGASTESPGM
NARRLATIVA
    HMGRclustalW{cucumismel}  SVTMPSIEVG TVGGGTQLAS QSACLNLLGV KGASKESPGA
NSRLLATIVA
    HMGRclustalW{rubbertre2}  SVTLPSIEVG TVGGGTQLAS QSACLNLLGV MGACKESPGS
YSRLLATIVA
    HMGRclustalW{rubbertre1}  SVTMPSIEVG TVGGGTQLAS QSACLNLLGV KGANKESPGS
NSRLLAAIVA
    HMGRclustalW{camptothec}  SVTMPSIEVG TVGGGTQLAS QSACLNLLGV KGASKEAPGS
NARLLATIVA
    HMGRclustalW{arabadops2}  SVSMPCIEVG TVGGGTQLAS QAACLNLLGV KGSNNEKPGS
NAQQLARIVA
    HMGRclustalW{chineseham}  SCTMPSIEIG TVGGGTNLLP QQACLQMLGV QGACKDNPGE
NARQLARIVC
```

FIG. 32PP

```
HMGRclustalW{chineseha2}   SCTMPSIEIG  TVGGGTNLLP  QQACLQMLGV  QGACKDNPGE
NARQLARIVC
HMGRclustalW{syrianhamst}  SCTMPSIEIG  TVGGGTNLLP  QQACLQMLGV  QGACKDNPGE
NARQLARIVC
   HMGRclustalW{      rat} SCTMPSIEIG  TVGGGTNLLP  QQACLQMLGV  QGACKDNPGE
NARQLARIVC
HMGRclustalW{      rabbit} SCTMPSIEIG  TVGGGTNLLP  QQACLQMLGV  QGACKDSPGE
NARQLARIVC
HMGRclustalW{       human} SCTMPSIEIG  TVGGGTNLLP  QQACLQMLGV  QGACKDNPGE
NARQLARIVC
HMGRclustalW{       mouse} SCTMPSIEIG  TVGGGTNLLP  QQACLQMLGV  QGACKDNPGE
NARQLARIVC
HMGRclustalW{     xenopus} SCTMPSIEIG  TVGGGTNLAP  QQACLQMLGV  QGASTETPGK
NACQLAQIVC
HMGRclustalW{sea urchin}   SCTMPSIELG  TVGGGTVLPP  QSACLQMMDV  KGSNIHGSGL
NASQLARIVC
HMGRclustalW{   cockroach} SCTMPSIEIG  TIGGGTVLPP  QAACLDMLGV  RGANEMCPGE
NANTLARIVC
HMGRclustalW{drosophila}   TCTMPSLEVG  TVGGGTGLPG  QSACLEMLGV  RGAHATRPGD
NAKKLAQIVC
HMGRclustalW{dictyostel}   TVTMPSIEVG  TVGGGTSLPA  QSACLDIIGV  KGSSSSKPGA
NADQLAKTIA
HMGRclustalW{schistosom}   SVTMPCLEVG  TVGGGTRLSG  QRACLDLLDL  SV.....D.R
PTEHLSRIIA
HMGRclustalW{archaeoglo}   GTIEIPMAVG  VIGGATKVNP  LAKISLKILG  VNTAEELARV  AAAL
HMGRclustalW{pseudomonas}  GTLEMPMPVG  LVGGATKTHP  LAQLSLRILG  VKTAQALAEI  AVAV Consensus       SVTMPSIEVG  TVGGGTQLAP  QSACLNLLGV  KGA-KESPGS
NARQLARIVA
                                NADH binding domain 2
```

FIG. 32QQ

```
                                    1051
1100
    HMGRclustalW{methanobac}   GAVLAGELSL MGALAAGHLA RAHSELGRG. ..........
    HMGRclustalW{methanococ}   AAVLAGELSL LGALAAGHLG KAHQELGR.. ..........
    HMGRclustalW{halobacter}   VGSLAGELSL LSALASRHLS SAHAELGR.. ..........
    HMGRclustalW{sulfolobus}   STVLSGELNL LAALSNKELG KAHAKLGRAM KV........
    HMGRclustalW{    yeast2}   CAVLAGELSL CSALAAGHLV QSHMTHNRK. ...TNKANELP
QPS.......
    HMGRclustalW{    yeast1}   CAVLAGELSL CAALAAGHLV QSHMTHNRKP AEPTKPNNLD
ATDI......
    HMGRclustalW{phycomyces}   .......... .......... .......... ..........
    HMGRclustalW{   fusarium}  AAVLAGELSL CSALAAGHLV RAHMQHNRSA APSRSTTPGS
SHDARLTGHD
    HMGRclustalW{    candida}  SIVLSGELSL VSALAAGHLV QSHMQHNRAA AKK.......
    HMGRclustalW{dictyoste2}   AAVLSGELSL MSALAAGHLV RSHLKGNRKT EAPAPQADTI
SMTHNLPHSD
    HMGRclustalW{wheat1}       .......... .......... .......... ..........
    HMGRclustalW{      rice}   GSVVAGRALL LAALASGHLV KSHMMYNRSS KDVAK.....
    HMGRclustalW{      corn}   GGVLAGELSL LSALAAGQLV KSHMKYNRSS KDVSS.....
    HMGRclustalW{wheat3}       .......... .......... .......... ..........
    HMGRclustalW{wheat2}       .......... .......... .......... ..........
    HMGRclustalW{   soybean}   GSVLAGELSL MSAIAAGQLV NSHMKYNRSS KDVTK.....
    HMGRclustalW{rubbertre3}   GSVLAGELSL MSAIAAGQLV NSHMKYNRSA KDVSK.....
    HMGRclustalW{rosyperiwi}   GSVLAGELSL MSAISAGQLV RSHMKYNRSS KDITN.....
    HMGRclustalW{    tomato}   GSVLAGELSL MSAISSGQLV NSHMKYNRST KDVTK.....
    HMGRclustalW{woodtobacc}   GSVLAGELSL MSAISAGQLV KSHMKYNRST KDVTK.....
    HMGRclustalW{    potato}   GSVLAGELSL MSAISAGQLV KSHMKYNRSI KDISK.....
    HMGRclustalW{    radish}   GAVLAGELSL MSAIAAGQLV RSHMKYNRSS RDISG.....
    HMGRclustalW{arabadopsis1} GAVLAGELSL MSAIAAGQLV RSHMKYNRSS RDISG.....
    HMGRclustalW{cucumismel}   GSVLAGELSL MSAIAAGQLV RSHMKYNRSS RDVSK.....
    HMGRclustalW{rubbertre2}   GSVLAGELSL MSAIAAGQLV KSHMKYNRSS KDVSK.....
    HMGRclustalW{rubbertre1}   GSVLAGELSL MSAIAAGQLV KSHMKYNRSS KDMSK.....
    HMGRclustalW{camptothec}   GSVLAGELSL MSAIAAGQLV NSHMKYNRSN KDVTK.....
    HMGRclustalW{arabadops2}   GSVLAGELSL MSAIAAGQLV KSHMKYNRSS RDIGP.....
    HMGRclustalW{chineseham}   GTVMAGELSL MAALAAGHLV RSHMVHNRSK INLQD.....
```

FIG. 32RR

```
   HMGRclustalW{chineseha2}    GTVMAGELSL MAALAAGHLV RSHMVHNRSK INLQD.....
   HMGRclustalW{syrianhamst}   GTVMAGELSL MAALAAGHLV RSHMVHNRSK INLQD.....
   HMGRclustalW{      rat}     GTVMAGELSL MAALAAGHLV RSHMVHNRSK INLQD.....
   HMGRclustalW{    rabbit}    GTVMAGELSL MAALAAGHLV KSHMIHNRSK INLQD.....
   HMGRclustalW{     human}    GTVMAGELSL MAALAAGHLV KSHMIHNRSK INLQD.....
   HMGRclustalW{     mouse}    GTVMAGELSL MAALAAGHLV RSHMVHNRSK INLQD.....
   HMGRclustalW{    xenopus}   STVMAGELSL MAALAAGHLV KSHMVHNRSK INLQD.....
   HMGRclustalW{sea urchin}    ATVMAGELSL MSALAAGHLV KSHMKHNRSA LNIASPLPSI
DEVATHRRSK
   HMGRclustalW{ cockroach}    GTVLAGELSL MSALAAGHLV KSHMRHNRSS VSTSG.....
   HMGRclustalW{drosophila}    ATVMAGELSL MAALVNSDLV KSHMRHNRSS IAVNSAN...
   HMGRclustalW{dictyostel}    SAVMAGELSL MSALSAGHLM KSHLQYNRAK TN........
   HMGRclustalW{schistosom}    GTVLAAELSL MAALDTDDLV KAHMHFNRAK QSTNSHSCSH
STTTDNNDNI
   HMGRclustalW{archaeoglo}    ..GLAQNFAA LRALATEGIQ RGHMELHARN LAIMAGATGD
EVDRVVEIMV
   HMGRclustalW{pseudomonas}   ..GLAQNLGA MRALATEGIQ RGHMALHARN IAVVAGARGD
EVDWVARQLV
            Consensus         GTVLAGELSL MSALAAGHLV KSHMK-NRSS KDVSK----- ------
----
```

FIG. 32SS

```
                                        1101
1152
   HMGRclustalW{methanobac}    .......... .......... ..........
..........
   HMGRclustalW{methanococ}    .......... .......... ..........
..........
   HMGRclustalW{halobacter}    .......... .......... ..........
..........
   HMGRclustalW{sulfolobus}    .......... .......... ..........
..........
   HMGRclustalW{      yeast2}  .......... ..NKGPPCKT SALL......
..........
   HMGRclustalW{      yeast1}  .......... ..NRLKDGSV TCIKS.....
..........
   HMGRclustalW{phycomyces}    .......... .......... ..........
..........
   HMGRclustalW{    fusarium}  QCPRALSVNN VDERRRYSEV KAIDE.....
..........
   HMGRclustalW{     candida}  .......... .......... ..........
..........
   HMGRclustalW{dictyoste2}    .......... .......... ..........
..........
        HMGRclustalW{wheat1}   .......... .......... ..........
..........
   HMGRclustalW{        rice}  .........A .....AS... ..........
..........
   HMGRclustalW{        corn}  .........T .....TATEK TRQREVDV..
..........
        HMGRclustalW{wheat3}   .......... .......... ..........
..........
        HMGRclustalW{wheat2}   .......... .......... ..........
..........
HMGRclustalW{         soybean} .........I .....S.... ..........
..........
   HMGRclustalW{rubbertre3}    .........I .....TF... ..........
..........
   HMGRclustalW{rosyperiwi}    .........I .....ASSQL ESDS......
..........
   HMGRclustalW{      tomato}  .........A .....SS... ..........
..........
   HMGRclustalW{woodtobacc}    .........A .....SS... ..........
..........
   HMGRclustalW{      potato}  .......... .......... ..........
..........
        HMGRclustalW{radish}   .........A .....TTTT. ..........
..........
HMGRclustalW{arabadopsis1}     .........A .....TTTTT TTT.......
..........
   HMGRclustalW{cucumismel}    .........L .....ES... ..........
..........
   HMGRclustalW{rubbertre2}    .........A .....AS... ..........
..........
   HMGRclustalW{rubbertre1}    .........A .....AS... ..........
..........
   HMGRclustalW{camptothec}    .........A .....SS... ..........
..........
   HMGRclustalW{arabadops2}    .........S .....SQVNR ..........
..........
   HMGRclustalW{chineseham}    .......... ...LQGTCTK KSA.......
..........
```

FIG. 32TT

```
HMGRclustalW{chineseha2}    ..........  ...LQGTCTK  KSA.......  ..........
..........
HMGRclustalW{syrianhamst}   ..........  ...LQGTCTK  KAA.......  ..........
..........
   HMGRclustalW{     rat}   ..........  ...LQGTCTK  KAA.......  ..........
..........
  HMGRclustalW{   rabbit}   ..........  ...LEGACTK  KAA.......  ..........
..........
 HMGRclustalW{    human}    ..........  ...LQGACTK  KTA.......  ..........
..........
 HMGRclustalW{    mouse}    ..........  ...LQGTCTK  KAA.......  ..........
..........
  HMGRclustalW{  xenopus}   ..........  ...LPGTCTK  KAA.......  ..........
..........
   HMGRclustalW{sea urchin} SVDFSALKES  SAAAPGTCTA  NAS.......  ..........
..........
   HMGRclustalW{ cockroach} .........S  ...EPSTPAC  KS........  ..........
..........
   HMGRclustalW{drosophila} ........NP  LNVTVSSCST  IS........  ..........
..........
   HMGRclustalW{dictyoste1} ..........  ..........  ..........  ..........
..........
   HMGRclustalW{schistosom} SNIYDNENVA  LSSKIPVTDN  SDIRESVHSL  HVKPFPVKSD
LSVNPEISHY TM
   HMGRclustalW{archaeoglo} RDGKIRLDYA  KEVLERLRS.  ..........  ..........
..........
   HMGRclustalW{pseudomonas} EYHDVRADRA VALLKQKRGQ  ..........  ..........
..........

Consensus       ---------A  ---LQGTCTK  KAA-------  ----------
----
```

FIG. 32UU

TRANSGENIC PLANTS CONTAINING ALTERED LEVELS OF STEROID COMPOUNDS

This application is a divisional of U.S. application Ser. No. 10/862,907, filed Jun. 7, 2004, now U.S. Pat. No. 7,544,863 that is a divisional application of U.S. patent application Ser. No. 09/885,723, filed Jun. 20, 2001, now U.S. Pat. No. 6,822,142, which application claims benefit of priority from U.S. Provisional Application Ser. No. 60/260,114, filed Jan. 5, 2001, each of the disclosures of which are incorporated herein by reference in their entirety.

TECHNICAL FIELD

The present invention relates to biotechnology with an emphasis on plant biotechnology, and particularly biotechnology affecting the biosynthesis of steroid compounds.

BACKGROUND

Enhancement of the nutritional or health benefits of oils through genetic engineering is being addressed throughout the agricultural community. Several approaches involve manipulation of already present cellular biosynthetic pathways. Steroid biosynthetic pathways are of current interest, particularly for the enhancement of health benefits from food oils.

Several related U.S. patents address increasing sterol accumulation in higher plants. Those patents include U.S. Pat. No. 5,589,619 "Process and Composition for increasing squalene and sterol accumulation in higher plants" (accumulation of squalene in transgenic plants by increasing HMGR activity) and U.S. Pat. No. 5,306,862 "Method and composition for increasing sterol accumulation in higher plants" (increasing HMGR activity to increase plant sterol accumulation—including sterol and cycloartenol, which affects insect resistance—in tobacco, tomato, corn, carrot, soybean, cotton, barley, *arabidopsis*, guayule and petunia; seeds with elevated sterol/cycloartenol, 7S promoter and CaMV promoters), U.S. Pat. No. 5,365,017 "Method and composition for increasing sterol accumulation in higher plants" (DNA construct with HMGR-CaMV 35S, transgenic plants, hybrid plants, corn, soy, barley, tomato, *Arabidopsis*), U.S. Pat. No. 5,349,126 "Process and composition for increasing squalene and sterol accumulation in higher plants" (increase in squalene and sterol accumulation by increasing HMGR activity in transgenic tobacco, cotton, soybean, tomato, alfalfa, *Arabidopsis*, corn, barley, carrot and guayule plants), and EP 486290 (enhancement of squalene and specific sterol [squalene zymosterol, cholest-7,24-dienol, cholest-5,7,24-trienol] accumulation in yeast by increasing HMGR activity in yeast deficient in enzymes that convert squalene to ergosterol).

In those patents, the amount of a protein exhibiting 3-hydroxy-3-methylglutaryl Coenzyme-A reductase (HMGR) activity is typically increased. HMGR widens a "bottleneck" near the beginning of a biosynthetic path to steroid production, permitting a higher carbon flux through steroid biosynthetic pathways and resulting in increased sterol accumulation.

U.S. Pat. No. 5,480,805 "Composition for modulating sterols in yeast" (enhancement of delta 8-7 isomerase activity-ERG2 enhances accumulation of specific sterols in yeast).

U.S. Pat. No. 5,460,949 "Method and composition for increasing the accumulation of squalene and specific sterols in yeast" (increasing squalene, zymosterol and specific sterols in yeast by increasing HMGR in yeast having decreased erg5 and erg6 activity—Sc and hamster HMGR).

WO 9845457 (SMTI, Erg6 from A.t., corn, yeast; transgenic plants with altered sterol levels_using DNA encoding an enzyme binding a first sterol and producing a second sterol—altered carotenoid, tocopherol, modified FA levels—HMGR, 5α-reductase, geranylgeranyl pyrophosphate synthase, phytoene synthase, phytoene desaturase, isopentenyl diphosphate isomerase).

Acetate is the metabolic precursor of a vast array of compounds vital for cell and organism viability. Acetyl coenzyme A (CoA) reacts with acetoacetyl CoA to form 3-hydroxy-3 methylglutaryl CoA (HMG-CoA). HMG-CoA is reduced to mevalonate in an irreversible reaction catalyzed by the enzyme HMG-CoA reductase. Mevalonate is phosphorylated and decarboxylated to isopentenyl-pyrophosphate (IPP). Through the sequential steps of isomerization, condensation and dehydrogenation, IPP is converted to geranyl pyrophosphate (GPP). GPP combines with IPP to form farnesyl pyrophosphate (FPP), two molecules of which are reductively condensed to form squalene, a 30-carbon precursor of sterols.

A key enzyme in sterol biosynthesis is 3-hydroxy-3-methylglutaryl-Coenzyme A reductase (HMG-CoA reductase or HMGR). Schaller et al. (Plant Physiol. 109: 761-770, 1995) found that over-expression of rubber HMGR (hmg1) genomic DNA in tobacco leads to the overproduction of sterol end-products (sitosterol, campesterol and stigmasterol) up to 6-fold in leaves. Further, the excess sterol was stored as sterylesters in lipid bodies. HMGR activity was increased by 4- to 8-fold.

Sterols are derivatives of a fused, reduced ring system, cyclopenta-[a]-phenanthrene, comprising three fused cyclohexane rings (A, B, and C) in a phenanthrene arrangement, and a terminal cyclopentane ring (D) having the formula (I) and carbon atom position numbering shown below:

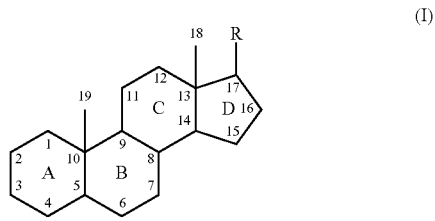

(I)

where R is an 8 to 10 carbon-atom side chain.

In plants, squalene is converted to squalene epoxide, which is then cyclized to form cycloartenol (4,4,14α-trimethyl-9β, 19-cyclo-5α-cholest-24-en-3β-ol). Cycloartenol has two methyl groups at position 4, a methyl group at position 14, a methylene bridge between the carbon atoms at positions 9 and 19 that forms a disubstituted cyclopropyl group at those positions, and includes an 8-carbon sidechain of the formula: $CH_3CH(CH_2)_2CH=C(CH_3)_2$. Squalene epoxide can alternatively be converted into pentacyclic sterols, containing five instead of four rings. Exemplary pentacyclic sterols include the phytoalexins and saponins.

Being one of the first sterols in the higher plant biosynthetic pathway, cycloartenol serves as a precursor for the production of numerous other sterols. In normal plants, cycloartenol is converted to predominantly 24-methylene cycloartenol (4,4, 14α-dimethyl-9β,19-cyclo-22,23-dihydro-ergosta-24(28)-en-3-β-ol), cycloeucalenol, (4,14α-trimethyl-9β,19 cyclo-5α-ergosta-24(28)-en-3β-ol), isofucosterol (5α-stigmasta-5-24(28)-dien-3β-ol), sitosterol (5α-stigmasta-5-en-3β-ol), stigmasterol-(stigmasta-5,-22-dien-3β-ol), campesterol (5α-ergosta-5-en-3β-ol), and cholesterol (5α-cholesta-5-en-3β-ol). These transformations are illustrated in FIG. 1.

Although sterols produced by plants, and particularly higher (vascular) plants, can be grouped by the presence or absence of one or more of several functionalities, plant sterols are classified into two general groups herein; i.e., those containing a double bond between the carbon atoms at positions 5 and 6 (delta-5 or Δ5 sterols) and those not containing a double bond between the carbon atoms at positions 5 and 6 (non-delta-5 sterols).

Exemplary naturally-occurring delta-5 plant sterols are isofucosterol, sitosterol, stigmasterol, campesterol, cholesterol, and dihydrobrassicasterol. Exemplary naturally occurring non-delta-5 plant sterols are cycloartenol, 24-methylene cycloartenol, cycloeucalenol, and obtusifoliol. The most abundant sterols of vascular plants are campesterol, sitosterol, and stigmasterol, all of which contain a double bond between the carbon atoms at positions 5 and 6 are classified as delta-5 sterols.

The HMG-CoA reductase enzymes of animals and yeasts are integral membrane glycoproteins of the endoplasmic reticulum. The intact enzyme comprises three regions: a catalytic region containing the active site of the enzyme; a membrane binding region anchoring the enzyme to the endoplasmic reticulum; and a linker region joining the catalytic and membrane binding regions of the enzymes. The membrane binding region occupies the amino-terminal (N-terminal) portion of the intact protein, whereas the catalytic region occupies the carboxy-terminal (C-terminal) portion of the protein, with the linker region constituting the remaining portion. M. E. Basson et al., *Mol. Cell Biol.,* 8(9):3797-3808 (1988).

The activity of HMG-CoA reductase in animals and yeasts is known to be subject to feedback inhibition by sterols. Such feedback inhibition requires the presence of the membrane binding region of the enzyme. See, e.g., G. Gil et al, *Cell,* 41:249-258 (1985); M. Bard and J. F. Downing, *J. Gen. Microbiol.,* 124:415-420 (1981).

Given that mevalonate is the precursor for sterols and other isoprenoids, it might be expected that increases in the amount or activity of HMG-CoA reductase would lead to increases in the accumulation of both sterols and other isoprenoids.

In mutant strains of the yeast *Saccharomyces cerevisiae* (*S. cerevisiae*) having abnormally high levels of HMG-CoA reductase activity, the production of two sterols, 4,14-dimethylzymosterol and 14-methylfucosterol is markedly increased above normal. Downing, et al., *Biochem. Biophys. Res. Comm.,* 94(3): 874-979 (1980).

When HMG-CoA reductase activity was increased by illumination in non-photosynthetic microorganisms, isoprenoid (carotenoid), but not sterol (ergosterol), synthesis was enhanced. Tada, et al., *Plant and Cell Physiology,* 23(4):615-621 (1982).

WO 9703202 discloses a method for identifying agents modulating sterol biosynthesis using a yeast acetoacetyl CoA thiolase (ERG10) gene linked to a reporter system to evaluate compounds, such as lovastatin and other HMG-CoA synthase inhibitors, that affect cholesterol biosynthesis.

U.S. Pat. No. 5,668,001 teaches a recombinant avian HMG-CoA synthase preparation useful for evaluating drugs that inhibit cholesterol biosythesis.

JP 09121863 discloses a plant with increased 3-hydroxy-3-methyl glutaryl coenzyme A reductase (HMGR) activity as a result of increasing the expression of a mutant protein kinase gene that regulates expression of the HMGR gene. The increased HMGR activity increases squalene, zymosterol, cholesta-7,24-dienol and cholest-5,7,24-trenol accumulation in yeast with ERG5 and ERG6 mutants.

EP 480730 "Plant-sterol accumulation and pest resistance-by increasing copy number of 3-hydroxy-3-methyl glutaryl coenzyme-A reductase gene in tobacco, tomato and corn WO 9913086 "Human Delta 7-sterol reductase polypeptide-useful for diagnosis or treatment of genetic defects e.g. hereditary Smith-Lemli-Opitz syndrome" teaches making and using the recombinant polypeptide with humans.

Chappell et al. U.S. Pat. No. 5,589,619 teaches that transformation of higher plants with truncated HMG-CoA reductase enhanced the production of squalene, cycloartenol and certain sterols, particularly compounds having unsaturations at the 5-position. Several intermediate sterols as are shown in FIG. 1 were also produced. It would be beneficial if the production of sitosterol and stigmasterol could be enhanced while lessening the accumulation of the intermediate sterols. The present invention provides avenues for enhancing production of sitosterol and stigmasterol and lessening the accumulation of the intermediate sterols.

Gonzalez et al. (Abstract of poster at Third Terpnet Meeting of the European Network on Plant Isoprenoids, May 29-30, 1997, Poitiers, France) over-expressed the *Arabidopsis* HMGR cDNA (hmg1 and hmg2) and found sterol overproduction with hmg1 only. They used two forms of the hmg1 gene, a full-length form and a truncated form containing only the catalytic domain. HMGRs have three domains, an N-terminal membrane spanning domain, a short linker domain, and a C-terminal catalytic domain. In this case the transgenic plants were also *Arabidopsis*. The difference between the full-length and truncated forms was a greater accumulation of pathway intermediates in the case of the truncated form. More importantly, the intermediates demonstrated as accumulating were cycloartenol, 24-methylenecycloartanol and obtusifoliol.

Finally, U.S. Pat. Nos. 5,365,017 and 5,306,862, both assigned to Amoco Corp., disclose a method for increasing sterol accumulation in plants by increasing the copy number of a gene having HMG-CoA reductase activity. These inventions disclose a method using hamster truncated HMGR that consisted of the catalytic domain and the linker domain. According to the claims the linker domain was essential for activity. They also demonstrated a greater accumulation of pathway intermediates such as cycloartenol.

BRIEF SUMMARY

The present invention relates to transgenic plants and their progeny having improved nutritional characteristics. More particularly, the present invention relates to transgenic plants and their progeny, the storage organs (e.g. seed, fruit and vegetable parts) of which contain modified levels of steroid compounds, such as (i) elevated levels of beneficial phytosterols (e.g., sitosterol), phytostanols (e.g., sitostanol), and esters thereof, relative to an otherwise identical plant transformed only with a truncated HMG-CoA reductase gene or a wild-type plant, and (ii) reduced levels of steroid pathway intermediate compounds (e.g. one or more of squalene, cycloartenol, 24-methylene cycloartenol, obtusifoliol, stigmasta-7-enol and campesterol) in their storage organs relative to an otherwise identical transgenic plant transformed only with a truncated HMG-CoA reductase gene. Nucleic acid sequences encoding enzymes that affect the biosynthesis and accumulation of steroid compounds in plants (HMG-CoA reductase and a steroid pathway enzyme), and methods for using these sequences to produce such transgenic plants, are also provided. These methods comprise, for example, introducing into cells nucleic acid sequences encoding enzymes that affect the levels of accumulated steroid pathway end products.

The present invention contemplates a recombinant construct or a recombinant vector that contains 2 DNA sequences. The first encodes a polypeptide exhibiting 3-hydroxy-3-methylglutaryl-Coenzyme A (HMG-CoA) reductase activity. The second DNA sequence encodes a polypeptide exhibiting the activity of another steroid pathway enzyme. Each polypeptide-encoding DNA sequence is operably linked in the 5' to 3' direction to a promoter and a transcription termination signal sequence independent of the other sequence. The promoter is located upstream and the termination sequence downstream of each polypeptide-encoding DNA sequence. The second DNA sequence encoding a steroid pathway enzyme can code for a squalene epoxidase enzyme, a sterol methyl transferase I enzyme, a sterol C4-demethylase enzyme, a obtusifoliol C14α-demethylase enzyme, a sterol C5-desaturase enzyme, or a sterol methyl transferase II enzyme. It is contemplated that HMG-CoA reductase and the steroid pathway enzyme activity comes from a mutant or truncated form of those enzymes, such as a truncated HMG-CoA reductase lacking the transmembrane region while retaining a functional catalytic domain. Examples of such preferred HMG CoA reductases include the truncated rubber and *Arabidopsis* HMG CoA reductases disclosed herein.

Preferably, the regulatory function of a promoter is substantially unaffected by cellular levels of squalene such as the CaMV 35S promoter. In one aspect, a promoter is seed-specific. In another aspect, a promoter is derived from a species in a different order from a host cell. In another aspect, the HMG-CoA reductase or steroid pathway enzymes is from a species in a different order from the order that of the host cell. The invention contemplates a construct or recombinant vector having more than one DNA sequence encoding a steroid pathway enzyme that do not have to be under the control of the same promoter. Preferably, a recombinant vector is a plant expression vector.

In another aspect of the invention, a transformed host cell comprises a recombinant construct or vector as described above. Preferably, a host cell is plant cell, preferably that plant cell is from canola, soybean, corn, maize, tobacco, cotton, rape, tomato or alfalfa. The invention contemplates a host cell in a cell culture, plants derived from transformed host cells, and storage organs (seeds, fruits and vegetable parts) from transgenic plants.

In addition to contemplating transgenic plants and seeds, the invention contemplates transgenic plant seeds capable of germinating into a transgenic plant and mutants, recombinants, genetically engineered derivatives thereof and hybrids derived therefrom. The plant over-accumulates steroid pathway products relative to a native, non-transgenic plant of the same strain, wherein said mutants, recombinants, genetically engineered derivatives thereof and hybrids derived therefrom maintain the ability to overaccumulate steroid pathway products.

The invention contemplates a process of increasing the formation of steroid pathway products in a transformed host cell as compared to an otherwise identical non-transformed host cell. Contemplated processes use the described recombinant constructs and vectors to transform host cells, then growing the host cells or regenerating transgenic plants therefrom.

In one aspect of the invention, the genome of a contemplated plant, its progeny, seeds or cell culture, comprises introduced DNA encoding an HMG-CoA reductase activity and introduced DNA encoding a steroid pathway enzyme that is a squalene epoxidase enzyme, a sterol methyl transferase I enzyme, a sterol C4-demethylase enzyme, a obtusifoliol C14α-demethylase enzyme, a sterol C5-desaturase enzyme, or a sterol methyl transferase II enzyme. The storage organs of such a plant contain an elevated level of total accumulated sterol, compared to storage organs of an otherwise identical plant, the genome of which does not comprise said introduced DNA. Further, the storage organs of the plant contain a reduced level of squalene, cycloartenol, 24-methylene cycloartenol, obtusifoliol, stigmasta-7-enol, or campesterol compared to the seeds of an otherwise identical plant or a plant comprising an introduced DNA encoding an HMG-CoA reductase enzyme.

The invention contemplates a method of producing a plant that accumulates an elevated level of sterol pathway products compared to a corresponding plant comprising no introduced DNA encoding a peptide, polypeptide, or protein that affects the biosynthesis and accumulation of a sterol pathway product, comprising sexually crossing plants to arrive at a plant comprising nucleic acid encoding an HMG CoA reductase and a steroid pathway enzyme, including crosses with a nurse cultivar. The plants, including apomicitic plants, uniform populations of the plants and their seeds and parts other than seeds are contemplated.

Another aspect of the invention is oils containing at least one sterol pathway product, extracted from the seeds of a contemplated plant. Preferably sitosterol, at least one sitosterol ester, or mixtures thereof, comprise at least about 57% by weight of the total sterol compounds of a contemplated oil. Preferably sitosterol, that at least one sitosterol ester, or mixtures thereof, comprise at least about 0.08% of the dry weight of a contemplated seed. Preferably, the oil has a reduced amount of squalene, cycloartenol, 24-methylene cycloartenol, obtusifoliol, stigmasta-7-enol, campesterol, or combinations thereof, compared to oil from a corresponding transgenic plant that does not contain introduced DNA encoding a squalene epoxidase enzyme, a sterol methyl transferase I enzyme, a sterol C4-demethylase enzyme, a obtusifoliol C14α-demethylase enzyme, a sterol C5-desaturase enzyme, a sterol methyl transferase II enzyme, or mixture thereof; wherein the reduction is in the range of from about 10% to about 100%.

Sitosterol ester compositions derived from transgenic plants of the present invention, their progeny or their seeds are also contemplated, preferably wherein an esterifying fatty acid has 2 to 22 carbon atoms in the main chain.

A further aspect of the invention is cholesterol-lowering compositions comprising contemplated oils and sitosterol ester compositions. Another further aspect of the invention is foods, food ingredients, or food compositions comprising contemplated oils.

Still further, the invention contemplates pharmaceutical compositions comprising a cholesterol-lowering effective amount of a contemplated oil, and a pharmaceutically acceptable carrier, excipient, or diluent.

A method of lowering the plasma concentration of low density lipoprotein cholesterol is contemplated, comprising orally administering to a human or animal subject an effective amount of an above composition. Also contemplated is a method of treating or preventing an elevated plasma concentration of low-density lipoprotein cholesterol, comprising orally administering to a human or animal subject an effective amount of a contemplated composition.

A related aspect of the invention is a method of making a food additive composition, comprising obtaining oil containing a sterol pathway product compound from seed of a contemplated transgenic plant and mixing the oil with an edible solubilizing agent, an effective amount of a dispersant, and optionally, an effective amount of an antioxidant.

Novel forms of two sterol pathway enzymes and the nucleic acids that encode them are disclosed: an *Arabidopsis* enzyme having nucleic acid similarity to a squalene epoxidase, and an *Arabidopsis* enzyme having nucleic acid similarity to an obtusifoliol C14α-demethylase enzyme. Thus, the invention contemplates an isolated DNA molecule having a nucleotide sequence of disclosure SEQ ID NO: 4, 6, 8, 10, 14, 15, 17 or the complements thereof. Also contemplated is a nucleotide sequence that hybridizes to the nucleotide sequence of SEQ ID NO:4, 6, 8, 10, 14, 15, 17 or their complements under a wash stringency equivalent to 0.5×SSC to 2×SSC, 0.1% SDS, at 55-65° C., and that encode a polypeptide having squalene epoxidase or obtusifoliol C14α-demthylase enzymatic activity. Preferably, that enzymatic activity is substantially similar to that of a disclosed squalene epoxidase or obtusifoliol C14α-demethylase, respectively. By substantially similar is meant having enzymatic activity differing from that of the disclosed enzymes by about 30% or less, preferably by about 20% or less, and more preferably by about 10% or less when assayed by standard enzymatic assays. Also contemplated is a nucleotide sequence encoding the same genetic information as said nucleotide sequence of SEQ ID NO: 4, 6, 8, 10, 14, 15, 17 or their complements or that hybridize as described above, but which is degenerate in accordance with the degeneracy of the genetic code. Recombinant constructs, vectors and transformed host cells comprising the novel isolated and purified nucleic acid sequences are also contemplated. In one embodiment, the vector is a plant vector and the host cell is a plant cell. Methods of producing the disclosed squalene epoxidase or obtusifoliol C14α-demethylase enzymes are also contemplated comprising culturing a transformed host cell for a time and under conditions conductive to the production of the squalene epoxidase or obtusifoliol C14α-demethylase enzyme, and recovering the produced squalene epoxidase or obtusifoliol C14α-demethylase enzyme.

Yet another aspect provides any of the above described transformed host cells, further comprising a recombinant construct or expression vector encoding a tocopherol synthesis pathway enzyme, and in particular, S-adenosylmethionine-dependent α-tocopherol methyltransferase. Also included are plants, seeds and storage organs comprising the transformed host cells.

Another aspect provides, a process of increasing the formation of steroid pathway products and tocopherols in a transformed host cell as compared to an otherwise identical non-transformed host cell comprising (1) transforming a host cell with a recombinant vector comprising (a) as operably linked components in the 5' to 3' direction, a promoter, a DNA sequence encoding a first polypeptide having 3-hydroxy-3-methylglutaryl-Coenzyme A reductase enzyme activity, and a transcription termination signal sequence; and (b) as operably linked components in the 5' to 3' direction, a promoter, a DNA sequence encoding at least one polypeptide having steroid pathway enzyme activity selected from the group consisting of squalene epoxidase enzyme activity, sterol methyl transferase I enzyme activity, sterol C4-demethylase enzyme activity, obtusifoliol C14α-demethylase enzyme activity, sterol C5-desaturase enzyme activity, and sterol methyl transferase II enzyme activity, and a transcription termination signal sequence; (2) transforming the host cell of (1) with a recombinant vector comprising as operably linked components, a promoter, a DNA sequence encoding a tocopherol synthesis pathway enzyme, and a transcription termination sequence; and (3) regenerating said transformed plant cell into said transgenic plant.

BRIEF DESCRIPTION OF THE DRAWINGS

These and other features, aspects, and advantages of the present invention will become better understood with regard to the following description, appended claims and accompanying figures where:

Figure 21:
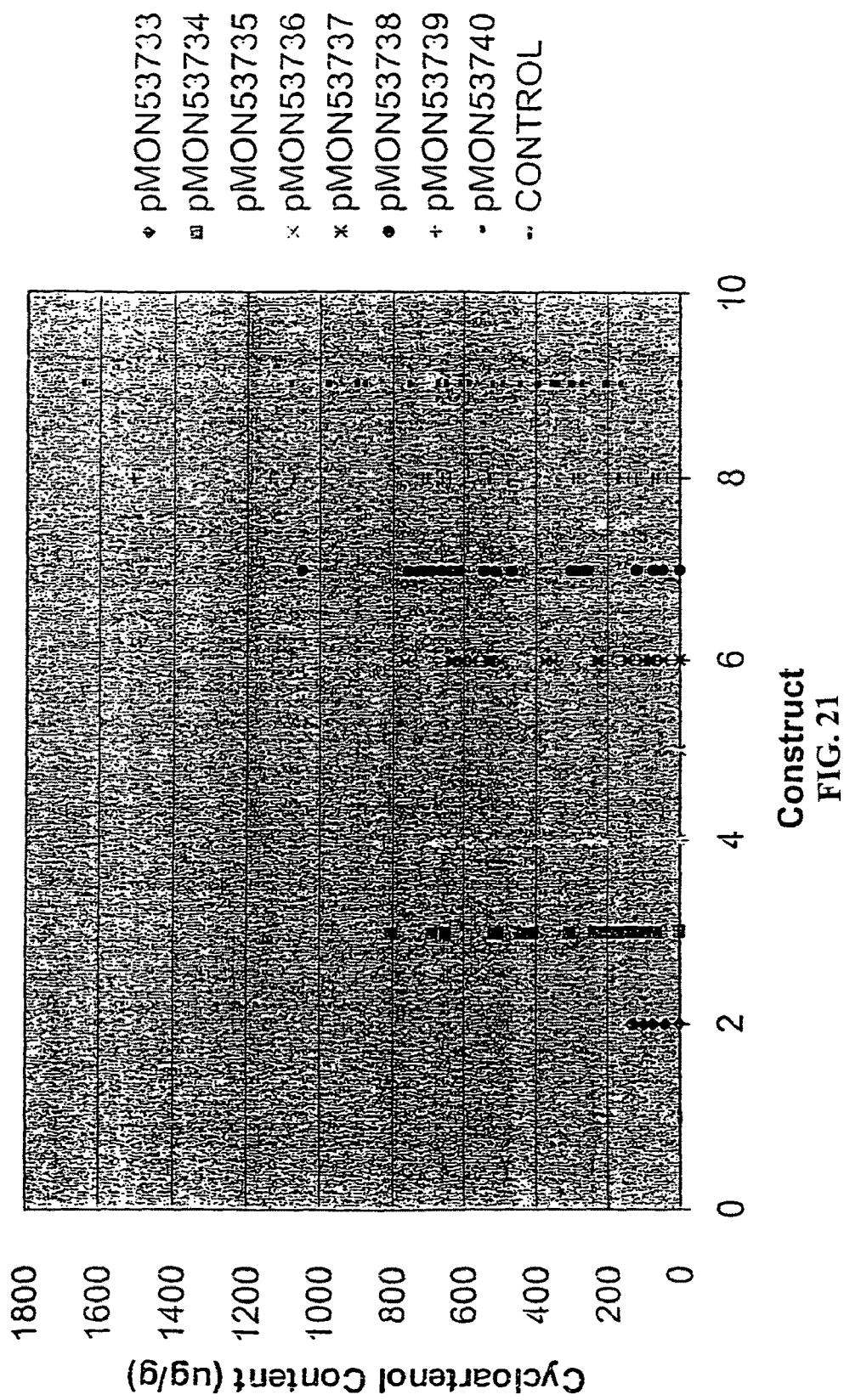

FIG. 21 is a graph comparing the cycloartenol content in micrograms of steroid compound per gram of seeds analyzed in transgenic *Arabidopsis* plants transformed with pMON53733 through pMON53740 compared to control plants.

Figure 22:
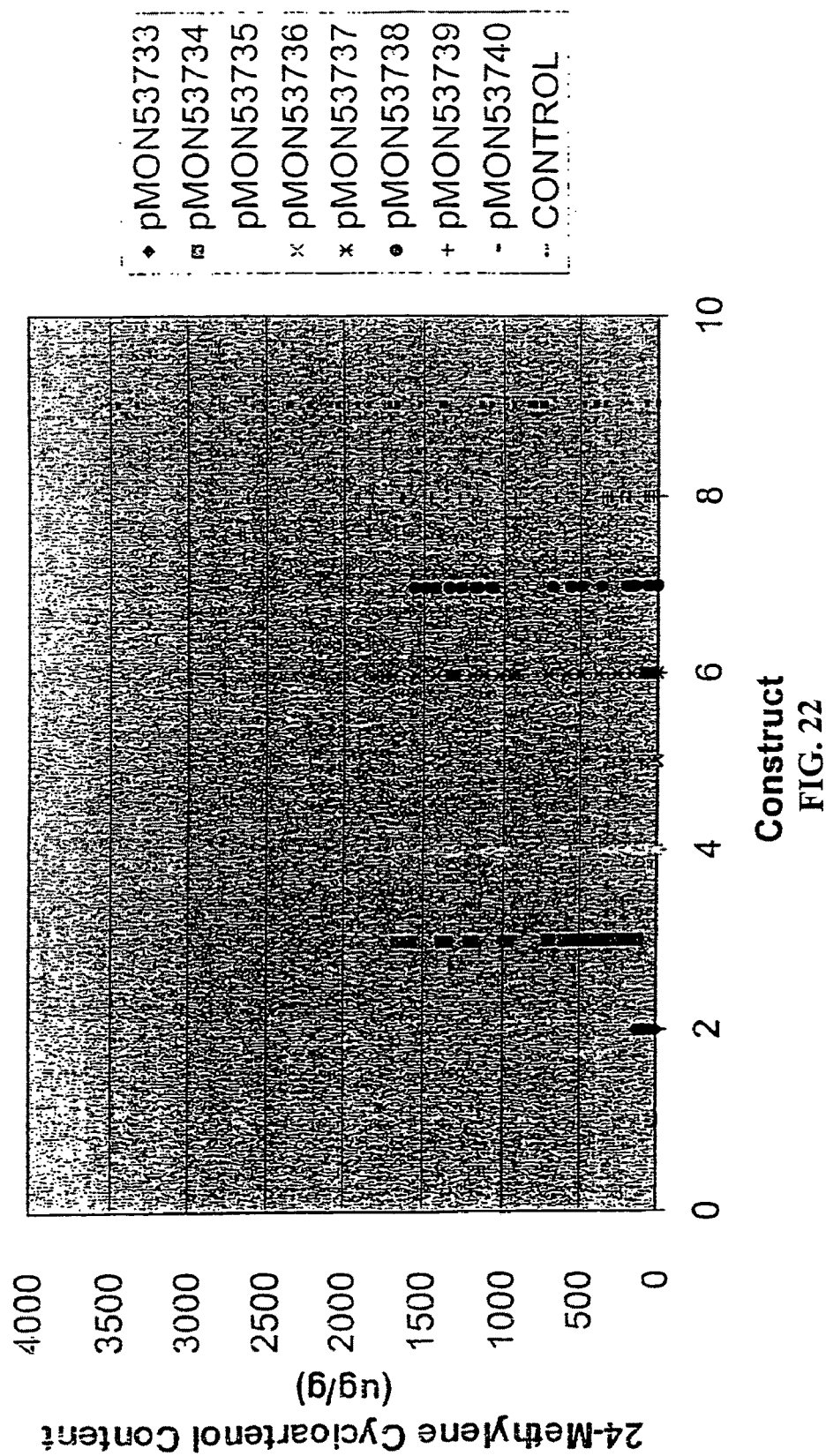

FIG. 22 is a graph comparing the 24-methylene cycloartenol content in micrograms of steroid compound per gram of seeds analyzed in transgenic *Arabidopsis* plants transformed with pMON53733 through pMON53740 compared to control plants.

Figure 23:
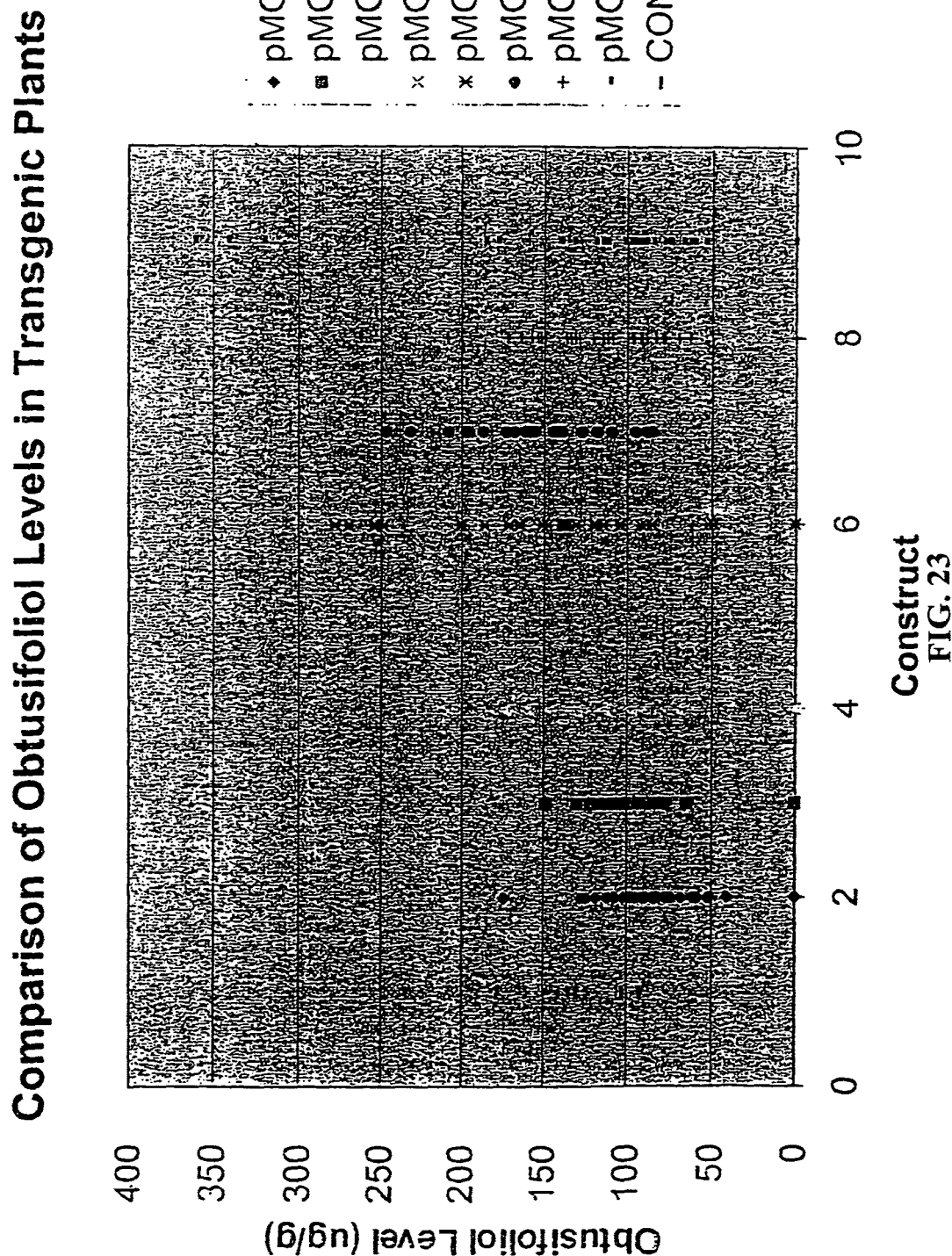

FIG. 23 is a graph comparing the obtusifoliol content in micrograms of steroid compound per gram of seeds analyzed in transgenic *Arabidopsis* plants transformed with pMON53733 through pMON53740 compared to control plants.

Figure 24:
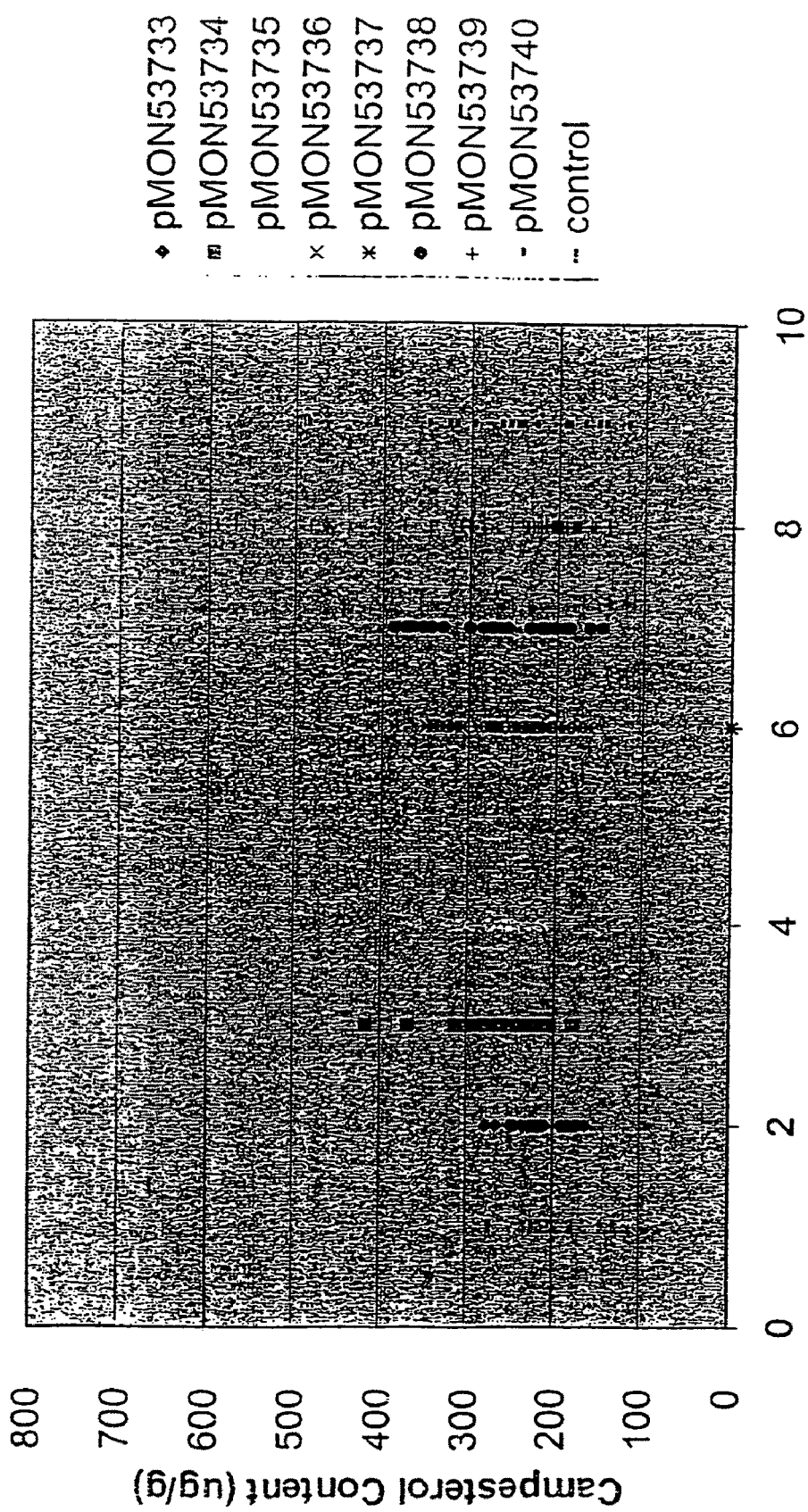

FIG. 24 is a graph comparing the campesterol content in micrograms of steroid compound per gram of seeds analyzed in transgenic *Arabidopsis* plants transformed with pMON53733 through pMON53740 compared to control plants.

Figure 25:
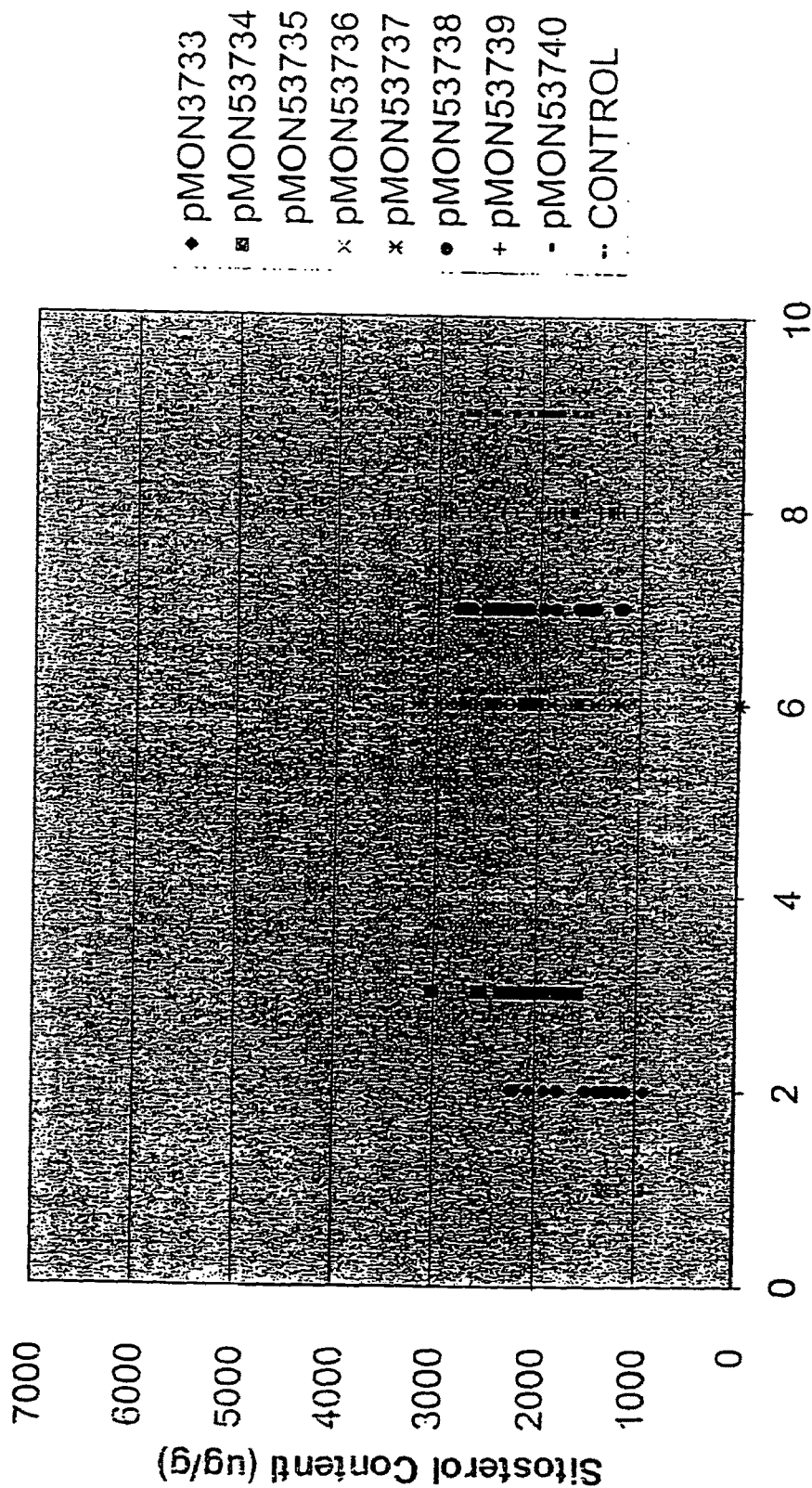

FIG. 25 is a graph comparing the sitosterol content in micrograms of steroid compound per gram of seeds analyzed in transgenic *Arabidopsis* plants transformed with pMON53733 through pMON53740 compared to control plants.

Figure 26:
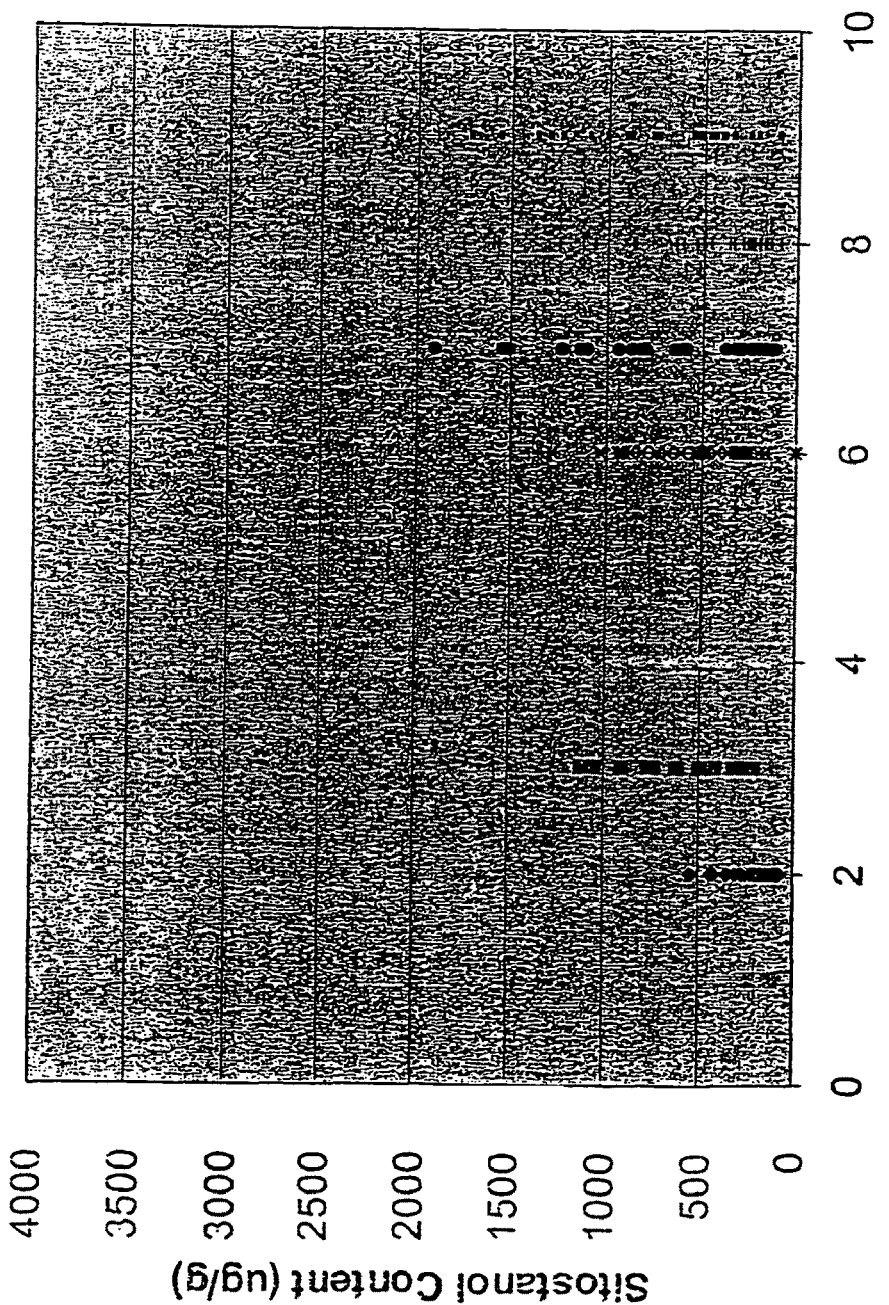

FIG. 26 is a graph comparing the sitostanol content in micrograms of steroid compound per gram of seeds analyzed in transgenic *Arabidopsis* plants transformed with pMON53733 through pMON53740 compared to control plants.

Figure 27:
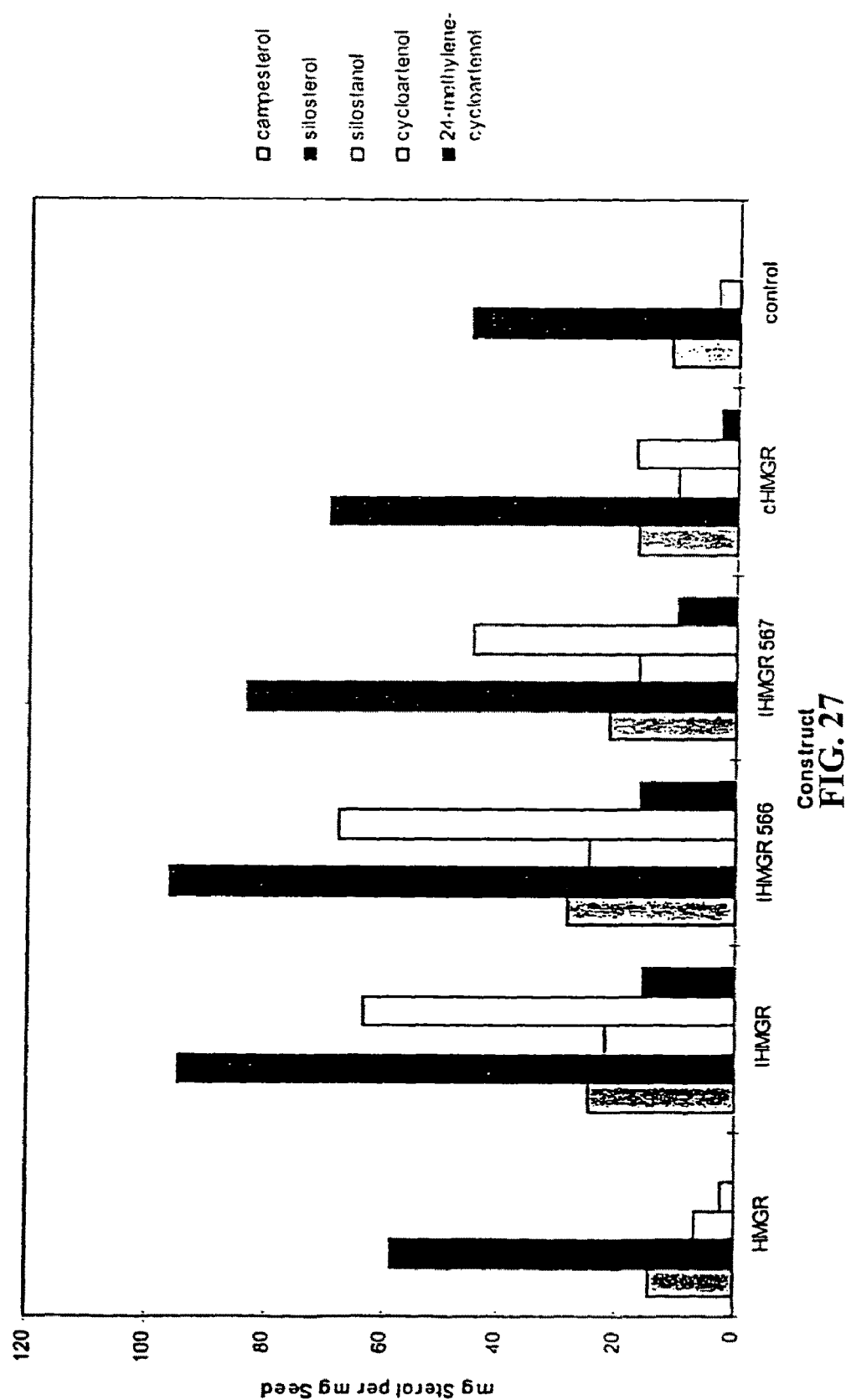

FIG. 27 is a sterol profile (histogram) of transgenic *Arabidopsis* harboring different forms of rubber HMGR.

Figure 28:
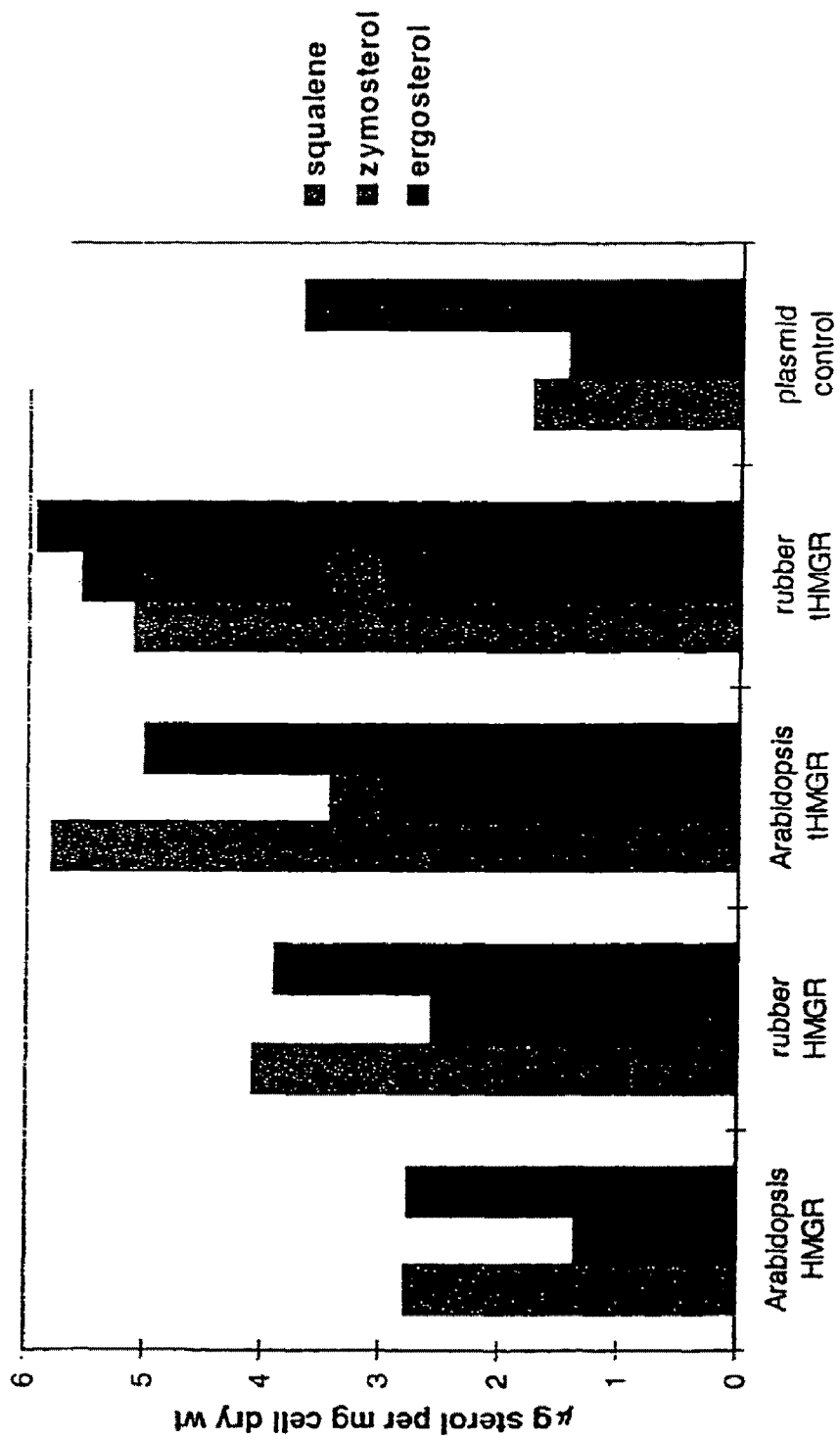

FIG. 28 is a graph of the squalene, zymosterol and erogosterol content in micrograms of sterol per milligram of cell dry weight from HMGR constructs in yeast HMGR1 knockout mutants for constructs having full length and truncated HMG CoA reductase (HMGR) sequences. The truncated sequences contain substantial portions of the catalytic region but lack the linker region and the transmembrane region of HMGR. These sequences are derived from *Arabidopsis* and rubber plants.

Figure 29:
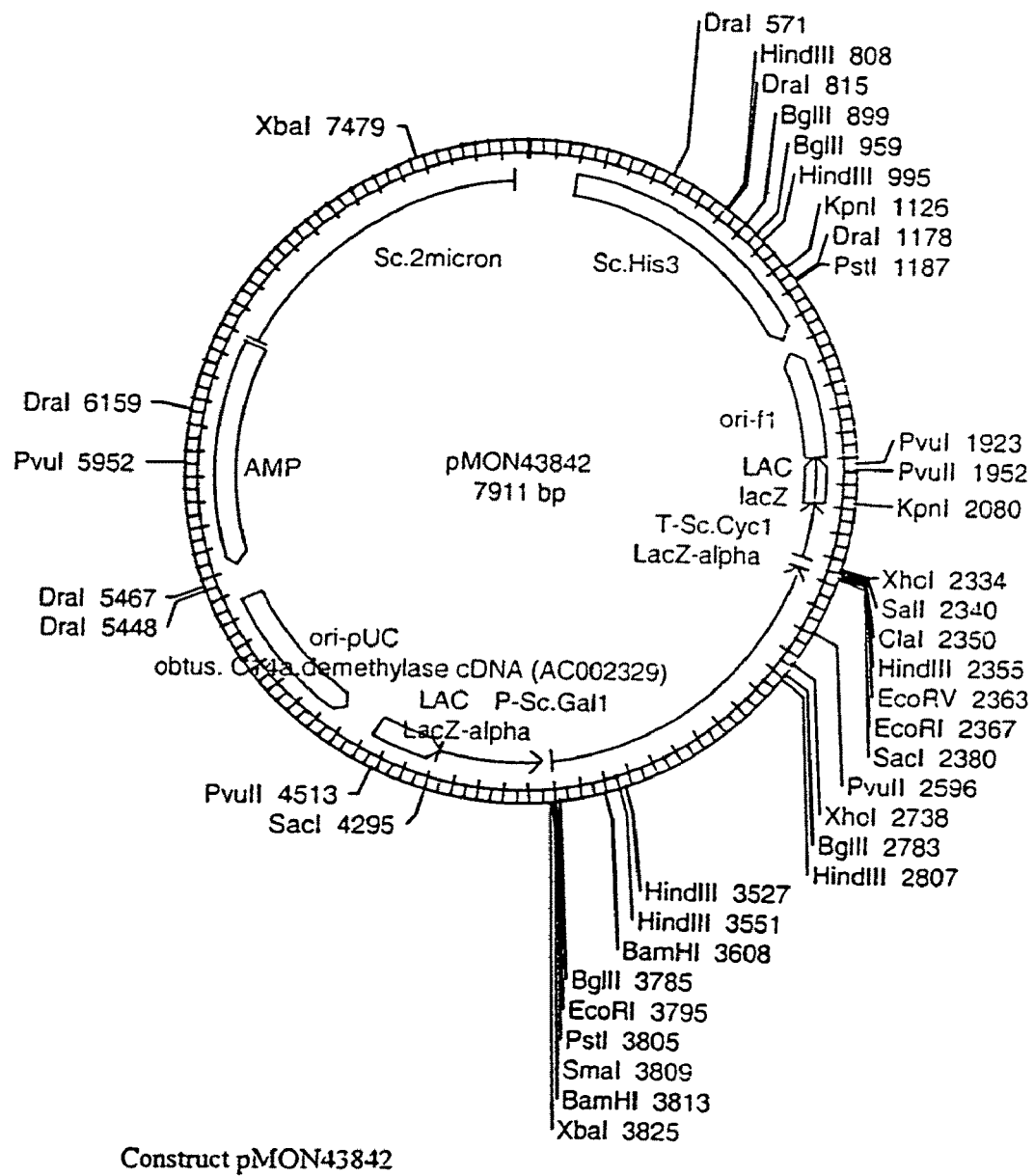

FIG. 29 is a map showing the structure of construct pMON43842. pMON43842 is a yeast expression vector carrying cDNA encoding *Arabidopsis* putative obtusifoliol C14α-demethylase (AC002329) in sense orientation driven by the p423Gal1 promoter. Sc.His3: HIS3 region from *Saccharomyces cerevisiae* encoding imidazoleglycerol-phosphate dehydratase for histidine synthesis; Ori-f1: bacteriophage f1 origin of replication; LAC: contains partial lacI coding sequence, promoter Plac, promoter Pt7, promoter Pt3, KS polylinker, and partial lacZ coding sequence; lacZ: partial coding sequence for beta-d-galactosidase or lacZ protein; T-Sc.Cyc1: a terminator from Cyc1-iso-1-cytochrome c from *Saccharomyces cerevisiae* to terminate transcription; obtus. C14α.demethylase (AC002329): cDNA encoding *Arabidopsis* putative obtusifoliol C14α-demethylase; P-Sc.Gal1: a promoter from Gal1-galactokinase of *Saccharomyces cerevisiae* to direct expression with galactose induction; LacZ-alpha: partial coding sequence for beta-d-galactosidase or lacZ protein; Ori-pUC: minimum sequence required for a functional origin of replication, sequence downstream of this region is known to affect copy number when expressed in bacteria; AMP: contains the P3 promoter and the beta-lactamase coding sequence, conferring resistance to ampicillin, penicillin, and carbenicillin; Sc.2 micron: 2 micron origin of replication.

Figure 30:
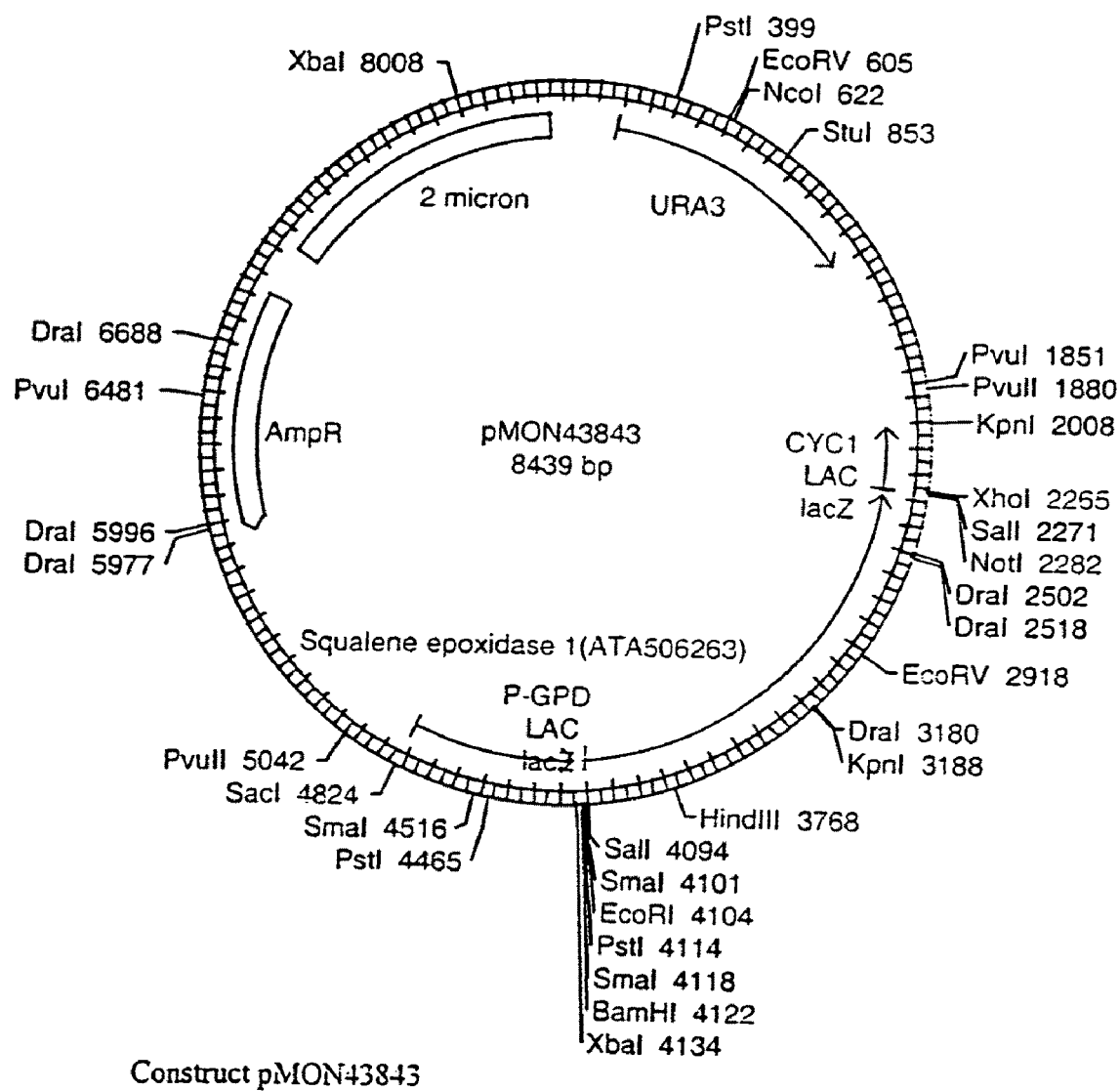

FIG. 30 is a map showing the structure of construct pMON43843. pMON43843 is a yeast expression vector carrying cDNA encoding *Arabidopsis* putative squalene epoxidase 1 (ATA506263) in sense orientation driven by the p423Gal1 promoter. Sc.His3: HIS3 region from *Saccharomyces cerevisiae* encoding imidazoleglycerol-phosphate dehydratase for histidine synthesis; Ori-f1: bacteriophage f1 origin of replication; LAC: contains partial lacI coding sequence, promoter Plac, promoter Pt7, promoter Pt3, KS polylinker, and partial lacZ coding sequence; lacZ: partial coding sequence for beta-d-galactosidase or lacZ protein; T-Sc.Cyc1: a terminator from Cyc1-iso-1-cytochrome c from *Saccharomyces cerevisiae* to terminates transcription; Squalene epoxidase 1 (ATA506263): cDNA encoding *Arabidopsis* putative squalene epoxidase 1 (ATA506263); P-Sc.Gal1: a promoter from Gal1-galactokinase of *Saccharomyces cerevisiae* to direct expression with galactose induction; LacZ-alpha: partial coding sequence for beta-d-galactosidase or lacZ protein; Ori-pUC: minimum sequence required for a functional origin of replication, sequence downstream of this region is known to affect copy number when expressed in bacteria; AMP: contains the P3 promoter and the beta-lactamase coding sequence, conferring resistance to ampicillin, penicillin, and carbenicillin; Sc.2 micron: 2 micron origin of replication.

Figure 31:
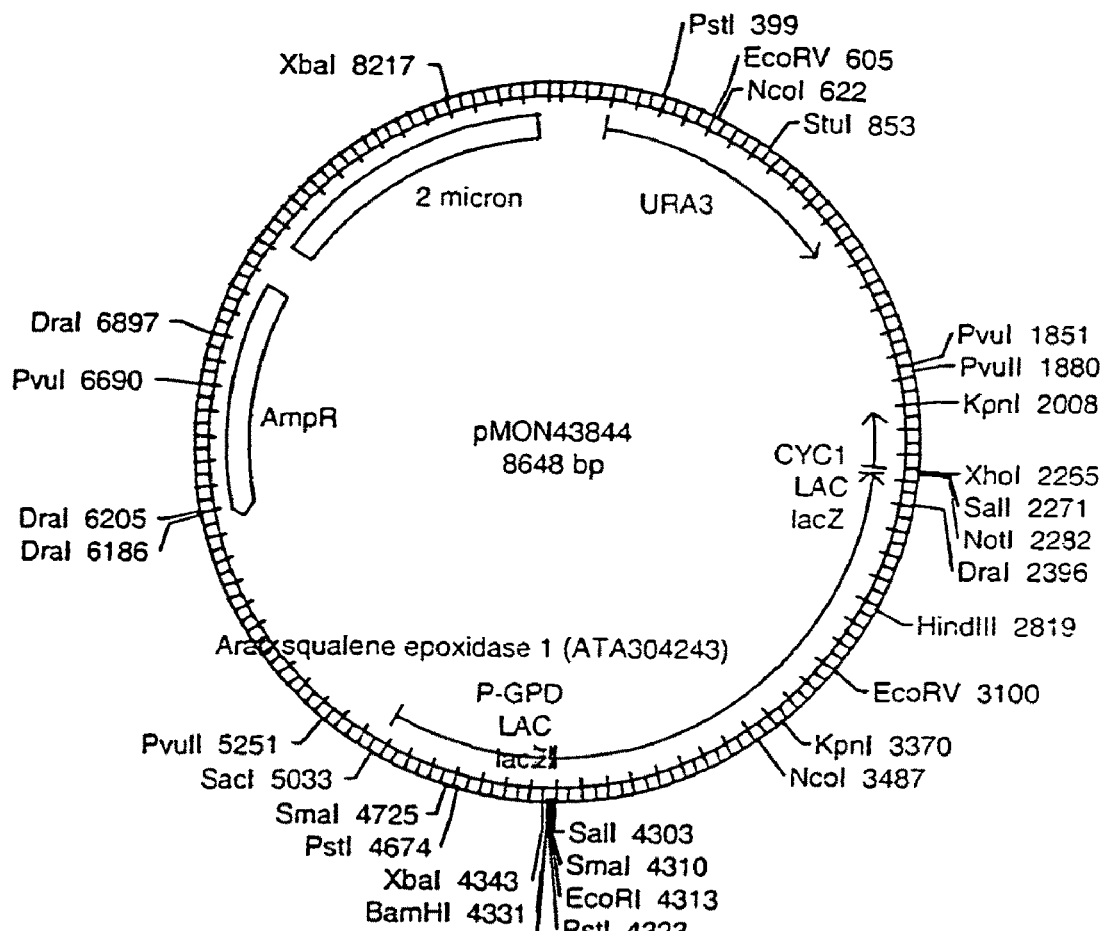

FIG. 31 is a map showing the structure of construct pMON43844. pMON43844 is a yeast expression vector carrying cDNA encoding *Arabidopsis* putative squalene epoxidase 1(ATA304243) in sense orientation driven by the p423Gal1 promoter. Sc.His3: HIS3 region from *Saccharomyces cerevisiae* encoding imidazoleglycerol-phosphate dehydratase for histidine synthesis; Ori-f1: bacteriophage f1 origin of replication; LAC: contains partial lacI coding sequence, promoter Plac, promoter Pt7, promoter Pt3, KS polylinker, and partial lacZ coding sequence; lacZ: partial coding sequence for beta-d-galactosidase or lacZ protein; T-Sc.Cyc1: a terminator from Cyc1-iso-1-cytochrome c from *Saccharomyces cerevisiae* to terminate transcription; Arab. squalene epoxidase 1 (ATA304243): cDNA encoding *Arabidopsis* putative squalene epoxidase 1 (ATA304243); P-Sc.Gal1: a promoter from Gal1-galactokinase of *Saccharomyces cerevisiae* to direct expression with galactose induction; LacZ-alpha: partial coding sequence for beta-d-galactosidase or lacZ protein; Ori-pUC: minimum sequence required for a functional origin of replication, sequence downstream of this region is known to affect copy number when expressed in bacteria; AMP: contains the P3 promoter and the beta-lactamase coding sequence, conferring resistance to ampicillin, penicillin, and carbenicillin; Sc.2 micron: 2 micron origin of replication.

FIG. 32 is a comparison of known HMG CoA reductase amino acid sequences. ClustalW alignment of forty-three non-redundant HMG-CoA reductase sequences to represent archaebacterial, eubacterial, fungal, plant and animal groups. The putative functional domains in the alignment marked as described below are based on the three dimensional structure of *Pseudomonas mevalonii* HMGR (Lawrence et al., 1995, Science 268:1758): boxed-HMGCoA binding domain, light shade-NAD(H) binding domain, underlined consensus-domains involved in catalysis, * underneath consensus and boldface-key histidine residue involved in catalysis. The putative phosphorylation site residues are marked with t and boldface, and are located at the C-terminal region of the protein, adjacent to a highly conserved arginine, marked with t and boldface. Also indicated are the conserved Glu (E), Lys (K), and Asp (D) residues, marked by E, K, and D, respectively. These residues are thought to be critical in catalysis, based on the crystal structure (Tabernero et al., 1999; PNAS 96(13):7167-71).

Appendices A through C show SEQ ID Nos: 1 through 3, respectively. Appendices D through G show SEQ ID Nos 20 thorough 23, respectively.

DETAILED DESCRIPTION

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

All publications, patents, patent applications, databases and other references cited in this application are herein incorporated by reference in their entirety as if each individual publication, patent, patent application, database or other reference were specifically and individually indicated to be incorporated by reference.

We have expressed the full-length forms of the rubber and *Arabidopsis* HMGRs driven by seed-specific promoters in transgenic canola and soybean. We have demonstrated sterol over-production up to 2-4 fold higher in seeds from these transgenic plants. We also demonstrated a higher accumulation of pathway intermediates in soybean than canola. These results were disclosed in PCT publication WO 00/61771. However, we have expressed a truncated form of the *Arabidopsis* hmg1 without the linker and membrane spanning domains in *Arabidopsis* and soybean. The results in *Arabidopsis* were similar to that demonstrated by Gonzalez et al. (1997) and we compared the sterol profiles of our transgenic plants with those produced by Gonzalez et al., using our methods to show they are comparable. We found the same types of pathway intermediates accumulating. However, in soybean seeds we have demonstrated the accumulation of squalene to a very high level (~3 mg/g seed which is around 100-fold higher than in nontransgenic controls). This is an unexpected result not disclosed or suggested in the prior art. Squalene is a precursor for sterols and in soybean it appears that there is a "bottleneck" in the further conversion of this precursor to sterols. Thus, it appears that there could be additional ways of over-producing sterols in soybean to levels greater than 10-fold which would include combining a truncated form of HMGR with other genes coding for enzymes down-stream of squalene.

This opens the potential to combine other genes such as squalene epoxidase for further enhancing the levels of desirable sterols. Such a combination has not been disclosed or suggested in the prior art. Squalene expoxidase catalyzes the addition of oxygen to squalene which is a 30-carbon linear isoprenoid chain thus allowing for cyclization to form cycloartenol. Additional enzymes downstream that can be also be manipulated are sterol methyltransferase 1, C-4 demethylase, C-14 demethylase, sterol methyltransferase 2, and C-5 desaturase that would all deplete other pathway intermediates shown to accumulate in soybeans. By using such strategies it is possible to convert all of the squalene and other intermediates to end sterols such as sitosterol, stigmasterol and campesterol. Thus, sterol level in soybean oils can be elevated from 0.3% up to 3.5%. Expression of the full-length rubber HMGR in soybeans results in a sterol level increase up to 2.7%.

Enhancement of 3-hydroxy-3-methylglutaryl-CoA reductase (HMG Co-A reductase) activity in certain cells results in increased sterol biosynthesis. See, e.g. Chappell, U.S. Pat. No. 5,589,619. The present discovery further contemplates an increase of steroid pathway end products such as Δ5 sterols and their stanol counterparts with a decreased accumulation of certain steroid pathway intermediates by also enhancing various specific steroid pathway enzyme activities, such that more of the steroid pathway intermediate compounds are converted to steroid pathway end products.

DNA sequences encoding squalene epoxidases are useful for removal of squalene accumulation, genes encoding sterol methyl transferase I enzymes are useful for removal of cycloartenol accumulation, genes encoding sterol C4-demethylase are useful for removal of 24-methylene cycloartenol accumulation, genes encoding obtusifoliol C14α-demethylases are useful for removal of accumulation of obtusifoliol, genes encoding sterol C5-desaturases are useful for removal of stigmasta-7-enol accumulation, and genes encoding sterol methyl transferase II enzymes are useful for the reduction of accumulated campesterol and concomitant increase of sitosterol.

Levels of sitostanol and sitostanol esters can be elevated further by approximately 2- to 40-fold over the transgenic plants of the art having only added genes for HMG CoA reductase by introducing additional genes encoding one or more of the following sterol pathway enzymes: a squalene epoxidase, a sterol methyl transferase I, a sterol C4-demethylase, an obtusifoliol C14α-demethylase, a sterol C5-desaturase, a sterol methyl transferase II.

As used herein, the term "structural coding sequence" means a DNA sequence which encodes for a peptide, polypeptide, or protein which may be made by a cell following transcription of the DNA to mRNA, followed by translation to the desired peptide, polypeptide, or protein.

The term "sterol" as applied to plants refers to any chiral tetracyclic isopentenoid which may be formed by cyclization of squalene oxide through the transition state possessing stereochemistry similar to the trans-syn-trans-anti-trans-anti configuration, i.e., protosteroid cation, and which retains a polar group at C-3 (hydroxyl or keto), an all-trans-anti stereochemistry in the ring system, and a side-chain 20R-configuration (Parker et al. (1992) In Nes et al., Eds., *Regulation of Isopentenoid Metabolism*, ACS Symposium Series No. 497, p. 110; American Chemical Society, Washington, D.C.). The numbering of the carbon atoms of a representative sterol (cholesterol) is shown in the following structure (FORMULA II):

As used herein, the term "sterol" refers to unsaturated hydroxyl group-containing derivatives of a fused, reduced ring system, cyclopenta[α]-phenanthrene, comprising three fused cyclohexane rings (A, B and C) in a phenanthrene arrangement, and a terminal cyclopentane ring (D). The exemplary steroid below (FORMULA II) illustrates the numbering system employed herein in describing the location of groups and substituents.

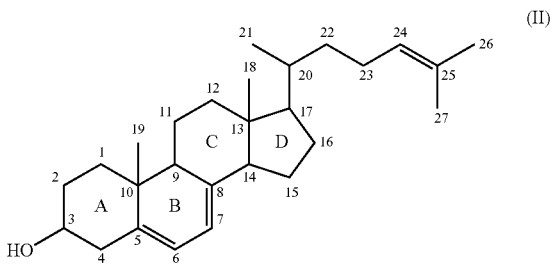
(II)

Sterols may or may not contain a C-5 to C-6 double bond, as this is a feature introduced late in the biosynthetic pathway (note Scheme 1, below). Sterols contain a $C_8$-$C_{10}$ side chain at the C-17 position, as shown above.

The term "phytosterol," which applies to sterols found uniquely in plants, refers to a sterol containing a C-5, and in some cases a C-22, double bond. Phytosterols are further characterized by alkylation of the C-17 side-chain with a methyl or ethyl substituent at the C-24 position. Major phytosterols include, but are not limited to, sitosterol, stigmasterol, campesterol, brassicasterol, etc. Cholesterol, which lacks a C-24 methyl or ethyl side chain, is found in plants but is not unique thereto, and is not a "phytosterol"

"Phytostanols" are saturated forms of phytosterols wherein the C-5 and, when present, C-22 double bond(s) is(are) reduced, and include, but are not limited to, sitostanol, campestanol, and 22-dihydrobrassicastanol.

"Phytosterol esters" and "phytostanol esters" are further characterized by the presence of a fatty acid or phenolic acid moiety rather than a hydroxyl group at the C-3 position.

The term "steroid compounds" includes sterols, phytosterols, phytosterol esters, phytostanols, and phytostanol esters.

The term "phytosterol compound" refers to at least one phytosterol, at least one phytosterol ester, or a mixture thereof.

The term "phytostanol compound" refers to at least one phytostanol, at least one phytostanol ester, or a mixture thereof.

The term "constitutive promoter" refers to a promoter that operates continuously in a cell, and which is not subject to quantitative regulation. The gene with which such a promoter is associated is always "turned on."

The terms "seed-specific," "fruit-specific," "plastid-specific," etc., as they apply to promoters refer to preferential or exclusive activity of these promoters in these organs or organelles, respectively. "Preferential expression" refers to promoter activity greater in the indicated organs or organelles than elsewhere in the plant. "Seed-specific" comprehends expression in the aleurone layer, endosperm, and/or embryo of the seed.

As used herein "isolated polynucleotide" means a polynucleotide that is free of one or both of the nucleotide sequences which flank the polynucleotide in the naturally-occurring genome of the organism from which the polynucleotide is derived. The term includes, for example, a polynucleotide or fragment thereof that is incorporated into a vector or expression cassette; into an autonomously replicating plasmid or virus; into the genomic DNA of a prokaryote or eukaryote; or that exists as a separate molecule independent of other polynucleotides. It also includes a recombinant polynucleotide that is part of a hybrid polynucleotide, for example, one encoding a polypeptide sequence.

As used herein "polynucleotide" and "oligonucleotide" are used interchangeably and refer to a polymeric (2 or more monomers) form of nucleotides of any length, either ribonucleotides or deoxyribonucleotides. Although nucleotides are usually joined by phosphodiester linkages, the term also includes polymeric nucleotides containing neutral amide backbone linkages composed of aminoethyl glycine units. This term refers only to the primary structure of the molecule. Thus, this term includes double- and single-stranded DNA and RNA. It also includes known types of modifications, for example, labels, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.), those containing pendant moieties, such as, for example, proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide. Polynucleotides include both sense and antisense strands.

The alternative nucleotide sequences described above are considered to possess substantially similar enzymatic activity to that of the polypeptide-encoding polynucleotide sequences of the present invention if they encode polypeptides having enzymatic activity differing from that of any of the polypeptides encoded by the polynucleotide sequences of the present invention by about 30% or less, preferably by about 20% or less, and more preferably by about 10% or less when assayed by standard enzymatic assays.

As used herein "effective amount" is intended to qualify the amount of an agent which will achieve the goal of a lessening in the severity and/or the frequency of incidence of a disease condition or disorder, over no treatment.

The phrase "steroid pathway products" refers to the products of steroid biosynthesis produced by the action of one or more of squalene epoxidase enzyme, sterol methyl transferase I enzyme, sterol C4-demethylase enzyme, obtusifoliol C14α-demethylase enzyme, sterol C5-desaturase enzyme, and sterol methyl transferase II enzyme. Specific examples of steroid pathway products include, but are not limited to, sitosterol, sitostanol, stigmasterol and stigmastanol.

In the context of the present disclosure, a "non-transformed" plant or cell refers to a plant or cells which does not comprise introduced polynucleotides encoding a polypeptide having 3-hydroxy-3-methylglutaryl-Coenzyme A reductase enzyme activity and at least one polypeptide having squalene epoxidase enzyme activity, sterol methyl transferase I enzyme activity, sterol C4-demethylase enzyme activity, obtusifoliol C14α-demethylase enzyme activity, sterol C5-desaturase enzyme activity, or sterol methyl transferase II enzyme activity. Thus, a plant or cell that contains introduced polynucleotide sequences other than those above, would still be considered "non-transformed."

As used herein, "peptide" and "protein" are used interchangeably and mean a compound that consists of two or more amino acids that are linked by means of peptide bonds.

I. Plant Steroid Biosynthesis

To aid the reader in understanding the present invention, descriptions of the sterol compound biosynthetic pathway are presented below. These descriptions identify enzymes useful in achieving the modifications to the biosynthesis and accumulation of sterol compounds described herein, and identify sources of nucleic acid sequences encoding these enzymes.

Various steps in the steroid compound biosynthetic pathway in plants are shown in Scheme 1, below. The numbers over the arrows refer to plant sterol compound biosynthetic pathway enzymes and genes as indicated in Table 1.

TABLE 1

Plant Sterol Compound Pathway Enzymes and Genes

| Enzyme | Step in Pathway | GenBank Gene ID |
|---|---|---|
| Acetoacetyl-CoA thiolase | 1 | X78116 |
| HMG-CoA synthase | 2 | X83882 |
| HMG-CoA reductase | 3 | X15032 |
| | | L19262 |
| Mevalonate kinase | 4 | X77793 |
| Phosphomevalonate kinase | 5 | Not available |
| Mevalonate pyrophosphate decarboxylase | 6 | Y14325 |
| Isopentenyl diphosphate isomerase | 7 | U49259 |
| | | U47324 |
| Farnesyl pyrophosphate synthase | 8 | X75789 |
| Squalene synthase | 9 | AF004560 |
| Squalene epoxidase | 10 | AB016883 |
| Squalene cyclase | 11 | U87266 |
| Sterol C-24 methyltransferase | 12, 18 | U71400 |
| Sterol C-4 demethylase | 13, 19 | Not available |
| Cycloeucalenol-obtusifoliol isomerase | 14 | Not available |
| Sterol C-14 demethylase | 15 | U74319 |
| Sterol C-14 reductase | 16 | PCT WO 97/48793 |
| Sterol C-8 isomerase | 17 | AF030357 |
| Sterol C-5 desaturase | 20 | X90454 |
| Sterol C-7 reductase | 21 | U49398 |
| Sterol C-24 isomerase | 22 | Klahre et al. (1998) Plant Cell 10: 1677-1690 |
| Sterol C-24 reductase | 23 | Same as 22 |
| Sterol C-22 desaturase | 24 | Not available |
| Sterol C-5 reductase | 25 | WO 00/61771 |

The plant sterol compound biosynthesis pathway has two distinct components. The early pathway reactions, leading from acetyl-CoA to squalene via mevalonic acid, are common to other isoprenoids. The later pathway reactions, leading from squalene to the major plant sterol compounds such as sitosterol, campesterol and stigmasterol, are committed biosynthetic reactions.

The early pathway reactions have been studied in fungi and plants (Lees et al., *Biochemistry and Function of Sterols*, Nes and Parish, Eds., CRC Press, 85-99 (1997); Newman and Chappell, *Biochemistry and Function of Sterols*, Nes and Parish, Eds., CRC Press, 123-134 (1997); Bach et al., *Biochemistry and Function of Sterols*, Nes and Parish, Eds., CRC Press, 135-150 (1997)).

Acetoacetyl CoA thiolase (EC 2.3.1.9) catalyzes the first reported reaction, which consists of the formation of acetoacetyl CoA from two molecules of acetyl CoA (Dixon et al., *J. Steroid Biochem. Mol. Biol.* 62: 165-171 (1997)). This enzyme has been purified from radish. A radish cDNA has been isolated by functional complementation in *Saccharomyces cerevisiae* (GeneBank Accession # X78116). A radish cDNA has also been screened against a cDNA library of *Arabidopsis thaliana* (Vollack and Bach, *Plant Physiology* 111: 1097-1107 (1996)).

HMGCoA synthase (EC 4.1.3.5) catalyzes the production of HMGCoA. This reaction condenses acetyl CoA with acetoacetyl CoA to yield HMGCoA. HMGCoA synthase has been purified from yeast. A plant HMGCoA synthase cDNA has also been isolated from *Arabidopsis thaliana* (Montamat et al., *Gene* 167: 197-201 (1995)).

HMGCoA reductase, also referred to as 3-hydroxy-3-methylglutaryl-coenzyme A (EC 1.1.1.34), catalyzes the reductive conversion of HMGCoA to mevalonic acid (MVA). This reaction is reported to play a role in controlling plant isoprenoid biosynthesis (Gray, *Adv. Bot. Res.* 14: 25-91 (1987); Bach et al., *Lipids* 26: 637-648 (1991); Stermer et al., *J. Lipid Res.* 35: 1133-1140 (1994). Plant HMGCoA reductase genes are often encoded by multigene families. The number of genes comprising each multigene family varies, depending on the species, ranging from two in *Arabidopsis thaliana* to at least seven in potato. Overexpression of plant HMGCoA reductase genes in transgenic tobacco plants has been reported to result in the overproduction of phytosterols (Schaller et al., *Plant Physiol.* 109: 761-770 (1995)).

Mevalonate kinase (EC 2.7.1.36) catalyzes the phosphorylation of mevalonate to produce mevalonate 5-phosphate. It has been reported that mevalonate kinase plays a role in the control of isoprenoid biosynthesis (Lalitha et al., *Indian. J. Biochem. Biophys.* 23: 249-253 (1986)). A mevalonate kinase gene from *Arabidopsis thaliana* has been cloned (GeneBank accession number X77793; Riou et al., *Gene* 148: 293-297 (1994)).

Phosphomevalonate kinase (EC 2.7.4.2) (MVAP kinase) is an enzyme associated with isoprene and ergosterol biosynthesis that converts mevalonate-5-phosphate to mevalonate-5-pyrophosphate utilizing ATP (Tsay et al., *Mol. Cell. Biol.* 11: 620-631 (1991)).

Mevalonate pyrophosphate decarboxylase ("MVAPP decarboxylase") (EC 4.1.1.33) catalyzes the conversion of mevalonate pyrophosphate to isopentenyl diphosphate ("IPP"). The reaction is reported to be a decarboxylation/dehydration reaction which hydrolyzes ATP and requires $Mg^{2+}$. A cDNA encoding *Arabidopsis thaliana* MVAPP decarboxylase has been isolated (Toth et al., *J. Biol. Chem.* 271: 7895-7898 (1996)). An isolated *Arabidopsis thaliana* MVAPP decarboxylase gene was reported to be able to complement the yeast MVAPP decarboxylase.

Isopentenyl diphosphate isomerase ("IPP:DMAPP") (EC 5.3.3.2) catalyzes the formation of dimethylallyl pyrophosphate (DMAPP) from isopentenyl pyrophosphate (IPP). Plant IPP:DMAPP isomerase gene sequences have been reported for this enzyme. It has also been reported that IPP:DMAPP isomerase is involved in rubber biosynthesis in a latex extract from *Hevea* (Tangpakdee et al., *Phytochemistry* 45: 261-267 (1997).

Farnesyl pyrophosphate synthase (EC 2.5.1.1) is a prenyltransferase which has been reported to play a role in providing polyisoprenoids for sterol compound biosynthesis as well as a number of other pathways (Li et al., *Gene* 17: 193-196 (1996)). Farnesyl pyrophosphate synthase combines DMAPP with IPP to yield geranyl pyrophosphate ("GPP"). The same enzyme condenses GPP with a second molecule of IPP to produce farnesyl pyrophosphate ("FPP"). FPP is a molecule that can proceed down the pathway to sterol compound synthesis, or that can be shuttled through other pathways leading to the synthesis of quinones or sesquiterpenes.

Squalene synthase (EC 2.5.1.21) reductively condenses two molecules of FPP in the presence of $Mg^{2+}$ and NADPH to form squalene. The reaction involves a head-to-head condensation, and forms a stable intermediate, presqualene diphosphate. The enzyme is subject to sterol demand regulation similar to that of HMGCoA reductase. The activity of squalene synthase has been reported to have a regulatory effect on the incorporation of FPP into sterol and other compounds for which it serves as a precursor (Devarenne et al., *Arch. Biochem. Biophys.* 349: 205-215 (1998)).

Squalene epoxidase (EC 1.14.99.7) (also called squalene monooxygenase) catalyzes the conversion of squalene to squalene epoxide (2,3-oxidosqualene), a precursor to the initial sterol molecule in the sterol compound biosynthetic pathway, cycloartenol. This is the first reported step in the pathway where oxygen is required for activity. The formation of squalene epoxide is also the last common reported step in sterol biosynthesis of animals, fungi, and plants.

The later pathway of sterol compound biosynthetic steps starts with the cyclization of squalene epoxide and ends with the formation of $\Delta5$-24-alkyl sterols in plants.

2,3-oxidosqualene cycloartenol cyclase (EC 5.4.99.8) (also called cycloartenol synthase) is the first step in the sterol compound pathway that is plant-specific. The cyclization of 2,3-oxidosqualene leads to lanosterol in animals and fungi, while in plants the product is cycloartenol. Cycloartenol contains a 9,19-cyclopropyl ring. The cyclization is reported to proceed from the epoxy end in a chair-boat-chair-boat sequence that is mediated by a transient C-20 carbocationic intermediate.

S-adenosyl-L-methionine:sterol C-24 methyl transferase ("SMT1") (EC 2.1.1.41) catalyzes the transfer of a methyl group from S-adenosyl-L-methionine to the C-24 center of the sterol side chain (Nes et al. (1991) *J. Biol. Chem.* 266(23): 15202-15212). This is the first of two methyl transfer reactions that have been reported to be an obligatory and rate-limiting step of the sterol compound-producing pathway in plants. The second methyl transfer reaction occurs later in the pathway after the $\Delta^{8-7}$ isomerase. The enzyme responsible for the second methyl transfer reaction is named SMTII (Bouvier-Nave, P. et al., (1997) *Eur. J. Biochem.*, 246: 518-529). An isoform, SMTII, catalyzes the conversion of cycloartenol to a $\Delta^{23(24)}$-24-alkyl sterol, cyclosadol (Guo et al. (1996) *Tetrahed. Lett.* 37(38):6823-6826).

Sterol C-4 demethylase catalyzes the first of several demethylation reactions, which results in the removal of the two methyl groups at C-4. While in animals and fungi the removal of the two C-4 methyl groups occurs consecutively, in plants it has been reported that there are other steps between the first and second C-4 demethylations. The C-4 demethylation is catalyzed by a complex of microsomal enzymes consisting of a monooxygenase, an NAD$^+$-dependent sterol 4-decarboxylase, and an NADPH-dependent 3-ketosteroid reductase.

Cycloeucalenol-obtusifoliol isomerase ("COI") catalyzes the opening of the cyclopropyl ring at C-9. The opening of the cyclopropyl ring at C-9 creates a double bond at C-8.

Sterol C-14 demethylase catalyzes demethylation at C-14, which removes the methyl group at C-14 and creates a double bond at that position. In both fungi and animals, this is the first step in the sterol synthesis pathway. Sterol 14-demethylation is mediated by a cytochrome P-450 complex.

Sterol C-14 reductase catalyzes a C-14 demethylation that results in the formation of a double bond at C-14 (Ellis et al., *Gen. Microbiol.* 137: 2627-2630 (1991)). This double bond is removed by a $\Delta^{14}$ reductase. The normal substrate is 4α-methyl-8,14,24 (24$^1$)-trien-3β-ol. NADPH is the normal reductant.

Sterol C-8 isomerase catalyzes a reaction that involves further modification of the tetracyclic rings or the side chain (Duratti et al., *Biochem. Pharmacol.* 34: 2765-2777 (1985)). The kinetics of the sterol isomerase-catalyzed reaction favor a $\Delta^8$ 6 $\Delta^7$ isomerase reaction that produces a $\Delta^7$ group.

Sterol C-5 desaturase catalyzes the insertion of the $\Delta^5$-double bond that normally occurs at the $\Delta^7$-sterol level, thereby forming a $\Delta^{5,7}$-sterol (Parks et al., *Lipids* 30: 227-230 (1995)). The reaction has been reported to involve the stereospecific removal of the 5α and 6α hydrogen atoms, biosynthetically derived from the 4 pro-R and 5 pro-S hydrogens of the (+) and (−) R-mevalonic acid, respectively. The reaction is obligatorily aerobic, and requires NADPH or NADH. The desaturase has been reported to be a multienzyme complex present in microsomes. It consists of the desaturase itself, cytochrome $b_5$, and a pyridine nucleotide-dependent flavoprotein. The $\Delta^5$-desaturase is reported to be a monooxygenase that utilizes electrons derived from a reduced pyridine nucleotide via cytochrome $b_5$.

Sterol C-7 reductase catalyzes the reduction of a $\Delta^7$-double bond in $\Delta^{5,7}$-sterols to generate the corresponding $\Delta^5$-sterol. It has been reported that the mechanism involves, like many other sterol enzymes, the formation of a carbocationic intermediate via electrophilic "attack" by a proton.

Sterol C-24(28) isomerase catalyzes the reduction of a $\Delta^{24(28)}$-$\Delta^{24}$, a conversion that modifies the side chain. The product is a $\Delta^{24(25)}$-24-alkyl sterol. Sterol C-24 reductase catalyzes the reduction of the $\square^{24(25)}$ double bond at C-24, which produces sitosterol. Recently, Klahre et al. ((1998) *Plant Cell* 10:1677-1690) discovered that both the isomerization and reduction steps are catalyzed by an enzyme coded by the same gene, i.e., DIM/DWF1.

Sterol C-22 desaturase (EC 2.7.3.9) catalyzes the formation of a double bond at C-22 on the side chain. This formation of a double bond at C-22 on the side chain marks the end of the sterol compound biosynthetic pathway, and results in the formation of stigmasterol (Benveniste (1986) *Annu. Rev. Plant Physiol.* 37:275-308). The C-22 desaturase in yeast, which is the reported final step in the biosynthesis of ergosterol in that organism, requires NADPH and molecular oxygen. In addition, the reaction is also reported to involve a cytochrome P450 that is distinct from a cytochrome P450 participating in demethylation reactions (Lees et al. (1995) *Lipids* 30: 221-226).

Phytosterols are biogenetic precursors of brassinosteroids, steroid alkaloids, steroid sapogenins, ecdysteroids, and steroid hormones. This precursor role of phytosterols is often described as a "metabolic" function. A common transformation of free sterols in tissues of vascular plants is the conjugation at the 3-hydroxy group of sterols with long-chain fatty acids to form steryl esters, or with a sugar, usually with a single molecule of β-D-glucose, to form steryl glycosides. Some of the steryl glycosides are additionally esterified, at the 6-hydroxy group of the sugar moiety, with long-chain fatty acids to form acylated steryl glycosides.

The existence of several enzymes that are specifically associated with the synthesis and breakdown of conjugated sterols has been reported (Wojciechowski, *Physiology and Biochemistry of Sterols*, eds. Patterson, Nes, AOCS Press, 361 (1991)). Enzymes involved in this process include: UDPGlc:Sterol glucosyltransferase, phospho(galacto)glyceride steryl glucoside acyltransferase, and sterylglycoside and sterylester hydrolases.

UDPGlc:sterol glucosyltransferase (EC 2.4.1.173) catalyzes glucosylation of phytosterols by glucose transfer from UDP-glucose ("UDPGl"). The formation of steryl glycosides can be measured using UDP-[$^{14}$C]glucose as the substrate. Despite certain differences in their specificity patterns, all reported UDPGlc:sterol glucosyltransferases preferentially glucosylate only sterols or sterol-like molecules that contain a C-3 hydroxy group, a β-configuration, and which exhibit a planar ring. It has been reported that UDPGlc:sterol glucosyltransferases are localized in the microsomes.

Phospho(galacto)glyceride steryl glucoside acyltransferase catalyzes the formation of acylated steryl glycosides from the substrate steryl glycoside by transfer of acyl groups from some membranous polar acyllipids to steryl glycoside molecules.

Acylglycerol:sterol acyltransferase (EC 2.3.1.26) catalyzes the reaction wherein certain acylglycerols act as acyl donors in a phytosterol esterification. In plants, the activity of acylglycerol:sterol acyltransferase is reported to be associated with membranous fractions. A pronounced specificity for shorter chain unsaturated fatty acids was reported for all acyltransferase preparations studied in plants. For example, acylglycerol:sterol acyltransferases from spinach leaves and mustard roots can esterify a number of phytosterols.

Sterylglycoside and sterylester hydrolases ("SG-hydrolases") catalyze the enzymatic hydrolysis of sterylglycosides to form free sterols. The SG-hydrolase activity is not found in mature, ungerminated seeds, is reported to emerge only after the third day of germination, and is found mainly in the cotyledons. It has been reported that phospho(galacto)glyceride:SG acyltranaferase may catalyze a reversible reaction. Enzymatic hydrolysis of sterylesters in germinating seeds of mustard, barley and corn is reported to be low in dormant seeds, but increases during the first ten days of germination. This activity is consistent with a decrease in sterylesters and an increase in free sterols over the same temporal period.

II. Processes for Modifying Steroid Compound Biosynthesis and Accumulation

In order to obtain seed producing oil containing elevated levels of phytostanols and phytostanol esters such as sitostanol and sitostanol esters, these recombinant constructs or expression cassettes can be introduced into plant cells by any number of conventional means known in the art and regenerated into fertile transgenic plants. The genome of such plants can then comprise introduced DNA encoding various steroid pathway enzymes, alone or in combination, that achieves the desirable effect of enhancing the levels of phytostanols, phytostanol esters, mixtures thereof in the oil of seed thereof.

Preferably, the genome can comprise introduced DNA encoding a HMG CoA reductase enzyme and an introduced DNA encoding one or more of a squalene epoxidase, a sterol methyl transferase I, a sterol C4-demethylase, an obtusifoliol C14α-demethylase, a sterol C5-desaturase, a sterol methyl transferase II. In each case, the foregoing introduced DNAs can be operatively linked to regulatory signals that cause seed-specific expression thereof.

The present invention encompasses not only such transgenic plants, but also transformed plant cells, including cells and seed of such plants, as well as progeny of such plants, for example produced from the seed. Transformed plant cells and cells of the transgenic plants encompassed herein can be grown in culture for a time and under appropriate conditions to produce oil containing elevated levels of phytosterols and/or phytostanols and their corresponding esters. Alternatively, the phytosterols, phytostanols, and their corresponding esters can be isolated directly from the cultures.

In addition, of course, seed obtained from the transgenic, progeny, hybrid, etc., plants disclosed herein can be used in methods for obtaining oil containing phytosterols, phytosterol esters, phytostanols, phytostanol esters, or mixtures thereof employing extraction and processing procedures known in the art. Note, in this regard, Kochhar (1983) *Prog. Lipid Res.* 22: 161-188.

The present invention also encompasses a method of producing a plant that accumulates an elevated level of sitosterol, at least one sitosterol ester, sitostanol, at least one sitostanol ester, or mixtures thereof, in seeds thereof compared to seeds of a corresponding plant comprising no introduced DNA encoding a polypeptide or protein that affects the biosynthesis of sterols, phytosterols, phytosterol esters, phytostanols, phytostanol esters, or combinations thereof, comprising sexually crossing a transgenic plant of the present invention with such a corresponding plant. The latter can be a non-transgenic plant, or a transgenic plant containing introduced DNA encoding a trait other than one affecting sterol, phytosterol, etc., biosynthesis. For example, such trait may be insect or herbicide resistance. Plants produced by this method also form part of the present invention.

Also included are plants that accumulate an elevated level of sitosterol, at least one sitosterol ester, sitostanol, at least one sitostanol ester, or mixtures thereof, in seeds thereof compared to seeds of a corresponding plant comprising no introduced DNA encoding a polypeptide or protein that affects the biosynthesis of sterols, phytosterols, phytosterol esters, phytostanols, phytostanol esters, or combinations thereof, which are apomictic.

A process of increasing the formation of steroid pathway products in a transformed host cell as compared to an otherwise identical non-transformed host cell comprising the following steps. A host cell is transformed with a recombinant vector comprising (a) as operably linked components in the 5' to 3' direction, a promoter, a DNA sequence encoding a polypeptide exhibiting 3-hydroxy-3-methylglutaryl-Coenzyme A reductase enzyme activity, and a transcription termination signal sequence; and (b) as operably linked components in the 5' to 3' direction, a promoter, a DNA sequence encoding a steroid pathway enzyme, and a transcription termination signal sequence. The steroid pathway enzyme is a squalene epoxidase enzyme, a sterol methyl transferase I enzyme, a sterol C4-demethylase enzyme, a obtusifoliol C14α-demethylase enzyme, a sterol C5-desaturase enzyme, and a sterol methyl transferase II enzyme. The transformed plant cell is regenerated into a transgenic plant.

A plant contemplated by this invention is a vascular, multicellular higher plant. Such higher plants will hereinafter by usually referred to simply as "plants". Such "plants" include both complete entities having leaves, stems, seeds, roots and the like as well as callus and cell cultures that are monocotyledonous and dicotyledonous. Dicotyledonous plants are a preferred embodiment of the present invention.

Preferred plants are members of the Solanaceae, Leguminosae, Ammiaceae, Brassicaceae, Gramineae, Carduaceae and Malvaceae families. Exemplary plant members of those families are tobacco, petunia and tomato (Solanaceae), soybean and alfalfa (Leguminosae), carrot (Ammiaceae), corn, maize and barley (Gramineae), *Arabidopsis* (Brassicaceae), guayule (Carduaceae), and cotton (Malvaceae). A preferred plant is tobacco of the strain *Nicotiana tabacum* (*N. Tabacum*), cotton of the strain Coker line 312-5A, soybean of the strain *Glycine max*, alfalfa of the strain RYSI or tomato of the strain *Lycopersicon esculentium*. Other plants include canola, maize and rape.

A transgenic plant contemplated by this invention is produced by transforming a plant cell or protoplast with an added, exogenous structural gene that encodes a polypeptide having HMG-CoA reductase activity and an exogenous structural gene that encodes at least one polypeptide have steroid pathway enzyme activity to produce a transformed plant cell, and regenerating a transgenic plant form the transformed plant cell. The encoded polypeptide is expressed both in the transformed plant cell or protoplast and the resulting transgenic plant. (The phrase "plant cell" will hereinafter be used to include a plant protoplast, except where plant protoplasts are specifically discussed).

A non-transgenic plant that serves as the source of the plant cell that is transformed, i.e. the precursor cell, is referred to herein as a "native, non-transgenic" plant. The native, non-transgenic plant is of the same strain as the formed transgenic plant.

Sterol production in a transgenic plant of the present invention is increased by increasing the activity of the enzyme HMG-CoA reductase, which enzyme catalyzes the conversion of 3-hydroxy-3-methylglutaryl Coenzyme A (HMG-CoA) to mevalonate and the activity of at least one other steroid pathway enzyme. As used herein, the term "specific activity" means the activity normalized to cellular protein content.

HMG-CoA reductase activity is increased by increasing the amount (copy number) of a gene encoding a polypeptide having HMG-CoA reductase catalytic activity. Expression of the increased amount of that encoded structural gene enhances the activity of that enzyme.

The amount of the expressed gene is increased by transforming a plant cell with a recombinant DNA molecule comprising a vector operatively linked to a DNA segment that encodes a polypeptide having HMG-CoA reductase activity, and a promoter suitable for driving the expression of that polypeptide in that plant cell, and culturing the transformed plant cell into a transgenic plant. Such a polypeptide includes intact as well as a catalytically active, truncated HMG-CoA reductase proteins.

Thus, a transformed plant cell and a transgenic plant have one or more added, exogenous genes that encode a polypeptide having HMG-CoA reductase activity and at least one other steroid pathway enzyme activity relative to a native, non-transgenic plant or untransformed plant cell of the same type. As such, a transformed plant cell or transgenic plant can be distinguished from an untransformed plant cell or native, nontransgenic plant by standard technology such as agarose separation of DNA fragments or mRNAs followed by transfer and appropriate blotting with DNA or RNA, e.g., Southern or Northern blotting, or by use of polymerase chain reaction technology, as are well known. Relative HMG-CoA reductase activity of the transformed cell or transgenic plant with untransformed cells and native, non-transgenic plants or cell cultures therefrom can also be compared, with a relative activity for that enzyme of about 1.5:1 for transgenic (transformed) to native (untransformed) showing transformation. Higher relative activity ratios such as about 15:1 have also been observed.

Sterol accumulation can also be used to distinguish between native, non-transgenic and transgenic plants. A transgenic plant has at least about twice the total sterol content as a native, non-transgenic plant where a single added gene is present. Greater differences up to about forty-fold have also been observed.

Sitostanol, sitostanol ester, and tocopherol biosynthesis and accumulation in plants can be modified in accordance with the present invention by variously expressing the nucleic acid coding sequences discussed above, alone or in combination, as described herein. The expression of sequences encoding sterol methyltransferase II enzymes facilitates the production of plants in which the biosynthesis and accumulation of campesterol, campestanol, and their esters can be reduced as these enzymes shunt sterol intermediates away from campesterol, and toward sitosterol and sitostanol.

III. DNA Encoding Useful Polypeptides

The present invention contemplates a recombinant construct or a recombinant vector that contains a DNA sequence encoding a polypeptide exhibiting 3-hydroxy-3-methylglutaryl-Coenzyme A (HMG-CoA) reductase activity and a DNA sequence encoding a polypeptide exhibiting the activity of a steroid pathway enzyme. Each polypeptide-encoding DNA sequence is operably linked in the 5' to 3' direction independent of the other sequence. Each DNA sequence in the 5' to 3' direction comprises a promoter, then the DNA sequence encoding the polypeptide then a transcription termination signal sequence. The steroid pathway enzyme is a squalene epoxidase enzyme, a sterol methyl transferase I enzyme, a sterol C4-demethylase enzyme, a obtusifoliol C14α-demethylase enzyme, a sterol C5-desaturase enzyme, or a sterol methyl transferase II enzyme. It is contemplated that HMG-CoA reductase and steroid pathway enzyme activities come from a mutant or truncated form of those enzymes, such as a truncated HMG-CoA reductase lacking the transmembrane region while retaining a functional catalytic domain. Several HMG CoA reductase sequences are known in the art. An amino acid alignment for these is shown in FIG. 32. The sources of the sequences used in building the multiple alignment are listed in Table 5.

TABLE 5

Sources of Sequences Used In Building The Multiple Alignment

| | | | | |
|---|---|---|---|---|
| methanobac | swissprot: hmdh_metth | Begin: 1 | End: 397 | O26662 *methanobacterium thermoautotrophicum*. 3-hydroxy-3-methylglutaryl-coenzyme a reductase (ec 1.1.1.34) (hmg-coa reductase). December 1998 |
| methanococ | swissprot: hmdh_metja | Begin: 1 | End: 405 | Q58116 *methanococcus jannaschii*. 3-hydroxy-3-methylglutaryl-coenzyme a reductase (ec 1.1.1.34) (hmg-coa reductase). July 1998 |
| halobacter | swissprot: hmdh_halvo | Begin: 1 | End: 403 | Q59468 *halobacterium volcanii (haloferax volcanii)*. 3-hydroxy-3-methylglutaryl-coenzyme a reductase (ec 1.1.1.34) (hmg-coa reductase). July 1998 |
| *sulfolobus* | swissprot: hmdh_sulso | Begin: 1 | End: 409 | O08424 *sulfolobus solfataricus*. 3-hydroxy-3-methylglutaryl-coenzyme a reductase (ec 1.1.1.34) (hmg-coa reductase). December 1998 |
| yeast2 | gp_pln1: yschmgcr2_1 | Begin: 1 | End: 1045 | M22255 *Saccharomyces cerevisiae* Yeast HMG-CoA reductase (HGM2) gene, complete cds; 3-hydroxy-3-methyl glutaryl coenzyme A reductase. April 1993 |
| yeast1 | gp_pln1: yschmgcr1_1 | Begin: 1 | End: 1054 | M22002 *Saccharomyces cerevisiae* Yeast HMG-CoA reductase (HGM1) gene, complete cds; 3-hydroxy-3-methyl-glutaryl coenzyme A reductase. April 1993 |
| *phycomyces* | swissprot: hmdh_phybl | Begin: 1 | End: 105 | Q12649 *phycomyces blakesleeanus*. 3-hydroxy-3-methylglutaryl-coenzyme a reductase (ec 1.1.1.34) (hmg-coa reductase) (fragment). November 1997 |

TABLE 5-continued

Sources of Sequences Used In Building The Multiple Alignment

| | | | | |
|---|---|---|---|---|
| *fusarium* | swissprot: hmdh_fusmo | Begin: 1 | End: 976 | Q12577 *fusarium moniliforme* (*gibberella fujikuroi*). 3-hydroxy-3-methylglutaryl-coenzyme a reductase (ec 1.1.1.34) (hmg-coa reductase). November 1997 |
| *candida* | gp_pln1: ab012603_1 | Begin: 1 | End: 934 | AB012603 *Candida utilis Candida utilis* HMG mRNA for HMG-CoA reductase, complete cds. July 1998 |
| dictyoste2 | swissprot: hmd2_dicdi | Begin: 1 | End: 481 | P34136 *dictyostelium discoideum* (slime mold). 3-hydroxy-3-methylglutaryl-coenzyme a reductase 2 (ec 1.1.1.34) (hmg-coa reductase 2) (fragment). 35735 |
| wheat1 | pir2: pq0761 | Begin: 1 | End: 150 | hydroxymethylglutaryl-CoA reductase (NADPH) (EC 1.1.1.34) (HMGR 10) - wheat (fragment) |
| rice | swissprot: hmdh_orysa | Begin: 1 | End: 509 | P48019 *oryza sativa* (rice). 3-hydroxy-3-methylglutaryl-coenzyme a reductase (ec 1.1.1.34) (hmg-coa reductase) (fragment). February 1996 |
| corn | sp_plant: o24594 | Begin: 1 | End: 579 | O24594 *zea mays* (maize). 3-hydroxy 3-methylglutaryl coenzyme a reductase (ec 1.1.1.88). May 1999 |
| wheat3 | pir2: pq0763 | Begin: 1 | End: 150 | hydroxymethylglutaryl-CoA reductase (NADPH) (EC 1.1.1.34) (HMGR 23) - wheat (fragment) |
| wheat2 | pir2: pq0762 | Begin: 1 | End: 150 | hydroxymethylglutaryl-CoA reductase (NADPH) (EC 1.1.1.34) (HMGR 18) - wheat (fragment) |
| soybean | gmtx6: 30820_1r59f1 | Begin: 101 | End: 259 | from proprietary soy sequence database |
| rubbertre3 | swissprot: hmd3_hevbr | Begin: 1 | End: 586 | Q00583 *hevea brasiliensis* (para rubber tree). 3-hydroxy-3-methylglutaryl-coenzyme a reductase 3 (ec 1.1.1.34) (hmg-coa reductase 3). July 1998 |
| rosyperiwi | swissprot: hmdh_catro | Begin: 1 | End: 601 | Q03163 *catharanthus roseus* (rosy periwinkle) (madagascar periwinkle). 3-hydroxy-3-methylglutaryl-coenzyme a reductase (ec 1.1.1.34) (hmg-coa reductase). July 1998 |
| tomato | swissprot: hmd2_lyces | Begin: 1 | End: 602 | P48022 *lycopersicon esculentum* (tomato). 3-hydroxy-3-methylglutaryl-coenzyme a reductase 2 (ec 1.1.1.34) (hmg-coa reductase 2). July 1998 |
| woodtobacc | swissprot: hmdh_nicsy | Begin: 1 | End: 604 | Q01559 *nicotiana sylvestris* (wood tobacco). 3-hydroxy-3-methylglutaryl-coenzyme a reductase (ec 1.1.1.34) (hmg-coa reductase). July 1998 |
| potato | gp_pln1: pothmgri_1 | Begin: 1 | End: 596 | L01400 *Solanum tuberosum* Potato hydroxymethylglutaryl coenzyme A reductase (hmgr) mRNA, complete cds; putative. April 1996 |
| radish | sp_plant: q43826 | Begin: 1 | End: 573 | Q43826 *raphanus sativus* (radish). hydroxymethylglutaryl-coa reductase (ec 1.1.1.34) (hydroxymethylglutaryl-coa reductase (nadph)) (3-hydroxy-3-methylglutaryl-coenzyme a red |
| arabadopsis1 | gp_pln1: athhmgcoar_1 | Begin: 1 | End: 592 | L19261 *Arabidopsis thaliana Arabidopsis thaliana* HMG-cOA reductase gene, complete cds. April 1994 |
| cucumismel | gp_pln1: ab021862_1 | Begin: 1 | End: 587 | AB021862 *Cucumis melo Cucumis melo* mRNA for HMG-CoA reductase, complete cds; putative. January 1999 |
| rubbertre2 | swissprot: hmd2_hevbr | Begin: 1 | End: 210 | P29058 *hevea brasiliensis* (para rubber tree). 3-hydroxy-3-methylglutaryl-coenzyme a reductase 2 (ec 1.1.1.34) (hmg-coa reductase 2) (fragment). 35735 |
| rubbertre1 | swissprot: hmd1_hevbr | Begin: 1 | End: 575 | P29057 *hevea brasiliensis* (para rubber tree). 3-hydroxy-3-methylglutaryl-coenzyme a reductase 1 (ec 1.1.1.34) (hmg-coa reductase 1). July 1998 |
| camptothec | swissprot: hmdh_camac | Begin: 1 | End: 593 | P48021 *camptotheca acuminata*. 3-hydroxy-3-methylglutaryl-coenzyme a reductase (ec 1.1.1.34) (hmg-coa reductase). November 1997 |
| arabadops2 | swissprot: hmd2_arath | Begin: 1 | End: 562 | P43256 *arabidopsis thaliana* (mouse-ear cress). 3-hydroxy-3-methylglutaryl-coenzyme a reductase 2 (ec 1.1.1.34) (hmg-coa reductase 2) (hmgr2). July 1998 |
| chineseham | swissprot: hmdh_crigr | Begin: 1 | End: 887 | P00347 *cricetulus griseus* (chinese hamster). 3-hydroxy-3-methylglutaryl-coenzyme a reductase (ec 1.1.1.34) (hmg-coa reductase). November 1997 |
| chineseha2 | gp_rod: cruhmg14_1 | Begin: 1 | End: 887 | L00183 *Cricetulus* sp. Hamster 3-hydroxy-3-methylglutaryl coenzyme A (HMG CoA) reductase gene, exons 19 and 20; 3-hydroxy-3-methylglutaryl coenzyme A (HMG CoA). April 1993 |
| syrianhamst | gp_rod: hamhmgcob_1 | Begin: 1 | End: 887 | M12705 *Mesocricetus auratus* Syrian hamster 3-hydroxy-3-methylglutaral coenzyme A reductase (HMG-CoA reductase) mRNA, complete cds; 3-hydroxy-3-methylglutaral coenzyme A red |
| rat | swissprot: hmdh_rat | Begin: 1 | End: 887 | P51639 *rattus norvegicus* (rat). 3-hydroxy-3-methylglutaryl-coenzyme a reductase (ec 1.1.1.34) (hmg-coa reductase). December 1998 |

TABLE 5-continued

Sources of Sequences Used In Building The Multiple Alignment

| | | | | |
|---|---|---|---|---|
| rabbit | swissprot: hmdh_rabit | Begin: 1 | End: 888 | Q29512 *oryctolagus cuniculus* (rabbit). 3-hydroxy-3-methylglutaryl-coenzyme a reductase (ec 1.1.1.34) (hmg-coa reductase). July 1999 |
| human | gp_pri2: humhmgcoa_1 | Begin: 1 | End: 888 | M11058 *Homo sapiens* Human 3-hydroxy-3-methylglutaryl coenzyme A reductase mRNA, complete cds; 3-hydroxy-3-methylglutaryl coenzyme A reductase. November 1994 |
| mouse | gp_rod: mushmgcoa_1 | Begin: 1 | End: 224 | M62766 *Mus musculus* Mouse HMG-CoA reductase mRNA, 3' end. April 1993 |
| xenopus | swissprot: hmdh_xenla | Begin: 1 | End: 883 | P20715 *xenopus laevis* (african clawed frog). 3-hydroxy-3-methylglutaryl-coenzyme a reductase (ec 1.1.1.34) (hmg-coa reductase). November 1997 |
| seaurchin | swissprot: hmdh_strpu | Begin: 1 | End: 932 | P16393 *strongylocentrotus purpuratus* (purple seaurchin). 3-hydroxy-3-methylglutaryl-coenzyme a reductase (ec 1.1.1.34) (hmg-coa reductase). November 1997 |
| cockroach | swissprot: hmdh_blage | Begin: 1 | End: 856 | P54960 *blattella germanica* (german cockroach). 3-hydroxy-3-methylglutaryl-coenzyme a reductase (ec 1.1.1.34) (hmg-coa reductase). November 1997 |
| drosophila | swissprot: hmdh_drome | Begin: 1 | End: 916 | P14773 *drosophila melanogaster* (fruit fly). 3-hydroxy-3-methylglutaryl-coenzyme a reductase (ec 1.1.1.34) (hmg-coa reductase). December 1998 |
| dictyoste1 | swissprot: hmd1_dicdi | Begin: 1 | End: 552 | P34135 *dictyostelium discoideum* (slime mold). 3-hydroxy-3-methylglutaryl-coenzyme a reductase 1 (ec 1.1.1.34) (hmg-coa reductase 1). November 1997 |
| schistosom | swissprot: hmdh_schma | Begin: 1 | End: 948 | P16237 *schistosoma mansoni* (blood fluke). 3-hydroxy-3-methylglutaryl-coenzyme a reductase (ec 1.1.1.34) (hmg-coa reductase). July 1998 |
| archaeoglo | swissprot: hmdh_arcfu | Begin: 1 | End: 436 | O28538 *archaeoglobus fulgidus*. 3-hydroxy-3-methylglutaryl-coenzyme a reductase (ec 1.1.1.34) (hmg-coa reductase). December 1998 |
| pseudomonas | gp_bct1: psehmgcoa_1 | Begin: 1 | End: 428 | M24015 *Pseudomonas mevalonii P. mevalonii* HMG-CoA reductase (mvaA) gene, complete cds; HMG-CoA reductase (EC 1.1.1.88). April 1993 |

These sequences, and their truncated counterparts, are useful in the present invention. Examples of such preferred HMG CoA reductases include the truncated rubber and *Arabidopsis* HMG CoA reductases disclosed herein.

Other enzyme-encoding DNAs can be introduced into plants to elevate even further the levels of desirable Δ5 sterols and their reduced stanol counterparts as well as other phytosterols and tocopherols. Thus, the DNA sequences contemplated for use in the present invention, which can be used alone or in various combinations as discussed below, include, but are not limited to, those encoding the following enzymes: 3-hydroxysteroid oxidases; steroid 5-reductases; sterol methyltransferases; sterol acyltransferases; and S-adenosylmethionine-dependent α-tocopherol methyltransferases.

In each case, the sequences encoding these enzymes can comprise an expression cassette comprising, operably linked in the 5' to 3'direction, a seed-specific promoter, the enzyme coding sequence, and a transcriptional termination signal sequence functional in a plant cell such that the enzyme is successfully expressed. For use in the methods disclosed herein, the recombinant constructs or expression cassettes can be incorporated in a vector, for example a plant expression vector. Such vectors can be transformed into host cells such as bacterial cells, for example during the preparation or modification of the recombinant constructs, and plant cells. Thus, the invention encompasses plants and seeds comprising such transformed plant cells.

It will be apparent to those of skill in the art that the nucleic acid sequences set forth herein, either explicitly, as in the case of the sequences set forth above, or implicitly with respect to nucleic acid sequences generally known and not present herein, can be modified due to the built-in redundancy of the genetic code and noncritical areas of the polypeptide that are subject to modification and alteration. In this regard, the present invention contemplates allelic variants of structural genes encoding a polypeptide having HMG-CoA reductase activity.

The previously described DNA segments are noted as having a minimal length, as well as total overall length. That minimal length defines the length of a DNA segment having a sequence that encodes a particular polypeptide having HMG-CoA reductase activity. As is well known in the art, as long as the required DNA sequence is present (including start and stop signals), additional base pairs can be present at either end of the segment and that segment can still be utilized to express the protein. This, of course, presumes the absence in the segment of an operatively linked DNA sequence that represses expression, expresses a further product that consumes the enzyme desired to be expressed, expresses a product other than the desired enzyme or otherwise interferes with the structural gene of the DNA segment.

Thus, as long as the DNA segment is free of such interfering DNA sequences, a DNA segment of the invention can be up to 15,000 base pairs in length. The maximum size of a recombinant DNA molecule, particularly a plant integrating vector, is governed mostly by convenience and the vector size that can be accommodated by a host cell, once all of the minimal DNA sequences required for replication and expression, when desired, are present. Minimal vector sizes are well known.

Also encompassed by the present invention are nucleotide sequences biologically functionally equivalent to those disclosed herein, that encode conservative amino acid changes within the amino acid sequences of the presently disclosed enzymes, producing "silent" changes therein. Such nucleotide sequences contain corresponding base substitutions based upon the genetic code compared to the nucleotide sequences encoding the presently disclosed enzymes. Substitutes for an amino acid within the enzyme sequences disclosed herein is selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral nonpolar (hydrophobic) amino acids such as alanine, leucine, isoleucine, valine, proline, phenylalanine, tryptophan, and methionine.

A. HMG-CoA Reductase

The introduction of an HMG CoA reductase gene into a cell results in a higher carbon throughput through the steroid synthesis pathway. The introduction of a truncated HMG CoA reductase gene (lacking the transmembrane region, resulting in a soluble HMG CoA reductase enzyme) provides higher HMG CoA reductase activity and thus increased delta-5 steroid compound production over the same case with an introduced full-length HMG CoA reductase gene. A useful truncated HMG CoA reductase nucleic acid encodes at least the catalytic domain.

Hydroxymethylglutaryl-CoA reductase is enzyme number 1.1.1.88, using the recommended nomenclature of the International Union of Biochemistry and Molecular Biology on the Nomenclature and Classification of Enzymes, *Enzyme Nomenclature* 1992, Edwin C. Webb, ed., Academic Press, Inc. (San Diego, Calif.: 1992), page 35.

The present invention contemplates transforming a plant cell with a structural gene that encodes a polypeptide having HMG-CoA reductase activity. The HMG-CoA reductase enzymes of both animal and yeast cells comprise three distinct amino acid residue sequence regions, which regions are designated the catalytic region, the membrane-binding region and the linker region.

The catalytic region contains the active site of the HMG-CoA reductase enzyme and comprises about forty percent of the COOH-terminal portion of intact HMG-CoA reductase enzyme.

The membrane-binding region contains hydrophobic amino acid residues and comprises about fifty percent of the $NH_2$-terminal portion of intact HMG-CoA reductase enzyme.

The linker region connects the catalytic and membrane-binding regions, and constitutes the remaining about ten percent of the intact enzyme.

As discussed in greater detail below, only the catalytic region of HMG-CoA reductase is needed herein to provide the desired enzyme activity. Thus, an exogenous structural gene that encodes a polypeptide corresponding to that catalytic region is the minimal HMG Co A reductase gene required for transforming plant cells in addition to one of the steroid pathway enzymes discussed below. The present invention therefore contemplates use of both intact and truncated structural genes that encode a polypeptide having HMG-CoA reductase activity.

A structural gene encoding a polypeptide having HMG-CoA reductase activity can be obtained or constructed from a variety of sources and by a variety of methodologies. See, e.g. Carlson et al., *Cell*, 28:145 (1982); Rine et al., *Proc. Natl. Acad. Sci. USA*, 80:6750 (1983). Exemplary of such structural genes are the mammalian and yeast genes encoding HMG-CoA reductase or the catalytic region thereof.

Figure 1:
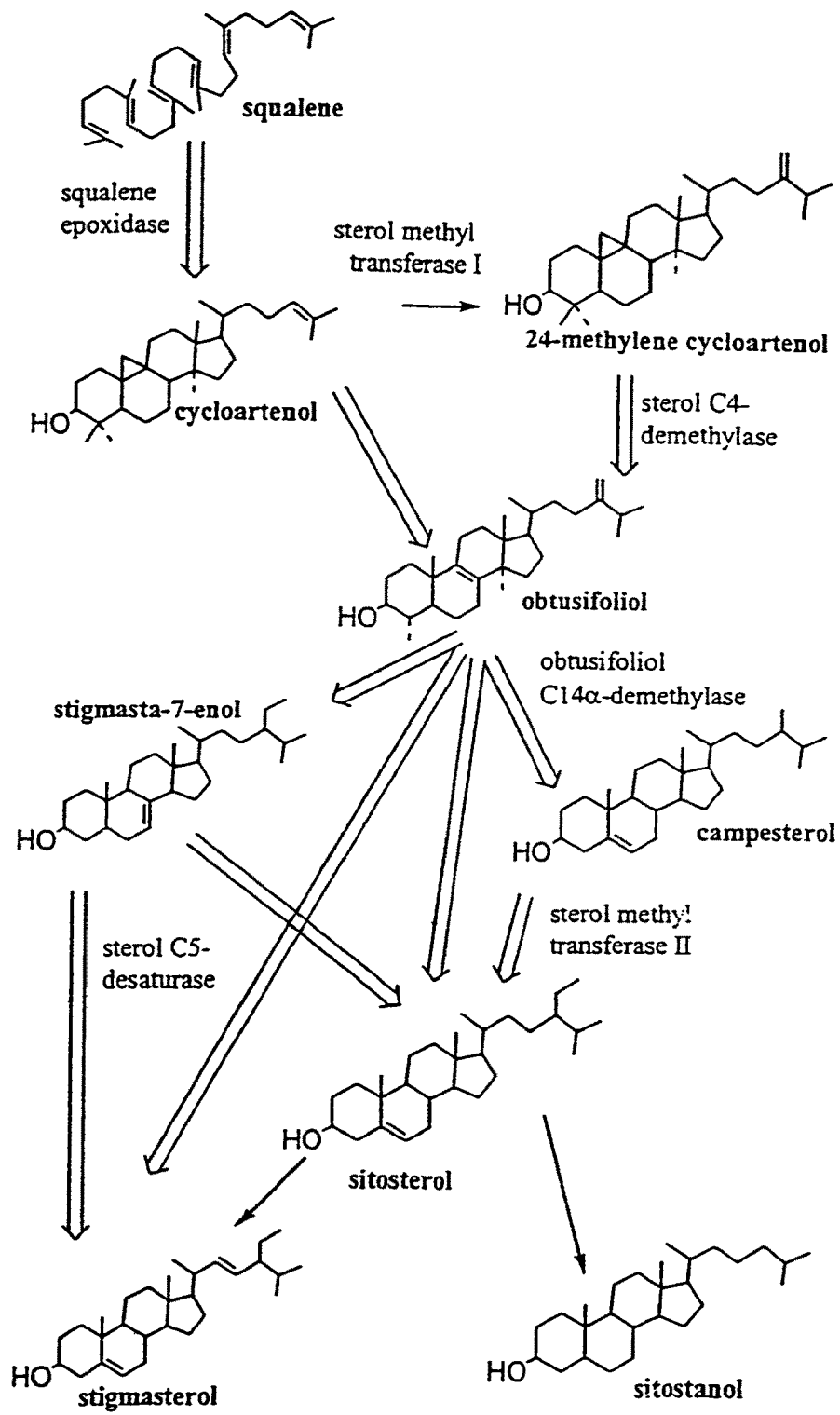
FIG. 1 is an abbreviated version of a plant steroid compound biosynthetic pathway that shows the enzymes affecting steroid compound biosynthesis and accumulation. These include: HMG-CoA reductase, squalene epoxidase, sterol methyl transferase I, sterol C4-demethylase, obtusifoliol C14α-demethylase, sterol C5 desaturase and sterol methyl transferase II.
Figure 2:
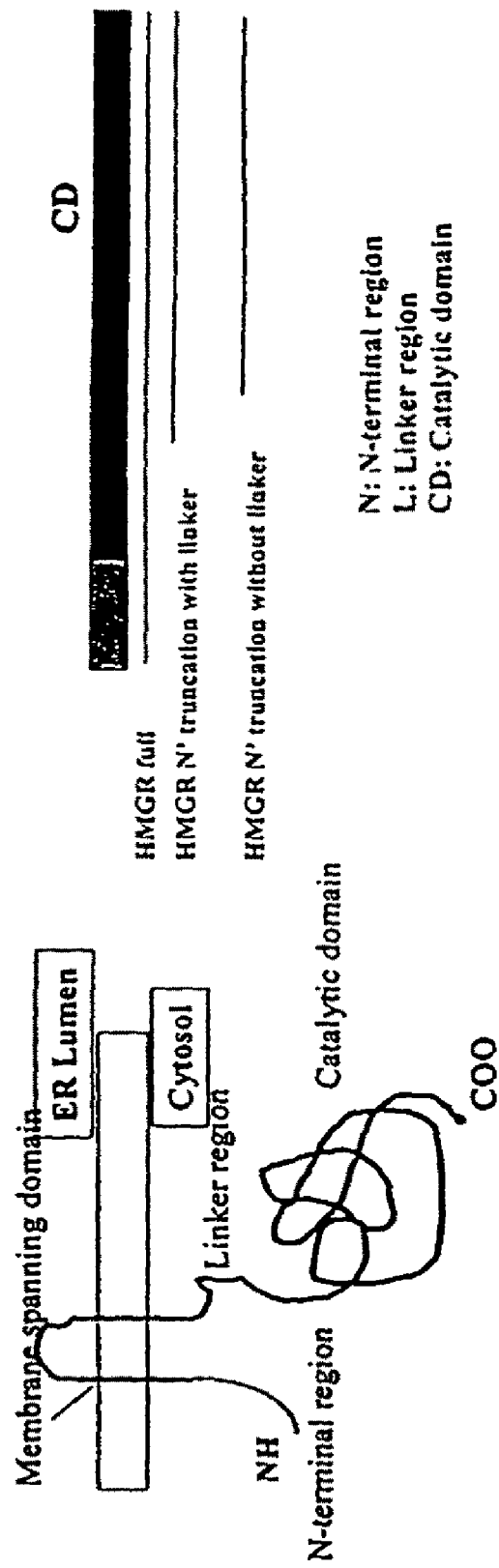
FIG. 2 depicts the forms of *Arabidopsis* and rubber HMGR1 tested in *Arabidopsis* and yeast to compare expression, activity and sterol production.

The disclosures of Chappell, et al., U.S. Pat. No. 5,349,126, are incorporated in full herein by reference. The mammalian genome contains a single gene encoding HMG-CoA reductase. The nucleotide sequence of the hamster and human gene for HMG-CoA reductase have been described in Chappell et al. A composite nucleotide sequence of DNA corresponds to the mRNA SEQ ID NO:1 of Chappell et al., as well as the derived amino acid residue sequence SEQ ID NO:2 of Chappell et al., for hamster HMG-CoA reductase is provided in FIG. 2 of Chappell et al, reprinted from Chin et al., *Nature*, 308:613 (1984). The composite nucleotide sequence of FIG. 2, SEQ ID NO:1 of Chappell et al., comprising about 4768 base pairs, includes the nucleotide sequence encoding the intact hamster HMG-CoA reductase enzyme.

Intact hamster HMG-CoA reductase comprises about 887 amino acid residues (SEQ ID NO:2 of Chappell et al.). A structural gene encoding an intact hamster HMG-CoA reductase enzyme of 887 amino acid residues comprises base pairs from about nucleotide position 164 to about nucleotide position 2824 of SEQ ID NO:1 of Chappell et al.

A preferred structural gene is one that encodes a polypeptide corresponding to only the catalytic region of the enzyme. Two catalytically active segments of hamster HMG-CoA reductase have been defined. Liscum et al., *J. Biol. Chem.*, 260(1):522 (1985). One segment containing a catalytic region has an apparent molecular weight of 62 kDa and comprises amino acid residues from about position 373 to about position 887. A second segment containing a catalytic region has an apparent molecular weight of 53 kDa segment and comprises amino acid residues from about position 460 to about position 887. The 62 kDa catalytically active segment is encoded by base pairs from about nucleotide position 1280 to about nucleotide position 2824 of SEQ ID NO:1 of Chappell et al. The 53 kDa catalytically active segment is encoded by base pairs from about nucleotide position 1541 to about nucleotide position 2824 of SEQ ID NO:1 of Chappell et al.

In a preferred embodiment, the utilized structural gene encodes the catalytic region and at least a portion of the linker region of HMG-CoA reductase. The linker region of hamster HMG-CoA reductase comprises amino acid residues from about position 340 to about position 373 or from about position 340 to about position 460, depending upon how the catalytic region is defined. These linker regions are encoded by base pairs from about nucleotide position 1180 to about nucleotide position 1283 or from about position 1180 to about position 1540, respectively of SEQ ID NO:1 of Chappell et al. The structural gene encoding the linker region is operatively linked to the structural gene encoding the catalytic region.

In one particularly preferred embodiment, a structural gene encoding a catalytically active, truncated HMG-CoA reductase enzyme can optionally contain base pairs encoding a small portion of the membrane region of the enzyme.

A structural gene encoding a polypeptide comprising a catalytically active, truncated or intact HMG-CoA reductase enzyme from other organisms such as yeast can also be used in accordance with the present invention.

Figure 3:
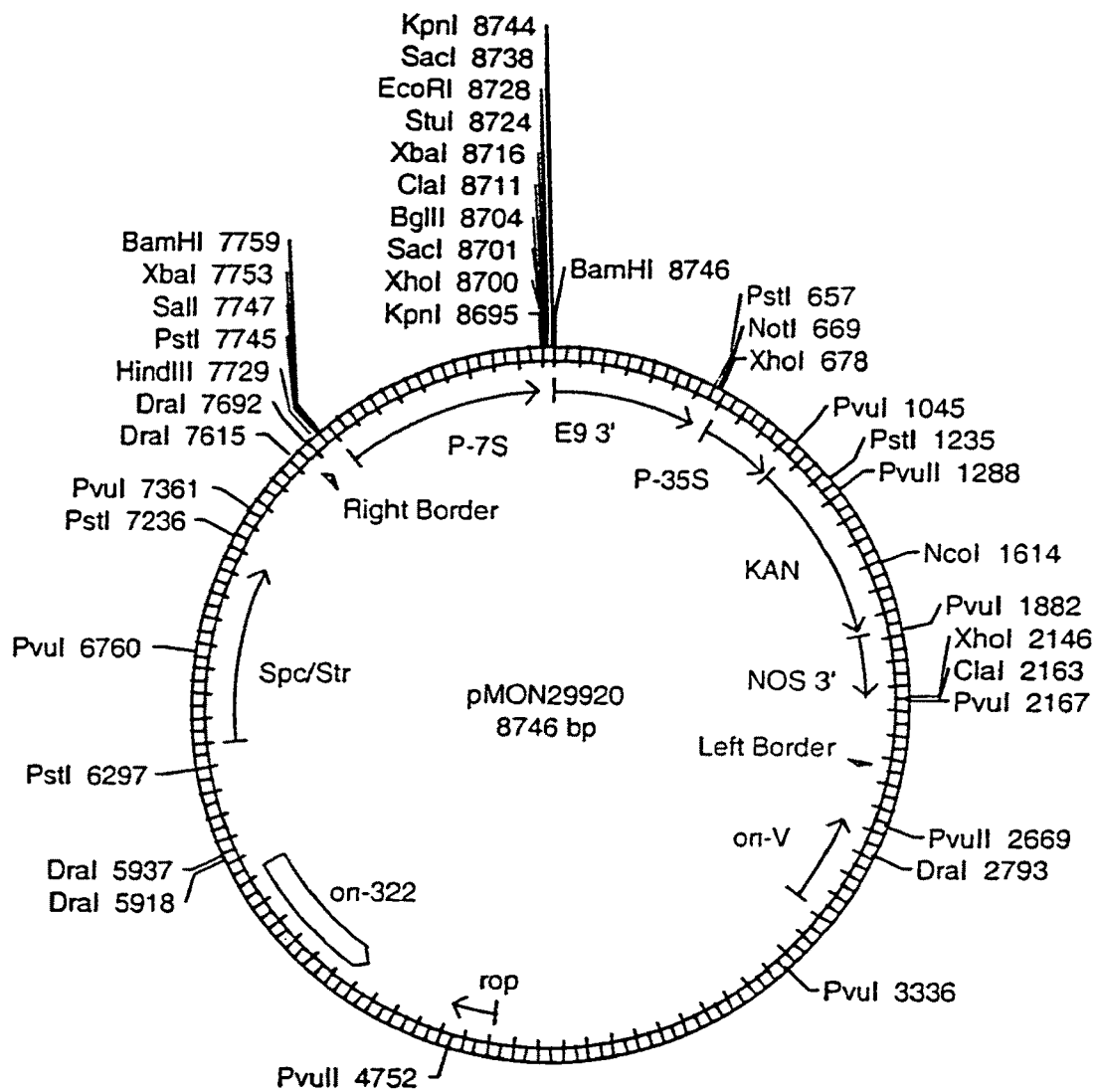
FIG. 3 is a map showing the structure of construct pMON29920. pMON29920 is a binary transformation vector with P-7S/E9 3' cassette and the KAN gene flanked by the two borders where P-7S is the promoter of alpha' beta conglycinin protein from soybean, E9 3' is the 3' end of pea rbc E9 gene and KAN is the coding sequence for NPTII that confers resistance to kanamycin. The NPTII gene is driven by the 35S promoter from cauliflower mosaic virus. Spc.Str is the coding region for Tn7 adenylyltransferase conferring resistance to spectinomycin and streptomycin; ori-V: the vegetative origin of replication; rop: coding region for repressor of primer; ori-322: minimum known sequence required for a functional origin of replication; NOS 3': the 3' termination end of nopaline synthase coding region.

Yeast cells contain two genes encoding HMG-CoA reductase. The two yeast genes, designated HMG1 and HMG2, encode two distinct forms of HMG-CoA reductase, designated HMG-CoA reductase 1 SEQ ID NO:3 of Chappell et al. are presented in FIG. 3 of Chappell et al., are taken from Basson et al. *Mol. Cell. Biol.*, 8(9):3797 (1988). The nucleotide base sequences of HMG2 SEQ ID NO:5 of Chappell et al. as well as the amino acid residue sequence of HMG-CoA reductase 2 SEQ ID NO:6 of Chappell et al. are set forth therein in the Sequence Listing.

The entire HMG1 gene comprises about 3360 base pairs SEQ ID NO:3 of Chappell et al. Intact HMG-CoA reductase 1 comprises an amino acid sequence of about 1054 amino acid residues SEQ ID NO:4 of Chappell et al. Thus, the minimal portion of the HMG1 gene that encodes an intact enzyme comprises base pairs from about nucleotide position 121 to about position 3282 of FIG. 3, SEQ ID NO:3 of Chappell et al.

The entire HMG2 gene comprises about 3348 base pairs SEQ ID NO:5 of Chappell et al. Intact HMG-CoA reductase 2 comprises about 1045 amino acid residues SEQ ID NO:6 of Chappell et al. Thus, the minimal portion of HMG2 gene that encodes intact HMG-CoA reductase 2 comprises base pairs from about nucleotide position 121 to about position 3255 of SEQ ID NO:5 of Chappell et al.

By analogy to the truncated hamster structural gene, structural genes encoding polypeptides comprising catalytically active, truncated HMG-CoA reductase enzymes from yeast can also be used in accordance with the present invention.

The catalytic region of HMG-CoA reductase 1 comprises amino acid residues from about residue 618 to about reside 1054: i.e., the COOH-terminus. A structural gene that encodes the catalytic region comprises base pairs from about nucleotide position 1974 to about position 3282 of FIG. 3 of Chappell et al.

The linker region of HMG-CoA reductase 1 comprises an amino acid sequence from about residue 525 to about residue 617. A structural gene that encodes the linker region comprises nucleotides from about position 1695 to about position 1973 of FIG. 3 of Chappell et al. A structural gene encoding the linker region of the enzyme operatively linked to the structural gene encoding the catalytic region of the enzyme.

Also by analogy to the truncated hamster gene, a truncated HMG1 gene can optionally contain nucleotide base pair sequences encoding a small portion of the membrane-binding region of the enzyme. Such a structural gene preferably comprises base pairs from about nucleotide position 121 to about position 147 and from about position 1695 to about position 3282 of FIG. 3 of Chappell et al.

A construct similar to those above from an analogous portion of yeast HMG-CoA reductase 2 can also be utilized.

A nucleic acid sequence encoding HMG-CoA reductase from *Hevea brasiliensis* has been disclosed by Chye et al. (1991) *Plant Mol. Biol.* 16: 567-577. A nucleic acid sequence encoding an *Arabidopsis thaliana* HMG-CoA reductase has been published by Caelles et al. (1989) *Plant Mol. Biol.* 13: 627-638, and is also available as GenBank accession number L19261. U.S. Pat. Nos. 5,306,862 and 5,365,017 disclose additional DNA sequences encoding HMG-CoA reductases.

The following sequences are listed by Genbank Accession numbers:

O26662 *methanobacterium thermoautotrophicum*. 3-hydroxy-3-methylglutaryl-coenzyme a reductase (ec 1.1.1.34) (hmg-coa reductase). 12/1998

Q58116 *methanococcus jannaschii*. 3-hydroxy-3-methylglutaryl-coenzyme a reductase (ec 1.1.1.34) (hmg-coa reductase). 7/1998

Q59468 *halobacterium volcanii* (*haloferax volcanii*). 3-hydroxy-3-methylglutaryl-coenzyme a reductase (ec 1.1.1.34) (hmg-coa reductase). 7/1998

O008424 *sulfolobus solfataricus*. 3-hydroxy-3-methylglutaryl-coenzyme a reductase (ec 1.1.1.34) (hmg-coa reductase). 12/1998

M22255 *Saccharomyces cerevisiae* Yeast HMG-CoA reductase (HGM2) gene, complete cds; 3-hydroxy-3-methyl glutaryl coenzyme A reductase. 4/1993

M22002 *Saccharomyces cerevisiae* Yeast HMG-CoA reductase (HGM1) gene, complete cds; 3-hydroxy-3-methyl-glutaryl coenzyme A reductase. 4/1993

Q12649 *phycomyces blakesleeanus*. 3-hydroxy-3-methyl-glutaryl-coenzyme a reductase (ec 1.1.1.34) (hmg-coa reductase) (fragment). 11/1997

Q12577 *fusarium moniliforme* (*gibberella fujikuroi*). 3-hydroxy-3-methylglutaryl-coenzyme a reductase (ec 1.1.1.34) (hmg-coa reductase). 11/1997

AB012603 *Candida utilis Candida utilis* HMG mRNA for HMG-CoA reductase, complete cds. 7/1998

P34136 *dictyostelium discoideum* (slime mold). 3-hydroxy-3-methylglutaryl-coenzyme a reductase 2 (ec 1.1.1.34) (hmg-coa reductase 2) (fragment).35735

PQ0761 hydroxymethylglutaryl-CoA reductase (NADPH) (EC 1.1.1.34) (HMGR 10)—wheat (fragment)

P48019 *oryza sativa* (rice). 3-hydroxy-3-methylglutaryl-coenzyme a reductase (ec 1.1.1.34) (hmg-coa reductase) (fragment). 2/1996

O24594 *zea mays* (maize). 3-hydroxy-3-methylglutaryl coenzyme a reductase (ec 1.1.1.88). 5/1999

PQ0763 hydroxymethylglutaryl-CoA reductase (NADPH) (EC 1.1.1.34) (HMGR 23)—wheat (fragment)

PQ0762 hydroxymethylglutaryl-CoA reductase (NADPH) (EC 1.1.1.34) (HMGR 18)—wheat (fragment) from proprietary soy sequence database Q00583 *hevea brasiliensis* (para rubber tree). 3-hydroxy-3-methylglutaryl-coenzyme a reductase 3 (ec 1.1.1.34) (hmg-coa reductase 3). 7/1998

Q03163 *catharanthus roseus* (rosy periwinkle) (madagascar periwinkle). 3-hydroxy-3-methylglutaryl-coenzyme a reductase (ec 1.1.1.34) (hmg-coa reductase). 7/1998

P48022 *lycopersicon esculentum* (tomato). 3-hydroxy-3-methylglutaryl-coenzyme a reductase 2 (ec 1.1.1.34) (hmg-coa reductase 2). 7/1998

Q01559 *nicotiana sylvestris* (wood tobacco). 3-hydroxy-3-methylglutaryl-coenzyme a reductase (ec 1.1.1.34) (hmg-coa reductase). 7/1998

L01400 *Solanum tuberosum* Potato hydroxymethylglutaryl coenzyme A reductase (hmgr) mRNA, complete cds; putative. 4/1996

Q43826 *raphanus sativus* (radish). hydroxymethylglu-taryl-coa reductase (ec 1.1.1.34) (hydroxymethylglutaryl-coa reductase (nadph)) (3-hydroxy-3-methylglutaryl-coenzyme a red L19261 *Arabidopsis thaliana Arabidopsis thaliana* HMG-cOA reductase gene, complete cds. 4/1994

AB021862 *Cucumis melo Cucumis melo* mRNA for HMG-CoA reductase, complete cds; putative. 1/1999

P29058 *hevea brasiliensis* (para rubber tree). 3-hydroxy-3-methylglutaryl-coenzyme a reductase 2 (ec 1.1.1.34) (hmg-coa reductase 2) (fragment).35735

P29057 *hevea brasiliensis* (para rubber tree). 3-hydroxy-3-methylglutaryl-coenzyme a reductase 1 (ec 1.1.1.34) (hmg-coa reductase 1). 7/1998

P48021 *camptotheca acuminata*. 3-hydroxy-3-methylglu-taryl-coenzyme a reductase (ec 1.1.1.34) (hmg-coa reductase). 11/1997

P43256 *arabidopsis thaliana* (mouse-ear cress). 3-hydroxy-3-methylglutaryl-coenzyme a reductase 2 (ec 1.1.1.34) (hmg-coa reductase 2) (hmgr2). 7/1998

P00347 *cricetulus griseus* (chinese hamster). 3-hydroxy-3-methylglutaryl-coenzyme A reductase (ec 1.1.1.34) (hmg-coA reductase). 11/1997

L00183 *Cricetulus* sp. Hamster 3-hydroxy-3-methylglutaryl coenzyme A (HMG CoA) reductase gene, exons 19 and 20; 3-hydroxy-3-methylglutaryl coenzyme A (HMG CoA). 4/1993

M12705 *Mesocricetus auratus* Syrian hamster 3-hydroxy-3-methylglutaral coenzyme A reductase (HMG-CoA reductase) mRNA, complete cds; 3-hydroxy-3-methylglutaral coenzyme A red P51639 *rattus norvegicus* (rat). 3-hydroxy-3-methylglutaryl-coenzyme a reductase (ec 1.1.1.34) (hmg-coa reductase). 12/1998

Q29512 *oryctolagus cuniculus* (rabbit). 3-hydroxy-3-methylglutaryl-coenzyme a reductase (ec 1.1.1.34) (hmg-coa reductase). 7/1999

M11058 *Homo sapiens* Human 3-hydroxy-3-methylglutaryl coenzyme A reductase mRNA, complete cds; 3-hydroxy-3-methylglutaryl coenzyme A reductase. 11/1994

M62766 *Mus musculus* Mouse HMG-CoA reductase mRNA, 3' end. 4/1993

P20715 *xenopus laevis* (african clawed frog). 3-hydroxy-3-methylglutaryl-coenzyme a reductase (ec 1.1.1.34) (hmg-coa reductase). 11/1997

P16393 *strongylocentrotus purpuratus* (purple sea urchin). 3-hydroxy-3-methylglutaryl-coenzyme a reductase (ec 1.1.1.34) (hmg-coa reductase). 11/1997

P54960 *blattella germanica* (german cockroach). 3-hydroxy-3-methylglutaryl-coenzyme a reductase (ec 1.1.1.34) (hmg-coa reductase). 11/1997

P14773 *drosophila melanogaster* (fruit fly). 3-hydroxy-3-methylglutaryl-coenzyme a reductase (ec 1.1.1.34) (hmg-coa reductase). 12/1998

P34135 *dictyostelium discoideum* (slime mold). 3-hydroxy-3-methylglutaryl-coenzyme a reductase 1 (ec 1.1.1.34) (hmg-coa reductase 1). 11/1997

P16237 *schistosoma mansoni* (blood fluke). 3-hydroxy-3-methylglutaryl-coenzyme a reductase (ec 1.1.1.34) (hmg-coa reductase). 7/1998

O28538 *archaeoglobus fulgidus*. 3-hydroxy-3-methylglutaryl-coenzyme a reductase (ec 1.1.1.34) (hmg-coa reductase). 12/1998

M24015 *Pseudomonas mevalonii P. mevalonii* HMG-CoA reductase (mvaA) gene, complete cds; HMG-CoA reductase (EC 1.1.1.88). 4/1993

B. Steroid Pathway Enzymes

The present invention contemplates nucleic acid sequences encoding polypeptides having the enzyme activity of the steroid pathway enzymes squalene epoxidase, sterol methyl transferase I, sterol C4-demethylase, obtusifoliol C14α-demethylase, sterol C5-desaturase and sterol methyl transferase II.

i. Squalene Epoxidase

Squalene epoxidase (also called squalene monooxygenase) catalyzes the conversion of squalene to squalene epoxide (2,3-oxidosqualene), a precursor to the initial sterol molecule in phytosterol biosynthetic pathway, cycloartenol. This is the first reported step in the pathway where oxygen is required for activity. The formation of squalene epoxide is also the last common reported step in sterol biosynthesis of animals, fungi and plants. Recently, several homologues of *Arabidopsis* and *Brassica* squalene epoxidase genes were reported (Schafer, U. A., Reed, D. W., Hunter, D. G., Yao, K., Weninger, A. M., Tsang, E. W., Reaney, M. J., MacKenzie, S. L., and Covello, P. S. (1999). Plant Mol. Biol. 39(4): 721-728). The same authors also have a PCT application disclosing the use of antisense technology with squalene epoxidase to elevate squalene levels in plants (WO 97/34003). However, to date there are no reports on functional characterization of any plant squalene epoxidase gene or enzyme.

Squalene Epoxidase, also known as squalene monooxygenase is enzyme reference number 1.14.99.7, *Enzyme Nomenclature* 1992, p. 146.

Several squalene epoxidase enzymes are known to the art. These include *Arabidopsis* squalene epoxidase protein sequence Accession No. AC004786 (SEQ ID NO:1), *Arabidopsis* squalene epoxidase Accession No. N64916 (SEQ ID NO:2), and *Arabidopsis* squalene epoxidase Accession No. T44667 (SEQ ID NO:3). Japanese patent application No. 07194381 A discloses a DNA encoding a mammalian squalene epoxidase.

In order to facilitate the modifications to sterol biosynthesis and accumulation described herein, the present invention also provides an isolated DNA molecule, comprising a nucleotide sequence selected from the group consisting of:

(a) *Arabidopsis* squalene epoxidase from clone ID ATA506263 disclosure SEQ ID NO:4, clone ID ATA304243 disclosure SEQ ID NO:6, clone ID ATA102071 disclosure SEQ ID NO: 8, clone ATA504158 disclosure SEQ ID NO:10, or the complement thereof;

(b) a nucleotide sequence that hybridizes to said nucleotide sequence of (a) under a wash stringency equivalent to 0.5× SSC to 2×SSC, 0.1% SDS, at 55-65° C., and which encodes a polypeptide having squalene epoxidase enzymatic activity substantially similar to that of the disclosed squalene epoxidase;

(c) a nucleotide sequence encoding the same genetic information as said nucleotide sequence of (a), but which is degenerate in accordance with the degeneracy of the genetic code; and (d) a nucleotide sequence encoding the same genetic information as said nucleotide sequence of (b), but which is degenerate in accordance with the degeneracy of the genetic code.

An additional aspect of the invention is the recombinant constructs and vectors (pMON48343, FIG. 30; pMON43844, FIG. 31) comprising nucleic acid sequences encoding the novel squalene epoxidase, as well as a method of producing the novel squalene epoxidase, comprising culturing a host cell transformed with the novel constructs or vectors for a time and under conditions conductive to the production of the squalene epoxidase, and recovering the squalene epoxidase produced thereby.

ii. Sterol Methyl Transferase I

S-adenosyl-L-methionine:sterol C-24 methyl transferases (SMT1 and SMT2) catalyze the transfer of a methyl group from a cofactor, S-adenosyl-L-methionine, to the C-24 center of the sterol side chain (Bach, T. J. and Benveniste, P. (1997), Prog. Lipid Res. 36: 197-226). SMT in higher plant cells are responsible for their capability to produce a mixture of 24-methyl and 24-ethyl sterols (Schaffer, A., Bouvier-Navé, Benveniste, P., Schaller, H. (2000) Lipids 35: 263-269). Functional characterization of the SMT using a yeast erg6 expression system demonstrated unambiguously that an SMT1 sequence encodes a cycloartenol-C24-methyltransferase and a SMT2 sequence encodes a 24-methylene lophenol-C24-methyltransferase in a given plant species (Bouvier-Navé, P., Husselstein, T., and Benveniste, P. (1998), Eur. J. Biochem. 246: 518-529). Several plant genes coding for SMT1 and SMT2 have been reported and reviewed (Schaffer, A., Bouvier-Navé, Benveniste, P., Schaller, H. (2000) Lipids 35: 263-269). Transgenic plants expressing homologues of either SMT1 or SMT2 have been studied (Schaffer, A., Bouvier-Navé, Benveniste, P., Schaller, H. (2000) Lipids 35: 263-269).

The use of these genes to modify plant sterol composition are also covered by two Monsanto patent applications (WO 98/45457 and WO 00/61771).

Sterol methyl transferase I enzymes known in the art are useful in the present invention. Examplary sequences include the known *Arabidopsis* sterol methyl transferase I protein sequence Accession No. U71400 (disclosure SEQ ID NO:20), the known tobacco sterol methyl transferase I protein sequence Accession No. U81312 (disclosure SEQ ID NO:21) and *Ricinus communes* sterol-C-methyltransferase, *Eur. J. Biochem.*, 246(2), 518-529 (1997). (Complete cds, Accession No. g2246457).

S-Adenosyl-L-Methionine-Sterol-C24-Methyltransferase—A nucleic acid sequence encoding an *Arabidopsis thaliana* S-adenosyl-L-methionine-sterol-C24-methyltransferase has been published by Husselstein et al. (1996) *FEBS Letters* 381: 87-92. $\Delta^{24}$-sterol C-methyltransferase is enzyme number 2.1.1.41, *Enzyme Nomenclature* 1992, page 160.

iii. Sterol C4-Demethylase

Sterol C-4 demethylase catalyses the first of several demethylation reactions, which results in the removal of the two methyl groups at C-4. While in animals and fungi the removal of the two C-4 methyl groups occurs consecutively, in plants it has been reported that there are other steps between the first and second C-4 demethylations (Bach, T. J. and Benveniste, P. (1997), Prog. Lipid Res. 36: 197-226). The C-4 demethylation is catalyzed by a complex of microsomal enzymes consisting of a monooxygenase, an NAD$^+$-dependent sterol 4-decarboxylase and an NADPH-dependent 3-ketosteroid reductase.

iv. Obtusifoliol C14α-Demethylase

Sterol C-14 demethylase catalyzes demethylation at C-14 which removes the methyl group at C-14 and creates a double bond at that position. In both fungi and animals, this is the first step in the sterol synthesis pathway. However, in higher plants, the 14α-methyl is removed after one C-4 methyl has disappeared. Thus, while lanosterol is the substrate for C-14 demethylase in animal and fungal cells, the plants enzyme uses obtusifoliol as substrate. Sterol 14-demethylation is mediated by a cytochrome P-450 complex. The mechanism of 14α-methyl removal involves two oxidation steps leading to an alcohol, then an aldehyde at C-29 and a further oxidative step involving a deformylation leading to formic acid and the sterol product with a typical 8,14-diene (Aoyama, Y., Yoshida, Y., Sonoda, Y., and Sato, Y. (1989) J. Biol. Chem. 264: 18502-18505). Obtusifoliol 14α-demethylase from *Sorghum bicolor* (L) Moench has been cloned using a gene-specific probe generated using PCR primers designed from an internal 14 amino acid sequence and was functionally expressed in *E. coli* (Bak, S. Kahn, R. A., Olsen, C. E. and Halkier, B. A. (1997) The Plant Journal 11(2): 191-201). Also, *Saccharomyces cerevisiae* CYP51A1 encoding lanosterol-14-demethylase was functionally expressed in tobacco (Grausem, B., Chaubet, N., Gigot, C., Loper, J. C., and Benveniste, P. (1995) The Plant Journal 7(5): 761-770).

Sterol C-14 demethylase enzymes and sequences are known in the art. For example *Sorghum bicolor* obtusifoliol 14α-demethylase CYP51 mRNA, described in Plant J., 11(2):191-201 (1997) (complete cds Accession No. U74319). In order to facilitate the modifications to sterol biosynthesis and accumulation described herein, the present invention also provides an isolated DNA molecule, having a nucleotide sequence selected from the group consisting of:

(a) obtusifoliol C14α-demethylase from clone ID: ATA101105 disclosure SEQ ID NO:14, clone ID ATA202967 disclosure SEQ ID NO:15, clone ID ATA403931 disclosure SEQ ID NO:17, or the complement thereof;

(b) a nucleotide sequence that hybridizes to said nucleotide sequence of (a) under a wash stringency equivalent to 0.5× SSC to 2×SSC, 0.1% SDS, at 55-65° C., and which encodes a polypeptide having obtusifoliol C14α-demethylase enzymatic activity substantially similar to that of the disclosed obtusifoliol C14α-demethylase;

(c) a nucleotide sequence encoding the same genetic information as said nucleotide sequence of (a), but which is degenerate in accordance with the degeneracy of the genetic code; and (d) a nucleotide sequence encoding the same genetic information as said nucleotide sequence of (b), but which is degenerate in accordance with the degeneracy of the genetic code.

An additional aspect of the invention is the recombinant constructs and vectors (pMON43842, FIG. 29) comprising nucleic acid sequences encoding the novel obtusifoliol C14α-demethylase, as well as a method of producing the novel obtusifoliol C14α-demethylase, comprising culturing a host cell transformed with the novel constructs or vectors for a time and under conditions conductive to the production of the obtusifoliol C14α-demethylase, and recovering the obtusifoliol C14α-demethylase produced thereby.

v. Sterol C5-Desaturase

Sterol C-5 desaturase catalyzes the insertion of the $\Delta^5$-double bond that normally occurs at the $\Delta^7$-sterol level, thereby forming a $\Delta^{5,7}$-sterol (Parks et al., *Lipids* 30:227-230 (1995)). The reaction has been reported to involve the stereospecific removal of the 5α and 6α hydrogen atoms, biosynthetically derived from the 4 pro-R and 5 pro-S hydrogens of the (+) and (−) R-mevalonic acid, respectively (Goodwin, T. W. (1979) Annu. Rev. Plant Physiol. 30: 369-404). The reaction is obligatorily aerobic and requires NADPH or NADH. The desaturase has been reported to be a multienzyme complex present in microsomes. It consists of the desaturase itself, cytochrome $b_5$ and a pyridine nucleotide-dependent flavoprotein. The $\Delta^5$-desaturase is reported to be a mono-oxygenase that utilizes electrons derived from a reduced pyridine nucleotide via cytochrome$_b$ (Taton, M., and Rahier, A. (1996) Arch. Biochem. Biophys. 325: 279-288). An *Arabidopsis thaliana* cDNA encoding a sterol-C5-desaturase was cloned by functional complementation of a yeast mutant, erg3 defective in ERG3, the gene encoding the sterol C5-desaturase required for ergosterol biosynthesis (Gachotte D., Husselstein, T., Bard, M., Lacroute F., and Benveniste, P. (1996) The Plant Journal 9(3): 391-398). Known sterol C5-desaturase enzymes are useful in the present invention, including *Arabidopsis* sterol C5-desaturase protein sequence Accession No. X90454, disclosure SEQ ID NO:23, and the *Arabidopsis thaliana* mRNA for sterol-C5-desaturase described in Plant J. 9(3):391-398 (1996) (complete cds Accession No. g1061037).

The NCBI (National Center for Biotechnology Information) database shows 37 sequences for sterol desaturase that are useful in the present invention. The following are exemplary of such sequences. From yeast: C5 sterol desaturase NP_013157 (*Saccharomyces cerevisiae*); hypothetical C5 sterol desaturase-fission T40027 (*Schizosaccharomyces pombe*); C5 sterol desaturase-fission T37759 (*Schizosaccharomyces pombe*); C5 sterol desaturase JQ1146 (*Saccharomyces cerevisiae*); C5 sterol desaturase BAA21457 (*schizosaccharomyces pombe*); C5 sterol desaturase CAA22610 (*Schizosaccharomyces pombe*); putative C5 sterol desaturase CAA16898 (*Schizosaccharomyces pombe*); probable C5 sterol desaturase 013666 (erg3_schpo); C5 sterol desaturase P50860 (Erg3_canga); C5 sterol desaturase P32353 (erg3_yeast); C5,6 desaturase AAC99343 (*Candida albicans*); C5 sterol desaturase BAA20292 (*Saccharomyces cer-* evisiae); C5 sterol desaturase AAB39844 (*Saccharomyces cerevisiae*); C5 sterol desaturase AAB29844 (*Saccharomyces cerevisiae*); C5 sterol desaturase CAA64303 (*Saccharomyces cerevisiae*); C5 sterol desaturase AAA34595 (*Saccharomyces cerevisiae*); C5 sterol desaturase AAA34594 (*Saccharomyces cerevisiae*). From plants: C5 sterol desaturase S71251 (*Arabidopsis thaliana*); putative sterol-C5-desaturase AAF32466 (*Arabidopsis thaliana*); sterol-C5-desaturase AAF32465 (*Arabidopsis thaliana*); putatuve sterol desaturase AAF22921 (*Arabidopsis thaliana*); delta7 sterol C5 desaturase (*Arabidopsis thaliana*); sterol C5(6) desaturase homolog AAD20458 (*Nicotiana tabacum*); sterol C5 desaturase AAD12944 (*Arabidopsis thaliana*); sterol C5,6 desaturase AAD04034 (*Nicotiana tabacum*); sterol C5 desaturase CAA62079 (*Arabidopsis thaliana*). From mammals: sterol-C5-desaturase (*Mus musculus*) BAA33730; sterol-C5-desaturase BAA33729 (*Homo sapiens*); lathosterol oxidase CAB65928 (*Leishmania major*); lathosterol oxidase (lathosterol 5-desaturase) O88822 (*Mus musculus*); lathosterol 5-desaturase O75845 (*Homo sapiens*); delta7 sterol C5 desaturase AAF00544 (*Homo sapiens*). Others: fungal sterol C5 desaturase homolog BAA18970 (*Homo sapiens*).

For DNA sequences encoding a sterol-C5-desaturase useful in the present invention, the NCBI_nucleotide search for "sterol desaturase" came up with 110 sequences. The following are exemplary of such sequences. NC_001139 (*Saccharomyces cerevisiae*); NC_001145 (*Saccharomyces cerevisiae*); NC_001144 (*Saccharomyces cerevisiae*); AW700015 (*Physcomitrella patens*); AB004539 (*Schizosaccharomyces pombe*); and AW596303 (*Glycine max*); AC012188 (*Arabidopsis thaliana*).

vi. Sterol Methyl Transferase II

The combination of introduction of an HMG-CoA reductase gene along with a sterol methyl transferase II gene into a cell serves to reduce steroid pathway intermediate compound accumulation in addition to reducing the accumulation of 24-methyl sterols such as campesterol.

Known sterol methyl transferase II enzymes are useful in the present invention, including *Arabidopsis* sterol methyl transferase II protein sequence (complete mRNA cds from FEBS Lett. 381(12):87-92 (1996) Accession No. X89867), disclosure SEQ ID NO:22.

Recombinant constructs encoding any of the forgoing enzymes affecting the steroid biosynthetic pathway can be incorporated into recombinant vectors comprising the recombinant constructs comprising the isolated DNA molecules. Such vectors can be bacterial or plant expression vectors.

IV. Recombinant Constructs and Vectors

The present invention contemplates a recombinant construct that contains a DNA sequence encoding a polypeptide exhibiting 3-hydroxy-3-methylfluaryl-Coenzyme A (HMG-CoA) reductase activity and a DNA sequence encoding a polypeptide exhibiting the activity of a steroid pathway enzyme. Each polypeptide-encoding DNA sequence is operably linked in the 5' to 3' direction independent of the other sequence. Each DNA sequence in the 5' to 3' direction comprises a promoter, then the DNA sequence encoding the polypeptide then a transcription termination signal sequence. The steroid pathway enzyme is a squalene epoxidase enzyme, a sterol methyl transferase I enzyme, a sterol C4-demethylase enzyme, a obtusifoliol C14α-demethylase enzyme, a sterol C5-desaturase enzyme, or a sterol methyl transferase II enzyme.

Preferably, the promoters in the recombinant construct are seed-specific promoters. In one embodiment, the promoter is derived from a species in a different order from the host cell. In other embodiments, the encoded HMG CoA reductase and/or steroid pathway enzymes is(are) from a species in a different order from the order that of the host cell.

It is contemplated that a construct comprises more than one of the DNA sequences encoding a steroid pathway enzyme.

The invention also contemplates a recombinant vector comprising the above-described recombinant construct, wherein that vector is preferably a plant expression vector.

A recombinant DNA molecule of the present invention can be produced by operatively linking a vector to a useful DNA segment discussed herein to form a plasmid. A vector capable of directing the expression of a polypeptide having HMG-CoA reductase activity is referred to herein as an HMG-CoA reductase "plant integrating vector".

Figure 5:
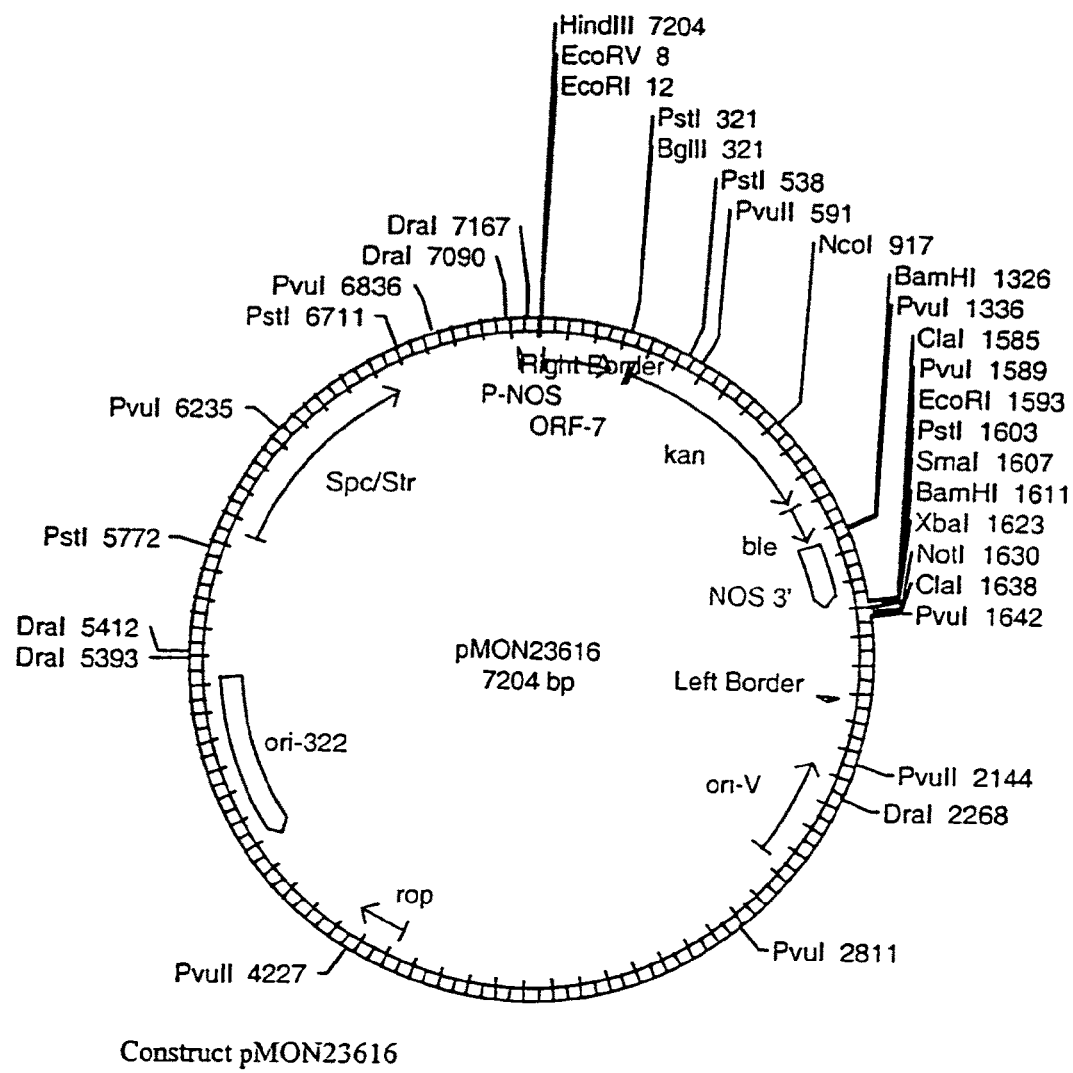
FIG. 5 is a map showing the structure of construct pMON23616. pMON23616 is a plant expression vector containing P-NOS/ORF-7/KAN/NOS-3' cassette. P-NOS: NOS promoter from *Agrobacterium tumefaciens* pTiT37; ORF-7: a short open reading frame that attenuates expression of KAN in plants; KAN: coding sequence of NPTII gene that confers resistance to kanamycin and neomycin; ble: confers resistance to bleomycin; NOS 3': 3' termination end of nopaline synthase coding region; Left Border: Octapine left border from Octapine Ti plasmid pTiA6; ori-V: the vegetative origin of replication; rop: coding region for repressor of primer; Spc/Str: coding region for Tn7 adenylyltransferase conferring resistance to spectinomycin and streptomycin.

Such plant integrating vectors contain control elements that direct and regulate expression, including a promoter, a marker, a terminator and insertion sequence (e.g. FIG. 5). The polypeptide coding genes are operatively linked to the plant integrating vector to allow the promoter sequence to direct RNA polymerase binding and expression of the desired polypeptide coding gene.

Useful in expressing the polypeptide coding gene are promoters that are inducible, viral, synthetic, constitutive as described by Poszkowski et al., *EMBO J.,* 3:2719 (1989) and Odell et al., *Nature,* 313:810 (1985), and temporally regulated, spatially regulated and spatiotemporally regulated as given in Chau et al., *Science,* 244:174-181 (1989). The promoter preferably comprises a promoter sequence whose function in regulating expression of the structural gene is substantially unaffected by the amount of sterol or squalene in the cell. As used herein, the term "substantially unaffected" means that the promoter is not responsive to direct feedback control by the sterols or squalene accumulated in transformed cells or transgenic plants.

A promoter is also selected for its ability to direct the transformed plant cell's or transgenic plant's transcriptional activity to the structural gene encoding a polypeptide having HMG-CoA reductase activity. Structural genes can be driven by a variety of promoters in plant tissues. Promoters can be near-constitutive, such as the CaMV 35S promoter, or tissue specific or developmentally specific promoters affecting dicots or monocots.

As exemplified and discussed in detail herein, where the near-constitutive promoter CaMV 35S is used to transform tobacco plants, increases in total sterol and squalene accumulation are found in a variety of transformed plant tissues (e.g. callus, leaf, seed and root). Alternatively, the effects of transformation (e.g. increased amount of a gene coding for HMG-CoA reductase, increased total sterol accumulation and increased squalene accumulation) can be directed to specific plant tissues by using plant integrating vectors containing a tissue-specific promoter.

An exemplary tissue-specific promoter is the Lectin promoter, which is specific for seed tissue. The Lectin protein in soybean seeds is encoded by a single gene (Le1) that is only expressed during seed maturation and accounts for about 2 to about 5 percent of total seed mRNA. The Lectin gene and seed-specific promoter have been fully characterized and used to direct seed specific expression in transgenic tobacco plants. See, e.g., Vodkin et al., *Cell,* 34:1023 (1983) and Lindstrom et al., *Developmental Genetics,* 11:160 (1990).

A plant integrating vector containing a structural gene coding for a polypeptide having HMG-CoA reductase activity is engineered to be under control of the Lectin promoter and that vector is introduced into soybean plants using a protoplast transformation method. E. G. Dhir et al., *Plant Cell Reports,* 10:97 (1991). The expression of the polypeptide having HMG-CoA reductase activity is directed specifically to the seeds of the transgenic plant. In this way, a transgenic soybean seed having increased squalene accumulation is produced. Such seeds can then be used to extract oil containing enhanced levels of squalene. As set forth hereinafter, such squalene-enhanced oil is characterized by a greater thermal stability when compared to non-squalene-enhanced oil.

In the present invention, a plant has an exogenously provided structural gene for HMG-CoA reductase and at least one of the six enumerated steroid pathway enzymes, a squalene epoxidase enzyme, a sterol methyl transferase I enzyme, a sterol C4-demethylase enzyme, a obtusifoliol C14α-demethylase enzyme, a sterol C5-desaturase enzyme, or a sterol methyl transferase II enzyme. The plant or seed thus containing these added genes is contemplated, while the methods to arrive at a plant or seed according to the invention are open to the multitude of methods contemplated by a person of ordinary skill in the art. In particular, all of the added structural genes do not have to have been added at the same time, or by the same route. Thus, for example, the HMG-CoA reductase activity may result from a cross with a plant made according to a process of U.S. Pat. No. 5,349,126, while a steroid pathway enzyme is added by nucleic acid bombardment to that plant. Further, when more than one nucleotide sequence encoding a steroid pathway enzyme is present in a contemplated plant, the expression of the gene does not have to be under the control of the same promoter, or even the same type of promoter.

The choice of which plant integrating vector and ultimately to which promoter a polypeptide coding gene is operatively linked depends directly on the functional properties desired, e.g. the location and timing of protein expression, and the host cell to be transformed. These are well known limitations inherent in the art of constructing recombinant DNA molecules. However, a vector useful in practicing the present invention is capable of directing the expression of the polypeptide coding gene, i.e., the gene encoding HMG-CoA reductase activity, included in the DNA segment to which it is operatively linked.

Typical vectors useful for expression of genes in higher plants are well known in the art and include vectors derived from the tumor-inducing (Ti) plasmid of *Agrobacterium tumefaciens*, described by Rogers et al., *Meth. Enzymol.*, 153:253-277 (1987). However, several other plant integrating vector systems are known to function in plants including pCaMVCN transfer control vector described by Fromm et al. *Proc. Nat. Acad. Sci. USA,* 82:5824 (1985). Plasmid pCaMVCN (available from Pharmacia, Piscataway, N.J.) includes the cauliflower mosaic virus CaMV 35S promoter.

The use of retroviral plant integrating vectors to form the recombinant DNAs of the present invention is also contemplated. As used herein, the term "retroviral plant integrating vector" refers to a DNA molecule that includes a promoter sequence derived from the long terminal repeat (LTR) region of a retrovirus genome.

In preferred embodiments, the vector used to express the polypeptide coding gene includes a selection marker that is effective in a plant cell, preferably a drug resistance selection marker. One preferred drug resistance marker is the gene whose expression results in kanamycin resistance; i.e., the chimeric gene containing the nopaline synthase promoter, Tn5 neomycin phosphotransferase II and nopaline synthase 3' nontranslated region described by Rogers et al., in *Methods for Plant Molecular Biology*, A. Weissbach and H. Weissbach eds., Academic Press Inc., San Diego, Calif. (1988).

A variety of methods have been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

Alternatively, synthetic linkers containing one or more restriction endonuclease sites can be used to join the DNA segment to the plant integrating vector. The synthetic linkers are attached to blunt-ended DNA segments by incubating the blunt-ended DNA segments with a large excess of synthetic linker molecules in the presence of an enzyme that is able to catalyze the ligation of blunt-ended DNA molecules, such as bacteriophage T4 DNA ligase. Thus, the products of the reaction are DNA segments carrying synthetic linker sequences at their ends. These DNA segments are then cleaved with the appropriate restriction endonuclease and ligated into a plant integrating vector that has been cleaved with an enzyme that produces termini compatible with those of the synthetic linker. Synthetic linkers containing a variety of restriction endonuclease sites are commercially available from a number of sources including New England BioLabs, Beverly, Mass.

Also contemplated by the present invention are RNA equivalents of the above-described recombinant DNA molecules.

A preferred recombinant DNA molecules utilized in accordance with the present invention are pMON53733-pMON53740 (FIGS. 13-20).

A. Promoters and Target Tissues

Promoters useful in the present invention include those that confer appropriate cellular and temporal specificity of expression. Such promoters include those that are constitutive or inducible, environmentally- or developmentally-regulated, or organelle-, cell-, or tissue-specific. Preferred promoters for use with the present invention promote expression of the introduced enzymes in the seed in the cytosol, although expression in plasids or organelles of the seeds is also contemplated.

Often-used constitutive promoters include the CaMV 35S promoter (Odell et al. (1985) *Nature* 313: 810), the enhanced CaMV 35S promoter, the Figwort Mosaic Virus (FMV) promoter (Richins et al. (1987) *NAR* 20: 8451), the mannopine synthase (mas) promoter, the nopaline synthase (nos) promoter, and the octopine synthase (ocs) promoter.

Useful inducible promoters include heat-shock promoters (Ou-Lee et al. (1986) *Proc. Natl. Acad. Sci. USA* 83: 6815; Ainley et al. (1990) *Plant Mol. Biol.* 14: 949), a nitrate-inducible promoter derived from the spinach nitrite reductase gene (Back et al. (1991) *Plant Mol. Biol.* 17: 9), hormone-inducible promoters (Yamaguchi-Shinozaki et al. (1990) *Plant Mol. Biol.* 15: 905; Kares et al. (1990) *Plant Mol. Biol.* 15: 905), and light-inducible promoters associated with the small subunit of RuBP carboxylase and LHCP gene families (Kuhlemeier et al. (1989) *Plant Cell* 1: 471; Feinbaum et al. (1991) *Mol. Gen. Genet.* 226: 449; Weisshaar et al. (1991) *EMBO J.* 10: 1777; Lam and Chua (1990) *Science* 248: 471; Castresana et al. (1988) *EMBO J.* 7: 1929; Schulze-Lefert et al. (1989) *EMBO J.* 8: 651).

Examples of useful tissue-specific, developmentally-regulated promoters include fruit-specific promoters such as the E4 promoter (Cordes et al. (1989) *Plant Cell* 1:1025), the E8 promoter (Deikman et al. (1988) *EMBO J.* 7: 3315), the kiwifruit actinidin promoter (Lin et al. (1993) *PNAS* 90: 5939), the 2A11 promoter (Houck et al., U.S. Pat. No. 4,943, 674), and the tomato pZ130 promoter (U.S. Pat. Nos. 5,175, 095 and 5,530,185); the β-conglycinin 7S promoter (Doyle et al. (1986) *J. Biol. Chem.* 261: 9228; Slighton and Beachy (1987) *Planta* 172: 356), and seed-specific promoters (Knutzon et al. (1992) *Proc. Natl. Acad. Sci. USA* 89: 2624; Bustos et al. (1991) *EMBO J.* 10: 1469; Lam and Chua (1991) *J. Biol. Chem.* 266: 17131; Stayton et al. (1991) *Aust. J. Plant. Physiol.* 18: 507). Fruit-specific gene regulation is discussed in U.S. Pat. No. 5,753,475. Other useful seed-specific promoters include, but are not limited to, the napin, phaseolin, zein, soybean trypsin inhibitor, 7S, ADR12, ACP, stearoyl-ACP desaturase, oleosin, *Lasquerella* hydroxylase, and barley aldose reductase promoters (Bartels (1995) *Plant J.* 7: 809-822), the EA9 promoter (U.S. Pat. No. 5,420,034), and the Bce4 promoter (U.S. Pat. No. 5,530,194). Useful embryo-specific promoters include the corn globulin 1 and oleosin promoters. Useful endosperm-specific promoters include the rice glutelin-1 promoter, the promoters for the low-pI α-amylase gene (Amy32b) (Rogers et al. (1984) *J. Biol. Chem.* 259: 12234), the high-pI α-amylase gene (Amy 64) (Khurseed et al. (1988) *J. Biol. Chem.* 263: 18953), and the promoter for a barley thiol protease gene ("Aleurain") (Whittier et al. (1987) *Nucleic Acids Res.* 15: 2515).

Appropriate target tissues of plants for enhanced production of sterol compounds such as sitosterol, sitosterol esters, sitostanol, sitostanol esters, and tocopherols, and reduced production of campesterol, campestanol, and esters thereof, include, but are not limited to, fruits, flowers, seeds, roots, tubers, leaves, stems, buds, and other vegetable parts of plants. Within seeds, appropriate organ compartments include the embryo, the endosperm, and the aleurone layer. Within any of the noted target tissues, appropriate cellular compartments include, but are not limited to, the cell cytoplasm and plastids (e.g., proplastids, chloroplasts, chromoplasts, leucoplasts, amyloplasts, etc.).

B. Vectors

In plants, transformation vectors capable of introducing encoding DNAs involved in sterol compound and tocopherol biosynthesis are easily designed, and generally contain one or more DNA coding sequences of interest under the transcriptional control of 5' and 3' regulatory sequences. Such vectors generally comprise, operatively linked in sequence in the 5' to 3' direction, a promoter sequence that directs the transcription of a downstream heterologous structural DNA in a plant; optionally, a 5' non-translated leader sequence; a nucleotide sequence that encodes a protein of interest; and a 3' non-translated region that encodes a polyadenylation signal which functions in plant cells to cause the termination of transcription and the addition of polyadenylate nucleotides to the 3' end of the mRNA encoding the protein. Plant transformation vectors also generally contain a selectable marker. Typical 5'-3' regulatory sequences include a transcription initiation start site, a ribosome binding site, an RNA processing signal, a transcription termination site, and/or a polyadenylation signal. Vectors for plant transformation have been reviewed in Rodriguez et al. (1988) *Vectors: A Survey of Molecular Cloning Vectors and Their Uses*, Butterworths, Boston; Glick et al. (1993) *Methods in Plant Molecular Biology and Biotechnology* CRC Press, Boca Raton, Fla.; and Croy (1993) In *Plant Molecular Biology Labfax*, Hames and Rickwood, Eds., BIOS Scientific Publishers Limited, Oxford, UK.

The use of transit peptides, e.g. translational fusion peptides, are not preferred for use in conjunction with the enzymes of the present invention, where the sterol synthetic compounds are present primarily in the cellular cytosol.

V. Cell Transformation and Plant Regeneration

The amount of a gene coding for a polypeptide having HMG-CoA reductase activity is increased by transforming a desired plant cell with a suitable vector that contains that added exogenous structural gene. Expression of that gene in the transformed plant cell and transgenic plants developed from that transformed plant cell enhances the activity of HMG-CoA reductase.

Methods for transforming polypeptide-coding genes into plant cells include *Agrobacterium*-mediated plant transformation, protoplast transformation, gene transfer into pollen, injection into reproductive organs and injection into immature embryos. Each of these methods has distinct advantages and disadvantages. Thus, one particular methods of introducing genes into a particular plant strain may not necessarily be the most effective for another plant strain, but it is well known which methods are useful for a particular plant strain.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., *Biotechnology*, 3:629 (1984) and Rogers et al., *Methods in Enzymology*, 153:253-277 (1987). Further the integration of the T8-DNA is a relatively precise process resulting in few rearrangements. The region of DNA to be transferred is defined by the border sequences, and intervening DNA is usually inserted into the plant genome as described by Spielmann et al., *Mol. Gen. Genet.*, 205:34 (1986) and Jorgensen et al, *Mol. Gen. Genet.*, 207:471 (1987).

Modern *Agrobacterium* transformation vectors are capable of replication in *E. coli* as well as *Agrobacterium*, allowing for convenient manipulations as described by Klee et al., in *Plant DNA Infectious Agents*, T. Hohn and J. Schell, eds., Springer-Verlag, New York (1985) pp. 179-203.

Moreover, recent technological advances in vectors for *Agrobacterium*-mediated gene transfer have improved the arrangement of genes and restriction sites in the vectors to facilitate construction of vectors capable of expressing various polypeptide coding genes. The vectors described by Rogers et al., *Meth. Enzymol.*, 153:253 (1987), have convenient multi-linker regions flanked by a promoter and a polyadenylation site for directed expression inserted polypeptide conding genes and are suitable for present purposes.

In addition, *Agrobacteria* containing both armed and disarmed Ti genes can be used for the transformations. Both types of transforming systems are illustrated herein. Transformants from the former system result in callus from which the desired squalene or sterol can be obtained, whereas transformants obtained from the latter, disarmed Ti genes can be regenerated into complete transgenic plants from whose tissues, e.g. leaf, seed and root, the desired chemicals can be obtained.

In those plant strains where *Agrobacterium*-mediated transformation is efficient, it is the method of choice because of the facile and defined nature of the gene transfer.

*Agrobacterium*-mediated transformation of leaf disks and other tissues, such as cotyledons and hypocotyls, appears to be limited to plant strains that *Agrobacterium* naturally infects. *Agrobacterium*-mediated transformation is the most efficient in dicotyledonous plants. Few monocots appear to be natural hosts for *Agrobacterium*, although transgenic plants have been produced in the monocot, asparagus, using *Agrobacterium* vectors as described by Bytebier et al., *Proc. Natl. Acad. Sci. USA,* 84:5345 (1987). Therefore, commercially important cereal grains such as rice, corn, and wheat must usually be transformed using alternative methods. However, as mentioned above, the transformation of asparagus using *Agrobacterium* can also be achieved.

A transgenic plant formed using *Agrobacterium* transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one more than one added gene as here, it is believed that a more accurate name for such a plant is an independent segregant, because the added, exogenous gene segregates independently during mitosis and meiosis. A transgenic plant containing a single structural gene that encodes a polypeptide having HMG-CoA reductase activity and at least one of the enumerated 6 steroid pathway enzymes; i.e., and independent segregant, is a preferred transgenic plant.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains the added genes according to the invention, germinating some of the seed produced and analyzing the resulting plants produced for enhanced HMG-CoA reductase activity, steroid pathway product accumulation or both, relative to a control (native, non-transgenic) or an independent segregant transgenic plant.

A homozygous transgenic plant exhibits enhanced HMG-CoA reductase activity as compared to a native, non-transgenic plant and an independent segregant transgenic plant.

It is to be understood that two different transgenic plants can also be mated to produce offspring that contain two independently segregating added, exogenous genes. Selfing of appropriate progeny can produce plants that are homozygous for both added, exogenous genes that encode a polypeptide having HMG-CoA reductase activity. Back-crossing to a parental plant and outcrossing with a non-transgenic plant are also contemplated.

A. Host Cells and Transformed Plant Cells

Cells modified according to the present invention are contemplated at each stage of the processes of the invention. As a result of the invention comprising at least two genes, there are several means to accomplish that end. In some embodiments of the invention, the intermediate steps include transformation of nucleic acids comprising some or all of the genes into host cells.

The nucleic acid sequence encoding a polypeptide exhibiting HMGR activity does not have to be in the same orientation as a nucleic acid sequence encoding a polypeptide exhibiting the activity of a steroid pathway enzyme. The coding nucleic acids can be under the control of different promoters or be in different orientations. For the host plant cell useful in carrying out the steroid compound biosynthesis according to the invention, the minimum that is required is the coding nucleic acids be in the same host cell. As long as the HMGR and a steroid pathway enzyme coding sequences are present in the same host cell, they do not have to be on the same DNA molecule or under the control of the same promoter, nor do they have to be derived from the same vector or construct.

Host cells are useful for making, storing, reproducing or manipulating nucleic acid constructs of the invention. Contemplated host cells are eukaryotic cells, such as yeast or plant cells. Any plant cells can be utilized with the present invention. Some particularly useful agriculturally significant plant cells are canola, soybean, corn, maize, tobacco, cotton, rape, tomato and alfalfa. Other common plant varieties are carrot, barley, *arabidopsis*, guayule and petunia. Prokaryotic host cells containing constructs and/or vectors according to the invention are also contemplated (e.g. *E. coli*).

One embodiment of the invention is a transformed host cell containing inter alia a recombinant construct that encodes both a DNA sequence encoding a polypeptide exhibiting 3-hydroxy-3-methylglutaryl-Coenzyme A reductase enzyme activity and a DNA sequence encoding a steroid pathway enzyme, where the steroid pathway enzyme is as described in detail above. In a preferred embodiment, those coding DNA sequences are operably linked to a promoter and a transcription termination signal sequence. In the coding sense direction of the construct, the components of the construct are operably linked in the 5' to 3' direction as a promoter, the DNA sequence encoding sequence and a transcription termination signal sequence.

Another embodiment of the invention is host cell that has been transformed with a recombinant vector that has such a construct. As discussed herein, in one embodiment of the invention, such a recombinant vector is a plant expression vector. Preferably such a host cell is a plant cell.

Methods of culturing various eukaryotic and prokaryotic cell cultures are well known in the art. The present invention contemplates cell cultures of transformed host cells. Transformed plant cells include transformed protoplasts and other types of host cell intermediates as well as plant cell cultures.

Non-limiting examples of plants that can be used in the practice of the invention include, acacia, alfalfa, aneth, apple, apricot, artichoke, arugula, asparagus, avocado, banana, barley, beans, beet, blackberry, blueberry, broccoli, brussel sprouts, cabbage, canola, cantaloupe, carrot, cassava, cauliflower, celery, cherry, chicory, cilantro, citrus, clementines, coffee, corn, cotton, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, mango, melon, mushroom, nectarine, nut, oat, oil palm, oil seed rape, okra, onion, orange, ornamental plants, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, watermelon, wheat, yam, and zucchini.

Plants particularly attractive for the steroid pathway modifications described herein include those that produce carbon substrates which can be employed for synthesis of these compounds. Non-limiting examples of such plants include various monocots and dicots, including high oil seed plants such as high oil seed *Brassica* (e.g., *Brassica nigra*, *Brassica napus*, *Brassica hirta*, *Brassica rapa*, *Brassica campestris*, *Brassica carinata*, and *Brassica juncea*), soybean (*Glycine max*), castor bean (*Ricinus communes*), cotton, safflower (*Carthamus tinctorius*), sunflower (*Helianthus annuus*), flax (*Linum usitatissimum*), corn (*Zea mays*), coconut (*Cocos nucifera*), palm (*Elaeis guineensis*), oilnut trees such as olive (*Olea europaea*), sesame, and peanut (*Arachis hypogaea*), as well as *Arabidopsis*, tobacco, wheat, barley, oats, amaranth, potato, rice, tomato, and legumes (e.g., peas, beans, lentils, alfalfa, etc.).

Enhancement of sitostanol compound production by the methods discussed herein is expected to result in yields of sitostanol, sitostanol esters, or mixtures thereof in an amount of at least about 57% by weight, preferably from about 57% to about 90% by weight, and more preferably from about 57% to about 65% by weight of the total sterol compounds present in seed oil. Expressed on a seed dry weight basis, sitostanol, sitostanol esters, or mixtures thereof are expected to be present in an amount of at least about 0.08%, preferably from about 0.08% to about 0.8%, and more preferably from about 0.08% to about 0.4% of seed dry weight.

B. Processes of Transformation

A variety of different methods can be employed to introduce transformation/expression vectors into plant protoplasts, cells, callus tissue, leaf discs, meristems, etc., to generate transgenic plants. These methods include, for example, Agrobacterium-mediated transformation, particle gun delivery, microinjection, electroporation, polyethylene glycol-mediated protoplast transformation, liposome-mediated transformation, etc. (reviewed in Potrykus (1991) Ann. Rev. Plant Physiol. Plant Mol. Biol. 42: 205).

In general, transgenic plants comprising cells containing and expressing nucleic acids encoding enzymes facilitating the modifications in sterol compound and tocopherol biosynthesis and accumulation described herein can be produced by transforming plant cells with a DNA construct as described above via any of the foregoing methods; selecting plant cells that have been transformed on a selective medium; regenerating plant cells that have been transformed to produce differentiated plants; and selecting a transformed plant that expresses the enzyme-encoding nucleotide sequence(s) at a level such that the amount of sitosterol, sitosterol esters, sitostanol, sitostanol esters, tocopherol compound(s), and campesterol/campestanol and their esters is within the ranges described herein.

The encoding DNAs can be introduced either in a single transformation event (all necessary DNAs present on the same vector), a co-transformation event (all necessary DNAs present on separate vectors that are introduced into plants or plant cells simultaneously), or by independent transformation events (all necessary DNAs present on separate vectors that are introduced into plants or plant cells independently). Traditional breeding methods can subsequently be used to incorporate the desired combination of enzymes into a single plant, and to produce hybrid progeny of the invention plants.

Specific methods for transforming a wide variety of dicots and obtaining transgenic plants are well documented in the literature (Gasser and Fraley (1989) Science 244: 1293; Fisk and Dandekar (1993) Scientia Horticulturae 55: 5; Christou (1994) Agro Food Industry Hi Tech, p. 17; and the references cited therein).

Apomixis is a genetically controlled method of reproduction in plants where the embryo is formed without union of an egg and a sperm. There are three basic types of apomictic reproduction: 1) apospory where the embryo develops from a chromosomally unreduced egg in an embryo sac derived from the nucleus, 2) diplospory where the embryo develops from an unreduced egg in an embryo sac derived from the megaspore mother cell, and 3) adventitious embryony where the embryo develops directly from a somatic cell. In most forms of apomixis, psuedogamy or fertilization of the polar nuclei to produce endosperm is necessary for seed viability. In apospory, a "nurse" cultivar can be used as a pollen source for endosperm formation in seeds. The nurse cultivar does not affect the genetics of the aposporous apomictic cultivar since the unreduced egg of the cultivar develops parthenogenetically, but makes possible endosperm production.

Apomixis is economically important, especially in transgenic plants, because it causes any genotype, no matter how heterozygous, to breed true. Thus, with apomictic reproduction, heterozygous transgenic plants can maintain their genetic fidelity throughout repeated life cycles. Methods for the production of apomictic plants are known in the art. See, U.S. Pat. No. 5,811,636 and references cited therein which are herein incorporated by reference.

The present invention also encompasses uniform populations of any of the plants discussed herein.

Successful transformation and plant regeneration have been achieved in the monocots as follows: asparagus (Asparagus officinalis; Bytebier et al. (1987) Proc. Natl. Acad. Sci. USA 84: 5345); barley (Hordeum vulgarae; Wan and Lemaux (1994) Plant Physiol. 104: 37); maize (Zea mays; Rhodes et al. (1988) Science 240: 204; Gordon-Kamm et al. (1990) Plant Cell 2: 603; Fromm et al. (1990) Bio/Technology 8: 833; Koziel et al. (1993) Bio/Technology 11: 194); oats (Avena sativa; Somers et al. (1992) Bio/Technology 10: 1589); orchardgrass (Dactylis glomerata; Horn et al. (1988) Plant Cell Rep. 7: 469); rice (Oryza sativa, including indica and japonica varieties; Toriyama et al. (1988) Bio/Technology 6: 10; Zhang et al. (1988) Plant Cell Rep. 7: 379; Luo and Wu (1988) Plant Mol. Biol. Rep. 6: 165; Zhang and Wu (1988) Theor. Appl. Genet. 76: 835; Christou et al. (1991) Bio/Technology 9: 957); rye (Secale cereale; De la Pena et al. (1987) Nature 325: 274); sorghum (Sorghum bicolor; Cassas et al. (1993) Proc. Natl. Acad. Sci. USA 90: 11212); sugar cane (Saccharum spp.; Bower and Birch (1992) Plant J. 2: 409); tall fescue (Festuca arundinacea; Wang et al. (1992) Bio/Technology 10: 691); turfgrass (Agrostis palustris; Zhong et al. (1993) Plant Cell Rep. 13: 1); and wheat (Triticum aestivum; Vasil et al. (1992) Bio/Technology 10: 667; Weeks et al. (1993) Plant Physiol. 102: 1077; Becker et al. (1994) Plant J. 5: 299).

Plant transformation vectors capable of delivering DNAs (genomic DNAs, plasmid DNAs, cDNAs, or synthetic DNAs) encoding plant-derived or other enzymes that affect the biosynthesis and accumulation of sterol compounds and tocopherols in plants for optimizing the pools of sitosterol, sitostanol, esters of either, and tocopherols, and for reducing the levels of campesterol, campestanol, and/or their esters, can be easily designed by art-recognized methods. Various strategies can be employed to introduce these encoding DNAs into plants to produce transgenic plants that biosynthesize and accumulate desirable levels of various sterol compounds and tocopherols, including:

1. Transforming individual plants with an encoding DNA of interest. Two or more transgenic plants, each containing one of these DNAs, can then be grown and cross-pollinated so as to produce hybrid plants containing the two DNAs. The hybrid can then be crossed with the remaining transgenic plants in order to obtain a hybrid plant containing all DNAs of interest within its genome.

2. Sequentially transforming plants with plasmids containing each of the encoding DNAs of interest, respectively.

3. Simultaneously cotransforming plants with plasmids containing each of the encoding DNAs, respectively.

4. Transforming plants with a single plasmid containing two or more encoding DNAs of interest.

5. Transforming plants by a combination of any of the foregoing techniques in order to obtain a plant that expresses a desired combination of encoding DNAs of interest.

Traditional breeding of transformed plants produced according to any one of the foregoing methods by successive rounds of crossing can then be carried out to incorporate all the desired encoding DNAs in a single homozygous plant line (Nawrath et al. (1994) Proc. Natl. Acad. Sci. USA 91: 12760; PCT International Publication WO 93/02187), or to produce hybrid offspring.

In methods 2 and 3, the use of vectors containing different selectable marker genes to facilitate selection of plants containing two or more different encoding DNAs is advantageous. Examples of useful selectable marker genes include those conferring resistance to kanamycin, hygromycin, sulphonamides, glyphosate, bialaphos, and phosphinothricin.

C. Processes of Regeneration

Processes of regeneration of plants from transformed protoplasts are known in the art.

D. Transgenic Plants and Progeny

The present invention contemplates the plants that contain the exogenous constructs according to the present invention, such that a plant comprises at least one transformed plant cell comprising a nucleic acid construct. The nucleic acid construct, as described above has as operably linked components in the 5' to 3' direction, a promoter, a DNA sequence encoding a polypeptide exhibiting 3-hydroxy-3-methylglutaryl-Coenzyme A reductase enzyme activity, and a transcription termination signal sequence. The plant also comprises a nucleic acid construct that has as operably linked components in the 5' to 3' direction, a promoter, a DNA sequence encoding a steroid pathway enzyme, and a transcription termination signal sequence. The steroid pathway enzyme is a squalene epoxidase enzyme, a sterol methyl transferase I enzyme, a sterol C4-demethylase enzyme, a obtusifoliol C14α-demethylase enzyme, a sterol C5-desaturase enzyme, or a sterol methyl transferase II enzyme. In one embodiment, the nucleic acid constructs are recombinant constructs.

In one embodiment of the present invention a transgenic plant can be produced in accordance with the processes discussed elsewhere herein. One method to arrive at the above construct-containing plant is to transform the plant cell with a recombinant vector harboring such a construct. Other methods involve direct transfer of the exogenous construct into the plant cell. The methods of arriving at a plant cell having exogenous nucleic acids are well known in art and are applicable to the present invention. In one embodiment, the nucleic acid constructs are recombinant constructs. In a preferred embodiment, the recombinant vector is a plant expression vector.

The present invention contemplates a plant, the genome of which comprises introduced DNA. That introduced DNA has at least two components. One component is a DNA encoding a 3-hydroxy-3-methylglutaryl-Coenzyme A reductase enzyme. The other component is DNA encoding a steroid pathway enzyme that is a squalene epoxidase enzyme, a sterol methyl transferase I enzyme, a sterol C4-demethylase enzyme, a obtusifoliol C14α-demethylase enzyme, a sterol C5-desaturase enzyme, or a sterol methyl transferase II enzyme. The storage organs, preferably seeds, of such a plant contain an elevated level of total accumulated sterol, compared to storage organs of an otherwise identical plant, the genome of which does not comprise the introduced DNA. The introduced DNAs are operatively linked to regulatory signals, preferably that cause seed-specific expression of said introduced DNAs. The seeds of such a plant contain a reduced level of squalene, cycloartenol, 24-methylene cycloartenol, obtusifoliol, stigmasta-7-enol, or campesterol compared to the seeds of an otherwise identical plant or compared to a plant comprising an introduced DNA encoding a HMG CoA reductase enzyme without the contemplated steroid pathway enzyme.

Also contemplated is a plant with introduced DNA, as described above, that produces seed having an elevated level of a steroid pathway product, compared to a corresponding transgenic or non-transgenic plant that does not contain said introduced DNA.

The invention also contemplates a plant comprising introduced DNA encoding (i) an HMGR enzyme and (ii) a squalene epoxidase enzyme, a sterol methyl transferase I enzyme, a sterol C4-demethylase enzyme, a obtusifoliol C14α-demethylase enzyme, a sterol C5-desaturase enzyme, a sterol methyl transferase II enzyme, or mixtures thereof, wherein said plant that produces a storage organ (preferably a seed) having an elevated level of a sterol pathway product compared to a corresponding transgenic or non-transgenic plant that does not contain said introduced DNA.

The invention also contemplates a plant having introduced DNA, as described above, that produces a storage organ (preferably a seed) having a reduced level of squalene, cycloartenol, 24-methylene cycloartenol, obtusifoliol, stigmasta-7-enol, campesterol, or mixtures thereof, compared to a corresponding transgenic plant that comprises introduced DNA encoding an HMGR enzyme but that does not contain introduced DNA encoding a squalene epoxidase enzyme, a sterol methyl transferase I enzyme, a sterol C4-demethylase enzyme, a obtusifoliol C14α-demethylase enzyme, a sterol C5-desaturase enzyme, a sterol methyl transferase II enzyme, or mixtures thereof.

For any of the above plants, an embodiment is contemplated wherein the introduced nucleic acid has regulatory signals that cause seed-specific expression of said introduced DNAs.

The progeny of the above-described plants are also considered an embodiment of the present invention, as are plant cells or transformed plant cells. Cultures of those plant cells are also contemplated. Plants produced from seeds having introduced DNA are also embodiments of the present invention.

A further embodiment of the present invention is a method of producing a plant that accumulates an elevated level of sterol pathway products, in seed of said plant compared to seed of a corresponding plant comprising no introduced DNA encoding a peptide, polypeptide, or protein that affects the biosynthesis and accumulation of a sterol pathway product, comprising sexually crossing a plant having introduced nucleic acid with the corresponding plant having no introduced DNA. Plants, including apomictic plants produced by this method are contemplated.

Another embodiment is a seed resulting from a cross of a plant having introduced DNA, described above, with a nurse cultivar. Also contemplated are seeds of any of the above-described plants. Also part of the present invention plant parts, other than a seed of any of the above-described plants.

Uniform populations of the above-described plants are also contemplated.

E. Stability of Transgene Expression

As several overexpressed enzymes may be required to produce optimal levels of substrates for the biosynthesis of sterol compounds and tocopherols, the phenomenon of co-suppression may influence transgene expression in transformed plants. Several strategies can be employed to avoid this potential problem (Finnegan and McElroy (1994) *Bio/Technology* 12: 883).

One commonly employed approach is to select and/or screen for transgenic plants that contain a single intact copy of the transgene or other encoding DNA (Assaad et al. (1993) *Plant Mol. Biol.* 22: 1067; Vaucheret (1993) *C.R. Acad. Sci. Paris, Science de la vie/Life Sciences* 316: 1471; McElroy and Brettell (1994) *TIBTECH* 12: 62). Agrobacterium-mediated transformation technologies are preferred in this regard.

Inclusion of nuclear scaffold or matrix attachment regions (MAR) flanking a transgene has been shown to increase the level and reduce the variability associated with transgene expression in plants (Stief et al. (1989) *Nature* 341: 343; Breyne et al. (1992) *Plant Cell* 4: 463; Allen et al. (1993) *Plant Cell* 5: 603); Mlynarova et al. (1994) *Plant Cell* 6: 417; Spiker and Thompson (1996) *Plant Physiol.* 110: 15). Flanking a transgene or other encoding DNA with MAR elements may overcome problems associated with differential base composition between such transgenes or encoding DNAs and integrations sites, and/or the detrimental effects of sequences adjacent to transgene integration sites.

The use of enhancers from tissue-specific or developmentally-regulated genes may ensure that expression of a linked transgene or other encoding DNA occurs in the appropriately regulated manner.

The use of different combinations of promoters, plastid targeting sequences, and selectable markers for introduced transgenes or other encoding DNAs can avoid potential problems due to trans-inactivation in cases where pyramiding of different transgenes within a single plant is desired.

Finally, inactivation by co-suppression can be avoided by screening a number of independent transgenic plants to identify those that consistently overexpress particular introduced encoding DNAs (Register et al. (1994) *Plant Mol. Biol.* 25: 951). Site-specific recombination in which the endogenous copy of a gene is replaced by the same gene, but with altered expression characteristics, should obviate this problem (Yoder and Goldsbrough (1994) *Bio/Technology* 12: 263).

Any of the foregoing methods, alone or in combination, can be employed in order to insure the stability of transgene expression in transgenic plants of the present invention.

F. Hybrid Plants

The invention contemplates a plant having introduced DNA encoding an HMGR and at least one of the six steroid pathway enzymes, as described in detail above. It is contemplated that a transgenic plant having DNA encoding an HMGR, as is known in the art, might be crossed with a transgenic plant having DNA encoding at least one of the six steroid pathway enzymes.

Also contemplated as a hybrid plant according to the invention is a plant that is a hybrid of a transgenic plant having introduced DNA encoding an HMGR and at least one of the six steroid pathway enzymes wherein the plant has been hybridized with another strain, yet still retains the introduced DNA.

G. Storage Organs

The term "storage organ" as used herein, refers to the seeds, fruits or vegetable parts of a plant. Most often the seed is important for use in the present invention. However, there are consumable embodiments, such as with potatoes or carrots, where the vegetable parts are preferred.

A contemplated embodiment of the present invention is a storage organ comprising at least one transformed host cell. The transformed host cell has at a minimum a construct according the invention as described above. Also contemplated are the embodiments when the construct has plant promoters, when the construct is recombinant, when the construct is part of a vector, and when the vector is a plant expression vector.

The invention contemplates a transgenic plant seed transformed with a vector comprising a DNA segment that encodes a polypeptide having HMG-CoA reductase activity, and a DNA segment that encodes a polypeptide having a steroid pathway enzyme, wherein the transgenic plant seed is capable of germinating into a transgenic plant that over-accumulates steroid pathway products relative to a native, non-transgenic plant of the same strain; and mutants, recombinants, genetically engineered derivatives thereof and hybrids derived therefrom, wherein said mutants, recombinants, genetically engineer derivatives thereof and hybrids derived therefrom maintain the ability to overaccumulate steroid pathway products.

Seed from a transgenic plant is grown in the field or greenhouse, and resulting sexually mature transgenic plants are self-pollinated to generate true breeding plants. The progeny from these plants become true breeding lines that are evaluated for steroid compound or squalene accumulation, preferably in the field under a range of environmental conditions.

The commercial value of a transgenic plant with increased steroid compound or squalene accumulation is enhanced if many different hybrid combinations are available for sale. The user typically grows more than one kind of hybrid based on such differences as time to maturity, standability or other agronomic traits. Additionally, hybrids adapted to one part of a country are not necessarily adapted to another part because of differences in such traits as maturity, disease and herbicide resistance. Because of this, steroid compound or squalene accumulation is preferably bred into a large number of parental lines so that many hybrid combinations can be produced.

Adding an enhanced steroid compound or squalene accumulation trait to an agronomically elite line is accomplished by a variety of techniques well known to those of skill in the art. For example, parent transgenic plants that are either homozygous or contain a single independent segregatable gene that encodes a polypeptide having HMG-CoA activity and thus for enhanced sterol or squalene accumulation are crossed with lines having other desirable traits such as herbicide resistance (U.S. Pat. No. 4,761,373) produce hybrids. Preferably, transgenic plants homozygous for enhanced sterol or squalene accumulation are used to generate hybrids.

For example, a transgenic plant homozygous for enhance sterol accumulation is crossed with a parent plant having other desired traits. The progeny, which are heterozygous or independently segregatable for enhanced sterol accumulation and their other desired traits. The backcrossing of progeny with the parent may have to be repeated more than once to obtain a transgenic plant that possesses all desirable traits.

Alternatively, transgenic plants with an enhanced sterol or squalene accumulation trait are made multiply transgenic by introducing into such plants other genes that encode and express other desirable traits, or are mutated as with radiation, e.g. X-rays or gamma rays, as in U.S. Pat. No. 4,616,099, whose disclosures are incorporated by reference. Thus, the present invention also contemplates mutants and genetically engineered derivatives of transgenic plants having enhanced sterol or squalene accumulation.

VI. Harvest

Besides seed, elevated levels of sterols, phytosterols, such as sitosterol, phytostanols, such as sitostanol, and esters thereof, can be found in other parts of the plants encompassed herein. While the seed-specific promoters contemplated in the present invention function preferentially in seed tissues, expression in other plant parts can be expected, depending upon the specificity of the particular promoter. In this case, promoters functional in plant plastids are less desirable than those primarily directing expression in the cellular cytosol, though it may be desirable to use promoters to drive expression of the recombinant constructs or expression cassettes disclosed herein in tissues and organs other than seeds. For example, elevated levels of sterols, phytosterols, etc., can be expected in fruits, as well as vegetable parts of plants other than seeds. Vegetable parts of plants include, for example, pollen, inflorescences, terminal buds, lateral buds, stems, leaves, tubers, and roots. Thus, the present invention also encompasses these and other parts of the plants disclosed herein that contain elevated levels of desirable phytosterol, and phytostanol.

Of course, a significant effect of introducing into plants the coding sequences disclosed herein will be on the content of phytosterols/phytostanols and their esters of seed oil. Therefore, additional aspects of the present invention include oil obtainable from the seed of the plants described herein, and methods for producing such plants and oil. Methods for extracting and processing seed oils are well known in the art.

Oils produced by the cells, plants, and methods disclosed herein are superior in phytosterol/phytostanol composition to conventional oils in a variety of ways. Oil of the present invention can contain an elevated level of at least one sterol, at least one phytosterol, at least one phytosterol ester, at least one phytostanol, at least one phytostanol ester, or mixtures thereof. Preferred compounds include sitosterol, sitostanol, and their esters.

Oil from seed of plants containing and expressing introduced DNA encoding a sterol methyltransferase II enzyme advantageously contains a reduced level of campesterol, at least one campesterol ester, campestanol, at least one campestanol ester, or mixtures thereof. The sterol methyltransferase II-encoding DNA can be introduced alone, or in combination with other introduced DNA sequences encoding enzymes affecting the biosynthesis of steroid compounds as discussed herein. Campesterol/campestanol and their esters are considered to be undesirable because they are readily absorbed in the intestine, while their safety in the blood is unknown. Employing the plants and methods disclosed herein, one can obtain seed oil comprising about 0% to about 19%, preferably about 0% to about 12%, more preferably about 5% to about 9% campesterol, at least one campesterol ester, campestanol, at least one campestanol ester, or mixtures thereof by weight of the total sterol compounds of the oil. (The levels of these compounds are difficult to express on a percent seed dry weight basis because different seeds contain different percentages of these compounds expressed on this basis) These values represent a reduction of about 10% to about 100% in the amount of these compounds compared to those in conventional oils.

Introduction into plant cells of the enzyme-encoding DNA sequences discussed above modifies the biosynthesis of sterol compounds carried out by the methods, and in the cells, plants, and seeds, disclosed herein. In particular, the expression of an HMG CoA reductase in conjunction with DNA sequences for a steroid pathway enzyme is expected to result in alteration of the steroid pathway product profiles in oil as the enhanced steroid pathway throughput produces substrates for the enhanced enzyme activity. The novel phytostanol ester compositions, e.g., sitostanol ester compositions, thus produced constitute another aspect of the present invention.

A. Harvest of Steroid Compounds

Methods for the derivation of steroid compounds from cells are well known in the art. The invention contemplates the recovery of biosynthesized steroid compounds from the leaves and/or stems of plants, from plant seeds, from plant's vegetative organs, from callouses, and from cell cultures of plants, yeasts or eukaryotic cells.

Different sources of steroid compounds are preferred for various plants. For use as a food or a food component as discussed later, the steroid compounds need not be isolated or purified to 100 percent purity. Steroid compound-enriched plants may be utilized directly.

For example, from tobacco or *Arabidopsis*, it may be preferable to extract a pulp of the leaves and stems. From tomato, potato, or corn, it may be preferable to use the tomato, potato or corn in the form of the familiar storage organs that are typically consumed either directly, or a derivative thereof, such as tomato paste, potato flakes, vegetable oil and many more that are well known in the food science arts.

If desired, after cultivation, the transgenic plant is harvested to recover the sterol or squalene product. This harvesting step can consist of harvesting a callus culture, the entire plant, or only the leaves, or roots of the plant. This step can either kill the plant or, if only a non-essential portion of the transgenic plant is harvested, can permit the remainder of the plant to continue to grow.

In preferred embodiments, this harvesting step further comprises the steps of:

(i) homogenizing at least a sterol-containing or a squalene-containing portion of the transgenic plant to produce a plant pulp and using the sterol- or squalene-containing pulp directly, as in dried pellets or tablets as where an animal food is contemplated; or (ii) extracting the squalene or sterol(s) from the plant pulp with an appropriate solvent such as an organic solvent or by supercritical extraction [Favati, et al., *J. Food Sci.* 53:1532 (1988) and the citations therein] to produce a sterol- or squalene-containing liquid solution or suspension; and (iii) isolating the squalene or sterol(s) from the solution or suspension.

At least a portion of the transgenic plant is homogenized to produce a plant pulp using methods well known to one skilled in the art. This homogenization can be done manually, by a machine, or by a chemical means as long as the transgenic plant portions are broken up into small pieces to produce a plant pulp. This plant pulp consists of a mixture of squalene or the sterol of interest, residual amounts of precursors, cellular particles and cytosol contents. This pulp can be dried and compressed into pellets or tablets and eaten or otherwise used to derive the benefits, or the pulp can be subjected to extraction procedures.

The sterol or squalene can be extracted from the plant pulp produced above to form a sterol- or -squalene-containing solution or suspension. Such extraction processes are common and well known to one skilled in this art. For example, the extracting step can consist of soaking or immersing the plant pulp in a suitable solvent. This suitable solvent is capable of dissolving or suspending the squalene or sterol present in the plant pulp to produce a sterol- or squalene-containing solution or suspension. Solvents useful for such an extraction process are well known to those skilled in the art and included several organic solvents and combinations thereof such as methanol, ethanol, isopropanol, acetone, acetonitrile, tetrahydrofuran (THF), hexane, and chloroform as well as water-organic solvent mixtures. A vegetable oil such as peanut, corn, soybean and similar oils can also be used for this extraction as can steam distillation.

A whole plant or callus culture with an added, exogenous structural gene for a polypeptide having HMG-CoA reductase activity is grown under suitable conditions for a period of time sufficient for squalene or sterols to be synthesized and accumulated. The sterol-squalene-containing plant cells, preferably in dried form, are then lysed chemically or mechanically, and the squalene or sterol is extracted from the lysed cells using a liquid organic solvent or steam distillation, as described before, to form a sterol- or squalene-containing liquid solution or suspension by usual means such as chromatography.

The squalene or sterol is isolated from the solution or suspension produced above using methods that are well known to those skilled in the art of squalene and sterol isolation. These methods include, but are not limited to, purification procedures based on solubility in various liquid media, chromatographic techniques such as column chromatography and the like.

The invention contemplates a sitosterol or sitostanol ester composition extracted from the seed of a transgenic plant of the invention. The invention also contemplates such a sitosterol or sitostanol ester wherein an esterifying fatty acid has 2 to 22 carbon atoms in the main chain.

B. Harvest of Oil

The novel biosynthetic composition of the oil in the transgenic plants is contemplated. Thus, the present invention contemplates oil containing at least one sterol pathway product, extracted from seed of a described transgenic plant. Preferably, sitosterol, at least one sitosterol ester, or mixtures thereof, comprise at least about 50% by weight of the total sterol compounds of the oil. Preferably, sitosterol, at least one sitosterol ester, or mixtures thereof, comprise at least about 0.08% of the dry weight of a contemplated seed. Preferably, the oil has a reduced amount of squalene, cycloartenol, 24-methylene cycloartenol, obtusifoliol, stigmasta-7-enol, campesterol, or mixtures thereof, compared to oil from a corresponding transgenic plant that does not contain introduced DNA encoding a squalene epoxidase enzyme, a sterol methyl transferase I enzyme, a sterol C4-demethylase enzyme, a obtusifoliol C14α-demethylase enzyme, a sterol C5-desaturase enzyme, a sterol methyl transferase II enzyme, or mixture thereof, and that reduction is in the range of from about 10% to about 100%.

Oil is extracted from transgenic plant seeds of the present invention by method well known in the art. By way of example, oil can be extracted from plant seeds using extraction methods set forth above for harvesting sterols and squalene from transgenic plants. Alternatively, oil can be extracted from transgenic plant seeds by usually used methods for obtaining seed oils such as by crushing he seeds to produced a pulp and then pressing the pulp to obtain oil. The pulp can also be extracted with appropriate solvents (e.g. benzene) to obtain the oil. *Industrial Chemistry: A Manual for the Student and Manufacturer*, ed. By A. Rogers and A. B. Aubert, D. Van Nostrand Co., New York, pages 547-548 (1912).

C. Uses of Oil

As discussed in the "Description of Related Art," phytostanols such as sitostanol are beneficial for lowering serum cholesterol (Ling et al. (1995) *Life Sciences* 57: 195-206) and preventing cardiac disease. Tocopherols act as antioxidants, and play a major role in protecting cells from damage caused by free radicals (Halliwell (1997) *Nutrition Review* 55: 44-60). As the amount of sitostanol in conventional vegetable and bran oils is low relative to that of other sterol compounds, the oils of the present invention are particularly useful for reducing the concentration of low density lipoprotein cholesterol in plasma.

Thus, further aspects of the present invention include the following:

Cholesterol-lowering compositions comprising the oils and sitostanol ester compositions disclosed herein. Such cholesterol-lowering compositions can take the form of, or be used in, foods, food products, processed foods, food ingredients, food additive compositions, or dietary supplements that contain oils and/or fats. Non-limiting examples include margarines; butters; shortenings; cooking oils; frying oils; dressings, such as salad dressings; spreads; mayonnaises; and vitamin/mineral supplements. Patent documents relating to such compositions include U.S. Pat. Nos. 4,588,717 and 5,244,887, and PCT International Publication Nos. WO 96/38047, WO 97/42830, WO 98/06405, and WO 98/06714. Additional non-limiting examples include toppings; dairy products such as cheese and processed cheese; processed meat; pastas; sauces; cereals; desserts, including frozen and shelf-stable desserts; dips; chips; baked goods; pastries; cookies; snack bars; confections; chocolates; beverages; unextracted seed; and unextracted seed that has been ground, cracked, milled, rolled, extruded, pelleted, defatted, dehydrated, or otherwise processed, but which still contains the oils, etc., disclosed herein.

Food additive compositions of the present invention can be made by a method comprising obtaining oil containing a phytostanol or phytostanol ester selected from sitostanol, at least one sitostanol ester, or mixtures thereof, from cultured cells, or seeds of a plant, of the present invention, and evenly distributing the oil or desired phytostanol compound in finely divided form throughout the food product or food additive composition to which it is added by dissolution or by suspension in an emulsion. For example, the oil or phytostanol compound can be dissolved in an edible solubilizing agent, or can be mixed with an edible solubilizing agent, an effective amount of a dispersant, and optionally, an effective amount of an antioxidant. Examples of useful edible solubilizing agents include, but are not limited to, monoglycerides, diglycerides, triglycerides, vegetable oils, tocopherols, alcohols, polyols, or mixtures thereof. Examples of useful antioxidants include, but are not limited to, tocopherols, such as α-tocopherol, ascorbic acid, inexpensive synthetic antioxidants, and mixtures thereof. Effective carriers for preparing emulsions or suspensions include water, alcohols, polyols, other edible compounds in which the oil or phytostanol compound is soluble or insoluble, and mixtures thereof. Examples of useful dispersants include, but are not limited to, lecithin, other phospholipids, sodium lauryl sulfate, fatty acids, salts of fatty acids, fatty acid esters, other detergent-like molecules, and mixtures thereof. Alternatively, the food additive composition can be made by a method comprising obtaining oil containing at least one tocopherol, and a phytostanol or phytostanol ester selected from sitostanol, at least one sitostanol ester, and mixtures thereof, from cultured cells, or seed of a plant, of the present invention, and mixing the oil with an edible solubilizing agent and an effective amount of a dispersant. Again, the edible solubilizing agent can include, but is not limited to, monoglycerides, diglycerides, triglycerides, vegetable oils, tocopherols, alcohols, polyols, or mixtures thereof, and the dispersant can include, but is not limited to, lecithin, other phospholipids, sodium lauryl sulfate, fatty acids, salts of fatty acids, fatty acid esters, other detergent-like molecules, and mixtures thereof.

The cholesterol-lowering compositions can also take the form of pharmaceutical compositions comprising a cholesterol-lowering effective amount of the oils or sitostanol ester compositions disclosed herein, along with a pharmaceutically acceptable carrier, excipient, or diluent. These pharmaceutical compositions can be in the form of a liquid or a solid. Liquids can be solutions or suspensions; solids can be in the form of a powder, a granule, a pill, a tablet, a gel, or an extrudate. U.S. Pat. No. 5,270,041 relates to sterol-containing pharmaceutical compositions.

Any of the foregoing cholesterol-lowering compositions can be used alone or in combination in methods to lower the risk of developing an elevated plasma concentration of low density lipoprotein cholesterol, to lower the plasma concentration of low density lipoprotein cholesterol, or to treat or prevent an elevated plasma concentration of low density lipoprotein cholesterol. Such methods comprise orally administering to a human or animal subject an effective amount of cholesterol-lowering composition. What constitutes an effective amount of cholesterol-lowering composition can be determined empirically, and depends in part on a variety of factors, including the age, weight, sex, diet, general medical condition of the subject, and the severity of hypercholesterolemia. Subjects undergoing treatment with the cholesterol-lowering combinations disclosed herein can be monitored by routine measurement of serum cholesterol levels to determine the effectiveness of therapy. Continuous analysis of the data obtained in this way permits modification of the treatment regimen during therapy so that optimal effective amounts of the cholesterol-lowering compositions of this invention are administered, and so that the duration of treatment can be determined as well. In this way, the treatment regimen/dosing schedule can be rationally modified over the course of treatment so as to achieve the lowest cholesterol-lowering effective amount of the present compositions which results in satisfactory anti-cholesterolemic effectiveness, and so that administration of these compositions is continued only so long as is necessary to successfully treat this condition. In general, an effective amount of a cholesterol-lowering composition of the present invention in the form of a phytostanol- or phytostanol ester-containing composition is in the range of from about 0.1 gm/day to about 4.5 gm/day. By way of example, a phytostanol ester composition, for example a sitostanol ester composition, can be administered in an amount in the range of from about 0.1 gm/day to about 4.5 gm/day, preferably from about 1 gm/day to about 4.5 gm/day, more preferably from about 2 gm/day to about 4.5 gm/day. A phytostanol composition, for example a sitostanol composition, can be administered in an amount in the range of from about 0.1 gm/day to about 3 gm/day, preferably from about 1 gm/day to about 3 gm/day, more preferably from about 2 gm/day to about 3 gm/day.

The cholesterol-lowering compositions of the present invention can be administered daily to patients in accordance with a number of different regimens. Fundamentally, these compositions should be administered in a cholesterol-lowering effective amount for a period of time effective to exert their anti-hypercholesterolemic preventing, reducing, or reversing action. Administration of the present cholesterol-lowering compositions should be continued until the hypercholesterolemic condition has been controlled or eliminated.

Another method encompassed by the present invention is that of achieving or improving effective absorption of sitostanol into a host, comprising producing at least one sitostanol ester by any of the methods disclosed herein, and administering this sitostanol ester to a host, which can be a human or animal. The sitostanol ester can be administered by a route selected from oral route, parenteral route, or topical route. The dose, which can be administered daily, can be up to about 10 milligrams of the sitostanol ester per kilogram of body weight. U.S. Pat. No. 5,202,045 relates to the use of stanol fatty acid esters to reduce serum cholesterol.

Also envisioned are plants which in addition to having increased levels of phytosterols and phytostanols due to the presence of constructs comprising sequences encoding 3-hydroxy-3-methylglutaryl-Coenzyme A reductase and at least one other sterol synthesis pathway enzyme, have increase levels of tocopherol due to the presence of constructs comprising sequences allowing the overexpression of enzymes in the tocopherol biosynthetic pathway.

Tocopherol levels vary in different plants, tissues, and developmental stages, indicating a highly regulated biosynthetic pathway. The production of homogentisic acid by p-hydroxyphenylpyruvate dioxygenase is likely to be a regulatory point for bulk flow through the pathway because of irreversible enzyme action and because homogentisic acid production is the first committed step in tocopherol biosynthesis (Norris et al., 1995, *Plant Cell* 7: 2139-2149). The other key regulatory step in tocopherol biosynthesis is the availability of the phytylpyrophosphate pool. Feeding studies (Furuya et al., 1987, *Phytochem.*, 26: 2741-2747) in safflower callus culture demonstrated 1.8-fold and 18-fold increases in tocopherol synthesis by feeding homogentisate and phytol, respectively. In meadow rescue leaf, vitamin E increases in the initial phase of foliar senescence when phytol is cleaved off from the chlorophylls and when free phytol is available (Peskier et al., 1989, *J. Plant Physiol.* 135: 428-432). These reports suggest tight coupling of tocopherol biosynthesis to the availability of homogentisic acid and phytol.

Transformation of plants with nucleic acid constructs that increase the biosynthetic activity of the tocopherol pathway can lead to increased production of particular tocopherol isomers, for example, α-tocopherol, are known in the art and can be found, for example, in PCT International publication WO 00/61771 which is incorporated herein by reference. Formation of α-tocopherol from other tocopherols occurs due to S-adenosylmethionine (SAM)-dependent methylases such as γ-tocopherol methyl transferase. Overexpression of methyl transferases in combination with 3-hydroxy-3-methylglutaryl-Coenzyme A reductase and at least one other sterol synthesis pathway enzyme as described herein is also contemplated in the present methods. Thus, any of the DNAs encoding enzymes of the tocopherol biosynthetic pathway, discussed above, are useful in the present invention. Transformation of plants with an early tocopherol biosynthesis gene is sufficient to produce plants having an elevated level of tocopherols. By "early tocopherol biosynthesis gene" is meant DNA encoding geranylgeranylpyrophosphate synthase, geranylgeranylpyrophosphate hydrogenase, 4-hydroxyphenylpyruvate dioxygenase, and phytyl/prenyl transferase. DNA encoding enzymes active in later steps of tocopherol biosynthesis ("secondary tocopherol biosynthesis genes") can be expressed to enhance carbon flux through the tocopherol pathway even further, and to produce specific tocopherol isomers. In this way, the tocopherol biosynthetic pathway can be modified to enhance production of any tocopherol compound of interest, such as α-tocopherol. As noted above, a variety of sources are available for the early tocopherol biosynthesis genes (and other tocopherol biosynthesis genes), and a gene from any of these sources can be utilized. If co-suppression occurs when a plant gene native to the target host plant is used to increase expression of a particular enzyme, a coding sequence from another source can be used as an alternative.

Preferred genes for introduction into plants to alter tocopherol quantity/quality include 3-deoxy-D-arabino-heptulosonate-7-P synthase (DAHP synthase), shikimate kinase, either or both of the prephenate dehydrogenases, 1-deoxy-d-xylulose 5-phosphate synthetase (DXS), 1-deoxy-d-xylulose 5-phosphate reductoisomerase (DXR), 4-diphosphocytidyl-2C-methyl-d-erythritol synthase (YgbP), 4-diphosphocytidyl-2C-methyl-d-erythritol kinase (YchB), 2C-methyl-d-erythritol 2,4-cyclodiphosphate synthase (YgbB), the gene product of GcpE, LytB (Altincicek et al., 2001, *J. Bacteriol.*, 183:2411-2416; Altincicek et al., 2001, *J. Immunol.*, 166: 3655-3658; Campos et al., 2001, *FEBS Lett.*, 488:170-173), geranylgeranylpyrophosphate synthase (GGPPS), geranylgeranylpyrophosphate hydrogenase (GGH), phytyl/prenyltransferase (PPT), 4-hydroxy-phenylpyruvate dioxygenase (HPPD), 2-methyl-6-phytylplastoquinol tocopherol methyltransferase I (MTI), tocopherol cyclase, γ-tocopherol methyltransferase (GMT) a plant slr 1736 gene (see Cyanobase http://www.kazusa.or.jp/cyanbase), a plant slr 1737 gene (see Cyanobase http://www.kazusa.or.jp/cyanbase), an ATPT2 gene (Smith et al., *Plant J.,* 11:83-92, 1977), and an AANT1 gene (Saint Guily et al., *Plant Physiol.,* 100:1069-1071, 1992).

4-hydroxy-phenylpyruvate dioxygenase and geranylgeranylpyrophosphate hydrogenase will increase the homogentisate and phytol pools, respectively. Enzymes that control fluxes through pathways are well known to be regulated in higher organisms such as plants. Therefore, 4-hydroxyphenylpyruvate dioxygenase and geranylgeranylpyrophosphate hydrogenase genes of microbial origin which are not subject to regulation in plants, or those from higher organisms (plants, algae, fungi, etc.) that are deregulated, are especially attractive in this regard. A non-limiting example is the microbial enzyme 4-amino-4-deoxyprephenate dehydrogenase (TyrA from *Erwinia herbicola*) which can replace prephenate aminotransferase, arogenate dehydrogenase and aminotransferase. Overexpression of enzymes such as 3-deoxy-arabino-heptulosonate 7-P (DAHP) synthase, prephenate dehydrogenase, and shikimate kinase would lead to increases in the levels of homogentisate. DNA encoding any of the tocopherol biosynthetic enzymes discussed herein can be introduced alone or in various combinations to enhance tocopherol quantity and/or alter tocopherol quality. When introduction of multiple enzymes is desirable, preferred combinations include, but are not limited to, 4-hydroxyphenylpyruvate dioxygenase (HPPD) plus geranyl geranylpyro-phosphate hydrogenase (GGH), geranylgeranylpyrophosphate synthase (GGPP synthase) plus geranylgeranylpyrophosphate hydrogenase (GGH), 4-amino-4-deoxyprephenate dehydrogenase (TyrA) plus phytylprenyltransferase (PPT), geranylgeranylpyro-phosphate hydrogenase (GGH) plus phytylprenyltransferase (PPT), geranylgeranylpyrophosphate synthase (GGPP synthase) plus phytylprenyltransferase (PPT), 2-methyl-6-phytylplastoquinol tocopherol methyltransferase I (MTI) plus phytylprenyltransferase (PPT), or 2-methyl-6-phytylplastoquinol tocopherol methyltransferase I (MTI), phytylprenyltransferase (PPT), 4-hydroxyphenylpyruvate dioxygenase (HPPD) and geranylgeranylpyrophosphate synthase (GGPP synthase).

Plants characterized by increase levels of sterol and tocopherol production can be produced by transforming plant cells or tissues genetically altered for increased sterol production by the methods described herein with additional nucleic acid constructs encoding tocopherol biosynthetic enzymes. Introduction of constructs encoding tocopherol pathway enzymes can be accomplished using standard methods in molecular biology such as those described herein or those described in PCT International Publication WO 00/61771. Introduction of constructs encoding 3-hydroxy-3-methylglutaryl-Coenzyme A reductase, at least one other sterol synthesis pathway enzyme, and at least one tocopherol synthesis pathway enzyme can be accomplished in a single transformation or in a series of transformations. For example, and without limitation, plant cells transformed with constructs encoding 3-hydroxy-3-methylglutaryl-Coenzyme A reductase, at least one other sterol synthesis pathway enzyme as described herein could be selected and then further transformed with additional constructs encoding one or more tocopherol synthesis pathway enzymes and in particular S-adenosylmethionine-dependent γ-tocopherol methyltransferase enzyme. Successfully transformed cells can then be selected and used to regenerate plants having increased levels of phytosterols and/or phytostanols as well as increased levels of tocopherol. Plants produced can then be "selfed", a technique well known in the art, to produce uniform populations of plants.

Alternatively, plants characterized by increased levels of tocopherols and phytosterols and/or phytostanols can be produced by traditional plant breeding methods. For example, plants transformed with nucleic acid constructs encoding 3-hydroxy-3-methylglutaryl-Coenzyme A reductase and at least one other sterol synthesis pathway enzyme can be sexually crossed with high tocopherol plants. Any plant transformed to produce increased levels of tocopherols and in particular α-tocopherols can be used. Non-limiting examples include plants produced by the methods described above and in PCT International publication WO 00/61771. If desired, the plants produced can be selfed to produce homozygous, uniform populations of plants.

Seed obtained from the transgenic, progeny, hybrid, etc., plants disclosed herein can be used in methods for obtaining oil containing phytosterols, phytosterol esters, phytostanols, phytostanol esters, or mixtures thereof along with tocopherols employing extraction and processing procedures known in the art. Note, in this regard, Kochhar (1983) *Prog. Lipid Res.* 22: 161-188. Alternatively, seeds with increased levels of tocopherols and phytosterols, phytosterol esters, phytostanols, phytostanol esters, or mixtures thereof; or fruits and vegetables with increased levels of tocopherols and phytosterols, phytosterol esters, phytostanols, phytostanol esters, or mixtures thereof, can be used directly.

Tocopherols and phytosterols and/or phytostanols can then be obtained from deodorized distillates of oil seed extracts and in particular soybean oil extracts. Such deodorized distillates are expected to contain increased levels of both tocopherols and phytosterols and/or phytostanol extracts. Oil extracts from plants and seed of the present invention are particularly valuable in that they allow the production of high sterol/tocopherol oils in a single process thus resulting in reduced purification costs, processing time and waste stream. Methods for the isolation of tocopherols and sterols from plant oils are well known in the art and can be found, for example, in U.S. Pat. Nos. 4,454,329; 5,097,012; 5,594,437; and 5,981,781.

EXAMPLES

The following examples are intended to provide illustrations of the application of the present invention. The following examples are not intended to completely define or otherwise limit the scope of the invention.

Example 1

Enhancement of Phytosterol Content in Seeds of Transgenic Plants by Seed-Specific Overexpression of Full-Length HMG-CoA Reductase (HMGR)

Figure 4:
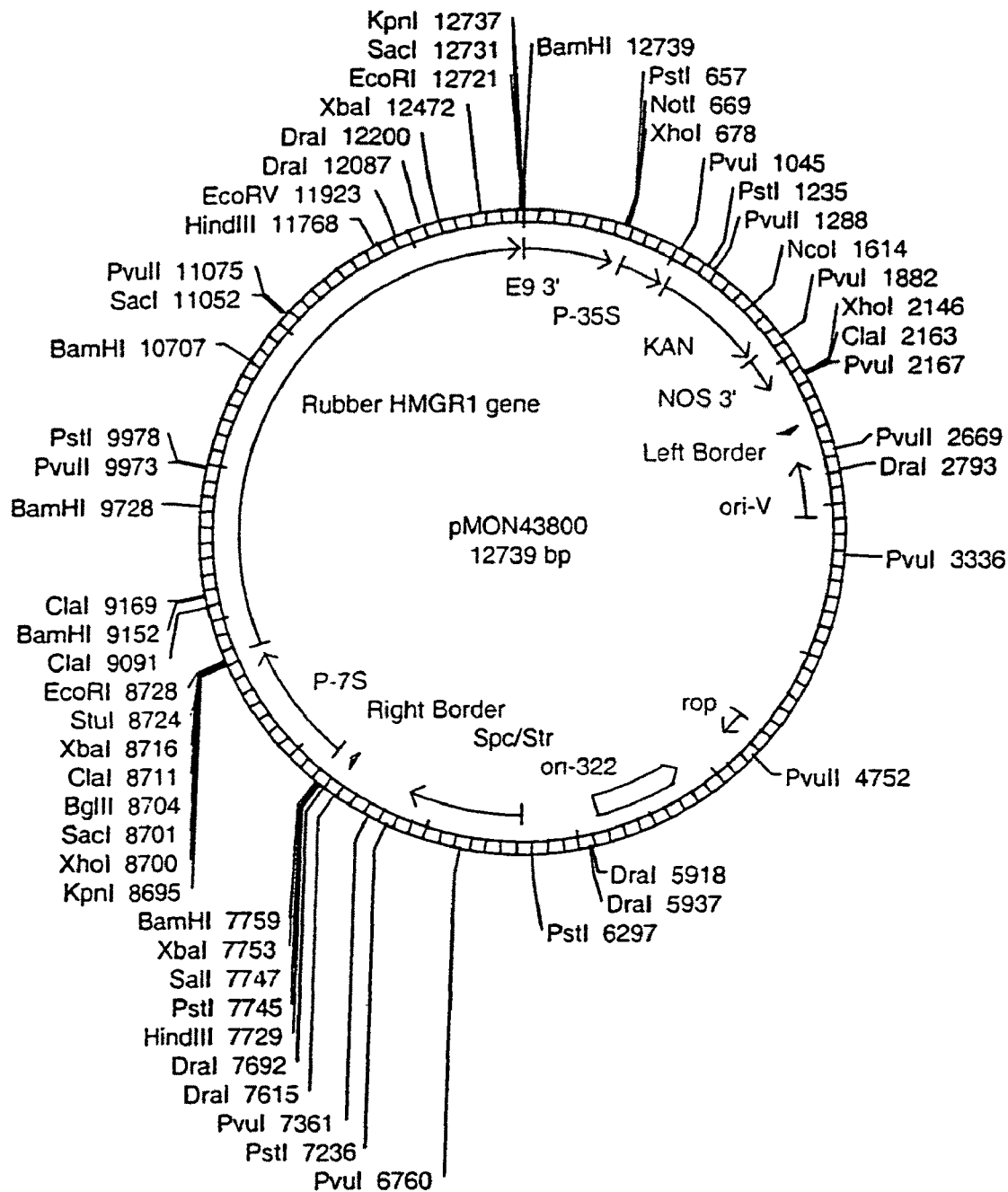
FIG. 4 is a map showing the structure of construct pMON43800. pMON43800 is a recombinant binary vector for *Agrobacterium*-mediated transformation, carrying the rubber HMGR1 gene cassette. The HMGR1 gene is driven by the 7S alpha' beta conglycinin promoter from soybean. P-7S: 7S promoter, rubber HMGR1 gene: coding sequence for 3-hydroxy-3-methylglutaryl reductase from *Hevea brasiliensis*; E9 3': 3' end of pea rbcs E9 gene; P-35S: 35S promoter from cauliflower mosaic virus; KAN: coding region for NPTII gene conferring resistance to kanamycin; NOS 3': 3' termination end of nopaline synthase coding region: Left Border: Octapine left border from Octapine Ti plasmid pTiA6; ori-V: the vegetative origin of replication; rop: coding region for repressor of primer; Spc/Str: coding region for Tn7 adenylyltransferase conferring resistance to spectinomycin and streptomycin.

In order to examine the ability of HMGR overexpression for increasing sterol compound levels in seeds, the following experiment was performed in *Glycine max*. A full-length HMGR gene from rubber genomic DNA was expressed in developing *Glycine max* seeds using the 7S promoter. This was achieved by excising the rubber HMGR gene from the plasmid pHEV15 (Schaller et al., (1995) *Plant Physiol.,* 109: 761-770) using EcoRI. The 3.8 Kb fragment was inserted into the EcoRI site of pMON29920 (FIG. 3) such that the HMGR gene is flanked by the 7S promoter on the 5' end and the E9 3' terminator to create pMON43800 (FIG. 4). This was next digested with SalI and NotI to release a 7.7 Kb fragment that was then blunt-ended at the Sal I end before ligating to pMON23616 (FIG. 5) that was first cut with SmaI and NotI. This created the pMON43818 binary vector that contains the rubber HMGR gene driven by 7S promoter and the NPTII gene selection marker driven by the NOS promoter and 3'

Figure 6:
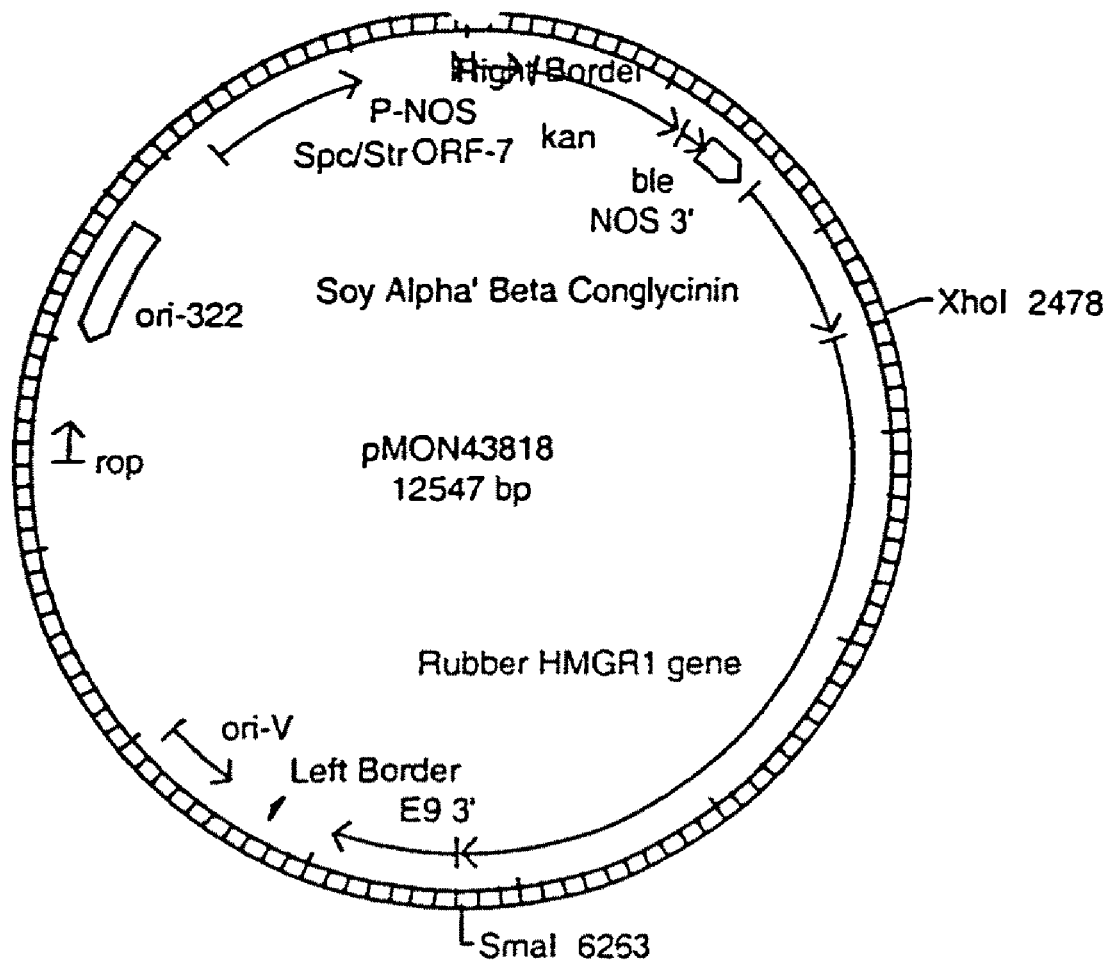
FIG. 6 is a map showing the structure of construct pMON43818. pMON43818 is a recombinant binary vector carrying the gene encoding rubber hydroxymethyl glutaryl CoA reductase1 (HMGR1) in sense orientation driven by the soybean alpha' beta conglycinin promoter. P-NOS: nopaline synthase gene promoter; kan: coding region for neomycin phospho transferase protein to confer resistance to kanamycin; NOS 3': 3' termination end of nopaline synthase coding region; Soy Alpha' Beta Conglycinin: 7S alpha' beta conglycinin gene promoter from soybean; Rubber HMGR1 gene: coding sequence for HMGR1 gene from *Hevea brasiliensis*; E9 3': 3' end of pea rbcS E9 gene; Left border: octopine left border, sequence essential for transfer of T-DNA into *Agrobacterium*; ori-V: plasmid origin of replication in *Agrobacterium*; rop: coding sequence for repressor of primer; Ori-322: origin of replication in *E. coli*; Spc/Str: coding region for Tn7 adenylyltransferase (AAD(3")) conferring resistance to spectinomycin and streptomycin; Right Border: right border sequence of T-DNA essential for integration into *Agrobacterium*.

NOS terminator. PMON43818 (FIG. 6) was used to transform *Agrobacterium tumefaciens* and transform *Glycine max* cotyledon explants as described in Example 2.

Seeds from 15 transgenic plants and one nontransgenic control plant were harvested at maturity. Sterol extraction and analysis on ten individual seeds per plant were performed as described in Example 2. Results are presented in Table 2.

TABLE 2

Sterol profile of transgenic soybean plants expressing rubber HMGR gene driven by 7s promoter. Event 1: control, events 2-16: 15 transgenic plants generated by 15 independent events using *Agrobacterium* mediated transformation.

| Event | Campesterol ug/g | Stigasterol ug/g | Sitosterol ug/g | Sitotanol ug/g | Others (Pathway intermediates) ug/g | Total ug/g | Intermediate accumulation (% of total sterol) |
|---|---|---|---|---|---|---|---|
| 1 | 161.9 | 148.2 | 551.3 | 36.8 | 264.8 | 1163 | 22.8 |
| 2 | 241.6 | 287.9 | 1128.8 | 96.6 | 1489.8 | 3244.5 | 46 |
| 3 | 442.4 | 320.1 | 1876.6 | 117.3 | 1728.4 | 4484.8 | 38.5 |
| 4 | 311.2 | 345.6 | 1645.6 | 113.8 | 1307.5 | 3723.6 | 35 |
| 5 | 395.5 | 323.0 | 1592.1 | 83.1 | 933.8 | 3327.5 | 28 |
| 6 | 370.5 | 301.6 | 1735.8 | 97.2 | 990.5 | 3495.6 | 28.3 |
| 7 | 351.0 | 307.0 | 1457.3 | 101.1 | 885.3 | 3101.7 | 28.5 |
| 8 | 248 | 172.4 | 1270.1 | 74.3 | 428.8 | 2193.6 | 19.5 |
| 9 | 221.1 | 140.7 | 1149 | 76.7 | 652.6 | 2240.1 | 29.1 |
| 10 | 234.2 | 184.8 | 1306.8 | 64.1 | 669.4 | 2459.3 | 27.2 |
| 11 | 156.5 | 125.4 | 679.2 | 38.8 | 142.3 | 1142.2 | 12.4 |
| 12 | 311.2 | 242.9 | 1457.3 | 67 | 418.6 | 2497 | 16.7 |
| 13 | 165.4 | 135.4 | 1320.1 | 59.7 | 1645.8 | 3326.4 | 49.4 |
| 14 | 190.8 | 152 | 1121.3 | 51.4 | 1040.7 | 2556.2 | 40.7 |
| 15 | 182.9 | 157.4 | 1118.5 | 55.2 | 376.6 | 1890.6 | 20 |
| 16 | 197.9 | 151.7 | 946.6 | 61.7 | 225.3 | 1583.2 | 14.2 |

Total sterols increased by 3.2- and 3.9-fold in the best performing plants (transgenic events 3 and 4). These two events also showed the highest increases of individual sterols. Campesterol increased by 2.7-fold, sitosterol by 3.4-fold, sitostanol by 3.2-fold and other sterols by 6.5-fold in event 3 while stigmasterol increased by 2.3-fold in event 4. The other sterols, which account for the highest increase in total sterols were pathway intermediates that included squalene, cycloartenol, 24-methylene cycloartenol, obtusifoliol, isofucosterol, and stigmasta-7-enol. These pathway intermediates normally form minor constituents in the sterol composition of seeds. However, in the transgenic seeds, probably due to increased carbon flux through the pathway, they accumulate in significant amounts. This suggests additional control points for sterol biosynthesis in plants such as squalene epoxidase, C-24 sterol methyltransferase, and C-14 obtusifoliol demethylase.

Example 2

Enhance Phytosterol Biosynthesis in Seeds of Transgenic Soybean Plants by Seed-Specific Expression of Catalytic Domain of HMG-CoA Reductase (HMGR) Alone and in Combination with Sterol Methyl Transferase II (SMTII)

In another embodiment of the present invention, the levels of sterol compounds, including sitosterol, sitostanol, campesterol, stigmasterol and at least one ester for each of the sterol compounds and mixture there of, can be elevated in plant seeds by overexpression of catalytic domain of plant-HMG-CoA reductases. One can transform a plant of interest using an expression cassette or vector comprising DNA encoding a polypeptide exhibiting 3-hydroxy-3-methylglutaryl-Coenzyme A reductase (HMG-CoA reductase or HMGR) activity.

Figure 11:
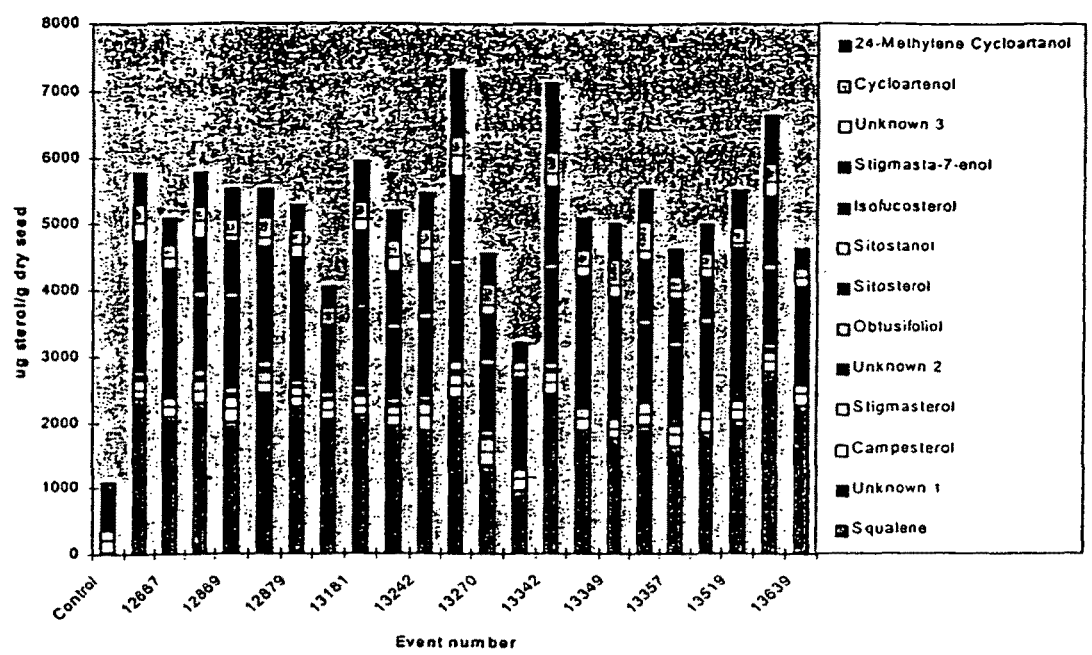
FIG. 11 is profile (histogram) of the sterol composition of R1 transgenic soybean seeds when *Arabidopsis* truncated HMGR (catalytic domain without linker) was overexpressed using seed-specific 7S promoter (data from pMON43057: p7S::At HMGR truncated).
Figure 12:
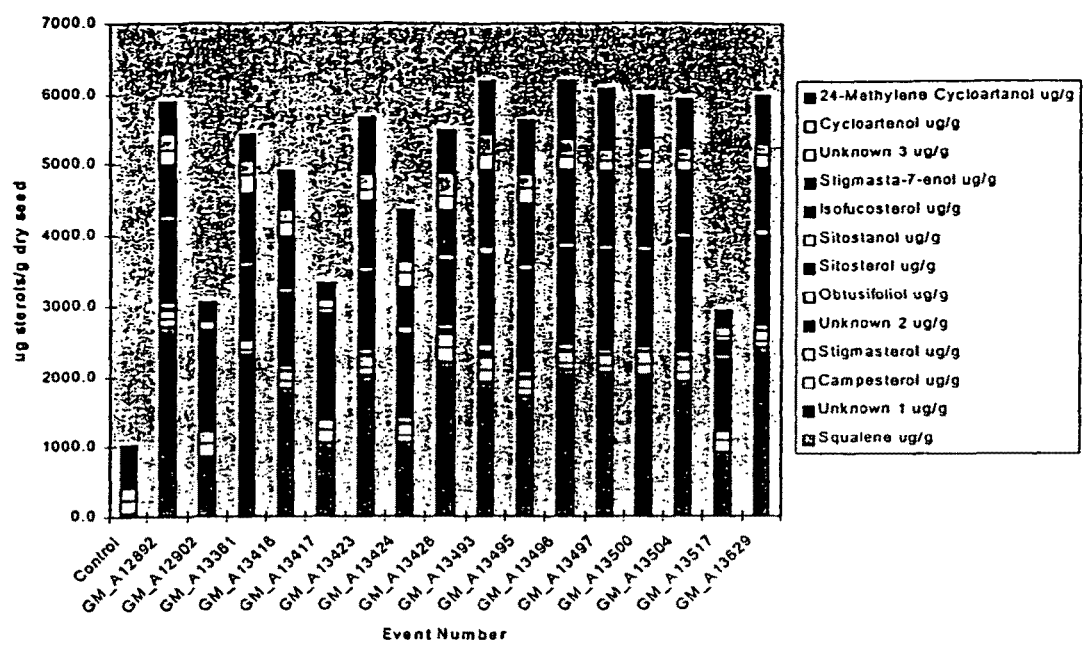
FIG. 12 is a profile (histogram) of the sterol composition of R1 transgenic soybean seeds when *Arabidopsis* truncated HMGR (catalytic domain without linker) and *Arabidopsis* SMTII were overexpressed (data from pMON43058:p7S::At HMGR truncated and p7S::At SMTII). The expression of the genes is controlled by the seed-specific 7S promoter.
Figure 13:
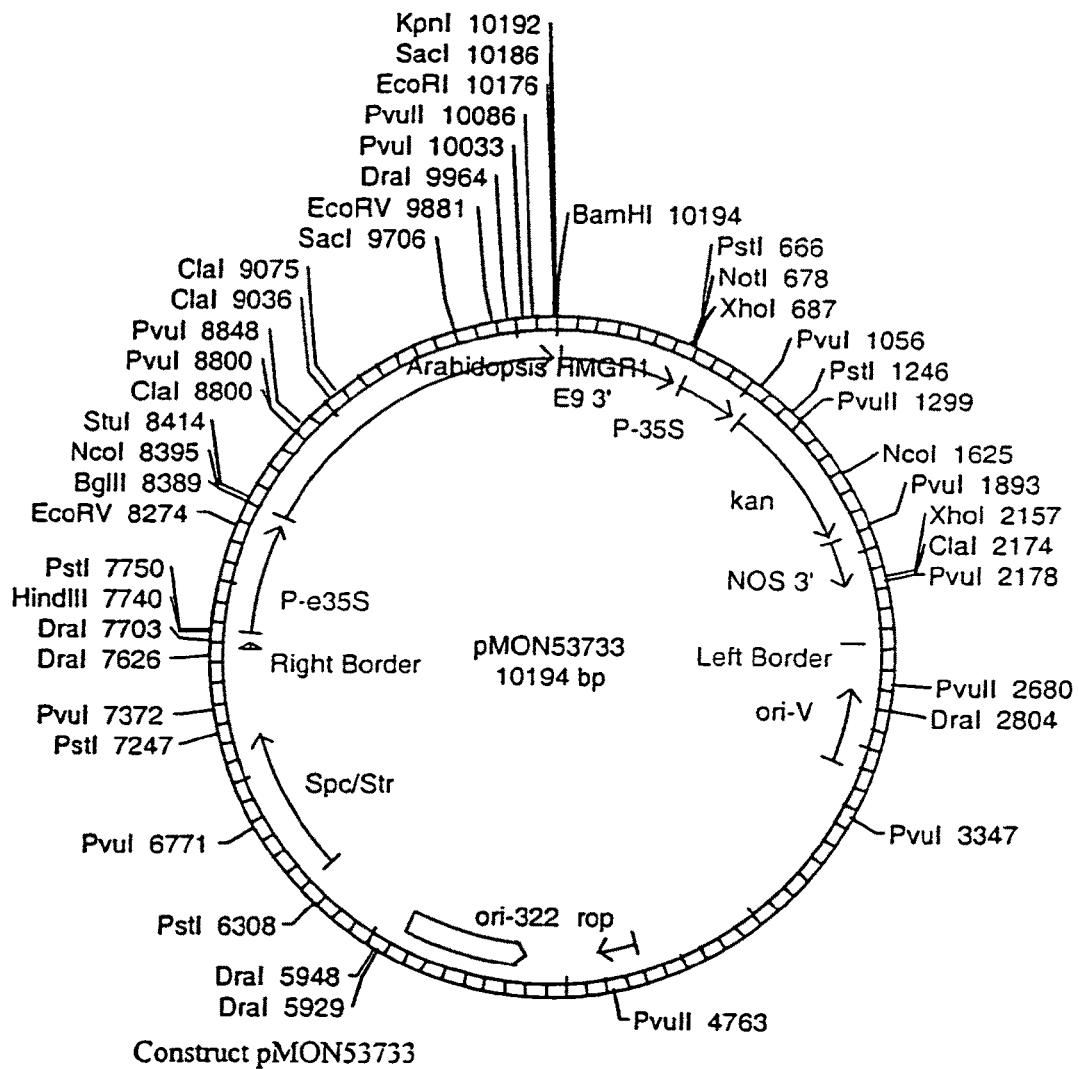
FIG. 13 is a map showing the structure of construct pMON53733. pMON53733 is a recombinant binary vector carrying the cDNA encoding full-length form of *Arabidopsis* hydroxymethyl glutaryl CoA reductase1 (HMGR1) in sense orientation driven by the enhanced cauliflower mosaic virus 35S promoter. P-35S: 35S promoter from cauliflower mosaic virus; kan: confers resistance to neomycin and kanamycin; NOS 3': 3' termination end of nopaline synthase coding region; Left border: octopine left border, sequence essential for transfer of T-DNA into *Agrobacterium*; ori-V: plasmid origin of replication in *Agrobacterium*; rop: coding sequence for repressor of primer; ori-322: origin of replication in *E. coli*; Spc/Str: coding region for Tn7 adenylyltransferase (AAD(3")) conferring resistance to spectinomycin and streptomycin; Right Border: right border sequence of T-DNA essential for integration into *Agrobacterium*; P-e35S: enhanced cauliflower mosaic virus promoter; *Arabidopsis* HMGR1: cDNA sequence encoding full-length form of *Arabidopsis* HMGR1; E9 3': 3' end of pea rbcs E9 gene.
Figure 14:
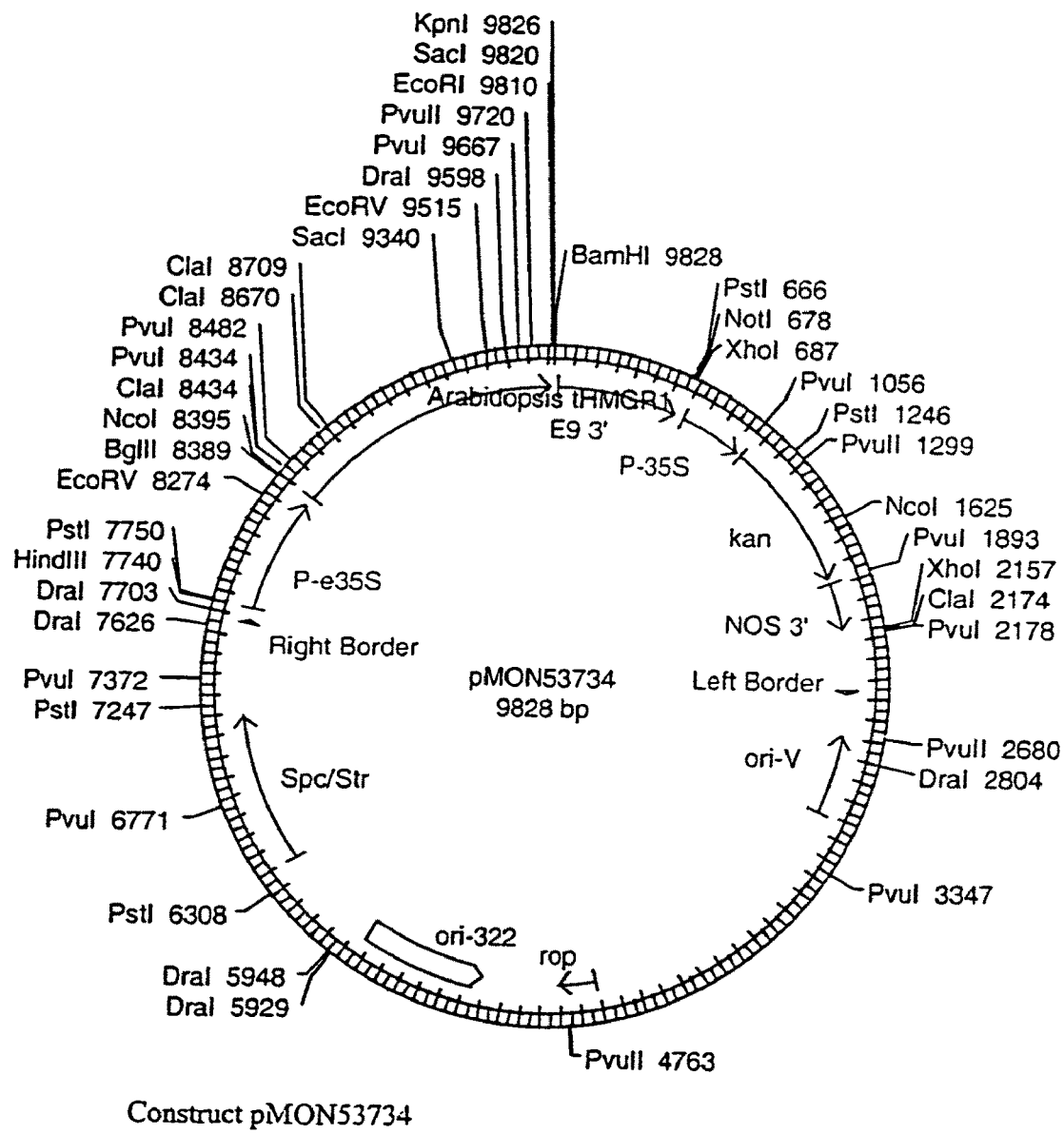
FIG. 14 is a map showing the structure of construct pMON53734. pMON53734 is a recombinant binary vector carrying the cDNA encoding catalytic domain with linker region of *Arabidopsis* hydroxymethyl glutaryl CoA reductase1 (HMGR1) in sense orientation driven by the enhanced cauliflower mosaic virus 35S promoter. P-35S: 35S promoter from cauliflower mosaic virus; kan: confers resistance to neomycin and kanamycin; NOS 3': 3' termination end of nopaline synthase coding region; Left border: octopine left border, sequence essential for transfer of T-DNA into *Agrobacterium*; ori-V: plasmid origin of replication in *Agrobacterium*; rop: coding sequence for repressor of primer; ori-322: origin of replication in *E. coli*; Spc/Str: coding region for Tn7 adenylyltransferase (AAD(3")) conferring resistance to spectinomycin and streptomycin; Right Border: right border sequence of T-DNA essential for integration into *Agrobacterium*; P-e35S: enhanced cauliflower mosaic virus promoter; *Arabidopsis* tHMGR1: cDNA sequence encoding catalytic domain with linker region of *Arabidopsis* HMGR1; E9 3': 3' end of pea rbcs E9 gene.
Figure 15:
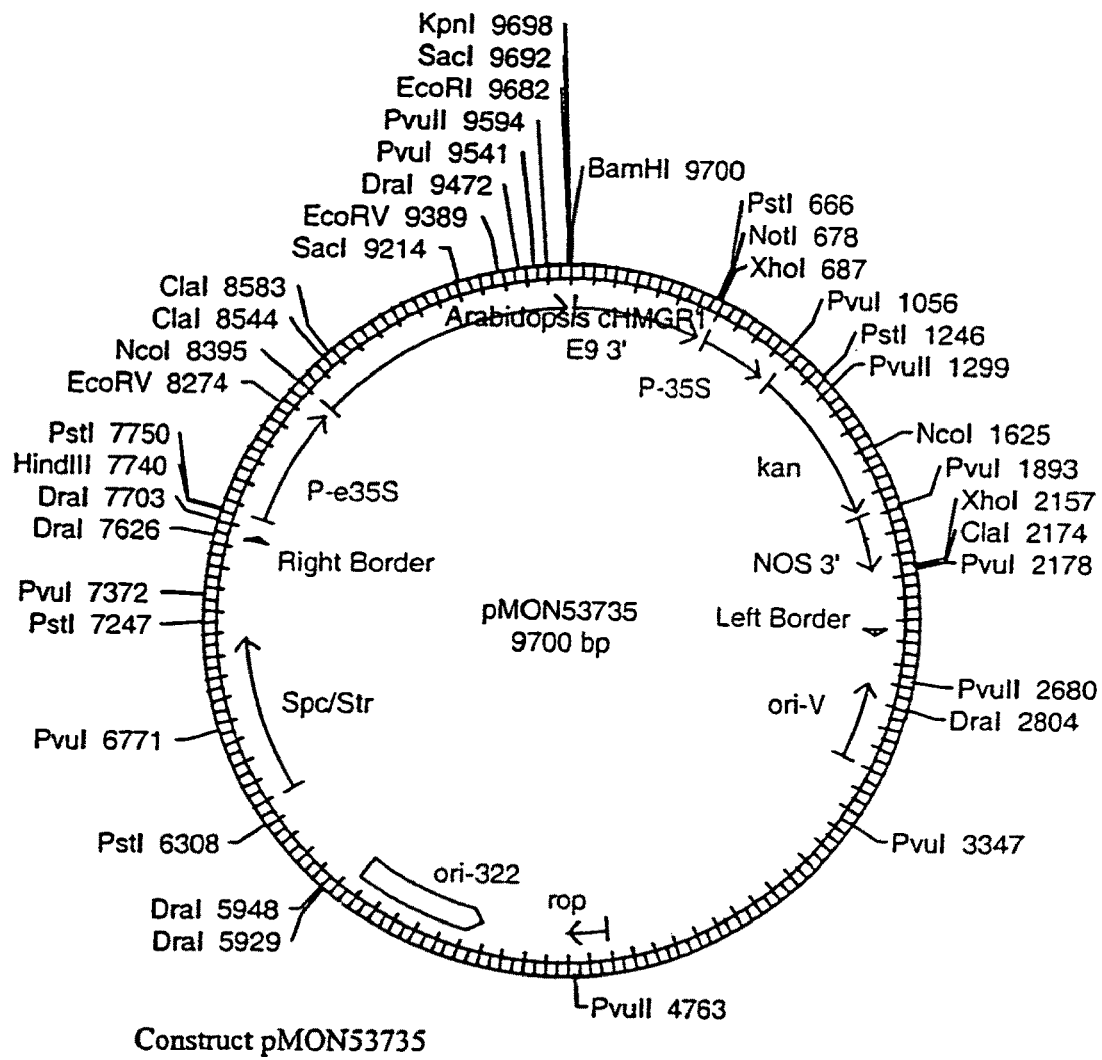
FIG. 15 is a map showing the structure of construct pMON53735. pMON53735 is a recombinant binary vector carrying the cDNA encoding catalytic domain without the linker region of *Arabidopsis* hydroxymethyl glutaryl CoA reductase1 (HMGR1) in sense orientation driven by the enhanced cauliflower mosaic virus 35S promoter. P-35S: 35S promoter from cauliflower mosaic virus; kan: confers resistance to neomycin and kanamycin; NOS 3': 3' termination end of nopaline synthase coding region; Left border: octopine left border, sequence essential for transfer of T-DNA into *Agrobacterium*; ori-V: plasmid origin of replication in *Agrobacterium*; rop: coding sequence for repressor of primer; ori-322: origin of replication in *E. coli*; Spc/Str: coding region for Tn7 adenylyltransferase (AAD(3")) conferring resistance to spectinomycin and streptomycin; Right Border: right border sequence of T-DNA essential for integration into *Agrobacterium*; P-e35S: enhanced cauliflower mosaic virus promoter; *Arabidopsis* cHMGR1: cDNA sequence encoding catalytic domain without the linker region of *Arabidopsis* HMGR1; E9 3': 3' end of pea rbcs E9 gene.
Figure 16:
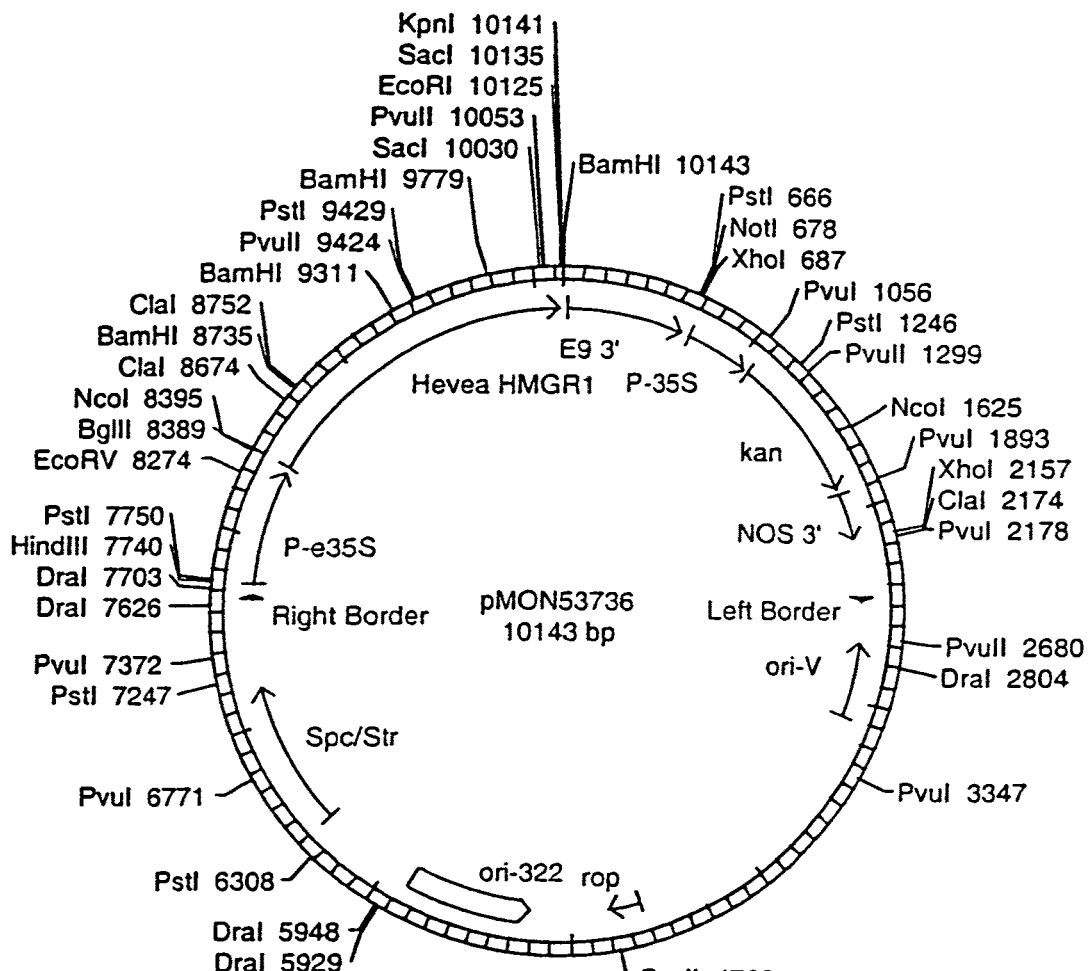
FIG. 16 is a map showing the structure of construct pMON53736. pMON53736 is a recombinant binary vector carrying the cDNA encoding full-length form of rubber (*Hevea brasiliensis*) hydroxymethyl glutaryl CoA reductase1 (HMGR1) in sense orientation driven by the enhanced cauliflower mosaic virus 35S promoter. P-35S: 35S promoter from cauliflower mosaic virus; kan: confers resistance to neomycin and kanamycin; NOS 3': 3' termination end of nopaline synthase coding region; Left border: octopine left border, sequence essential for transfer of T-DNA into *Agrobacterium*; ori-V: plasmid origin of replication in *Agrobacterium*; rop: coding sequence for repressor of primer; ori-322: origin of replication in *E. coli*; Spc/Str: coding region for Tn7 adenylyltransferase (AAD(3")) conferring resistance to spectinomycin and streptomycin; Right Border: right border sequence of T-DNA essential for integration into *Agrobacterium*; P-e35S: enhanced cauliflower mosaic virus promoter; *Hevea* HMGR1: cDNA sequence encoding full-length form of rubber HMGR1; E9 3': 3' end of pea rbcs E9 gene.
Figure 17:
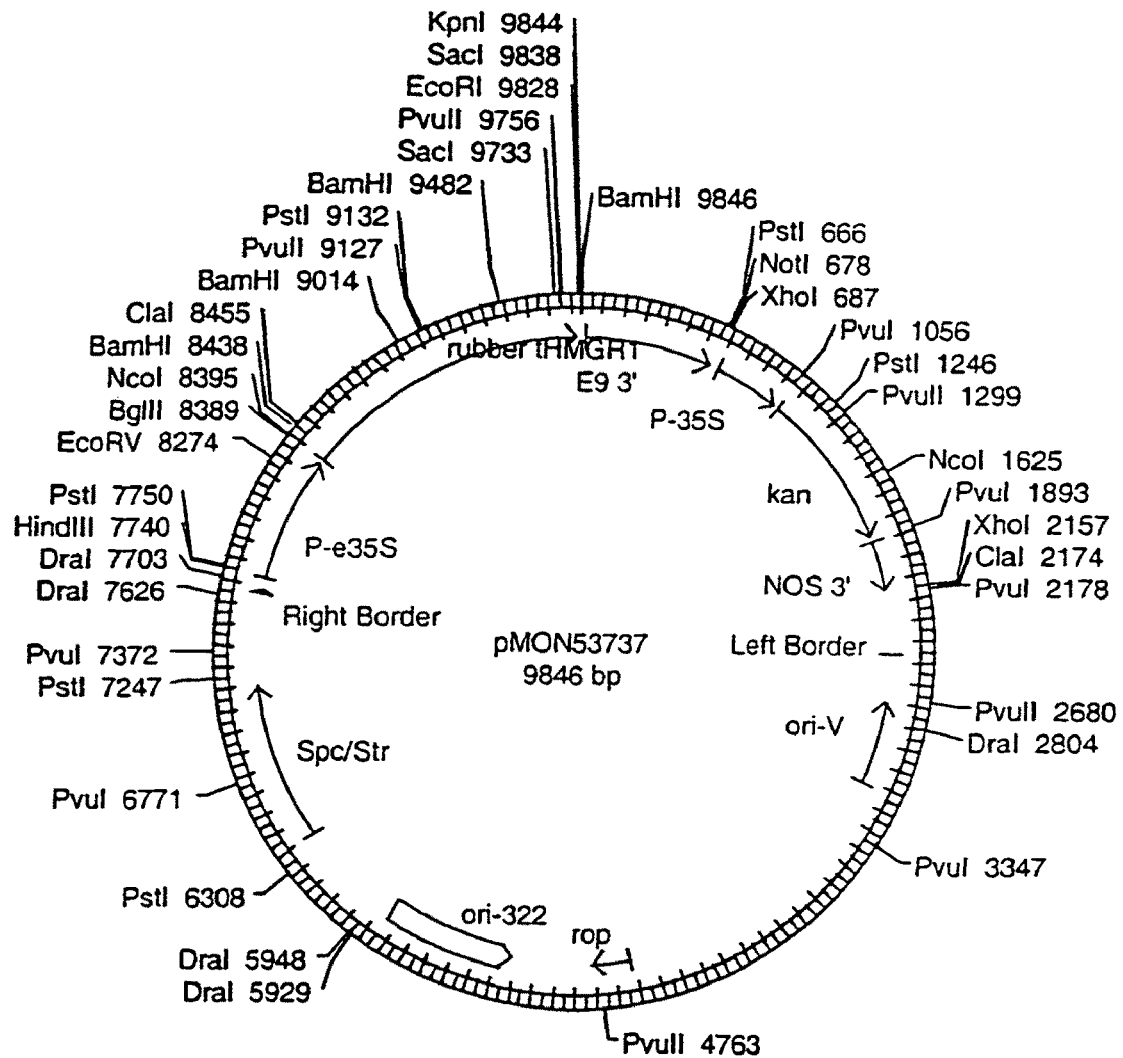
FIG. 17 is a map showing the structures of construct pMON53737. pMON53737 is a recombinant binary vector carrying the cDNA encoding catalytic domain with linker region of rubber (*Hevea brasiliensis*) hydroxymethyl glutaryl CoA reductase1 (HMGR1) in sense orientation_driven by the enhanced cauliflower mosaic virus 35S promoter. P-35S: 35S promoter from cauliflower mosaic virus; kan: confers resistance to neomycin and kanamycin; NOS 3': 3' termination end of nopaline synthase coding region; Left border: octopine left border, sequence essential for transfer of T-DNA into *Agrobacterium*; ori-V: plasmid origin of replication in *Agrobacterium*; rop: coding sequence for repressor of primer; ori-322: origin of replication in *E. coli*; Spc/Str: coding region for Tn7 adenylyltransferase (AAD(3")) conferring resistance to spectinomycin and streptomycin; Right Border: right border sequence of T-DNA essential for integration into *Agrobacterium*; P-e35S: enhanced cauliflower mosaic virus promoter; rubber tHMGR1: cDNA sequence encoding catalytic domain with linker region of rubber HMGR1; E9 3': 3' end of pea rbcs E9 gene.
Figure 18:
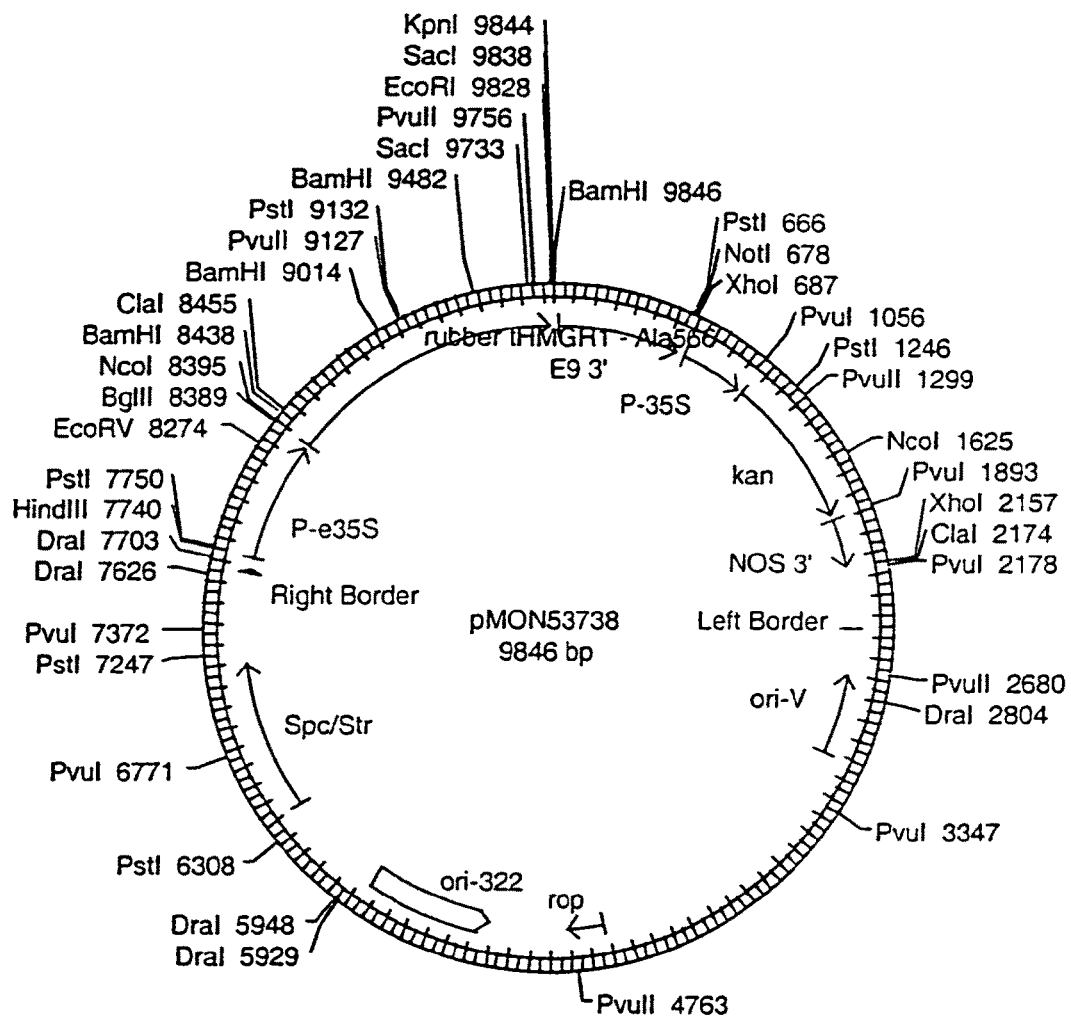
FIG. 18 is a map showing the structure of construct pMON53738. pMON53738 is a recombinant binary vector carrying the cDNA encoding mutant form of rubber (*Hevea brasiliensis*) hydroxymethyl glutaryl CoA reductase1 (HMGR1) in sense orientation driven by the enhanced cauliflower mosaic virus 35S promoter. In the mutant rubber HMGR1 the putative phosphorylation site, the serine amino acid residue at position 566 is changed to alanine amino acid residue (SEQ ID 23). P-35S: 35S promoter from cauliflower mosaic virus; kan: confers resistance to neomycin and kanamycin; NOS 3': 3' termination end of nopaline synthase coding region; Left border: octopine left border, sequence essential for transfer of T-DNA into *Agrobacterium*; ori-V: plasmid origin of replication in *Agrobacterium*; rop: coding sequence for repressor of primer; ori-322: origin of replication in *E. coli*; Spc/Str: coding region for Tn7 adenylyltransferase (AAD(3")) conferring resistance to spectinomycin and streptomycin; Right Border: right border sequence of T-DNA essential for integration into *Agrobacterium*; P-e35S: enhanced cauliflower mosaic virus promoter; rubber tHMGR1 Ala 566: cDNA sequence encoding catalytic domain with linker region of rubber HMGR1 in which serine amino acid residue at position 566 is changed to alanine amino acid residue using site directed mutagenesis; E9 3': 3' end of pea rbcs E9 gene.
Figure 19:
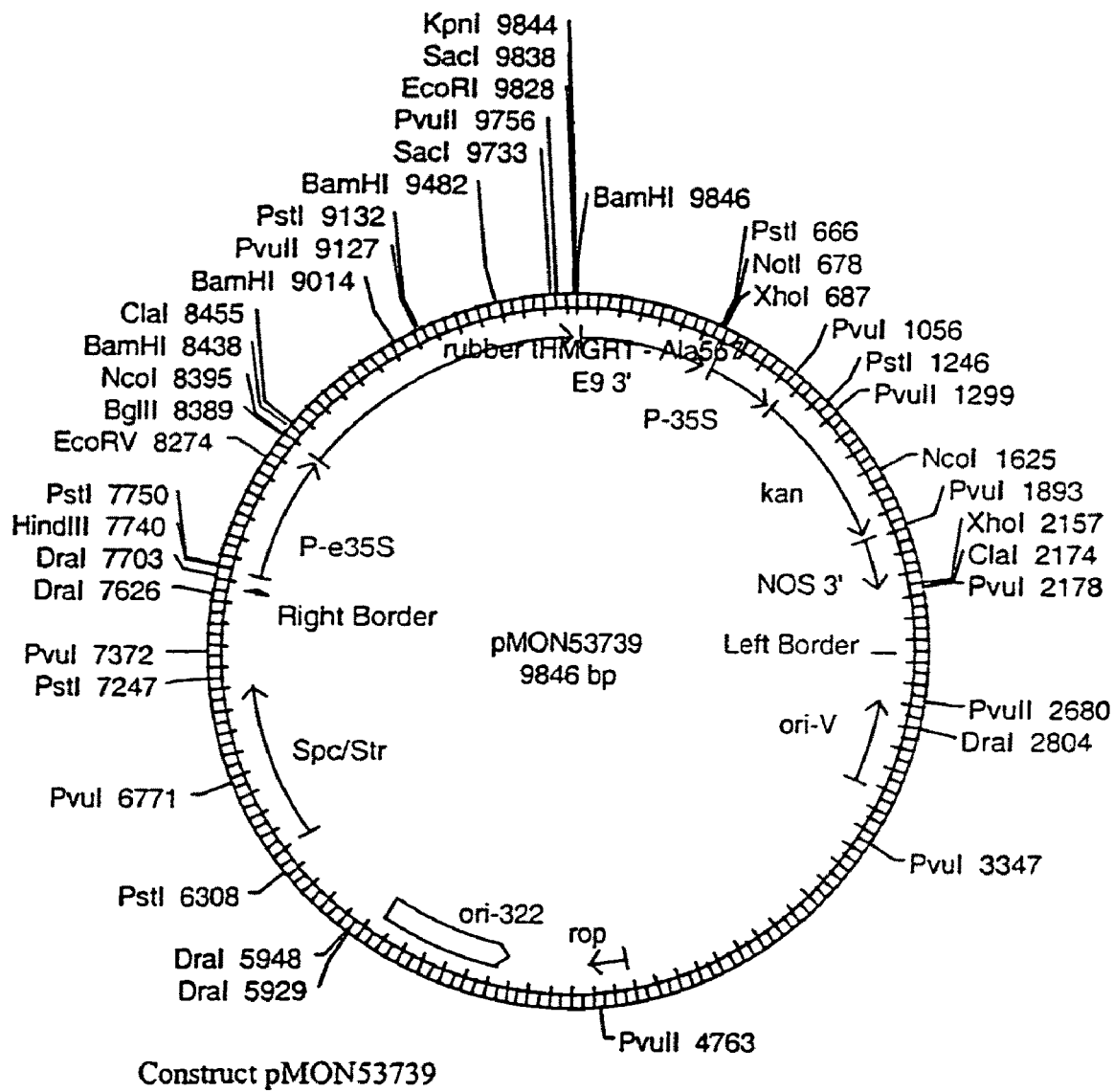
FIG. 19 is a map showing the structure of construct pMON53739. pMON53739 is a recombinant binary vector carrying the cDNA encoding mutant form of rubber (*Hevea brasiliensis*) hydroxymethyl glutaryl CoA reductase1 (HMGR1) in sense orientation driven by the enhanced cauliflower mosaic virus 35S promoter. In the mutant rubber HMGR1 the putative phosphorylation site, the serine amino acid residue at position 567 is changed to alanine amino acid residue (SEQ ID 24). P-35S: 35S promoter from cauliflower mosaic virus; kan: confers resistance to neomycin and kanamycin; NOS 3': 3' termination end of nopaline synthase coding region; Left border: octopine left border, sequence essential for transfer of T-DNA into *Agrobacterium*; ori-V: plasmid origin of replication in *Agrobacterium*; rop: coding sequence for repressor of primer; ori-322: origin of replication in *E. coli*; Spc/Str: coding region for Tn7 adenylyltransferase (AAD(3")) conferring resistance to spectinomycin and streptomycin; Right Border: right border sequence of T-DNA essential for integration into *Agrobacterium*; P-e35S: enhanced cauliflower mosaic virus promoter; rubber tHMGR1 Ala 567: cDNA sequence encoding catalytic domain with linker region of rubber HMGR1 in which serine amino acid residue at position 567 is changed to alanine amino acid residue using site directed mutagenesis; E9 3': 3' end of pea rbcS E9 gene.
Figure 20:
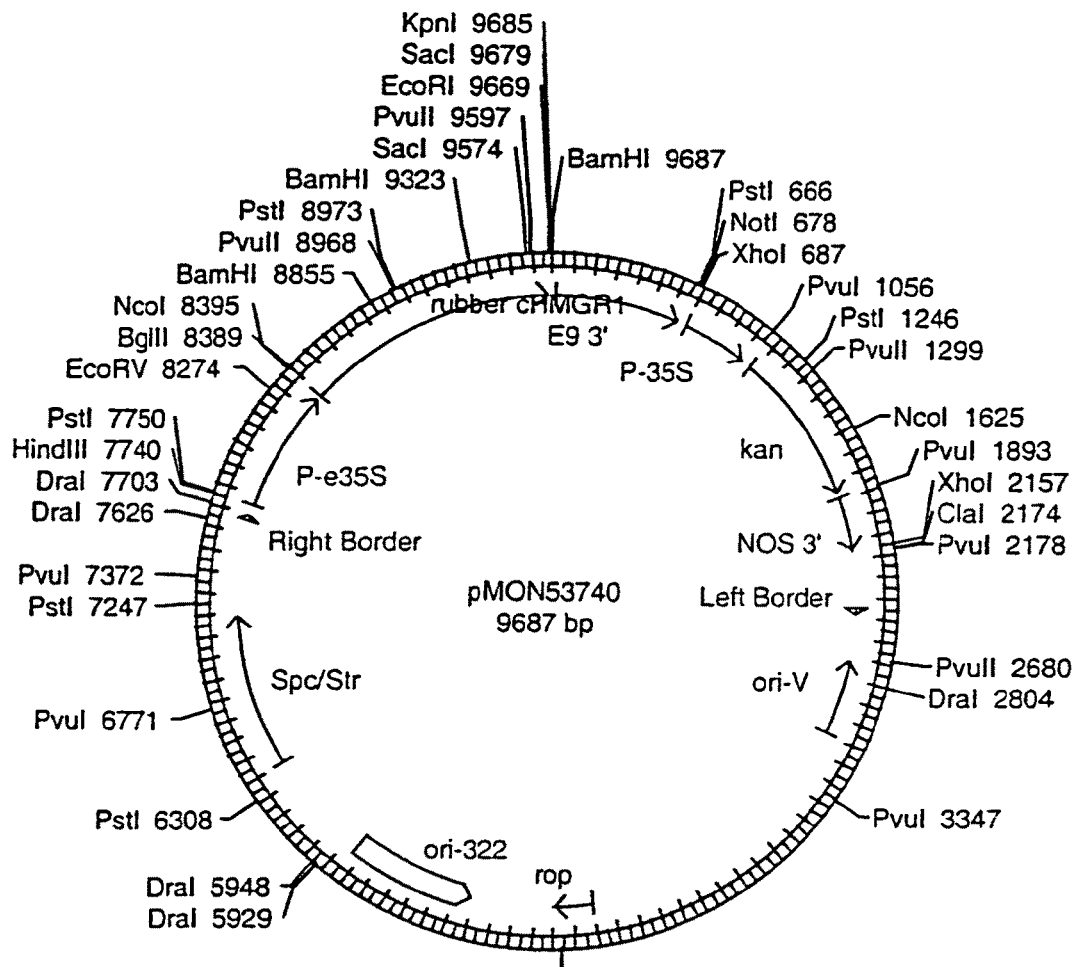
FIG. 20 is a map showing the structure of construct pMON53740. pMON53740 is a recombinant binary vector carrying the cDNA encoding catalytic domain without linker region of rubber (*Hevea brasiliensis*) hydroxymethyl glutaryl CoA reductase1 (HMGR1) in sense orientation driven by the enhanced cauliflower mosaic virus 35S promoter. P-35S: 35S promoter from cauliflower mosaic virus; kan: confers resistance to neomycin and kanamycin; NOS 3': 3' termination end of nopaline synthase coding region; Left border: octopine left border, sequence essential for transfer of T-DNA into *Agrobacterium*; ori-V: plasmid origin of replication in *Agrobacterium*; rop: coding sequence for repressor of primer; ori-322: origin of replication in *E. coli*; Spc/Str: coding region for Tn7 adenylyltransferase (AAD(3")) conferring resistance to spectinomycin and streptomycin; Right Border: right border sequence of T-DNA essential for integration into *Agrobacterium*; P-e35S: enhanced cauliflower mosaic virus promoter; rubber cHMGR1: cDNA sequence encoding catalytic domain without linker region of rubber HMGR1; E9 3': 3' end of pea rbcs E9 gene.

HMGR cDNAs from rubber have been successfully used to increase plant sterol levels in plant tissues (Schallet et al. (1995) *Plant Physiol.* 109: 761-770). Full-length and truncated forms of HMGR CDNAs encoding full-length and catalytic domain of HMGR, respectively, from *Arabidopsis* have also been used to overproduce sterols in transgenic *Arabidopsis* plants (Gonzalez et al. (1997) *Third Terpnet Meeting of the European Network on Plant Isoprenoids Abstracts*, Abstract No. 33, page 33). In the above examples however, the genes have not been specifically targeted to increase sterol levels in seeds. Another approach to enhance the nutritionally beneficial 24-ethyl sterols (sitosterol, sitostanol) and reduce the accumulation of 24-methyl sterols (campesterol) in seeds one can co-express two genes encoding the enzymes HMGR and sterol methyl transferse II (SMTII), each under the control of seed-specific promoter. Here we present evidence for such approaches: sterol composition of transgenic soybean seeds haboring truncated form (catalytic domain of HMGR without linker) of *Arabidopsis* HMGR1 is presented in FIG. 11 and Table 3. Sterol composition of transgenic soybean seeds haboring *Arabidopsis* HMGR1 (catalytic domain of HMGR without linker) and *Arabidopsis* SMTII is presented in FIG. 12 and Table 4.

Figure 7:
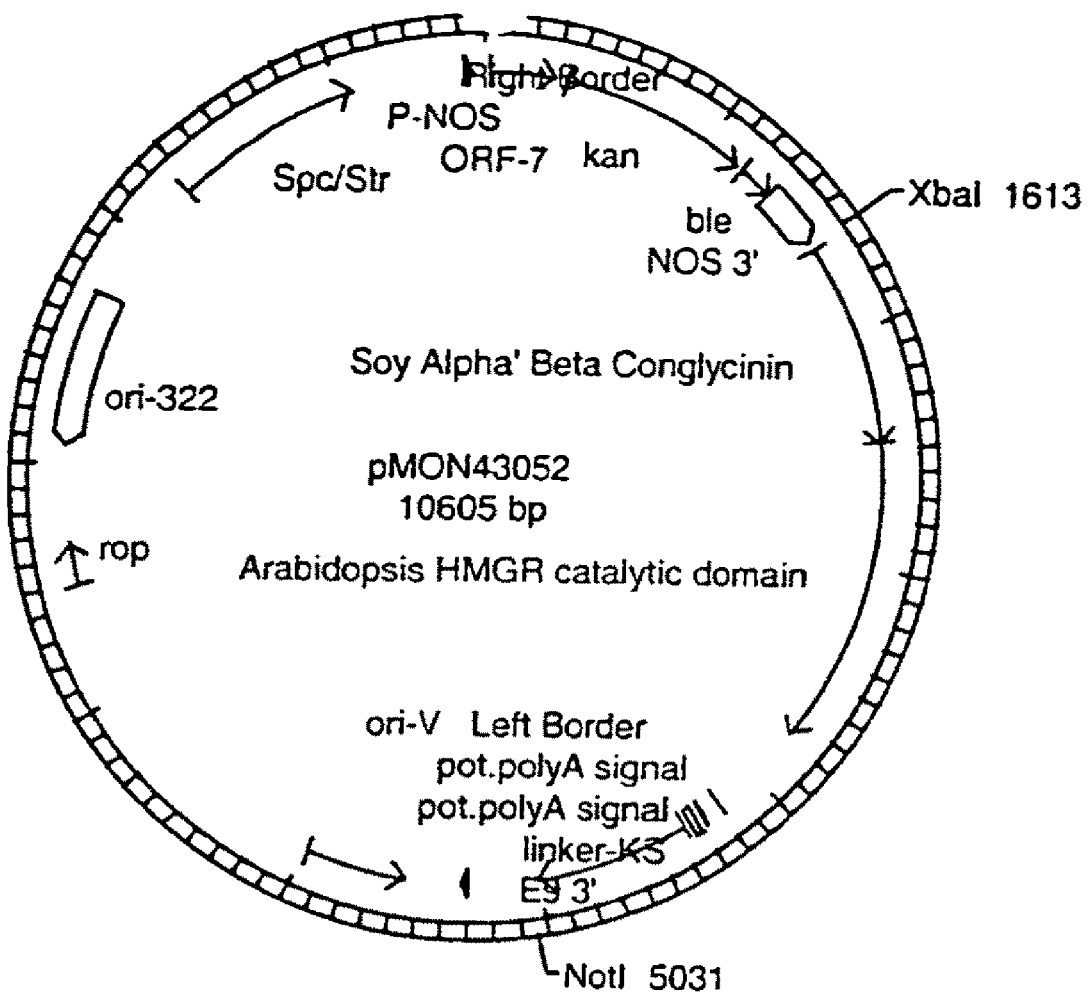
FIG. 7 is a map showing the structure of construct pMON43052. pMON43052 is a recombinant shuttle vector, carrying the cDNA fragment encoding the catalytic domain of *Arabidopsis* HMGR1 in sense orientation driven by the soybean alpha' beta conglycinin promoter. P-NOS: nopaline synthase gene promoter; kan: coding region for neomycin phosphotransferase protein to confer resistance to kanamycin; NOS 3': 3' termination end of nopaline synthase coding region; Soy Alpha' Beta Conglycinin: 7S alpha' beta conglycinin gene promoter from soybean; *Arabidopsis* HMGR catalytic domain: coding sequence for the catalytic domain of *Arabidopsis* HMGR1 protein; E9 3': 3' end of pea rbcs E9 gene; Left border: octopine left border, sequence essential for transfer of T-DNA into *Agrobacterium*; ori-V: plasmid origin of replication in *Agrobacterium*; rop: coding sequence for repressor of primer; Ori-322: origin of replication in *E. coli*; Spc/Str: coding region for Tn7 adenylyltransferase (AAD(3")) conferring resistance to spectinomycin and streptomycin; Right Border: right border sequence of T-DNA essential for integration into *Agrobacterium*.
Figure 8:
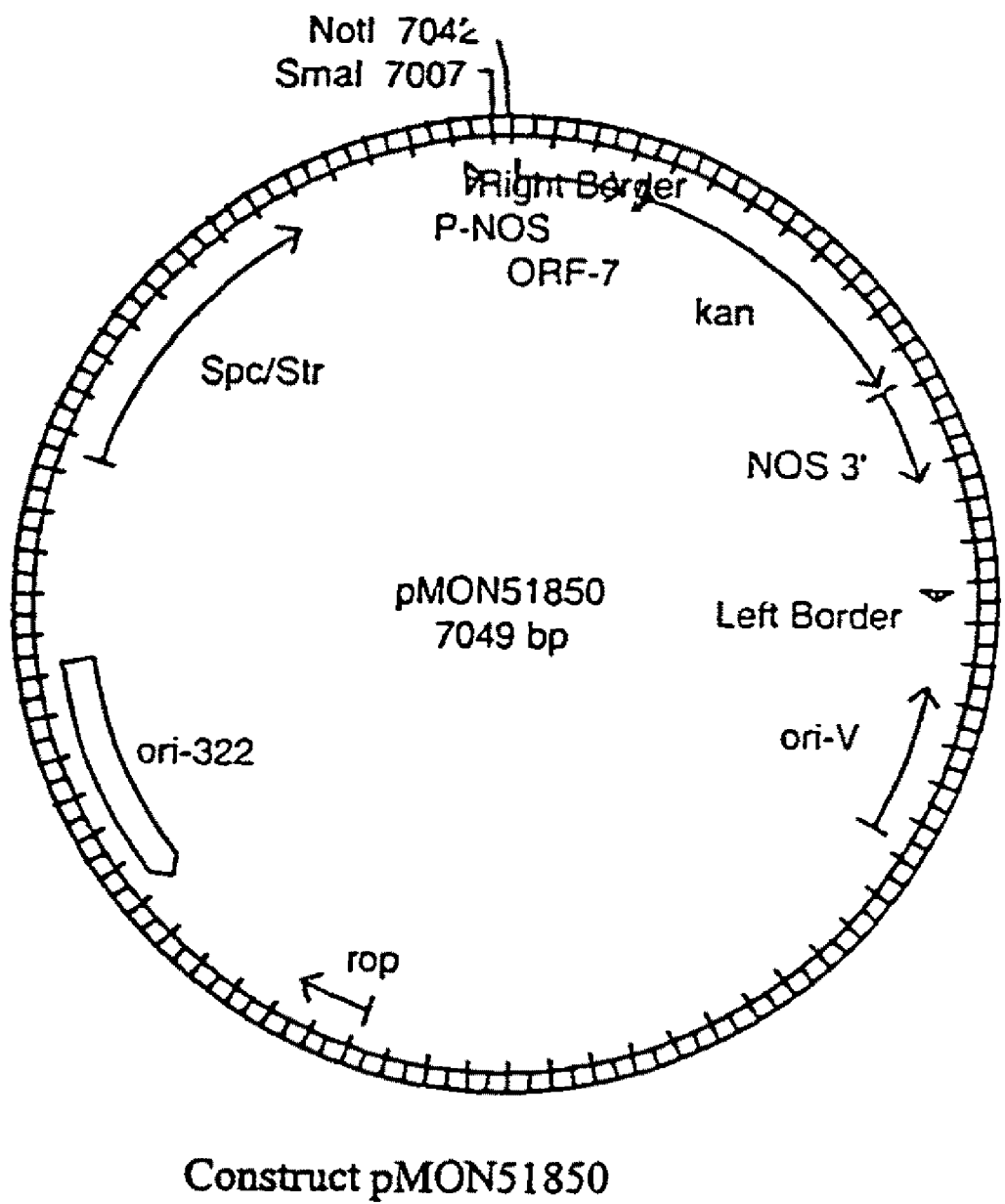
FIG. 8 is a map showing the structure of construct pMON51850. pMON51850 is a binary vector for *Agrobacterium* mediated transformation of soybean. P-NOS: nopaline synthase gene promoter; kan: coding region for neomycin phosphotransferase protein to confer resistance to kanamycin; NOS 3': 3' termination end of nopaline synthase coding region; Left border: octopine left border sequence essential for transfer of T-DNA into *Agrobacterium*; ori-V: plasmid origin of replication in *Agrobacterium*; rop: coding sequence for repressor of primer; ori-322: origin of replication in *E. coli*; Spc/Str: coding region for Tn7 adenylyltransferase (AAD(3")) conferring resistance to spectinomycin and streptomycin; Right Border: right border sequence of T-DNA essential for integration into *Agrobacterium*.
Figure 9:
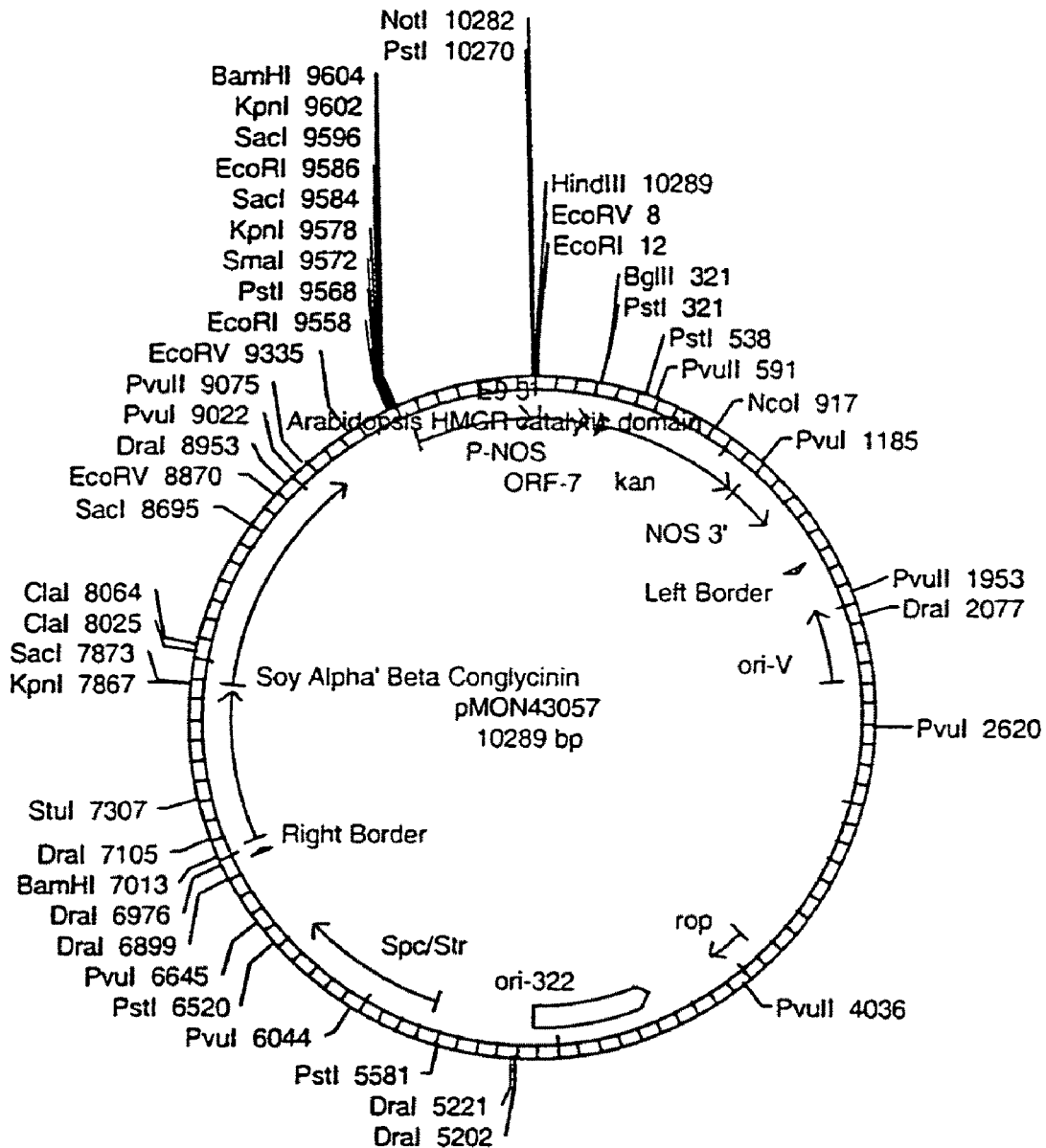
FIG. 9 is a map showing the structure of construct pMON43057. pMON43057 is a recombinant binary vector for *Agrobacterium* mediated transformation of soybean, carrying the gene cassette for expressing catalytic domain of HMGR1 from *Arabidopsis thaliana*. The catalytic domain of the HMGR1 cDNA is driven by soybean 7S alpha' beta conglycinin promoter. P-NOS: nopaline synthase gene promoter; kan: coding region for neomycin phosphotransferase protein to confer resistance to kanamycin; NOS 3': 3' termination end of nopaline synthase coding region; Left border: octopine left border sequence essential for transfer of T-DNA into *Agrobacterium*; ori-V: plasmid origin of replication in *Agrobacterium*; rop: coding sequence for repressor of primer; ori-322: origin of replication in *E. coli*; Spc/Str: coding region for Tn7 adenylyltransferase (AAD(3")) conferring resistance to spectinomycin and streptomycin; Right Border: right border sequence for transfer of T-DNA into *Agrobacterium*; Soy Alpha' Beta Conglycinin: soybean 7S alpha' beta conglycinin gene promoter; *Arabidopsis* HMGR catalytic domain: coding sequence for *Arabidopsis* HMGR1 catalytic domain; E9 3': 3' end of pea rbcS E9 gene.
Figure 10:
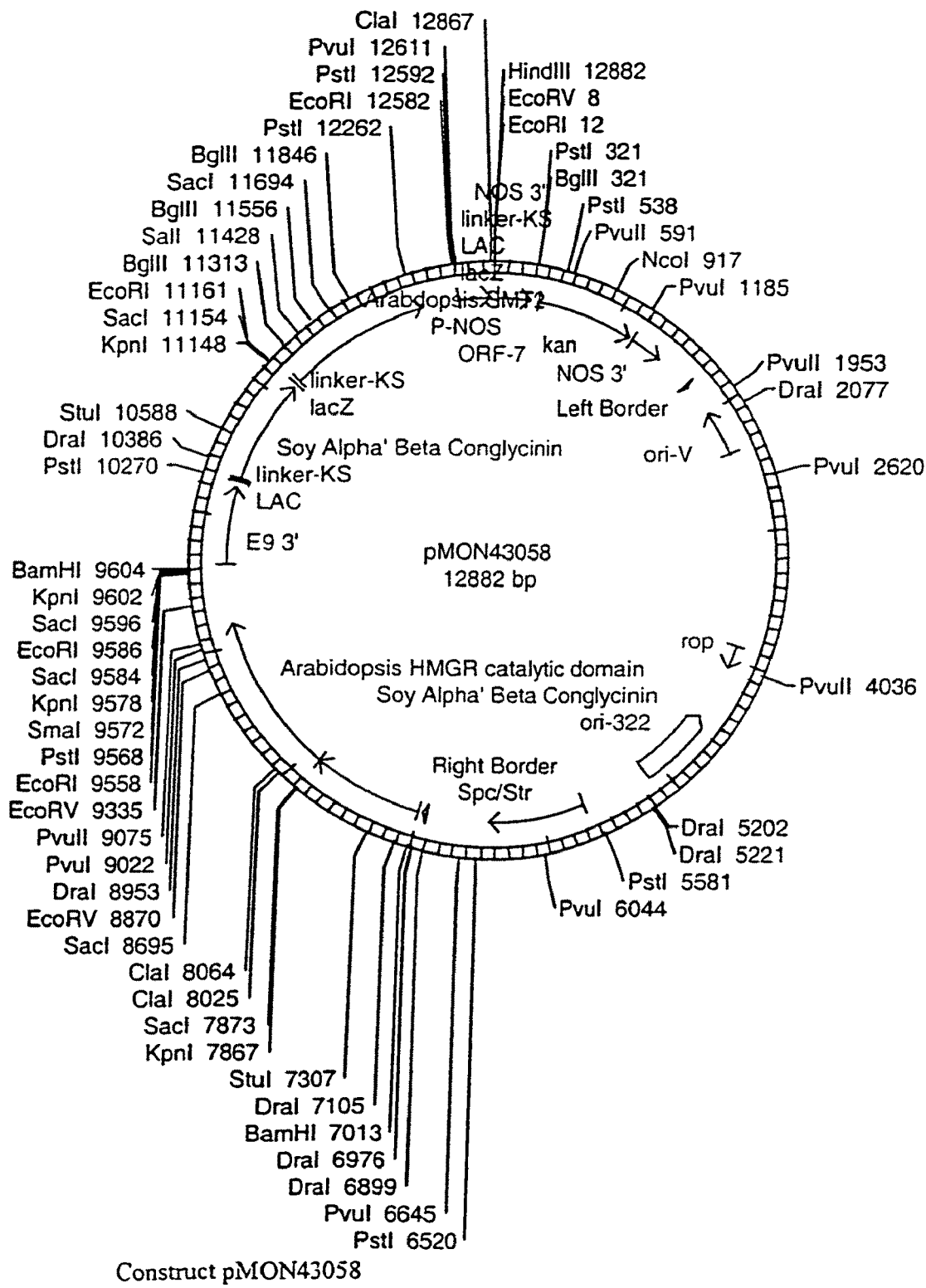
FIG. 10 is a map showing the structure of construct pMON43058. pMON43058 is a recombinant binary vector for *Agrobacterium*-mediated soybean transformation, carrying gene expression cassettes for catalytic domain of HMGR1 from *Arabidopsis thaliana* and SMTII from *Arabidopsis thaliana*. P-NOS: nopaline synthase gene promoter; kan: coding region for neomycin phosphotransferase protein to confer resistance to kanamycin; NOS 3': 3' termination end of nopaline synthase coding region; Left border: octopine left border sequence essential for transfer of T-DNA into *Agrobacterium*; ori-V: plasmid origin of replication in *Agrobacterium*; rop: coding sequence for repressor of primer; ori-322: origin of replication in *E. coli*; Spc/Str: coding region for Tn7 adenylyltransferase (AAD(3")) conferring resistance to spectinomycin and streptomycin; Right Border: right border sequence essential for transfer of T-DNA into *Agrobacterium*; Soy Alpha' Beta Conglycinin: 7S alpha' beta conglycinin gene promoter from soybean; *Arabidopsis* HMGR catalytic domain: sequence encoding the catalytic domain of *Arabidopsis* HMGR1; E9 3': 3' end of pea rbcs E9 gene; Soy Alpha' Beta Conglycinin: soybean 7S alpha'beta conglycinin gene promoter; *Arabidopsis* SMT2: cDNA encoding sterol methyl transferase II enzyme from *Arabidopsis thaliana* (accession no: X89867); NOS 3': 3' termination end of nopaline synthase coding region.

In order to examine whether overexpression of the catalytic domain of HMGR increases sterol levels in the seeds of transgenic soybean, the following experiment was performed in *Glycine max*. A truncated form of HMGR1 cDNA encoding only the catalytic domain of HMGR from *Arabidopsis* was expressed in developing seeds of *Glycine max* using the seed-specific 7S promoter. This was achieved by excising the cDNA fragment (HMGR1cd) encoding the HMGR1 catalytic domain from the plasmid pHMGR1cd (Dale et al., (1995) Eur. J. Biochem. 233: 506-513) using NdeI and SmaI enzymes resulting in the isolation of a 1.9 Kb fragment. The NdeI overhang was filled-in and the 1.9 Kb fragment was blunt-end ligated to vector pMON43818 (FIG. 6), previously XhoI (XhoI overhang was filled-in) and SmaI digested such that the HMGR1cd was flanked by the 7S promoter on the 5' end and the E9 3' terminator to create a recombinant vector pMON43052 (FIG. 7). This was next digested with XbaI and blunt-ended and then digested with NotI to release a 3.4 Kb fragment and ligated to pMON51850 (FIG. 8) that was digested with SmaI and NotI. The ligation created a recombinant binary vector pMON43057 (FIG. 9) that contained the cDNA fragment encoding the catalytic domain of *Arabidopsis* HMGR1, driven by 7S promoter and E9 3' terminator and the NPTII selectable marker gene driven by the NOS promoter and 3' NOS terminator. The pMON43057 was used for *Agrobacterium tumefaciens* mediated transformation of *Glycine max* cotyledon explants. The pMON43058 (FIG. 10) construct carrying both the catalytic domain of *Arabidopsis* HMGR1 and *Arabidopsis* SMTII, both driven by the 7S promoter, was also used for *Agrobacterium temefaciens*-mediated transformation of *Glycine max* in a similar manner described below.

Explants for transformation were prepared as follows: sterilized seeds were germinated on germination medium under light at 28° C. for 5-6 days. Germinated seeds were placed in the dark at 4° C. for 24 hours prior to excision. Seed coats were removed and hypocotyls of each seedling trimmed to a length of 0.5 cm to 1.0 cm in length. The cotyledons were then split open such that the hypocotyl was split down in the middle. The primary leaves and apical region of each cotyledon was removed to expose the wounding region. Wounding was performed with 3-7 shallow, scalpel scores in line with the embryo axis, ensuring that the apical bud was damaged. Wounded explants were incubated in the culture of *Agrobacterium tumefaciens* containing pMON43057. Incubation was for 1 hour at room temperature. Innoculated explants were then transferred to a co-culture medium and placed under light at 23° C. for 3-4 days. At this time explants were transferred to shooting medium without kanamycin selection and placed in a 25° C. light growth room for 4 days.

After 4 days on delay, explants were transferred to a 186 ppm kanamycin selection medium and placed in a 25° C. light growth room for 2 weeks. At the end of two weeks explants were transferred to 186 ppm Woody Plant medium and placed again in a 25° C. light growth room for another 2 weeks. Cultures were transferred every 2 weeks to fresh medium for approximately 18-21 weeks. At the 6 week transfer, the cotyledons and any dead material were removed from the explants, and the petiole was cut. At each subsequent 2 week transfer, the petiole was cut to expose fresh cells to the medium.

Transgenic shoots that were approximately ½" in length, with 2 nodes, 1 open trifoliate and an active growing point were selected, cut and transferred to rooting medium. Once a good root system was developed, the plants were sent to the greenhouse to grow up in soils in pots.

Seeds from the 15 transgenic plants and one nontransgenic control plant were harvested at maturity. Ten individual seeds from each plant were weighed and ground into fine powder using an electric grinder. A known amount of cholestane (usually 100 µg in 100 µl ethanol) was added to each approximately 50 mg powder sample. Sterol compounds were hydrolyzed directly from the ground tissue by saponification with 2 ml of 10% KOH in methanol by refluxing the material at 60° C. for 30 minutes. The refluxed samples were cooled to room temperature and filtered through glass wool. An equal volume of water was added to each filtrate, and the nonsaponifiables were extracted by partitioning three times with equal volumes of hexane. The hexane phases were pooled and evaporated. The residues were resuspended in 1 ml of acetone, and quantatively transferred to glass GC vials that were immediately capped. Sterols were analyzed by Gas Chromatography-Flame Ionizing Detector using the following conditions: Inlet temperature of 220° C., detector temperature of 320° C., and column oven temperature programmed from 220° C. to 320° C. with initial temperature for 1 minute and final temperature for 16 minutes and ramp rate of 8°/min. The column used was a glass capillary DB-5 column of 50 m length, 320 µm diameter, and a film thickness of 0.25 µm. The carrier gas was helium at a flow rate of 11.0 ml/min. Results are presented in Table 3 and Table 4.

To fully characterize the sterol compounds present in the transgenic seeds, a representative sample was also analyzed by Gas Chromatography-Mass Spectrometry (GC-MS) for confirmation of the sterol compounds present. The GC-MS conditions were as follows: inlet temp. 250° C., detector 320° C., oven programmed from 180° C. to 325° C. with initial equilibration time of 1.0 min ramping to 310° C. at 4°/min at then 20°/min to 325° C. The column was a DB-5 capillary glass column similar to the one used for GC-FID.

Majority of the transgenic lines harboring pMON43057 showed 3 to 5-fold increase in total sterols. The best performing transgenic lines, GM_A13342 and GM_A13634, showed 6.5- and 6.1-fold increase in total sterols, respectively. These lines showed 2- to 2.6-fold increase in sitosterol, 1.5 to 2.2-fold increase in sitostanol and no significant change in the campesterol levels. Hence the major proportion of the total sterol increase was accounted by the accumulation of pathway intermediates which include squalene, cycloartenol, 24-methylene cycloartenol, obtusifoliol, isofucosterol, and stigmasta-7-enol. The best performing transgenic lines, GM_A13342 and GM_A13634, showed 32.6- and 32.2-fold increase in pathway intermediates accumulation, respectively, as compared to the control. In all the transgenic lines harboring the pMON43057, 50-70% of the total increase was accounted by the increase in the pathway intermediates accumulation as compared to the control. The pathway intermediates include squalene, cycloartenol, 24-methylene cycloartenol, obtusifoliol, isofucosterol, and stigmasta-7-enol.

Six transgenic lines haboring pMON43058 produced 5.8- to 6-fold increase in total sterols and the rest of the 10 transgenic lines with the pMON43058 showed 3- to 5-fold increase in total sterols. The best performing transgenic lines showed about 2- to 3-fold increase in sitosterol and 4.5- to 6-fold increase in sitostanol levels. However, the campesterol accumulation was reduced by 50% in these lines. This was due to overexpression of the *Arabidopsis* SMTII enzyme which enhances the carbon flux towards the synthesis of 24-ethyl sterols thereby reducing the carbon flux through the pathway leading to the synthesis of 24-methyl sterols. As seen in pMON43057 transgenic lines, all of the transgenic lines harboring the pMON43058 also accumulated 50-60% of the total sterols in the form of pathway intermediates which are squalene, cycloartenol, 24-methylene cycloartenol, obtusifoliol, isofucosterol, and stigmasta-7-enol. These pathway intermediates normally form minor constituents in the sterol composition of seeds. However, in the transgenic seeds, probably due to increased carbon flux through the pathway, they accumulate in significant amounts. The pathway intermediates accumulation is highly significant when the truncated from of HMGR is overexpressed as compared to the full length form of HMGR suggesting that the overexpression of the truncated form of HMGR creates even greater increase in carbon flux through the pathway. This provides further evidence for additional control points for sterol biosynthesis in plants such as squalene epoxidase, sterol methyltransferase I, sterol C4-demethylase, obtusifoliol C14α-demethylase, sterol C5-desaturase, and sterol methyl transferase II.

Example 3

Enhancement of Phytosterol Biosynthesis in Seeds of Arabidopsis Transgenic Plants by Constitutive Expression of Different Forms of Arabidopsis and Rubber HMGR Enzymes Arabidopsis transgenic plants were generated using Agrobacterium mediated transformation of constructs (pMON53733, pMON53734, pMON53735, pMON53736, pMON53737, pMON53738, pMON53739, pMON53740) carrying cDNA encoding different forms of Arabidopsis and rubber HMGR enzymes driven by CaMV enhanced 35S promoter (FIGS. 13-20). The transformed Arabidopsis seeds carrying each of the above constructs were selected on kanamycin (50 µg/ml) medium to select for transformants expressing the selectable marker, the NPTII gene driven by CaMV 35S promoter. Kanamycin resistant Arabidopsis transgenic plants were grown in green house for maturity and seeds were collected from each of the transgenic lines for sterol analysis. About 50 mg of seeds from each transgenic line were weighed, homogenized and used for saponification to extract sterols as described in Example 2.

FIGS. 21-26 describe the sterol analysis data obtained from the transgenic lines carrying each of the above constructs. FIG. 27 shows the effect on different sterol end products and pathway intermediate accumulation when different forms of rubber HMGR cDNAs were expressed constitutively in transgenic Arabidopsis plants. When truncated rubber HMGR (with or without linker region) was overexpressed the total sterol accumulation in seeds increased by 2.9 to 3.7-fold as compared with the wild type control plants. The sterol end products such as campesterol and sitosterol showed 1.5 to 2-fold increase in the lines expressing truncated form of rubber HMGR (with and without linker). However the sitostanol end product accumulation in the transgenic lines harboring the truncated form of rubber HMGR (with and without linker) was enhanced by 2.8 to 7-fold. There is a significant accumulation of pathway intermediates such as cycloartenol and 24-methylene cycloartenol in the seeds of the transgenic lines transformed with the truncated form of rubber HMGR (with and without linker region). The wild type control plants used in the experiment do not accumulate both of the pathway intermediates.

Example 4

Comparison of Steroid Compounds from HMGR Constructs in a Yeast HMGR1 Knockout Mutant The effects on the sterol levels of the expression of various HMGR constructs expressed in a yeast HMGR1 knockout mutant were compared. Constructs containing a nucleic acid encoding the full length HMGR polypeptides from Arabidopsis and rubber were compared to those encoding a truncated Arabidopsis or rubber HMGR polypeptide that were lacking both the membrane binding and linker region of HMGR. The control yeast cells were transformed with a similar construct lacking a polypeptide encoding any form of HMGR.

Yeast cells transformed with Arabidopsis HMGR and rubber HMGR constructs accumulated approximately the same amounts of zymosterol and ergosterol, but more squalene than the control yeast.

Transformed yeast cells having rubber HMGR constructs accumulated about the same amount of ergosterol, but about twice as much squalene and zymosterol than the control yeast.

Transformed yeast cells having Arabidopsis tHMGR constructs accumulated three times as much squalene, twice as much zymosterol, and about 30 percent more ergosterol than the control yeast.

Transformed yeast cells having rubber tHMGR constructs accumulated three times as much squalene, four times as much zymosterol, and about 50 percent more ergosterol than the control yeast.

The data are shown in a FIG. 28, "Plant HMGR1 Constructs in Yeast HMGR1 Knockout Mutant".

Example 5

Gene Sequences for all Genes Listed in the Application

The sequences obtained from the NCBI public database are SEQ ID NO.: 1, 2, 3, 20, 21, 22, 23. These sequences are included in the appendix and denoted as follows:

```
Appendix A = SEQ ID NO. 1,
Appendix B = SEQ ID NO. 2,
Appendix C = SEQ ID NO. 3,
Appendix D = SEQ ID NO. 20,
Appendix E = SEQ ID NO. 21,
Appendix F = SEQ ID NO. 22,
Appendix G = SEQ ID NO. 23.

SEQ ID 1 = Arabidopsis squalene epoxidase protein
sequence (Accession NO: AC004786) See Appendix A SEQ ID 2 = Arabidopsis squalene epoxidase
(Accession NO: N64916) See Appendix B SEQ ID 3 = Arabidopsis squalene epoxidase
(Accession NO: T44667) See Appendix C SEQ ID 4 = Arabidopsis squalene epoxidase
(clone ID: ATA506263) nucleotide sequence
GAATTCCCGGGTCGACCCACGCGTCCGCTTATAGATAAGGATATGGCCTT

TACGAACGTTTGCCTATGGACGCTACTCGCCTTCATGCTGACTTGGACAG

TGTTCTACGTCACAAACAGGGGGAAGAAGGCGACGCAGTTGGCGGATGCG

GTGGTTGAAGAGCGAGAAGACGGTGCTACTGACGTTATCATCGTTGGGGC

TGGAGTAGGCGGCTCGGCTCTCGCATATGCTCTTGCTAAGGACGGGCGTC

GAGTCCATGTAATAGAGAGGGACCTGAGAGAACCAGAGAGAATCATGGGT

GAGTTTATGCAACCAGGAGGACGACTCATGCTCTCTAAGCTTGGTCTTGA

AGATTGTTTGGAGGGAATAGATGCCCAAAAAGCCACGGGCATGACAGTTT

ATAAGGACGGAAAAGAAGCAGTCGCATCTTTTCCCGTGGACAACAACAAT

TTTCCTTTTGATCCTTCGGCTCGATCTTTTCACAATGGCCGATTCGTCCA

ACGATTGCGGCAAAAGGCTTCTTCTCTTCCCAATGTGCGCCTGGAAGAAG

GAACGGTGAAGTCTTTGATAGAAGAAAAAGGAGTGATCAAAGGAGTGACA

TACAAAAATAGCGCAGGCGAAGAAACAACAGCCTTGGCACCTCTCACTGT

AGTATGCGACGGTTGCTACTCAAACCTTCGCCGGTCTCTTAATGACAACA

ATGCGGAGGTTCTGTCATACCAAGTTGGTTTTATCTCAAAGAACTGTCAG

CTTGAAGAACCCGAAAAGTTAAAGTTGATAATGTCTAAACCCTCCTTCAC
```

-continued

```
CATGTTGTATCAAATCAGCAGCACCGACGTTCGTTGTGTTTTTGAAGTTC
TCCCCAACAACATTCCTTCTATTTCAAATGGTGAAATGGCTACTTTCGTG
AAGAACACTATTGCTCCTCAGGTACCTTTAAAACTCCGCAAAATATTTTT
GAAAGGGATTGATGAAGGAGAACATATAAAAGCCATGCCAACAAAGAAGA
TGACAGCTACTTTGAGCGAGAAGAAAGGAGTGATTTTATTGGGAGATGCA
TTCAACATGCGTCATCCAGCAATCGCATCTGGAATGATGGTTTTATTATC
TGACATTCTCATTTTACGCCGTCTTCTCCAGCCATTAAGCAACCTTGGCA
ATGCGCAAAAAATCTCACAAGTTATCAAGTCCTTTTATGATATCCGCAAG
CCAATGTCAGCGACAGTTAACACGTTAGGAAATGCATTCTCTCAAGTGCT
AGTTGCATCGACGGACGAAGCAAAAGAGGCAATGAGACAAGGTTGCTATG
ATTACCTCTCTAGTGGTGGGTTTCGCACGTCAGGGATGATGGCTTTGCTA
GGCGGCATGAACCCTCGTCCGATCTCTCTCATCTATCATCTATGTGCTAT
CACTCTATCCTCCATTGGCCATCTACTCTCTCCATTTCCCTCTCCCCTTG
GCATTTGGCATAGCCTTCGACTTTTTGGTTTGGCTATGAAAATGTTGGTT
CCCCATCTCAAGGCTGAAGGAGTTAGCCAAATGTTGTTTCCAGTCAACGC
CGCCGCGTATAGCAAAAGCTATATGGCTGCAACGGCTCTTTAAAACACTG
GTGCTTTAAACTGCAAAATATAACACATATATAAATCCCGAATCTTTGTG
ATTCTGCATATATTGTGTTCTACAATTATTCTCATATAAATGAAAATTGT
TCTACGTAAAAGTAAAAGAAGGAATTGTAATACTAATAAAACGAGTTTT
TAATTCTGTTGAATGCTTGTGTATATTGGTGAAAAAAAAAAAAAAAAAA
AAAAAAAAAAAAAAAAAAAGGGCGGCCGC

SEQ ID 5 = Arabidopsis squalene epoxidase
(clone ID: ATA506263) amino acid translation
EFPGRPTRPLIDKDMAFTNVCLWTLLAFMLTWTVFYVTNRGKKATQLADA
VVEEREDGATDVIIVGAGVGGSALAYALAKDGRRVHVIERDLREPERIMG
EFMQPGGRLMLSKLGLEDCLEGIDAQKATGMTVYKDGKEAVASFPVDNNN
FPFDPSARSFHNGRFVQRLRQKASSLPNVRLEEGTVKSLIEEKGVIKGVT
YKNSAGEETTALAPLTVVCDGCYSNLRRSLNDNNAEVLSYQVGFISKNCQ
LEEPEKLKLIMSKPSFTMLYQISSTDVRCVFEVLPNNIPSISNGEMATFV
KNTIAPQVPLKLRKIFLKGIDEGEHIKAMPTKKMTATLSEKKGVILLGDA
FNMRHPAIASGMMVLLSDILILRRLLQPLSNLGNAQKISQVIKSFYDIRK
PMSATVNTLGNAFSQVLVASTDEAKEAMRQGCYDYLSSGGFRTSGMMALL
GGMNPRPISLIYHLCAITLSSIGHLLSPFPSPLGIWHSLRLFGLAMKMLV
PHLKAEGVSQMLFPVNAAAYSKSYMAATAL*

SEQ ID 6 = Arabidopsis squalene epoxidase
(clone ID: ATA304243) nucleotide sequence
GAATTCCCGGGTCGACCCACGCGTCCGCGGACGCGTGGGATTGAGAACAA
ATAGATTTGGTTATATATGGCTTTTACGCACGTTTGTTTATGGACGTTAG
TCGCCTTCGTGCTGACGTGGACGGTGTTCTACCTTACCAACATGAAGAAG
AAGGCGACGGATTTGGCTGATACGGTGGCTGAGGATCAAAAAGACGGTGC
TGCTGACGTCATTATCGTCGGGGCTGGTGTAGGTGGTTCGGCTCTCGCAT
ATGCTCTTGCTAAGGATGGGCGTGAGTACATGTGATCGAGAGGGACATG
```

```
AGAGAACCAGAAAGAATGATGGGTGAGTTTATGCAACCTGGCGGACGACT
CATGCTTTCTAAACTTGGCCTTCAAGATTGCTTGGAAGACATAGATGCAC
AGAAAGCCACGGGTTTGGCAGTTTATAAAGATGGAAAAGAAGCAGACGCA
CCTTTTCCAGTGGATAACAACAATTTTTCTTATGAACCTTCTGCTCGATC
TTTTCACAATGGCCGATTCGTCCAACAACTGCGTCGAAAGGCTTTTTCTC
TTTCCAATGTGCGCCTGGAAGAAGGAACGGTGAAGTCTTTACTAGAAGAA
AAAGGAGTGGTCAAAGGAGTGACATACAAGAATAAAGAAGGCGAAGAAAC
AACAGCCTTGGCACCTCTCACTGTGGTATGCGACGGTTGCTACTCAAACC
TTCGTCGGTCTCTTAATGATGACAACAATGCTGAGATTATGTCGTACATA
GTTGGTTACATCTCAAAGAATTGTCGGCTTGAAGAACCCGAAAAGCTACA
CTTGATATTGTCTAAACCATCTTTCACCATGGTATACCAATAAGCAGCA
CTGACGTTCGTTGTGGTTTTGAGGTTCTCCCCGAAAATTTTCCTTCTATT
GCAAATGGTGAAATGTCTACTTTCATGAAGAATACTATAGTTCCTCAGGT
ACCTCCAAAACTCCGCAAAATATTTTTGAAAGGTATAGATGAGGGAGCAC
ACATAAAAGTGGTGCCGGCAAAGCGCATGACATCTACTTTAAGCAAGAAG
AAAGGTGTGATTGTATTGGGAGATGCATTCAATATGCGTCATCCAGTTGT
TGCATCTGGAATGATGGTTTTACTGTCGGACATTCTCATTCTACGCCGTC
TTCTTCAGCCATTAAGCAACCTCGGCGATGCAAACAAAGTCTCAGAAGTT
ATCAATTCCTTTTATGATATCCGCAAGCCAATGTCGGCGACGGTTAACAC
ATTGGGAAATGCATTTTCTCAAGTACTAATTGGATCAACGGATGAAGCAA
AAGAGGCAATGAGACAGGGTGTCTATGATTACCTTTGTAGTGGCGGGTTT
CGTACGTCAGGGATGATGGCTCTGCTCGGCGGCATGAATCCTCGTCCTCT
CTCTCTCGTCTATCATCTTTGTGCCATCACTCTATCCTCCATTGGCCAAC
TGCTCTCTCCATTTCCCTCTCCCCTTCGCATTTGGCATAGCCTCAAGCTT
TTTGGTTTGGCCATGAAAATGTTGGTTCCCAATCTCAAAGCTGAAGGAGT
TAGCCAAATGTTGTTTCCAGCAAATGCAGCCGCGTATCACAAAAGCTATA
TGGCTGCAACCACTCTCTAAACTTTGATGCTCTCAATCGCAATATATATG
GAGCACGAATCTATGTGATTGTGCATTTGGTAAACGTGTATTGCAGTGCT
TATAATTATTAGTATGTAACGGGGAAAAGTTCTAAACACAAAAAAATAAA
CTTTTGAATGTTATATGTGTGAATTATTTTTGTTGTTACAAGTAATGCTC
TTTTTTTTTAGCTTCACACATGTATTATTGGAGCTAATTTTTTGTTTCTC
TGTTCTTTTATTTTTGTTTTCTTACTGTATTTACTTTGAAAAGTTTCGTT
TTATACATATTGGACATTTTTAAAAAAAAAAAAAAAAAAAAAAAAAAAA
AAAAAAAAAAAAAAAAAAAAAAAAAAAAAAAAAAAAAAAAAAAAAAAA
AAAAAAAAAAAAAAAAAAAAAAAAGGGCGGCCGC

SEQ ID 7 = Arabidopsis squalene epoxidase
(clone ID: ATA304243) amino acid translation
MAFTHVCLWTLVAFVLTWTVFYLTNMKKATDLADTVAEDQKDGAADVII
VGAGVGGSALAYALAKDGRRVHVIERDMREPERMMGEFMQPGGRLMLSKL
GLQDCLEDIDAQKATGLAVYKDGKEADAPFPVDNNNFSYEPSARSFHNGR
FVQQLRRKAFSLSNVRLEEGTVKSLLEEKGVVKGVTYKNKEGEETTALAP
LTVVCDGCYSNLRRSLNDDNNAEIMSYIVGYISKNCRLEEPEKLHLILSK
```

-continued

PSFTMVYQISSTDVRCGFEVLPENFPSIANGEMSTFMKNTIVPQVPPKLR

KIFLKGIDEGAHIKVVPAKRMTSTLSKKKGVIVLGDAFNMRHPVVASGMM

VLLSDILILRRLLQPLSNLGDANKVSEVINSFYDIRKPMSATVNTLGNAF

SQVLIGSTDEAKEAMRQGVYDYLCSGGFRTSGMMALLGGMNPRPLSLVYH

LCAITLSSIGQLLSPFPSPLRIWHSLKLFGLAMKMLVPNLKAEGVS QML

FPANAAAYHKSYMAATTL*

SEQ ID 8 = Arabidopsis squalene epoxidase
(clone ID: ATA102071) nucleotide sequence
AAATCATATTGAGAACAAATAGATTTGGTTATATATGGCTTTTACGCACG

TTTGTTTATGGACGTTAGTCGCCTTCGTGCTGACGTGGACGGTGTTCTAC

CTTACCAACATGAAGAAGAAGGCGACGGATTTGGCTGATACGGTGGCTGA

GGATCAAAAAGACGGTGCTGCTGACGTCATTATCGTCGGGGCTGGTGTAG

GTGGTTCGGCTCTCGCATATGCTCTGCTAAGTGTGCGCCTGGAAGAAGGA

ACGGTGAAGTCTTTACTAGAAGAAAAAGGAGTGGTCAAAGGAGTGACATA

CAAGAATAAAGAATGCGAACAAACAACAGCCTTGGCACCTCTCACTGTGG

TATGCGACGGTTGCTAATCAAACCTTCGTCGGTCTCTTAATG

SEQ ID 9 = Arabidopsis squalene epoxidase
(clone ID: ATA102071) amino acid translation
MAFTHVCLWTLVAFVLTWTVFYLTNMKKKATDLADTVAEDQKDGAADVII

VGAGVGGSALAYALLSVRLEEGTVKSLLEEKGVVKGVTYKNKECEQTTAL

APLTVVCDGC

SEQ ID 10 = Arabidopsis squalene epoxidase
(clone ID: ATA504158) nucleotide sequence
CACAAAGCAAAAAATCTCTGTAAAAGCAGAACGATAATGGAGTCACAAT

TATGGAATTGGATCTTACCTCTTTTGATCTCTTCTCCTCATCTCCTTC

GTCGCTTTCTATGGATTCTTCGTCAAACCGAAGCGGAACGGTCTCCGTCA

CGATCGGAAACTGTTTCTACCGTCACCTCCGACGTCGGATCTGTTAATA

TTACCGGAGATACTGTCGCTGATGTCATTGTTGTTGGAGCTGGTGTTGCT

GGTTCTGCTCTTGCTTATACTCTTGGAAAGGGGAAATTTAAACGCCGAGT

TCATGTGATTGAAAGAGATTTATCGGAGCCTGATCGTATTGTTGGGGAGT

TGTTACAGCCTGNGGGTTACCTCAAGTTACTGGAGTGTGGAATTGGAGAT

TGTGTGGAAGAAATAGATGCTCAGCNTGTGTATGGTTATGCACTTTTTAA

AAATGGG

SEQ ID 11 = Arabidopsis squalene epoxidase
(clone ID: ATA504158) amino acid translation
TKQKNLCKSRTIMESQLWNWILPLLISSLLISFVAFYGFFVKPKRNGLRH

DRKTVSTVTSDVGSVNITGDTVADVIVVGAGVAGSALAYTLGKGKFKRRV

HVIERDLSEPDRIVGELLQPXGYLKLLECGIGDCVEEIDAQXVYGYALFK

NG

SEQ ID 12 = Arabidopsis obtusifoliol
C14α-demethylase nucleotide sequence
(Accession NO: complement, join AC002329:
37461 . . . 38456, AC002329: 39121 . . . 39546)
(homolog of sorghum obtusifoliol C14α-demethylase)
nucleotide sequence
CGTGTTTTACAAATTTCCTTTGTTGGTTTTCCACAGATTTAAAGAACCCT

AACGAGAGAAAAAAATGGACTGGGATTACTATACGCTGTTGAAGACGAGT

GTGGCTATTATTATAGTGTTTGTTGTGGCCAAACTCATAACCTCCTCCAA

ATCCAAGAAGAAAACAAGTGTCGTCCCACTCCCTCCAGTTCTTCAAGCGT

GGCCTCCATTTATCGGATCCCTAATCCGCTTCATGAAAGGTCCAATAGTG

CTACTTAGAGAGGAATATCCTAAGCTTGGAAGTGTTTTCACAGTGAAGCT

TCTTCACAAAAACATCACTTTTCTCATCGGTCCCGAAGTCTCGTCCCACT

TTTTCAACGCTTATGAATCTGAACTCAGCCAGAAAGAAATTTACAAATTT

AATGTGCCTACTTTTGGCCCCGGAGTTGTGTTTGATGTTGACTATCCCGT

TCGGATGGAGCAGTTCCGATTCTTCTCCAGCGCTCTCAAGGATTACTTCT

CAAAATGGGGAGAAAGTGGGGAAGTGGATCTAAAGGCCGAGTTAGAGCGT

CTAATCACCTTGACTGCTAGTAGATGTCTATTGGGTCGAGAAGTCCGTGA

CCAACTTTTTGATGATGTTGCTCCATTGTTCCATGACCTTGATAAAGGCA

TGCAACCCATAAGTGTCATCTTCCCAAAGCTCCCCATTCCAGCTCACAAT

TGTCGTGACCGTGCTCGCGGAAAGATTGCAAAAATCTTTTCAAACATCAT

AGCAACAAGAAAACGCTCTGGTGACAAATCAGAGAACGACATGCTACAAT

GTTTCATCGACTCAAAGTACAAAGACGGTAGAGAGACAACTGAATCTGAA

GTAACTGGTTTGCTCATTGCTGGTTTGTTTGCAGGACAACATACAAGCTC

TATCACTGCCACATGGACCGGTGCTTATCTAATTCAAAACAAACACTGGT

GGTCCGCGGCTTTGGACGAGCAGAAGAAACTGATTGGAAAACATGGGGAC

AAGATCGACTACGATGTTTTGTCTGAGATGGATTTTCTGTTTCGCAGTGC

AAAAGAAGCTTTAAGGCTTCACCCTCCAAAGATCTTACTGCTGAGAACAG

TACACAGTGATTTCACCGTGACAACTCGAGAAGGAAAGCAATATGAGATA

CCAAAGGGTCATATCGTTGCAACTTCTCCTGCATTCGCCAACCGCTTACC

TCATGTCTACAAAGATCCGGAAAATTTTGATCCGGATAGATTTTCAAAGG

AAAGAGAAGAGGATAAAGCAGCTGGTTCGTGTTCATACATCTCTTTGGGA

GCTGGTAGGCACGAGTGTCCTGGTGGATCATTTGCGTTCTTGCAGATCAA

AGCCGTATGGTGTCACTTATTGAGAAACTTTGAGCTTGAGTTAGTGTCAC

CTTTCCCTGAAATCAACTGGAATGCTTTGGTCGTTGGTGCTAAAGGAAAT

GTCATGGTTCGTTACAAGCGTCGTCCCTTTTCTTAA

SEQ ID 13 = Arabidopsis obtusifoliol
C14α-demethylase nucleotide sequence (Accession
NO: complement, join AC002329: 37461 . . . 38456,
AC002329: 39121 . . . 39546) (homolog of sorghum
obtusifoliol C14α-demethylase) amino acid
translation
MDWDYYTLLKTSVAIIIVFVVAKLITSSKSKKKTSVVPLPPVLQAWPPFI

GSLIRFMKGPIVLLREEYPKLGSVFTVKLLHKNITFLIGPEVSSHFFNAY

ESELSQKEIYKFNVPTFGPGVVFDVDYPVRMEQFRFFSSALKDYFSKWGE

SGEVDLKAELERLITLTASRCLLGREVRDQLFDDVAPLFHDLDKGMQPIS

VIFPKLPIPAHNCRDRARGKIAKIFSNIIATRKRSGDKSENDMLQCFIDS

KYKDGRETTESEVTGLLIAGLFAGQHTSSITATWTGAYLIQNKHWWSAAL

DEQKKLIGKHGDKIDYDVLSEMDFLFRSAKEALRLHPPKILLLRTVHSDF

TVTTREGKQYEIPKGHIVATSPAFANRLPHVYKDPENFDPDRFSKEREED

KAAGSCSYISLGAGRHECPGGSFAFLQIKAVWCHLLRNFELELVSPFPEI

NWNALVVGAKGNVMVRYKRRPFS*

-continued

SEQ ID 14 = *Arabidopsis obtusifoliol* C14α-
demethylase (clone ID: ATA101105) nucleotide
sequence
GACACTATAGAAGAGCTATGACGTCGCATGCACGCGTACGTAAGCTCGGA

ATTCGGCTCGAGCTTGTTCACAAAAAGATTACTTTTCTTATTGGTCCTGA

AGTCTCTGCTCATTTTTTCAAAGCTTCTGAATCTGATCTTAGTCAGCAGG

AAGTGTATCAGTTCAATGTCCCTACTTTTGGTCCTGGAGTTGTTTTCGAT

GTTGATTATTCTGTTTCGTCAGGAGCAGTTCGGTTCTTCACTGAGGCACT

TAGAGTTAACAAGTTGAAGGGTTATGTGGATATGATGGTTACTGAAGCTG

AGGATTACTTCTCTAAATGGGGAGAGAGTGGTGAAGTTGATATTAAGGTT

GAGCTAGAGAGGCTCATCATCTTGACTGCAAGTGATGTTTACTGGGTCGA

GAAGTTCGTGATCAGCTTTTTGATGATGTCTCTGCTTTGTTCCATGACCT

TGACAATGGAATGCTTCCCATCAGTGCTTCCCATCAGTGTTCTCTTCCCA

TATCTCCCAATTCCAGCTCACCG

SEQ ID 15 = *Arabidopsis obtusifoliol* C14α-
demethylase (clone ID: ATA101105) amino acid
translation
HYRRAMTSHARVRKLGIRLELVHKKITFLIGPEVSAHFFKASESDLSQQE

VYQFNVPTFGPGVVFDVDYSVRQEQFGSSLRHLELTS

SEQ ID 16 = *Arabidopsis obtusifoliol* C14α-
demethylase (clone ID: ATA202967) nucleotide
sequence
TCGACCCCGCGTCCGCGGACGCGTGGGATCAGCTTCAAGCTTAAGAGAGC

TTCGAAAGCGAAAGCGACGATTTCTTCTCCATCGTGAGAGCAAATCTCCA

GAGCCGTTTTCTCTTCTTCTTCCTCCTCGCGCCGTCTCTGAAACTCC

ATCATCGTATCAATCAAATTGCTTCCTCCTCCAAATTGAAAAACAATGGA

ATTGGATTCGGAGAACAAATTGTTGAAGACGGGTTTGGTTATAGTGGCGA

CACTTGTTATAGCCAAACTCATCTTCTCTTTCTTCACTTCTGATTCTAAG

AAGAAGCGTCTTCCTCCTACTCTTAAAGCTTGGCCTCCATTGGTTGGAAG

TCTTATCAAATTCTTGAAAGGACCTATTATTATGCTTAGAGAGGAATACC

CTAAGCTTGGAAGTGTGTTTACTGTTAATCTTGTTCACAAAAAGATTACT

TTTCTTATTGGTCCTGAAGTCTCTGCTCATTTTTTCAAAGCTTCTGAATC

TGATCTTAGTCAGCAGGAAGTGTATCAGTTCAATGTCCCTACTTTTGGTC

CTGGAGTTGTTTTCGATGTTGATTATTCTGTTCGTCAGGAGCAGTTTCGG

TTCTTCACTGAGGCACTTAGAGTTAACAAGTTGAAGGGTTATGTGGATAT

GATGGTTACTGAAGCTGAGGATTACTTCTCTAAATGGGGAGAGAGTGGTG

AAGTTGATATTAAGGTTGAGCTAGAGAGGCTCATCATCTTGACTGCAAGT

AGATGTTTACTGGGTCGAGAAGTTCGTGATCAGCTTTTTGATGATGTCTC

TGCTTTGTTCCATGACCTTGACAATGGAATGCTTCCCATCAGTGTTCTCT

TCCCATATCTCCCAATTCCAGCTCACCGCCGTCGTGACCGTGCCCGAGAA

AAGCTTTCGGAGATTTTCGCAAAAATCATTGGGTCGAGAAAACGCTCTGG

AAAAACAGAACGACATGCTGCAGTGTTTCATCGAATCAAAGTACAAAG

ATGGTAGACAGAACCGAATCGAAGTCACTGGTTTGCTCATTGCTGCT

CTGTtGCAGGACAACACACGAGCTCTATCACTTCCACCTGGACCGGTGC

TTATCTGATGCGATACAAAGAGTACTTCTCAGCTGCTCTTGATGAGCAGA

AGAACCTGATTGCGAAACATGGAGACAAGATCGATCATGATATCTTATCC

GAGATGGATGTTCTCTACCGCTGCATTAAGGAAGCGTTGAGGCTTCACCC

TCCACTCATCATGTTAATGAGAGCCTCGCACAGTGATTTCAGCGTGACAG

CTCGGGATGGAAAAACTTACGATATCCCAAAGGGTCACATCGTTGCAACC

TCCCCTGCATTTGCCAACCGCTTACCGCACATCTTCAAAGACCCCGACAC

CTACGACCCAGAAAGATTCTCCCCTGGAAGAGAAGAGGACAAAGCCGCAG

GGGCATTCTCGTACATTGCATTCGGAGGGGGAAGGCACGGGTGCCTTGGA

GAGCCGTTTGCTTACCTGCAGATCAAAGCCATATGGAGTCATTTGTTGAG

GAACTTCGAGCTTGAGCTAGTTTCACCGTTCCCTGAGATTGACTGGAACG

CTATGGTGGTTGGAGTTAAAGGCAATGTGATGGTGCGTTACAAGAGGCgc

CAGCTTTCTTAAAGACAAGTTTAAGGTTATTGCAGCTTTGGATTTTCTC

TCTGGTTTCTGCTTTGCTTTTGTCCCTCTCTGGTTTTAGTTTTGTTGTTG

AATAATTCTTCTGTTTTTATAAACTGTTGTTACTCTTTAATTGACATTTA

TTTTTAAGCTTCCTAAGTTTGTGGTTCAAAAAAAAAAAAAGGCGGCGTTA

CT

SEQ ID 17 = *Arabidopsis obtusifoliol* C14α-
demethylase (clone ID: ATA202967) amino acid
translation
MELDSENKLLKTGLVIVATLVIAKLIFSFFTSDSKKKRLPPTLKAWPPLV

GSLIKFLKGPIIMLREEYPKLGSVFTVNLVHKKITFLIGPEVSAHFFKAS

ESDLSQQEVYQFNVPTFGPGVVFDVDYSVRQEQFRFFTEALRVNKLKGYV

DMMVTEAEDYFSKWGESGEVDIKVELERLIILTASRCLLGREVRDQLFDD

VSALFHDLDNGMLPISVLFPYLPIPAHRRRDRAREKLSEIFAKIIGSRKR

SGKTENDMLQCFIESKYKDGRQTTESEVTGLLIAALFAGQHTSSITSTWT

GAYLMRYKEYFSAALDEQKNLIAKHGDKIDHDILSEMDVLYRCIKEALRL

HPPLIMLMRASHSDFSVTARDGKTYDIPKGHIVATSPAFANRLPHIFKDP

DTYDPERFSPGREEDKAAGAFSYIAFGGGRHGCLGEPPFAYLQIKAIWSHL

LRNFELELVSPFPEIDWNAMVVGVKGNVMVRYKRRQLS*

SEQ ID 18 = *Arabidopsis obtusifoliol* C14α-
demethylase (clone ID: ATA403931) nucleotide
sequence
TCGACCCCGCGTCCGCGGACGCGTGGGATCAGCTTCAAGCTTAAGAGAGC

TTCGAAAGCGAAAGCGACGATTTCTTCTCCATCGTGAGAGCAAATCTCCA

GAGCCGTTTTCTCTTCTTCTTCCTCCTCGCGCCGTCTCTGAAACTCC

ATCATCGTATCAATCAAATTGCTTCCTCCTCCAAATTGAAAAACAATGGA

ATTGGATTCGGAGAACAAATTGTTGAAGACGGGTTTGGTTATAGTGGCGA

CACTTGTTATAGCCAAACTCATCTTCTCTTTCTTCACTTCTGATTCTAAG

AAGAAGCGTCTTCCTCCTACTCTTAAAGCTTGGCCTCCATTGGTTGGAAG

TCTTATCAAATTCTTGAAAGGACCTATTATTATGCTTAGAGAGGAATACC

CTAAGCTTGGAAGTGTGTTTACTGTTAATCTTGTTCACAAAAAGATTACT

TTTCTTATTGGTCCTGAAGTCTCTGCTCATTTTTTCAAAGCTTCTGAATC

TGATCTTAGTCAGCAGGAAGTGTATCAGTTCAATGTCCCTACTTTTGGTC

CTGGAGTTGTTTTCGATGTTGATTATTCTGTTCGTCAGGAGCAGTTTCGG

-continued

TTCTTCACTGAGGCACTTAGAGTTAACAAGTTGAAGGGTTATGTGGATAT

GATGGTTACTGAAGCTGAGGATTACTTCTCTAAATGGGGAGAGAGTGGTG

AAGTTGATATTAAGGTTGAGCTAGAGAGGCTCATCATCTTGACTGCAAGT

AGATGTTTACTGGGTCGAGAAGTTCGTGATCAGCTTTTTGATGATGTCTC

TGCTTTGTTCCATGACCTTGACAATGGAATGCTTCCCATCAGTGTTCTCT

TCCCATATCTCCCAATTCCAGCTCACCGCCGTCGTGACCGTGCCCGAGAA

AAGCTTTCGGAGATTTTCGCAAAAATCATTGGGTCGAGAAAACGCTCTGG

AAAAACAGAGAACGACATGCTGCAGTGTTTCATCGAATCAAAGTACAAAG

ATGGTAGACAGACAACCGAATCTGAAGTCACTGGTTTGCTCATTGCTGCT

CTGTtTGCAGGACAACACACGAGCTCTATCACTTCCACCTGGACCGGTGC

TTATCTGATGCGATACAAAGAGTACTTCTCAGCTGCTCTTGATGAGCAGA

AGAACCTGATTGCGAAACATGGAGACAAGATCGATCATGATATCTTATCC

GAGATGGATGTTCTCTACCGCTGCATTAAGGAAGCGTTGAGGCTTCACCC

TCCACTCATCATGTTAATGAGAGCCTCGCACAGTGATTTCAGCGTGACAG

CTCGGGATGGAAAAACTTACGATATCCCAAAGGGTCACATCGTTGCAACC

TCCCCTGCATTTGCCAACCGCTTACCGCACATCTTCAAAGACCCCGACAC

CTACGACCCAGAAGATTCTCCCCTGGAAGAGAAGAGGACAAAGCCGCAG

GGGCATTCTCGTACATTGCATTCGGAGGGGGAAGGCACGGGTGCCTTGGA

GAGCCGTTTGCTTACCTGCAGATCAAAGCCATATGGAGTCATTTGTTGAG

GAACTTCGAGCTTGAGCTAGTTTCACCGTTCCCTGAGATTGACTGGAACG

CTATGGTGGTTGGAGTTAAAGGCAATGTGATGGTGCGTTACAAGAGGCgc

CAGCTTTCTTAAAGACAAGTTTAAGGTTATTGCAGCTTTGGATTTTTCTC

TCTGGTTTCTGCTTTGCTTTTGTCCCTCTCTGGTTTTAGTTTTGTTGTTG

AATAATTCTTCTGTTTTTATAAACTGTTGTTACTCTTTAATTGACATTTA

TTTTTAAGCTTCCTAAGTTTGTGGTTCAAAAAAAAAAAAGGCGGCGTTA

CT

SEQ ID 19 = Arabidopsis obtusifoliol C14α-
demethylase (clone ID: ATA403931) amino acid
translation
MELDSENKLLKTGLVIVATLVIAKLIFSFFTSDSKKKRLPPTLKAWPPLV

GSLIKFLKGPIIMLREEYPKLGSVFTVNLVHKKITFLIGPEVSAHFFKAS

ESDLSQQEVYQFNVPTFGPGVVFDVDYSVRQEQFRFFTEALRVNKLKGYV

DMMVTEAEDYFSKWGESGEVDIKVELERLIILTASRCLLGREVRDQLFDD

VSALFHDLDNGMLPISVLFPYLPIPAHRRRDRAREKLSEIFAKIIGSRKR

SGKTENDMLQCFIESKYKDGRQTTESEVTGLLIAALFAGQHTSSITSTWT

GAYLMRYKEYFSAALDEQKNLIAKHGDKIDHDILSEMDVLYRCIKEALRL

HPPLIMLMRASHSDFSVTARDGKTYDIPKGHIVATSPAFANRLPHIFKDP

DTYDPERFSPGREEDKAAGAFSYIAFGGGRHGCLGEPFAYLQIKAIWSHL

LRNFELELVSPFPEIDWNAMVVGVKGNVMVRYKRRQLS*

SEQ ID 20 = Arabidopsis sterol methyl
transferase I protein sequence (Accession NO:
U71400) See Appendix D SEQ ID 21 = Tobacco sterol methyl transferase I
protein sequence (from Prof. Pierre Benveniste
Accession NO: U81312) See Appendix E SEQ ID 22 = Arabidopsis sterol methyl
transferase II protein sequence (Accession NO:
X89867) (from Prof. Pierre Benveniste) See
Appendix F SEQ ID 23 = Arabidopsis sterol C5-desaturase
protein sequence (Accession NO: X90454) See
Appendix G SEQ ID 24 = Rubber truncated HMGR1m1 (S566 to A)
nucleotide sequence
ATGGCACGCGCCTCCCATGACGTGTGGGACCTCGAAGATACGGATCCCAA

CTACCTCATCGATGAAGATCACCGTCTCGTTACTTGCCCTCCCGCTAATA

TATCTACTAAGACTACCATTATTGCCGCACCTACCAAATTGCCTACCTCG

GAACCCTTAATTGCACCCTTAGTCTCGGAGGAAGACGAAATGATCGTCAA

CTCCGTCGTGGATGGGAAGATACCCTCCTATTCTCTGGAGTCGAAGCTCG

GGGACTGCAAACGAGCGGCTGCGATTCGACGCGAGGCTTTGCAGAGGATG

ACAAGGAGGTCGCTGGAAGGCTTGCCAGTAGAAGGGTTCGATTACGAGTC

GATTTTAGGACAATGCTGTGAAATGCCAGTGGGATACGTGCAGATTCCGG

TGGGGATTGCGGGGCCGTTGTTGCTGAACGGGCGGGAGTACTCTGTTCCA

ATGGCGACCACCGGAGGGTTGTTTGGTGGCGAGCACTAATAGAGGGTGTAA

GGCGATTTACTTGTCAGGTGGGGCCACCAGCGTCTTGTTGAAGGATGGCA

TGACAAGAGCGCCTGTTGTAAGATTCGCGTCGGCGACTAGAGCCGCGGAG

TTGAAGTTCTTCTTGGAGGATCCTGACAATTTTGATACCTTGGCCGTAGT

TTTTAACAAGTCCAGTAGATTTGCGAGGCTCCAAGGCATTAAATGCTCAA

TTGCTGGTAAGAATCTTTATATAAGATTCAGCTGCAGCACTGGCGATGCA

ATGGGGATGAACATGGTTTCTAAAGGGGTTCAAAACGTTCTTGAATTTCT

TCAAAGTGATTTTTCTGATATGGATGTCATTGGAATCTCAGGAAATTTTT

GTTCGGATAAGAAGCCTGCTGCTGTAAATTGGATTGAAGGACGTGGCAAA

TCAGTTGTTTGTGAGGCAATTATCAAGGAAGAGGTGGTGAAGAAGGTGTT

GAAAACCAATGTGGCCTCCCTAGTGGAGCTTAACATGCTCAAGAATCTTG

CTGGTTCTGCTGTTGCTGGTGCTTTGGGTGGATTTAATGCCCATGCAGGC

AACATCGTATCTGCAATCTTTATTGCCACTGGCCAGGATCCAGCACAGAA

TGTTGAGAGTTCTCATTGCATTACCATGATGGAAGCTGTCAATGATGGAA

AGGATCTCCATATCTCTGTGACCATGCCCTCCATTGAGGTGGGTACAGTC

GGAGGTGGAACTCAACTTGCATCTCAGTCTGCTTGTCTCAATTTGCTTGG

GGTGAAGGGTGCAAACAAAGAGTCGCCAGGATCAAACTCAAGGCTCCTTG

CTGCCATCGTAGCTGGTTCAGTTTTGGCTGGTGAGCTCTCCTTGATGTCT

GCCATTGCAGCTGGGCAGCTTGTCAAGAGTCACATGAAGTACAACAGAGC

CAGCAAAGATATGTCTAAAGCTGCATCTTAG

SEQ ID 25 = Rubber truncated HMGR1m1 (S566 to A)
amino acid translation
MARASHDVWDLEDTDPNYLIDEDHRLVTCPPANISTKTTIIAAPTKLPTS

EPLIAPLVSEEDEMIVNSVVDGKIPSYSLESKLGDCKRAAAIRREALQRM

TRRSLEGLPVEGFDYESILGQCCEMPVGYVQIPVGIAGPLLLNGREYSVP

```
MATTEGCLVASTNRGCKAIYLSGGATSVLLKDGMTRAPVVRFASATRAAE

LKFFLEDPDNFDTLAVVFNKSSRFARLQGIKCSIAGKNLYIRFSCSTGDA

MGMNMVSKGVQNVLEFLQSDFSDMDVIGISGNFCSDKKPAAVNWIEGRGK

SVVCEAIIKEEVVKKVLKTNVASLVELNMLKNLAGSAVAGALGGFNAHAG

NIVSAIFIATGQDPAQNVESSHCITMMEAVNDGKDLHISVTMPSIEVGTV

GGGTQLASQSACLNLLGVKGANKESPGSNSRLLAAIVAGSVLAGELSLMS

AIAAGQLVKSHMKYNRASKDMSKAAS

SEQ ID. 26 = Rubber truncated HMGR1m2 (S567 to
A) nucleotide sequence
ATGGCACGCGCCTCCCATGACGTGTGGGACCTCGAAGATACGGATCCCAA

CTACCTCATCGATGAAGATCACCGTCTCGTTACTTGCCCTCCCGCTAATA

TATCTACTAAGACTACCATTATTGCCGCACCTACCAAATTGCCTACCTCG

GAACCCTTAATTGCACCCTTAGTCTCGGAGGAAGACGAAATGATCGTCAA

CTCCGTCGTGGATGGGAAGATACCCTCCTATTCTCTGGAGTCGAAGCTCG

GGGACTGCAAACGAGCGGCTGCGATTCGACGCGAGGCTTTGCAGAGGATG

ACAAGGAGGTCGCTGGAAGGCTTGCCAGTAGAAGGGTTCGATTACGAGTC

GATTTTAGGACAATGCTGTGAAATGCCAGTGGGATACGTGCAGATTCCGG

TGGGGATTGCGGGGCCGTTGTTGCTGAACGGGCGGGAGTACTCTGTTCCA

ATGGCGACCACGGAGGGTTGTTTGGTGGCGAGCACTAATAGAGGGTGTAA

GGCGATTTACTTGTCAGGTGGGGCCACCAGCGTCTTGTTGAAGGATGGCA

TGACAAGAGCGCCTGTTGTAAGATTCGCGTCGGCGACTAGAGCCGCGGAG

TTGAAGTTCTTCTTGGAGGATCCTGACAATTTTGATACCTTGGCCGTAGT

TTTTAACAAGTCCAGTAGATTTGCGAGGCTCCAAGGCATTAAATGCTCAA

TTGCTGGTAAGAATCTTTATATAAGATTCAGCTGCAGCACTGGCGATGCA

ATGGGGATGAACATGGTTTCTAAAGGGGTTCAAAACGTTCTTGAATTTCT

TCAAAGTGATTTTTCTGATATGGATGTCATTGGAATCTCAGGAAATTTTT

GTTCGGATAAGAAGCCTGCTGCTGTAAATTGGATTGAAGGACGTGGCAAA

TCAGTTGTTTGTGAGGCAATTATCAAGGAAGAGGTGGTGAAGAAGGTGTT

GAAAACCAATGTGGCCTCCCTAGTGGAGCTTAACATGCTCAAGAATCTTG

CTGGTTCTGCTGTTGCTGGTGCTTTGGGTGGATTTAATGCCCATGCAGGC

AACATCGTATCTGCAATCTTTATTGCCACTGGCCAGGATCCAGCACAGAA

TGTTGAGAGTTCTCATTGCATTACCATGATGGAAGCTGTCAATGATGGAA

AGGATCTCCATATCTCTGTGACCATGCCCTCCATTGAGGTGGGTACAGTC

GGAGGTGGAACTCAACTTGCATCTCAGTCTGCTTGTCTCAATTTGCTTGG

GGTGAAGGGTGCAAACAAAGAGTCGCCAGGATCAAACTCAAGGCTCCTTG

CTGCCATCGTAGCTGGTTCAGTTTTGGCTGGTGAGCTCTCCTTGATGTCT

GCCATTGCAGCTGGGCAGCTTGTCAAGAGTCACATGAAGTACAACAGATC

CGCCAAAGATATGTCTAAAGCTGCATCTTAG

SEQ ID 27 = Rubber truncated HMGR1m2 (S567 to A)
amino acid translation
MARASHDVWDLEDTDPNYLIDEDHRLVTCPPANISTKTTIIAAPTKLPTS

EPLIAPLVSEEDEMIVNSVVDGKIPSYSLESKLGDCKRAAAIRREALQRM

TRRSLEGLPVEGFDYESILGQCCEMPVGYVQIPVGIAGPLLLNGREYSVP

MATTEGCLVASTNRGCKAIYLSGGATSVLLKDGMTRAPVVRFASATRAAE

LKFFLEDPDNFDTLAVVFNKSSRFARLQGIKCSIAGKNLYIRFSCSTGDA

MGMNMVSKGVQNVLEFLQSDFSDMDVIGISGNFCSDKKPAAVNWIEGRGK

SVVCEAIIKEEVVKKVLKTNVASLVELNMLKNLAGSAVAGALGGFNAHAG

NIVSAIFIATGQDPAQNVESSHCITMMEAVNDGKDLHISVTMPSIEVGTV

GGGTQLASQSACLNLLGVKGANKESPGSNSRLLAAIVAGSVLAGELSLMS

AIAAGQLVKSHMKYNRSAKDMSKAAS
```

Example 6

*Arabidopsis* Obtusifoliol C14α-demethylase Constructs

The *Arabidopsis* obtusifoliol C14α-demethylase gene was amplified from two separate *Arabidopsis* mRNA samples (SIN 2 and Keto-10) through use of primers BXK33 and BXK34, as described below.

BXK33 (SEQ ID 28): 5'-GAGATCTGAACCCTAACGAGAG-3'

BXK34 (SEQ ID 29): 5'-GGAGCTCTTAAGAAAAGGGACGACGC-3'

The primer BXK33 has a Bgl II cleavage site shown in bold. The primer BXK34 has a Sac I cleavage site shown in bold. The actual size of the structural gene is 1.445 Kb.

The *Arabidopsis* mRNA was amplified using a Perkin Elmer GeneAmp RT-PCR kit. The reverse transcription reaction used 25 mM MgCl$_2$ (4 μl; 5 mM final), 10×PCR buffer (2 μl), di DEPC water (1 μl), 2 μl each of 1 mM solution of each of four dNTPs (dGTP, dATP, dUTP, dCTP), RNase inhibitor (1 μl of 10 units per μl stock), MMLV reverse transcriptase (1 μl of a 2.5 U/μl stock), Oligo d(T) 16 Primer (1 μl of a 2.5 μM stock), and 2 μl of an *Arabidopsis* polyA RNA sample. The reaction mix was incubated at room temperature (about 20° C.) for 10 minutes, then in a PCR machine for one cycle (15 min. at 42° C., 5 min. at 99° C. and 5 min. at 4° C.).

Separate primer-mediated amplification reactions were carried out using Taq DNA polymerase and Vent DNA polymerase to obtain *Arabidopsis* obtusifoliol C14α-demethylase cDNA from the amplified mRNA sample.

| Taq PCR Reaction | Vent PCR Reaction |
| --- | --- |
| 4 μl 25 mM MgCl$_2$ | 4 μl 25 mM MgCl$_2$ |
| 8 μl 10X PCR buffer II | 8 μl 10X Vent PCR buffer |
| 65.5 μl di DEPC water | 65.5 μl di DEPC water |
| 0.5 μl AmpliTaq polymerase | 0.5 μl Vent polymerase |

After 1 minute and 35 seconds at 95° C., 1 μl each of 15 μM stocks of the upstream and downstream primers (BXK33 and BXK34) were added to the PCR reaction (100 μl total PCR reaction volume) and the PCR reaction solutions were subjected to 35 cycles (95° C. for 15 seconds, then 60° C. for 30 seconds). The amplified PCR reaction was then maintained at 72° C. for 7 minutes and then stored at 4° C. An amplification positive control reaction was carried out under the same conditions with DM151 and DM152 primers.

DM151 (SEQ ID 30): 5'-GTCTCTGAATCAGAAATCCTTCTATC-3'

DM152 (SEQ ID 31); 5'-CATGTCAAATTTCACTGCTTCATCC-3'

Electrophoresis of the nucleic acid solutions after PCR amplification displayed an amplification product corresponding approximately to the size of the desired 1.445 Kb structural gene. The fragment was cloned into an M13 vector. A representative sequencing reaction consisted of: 10 μl of plasmid DNA (200-500 ng), 2 μl of M13 Forward or Reverse primer (15 picomoles) and 8 μl of Big Dye Terminator Reaction Mix (PE Applied Biosci.). The clone copy of ATA101105 was called CPR17398. The sequence of the selected clone (*Arabidopsis* obtusifoliol C14α-demethylase) is identified as SEQ ID NO:9.

The predicted polypeptide sequence for the cloned *Arabidopsis* obtusifoliol C14α-demethylase sequence was subjected to a BLAST search in the public database and found to align with the sorghum obtusifoliol 14-alpha demethylase polypeptide (ATA101105/U74319/g1658192; and g1216657/U74319) exhibiting 75-78% sequence identity and 87-90% sequence homology. The cloned nucleic acid encoding *Arabidopsis* obtusifoliol C14α-demethylase (SEQ ID No:9) is missing the 5' end.

The 5' terminal portion of the structural gene was obtained by the RACE (Rapid Amplification of cDNA Ends) PCR using primers BXK39 and BXK40 per manufacturer's instructions (Clontech).

BXK39 (SEQ ID 32):
5'-GAGATCTCCACAGATTTAAAGAACCCTAACG-3'

BXK40 (SEQ ID 33):
5'-GGAGCTCGGTTTTTAAGAAAAGGGACGACGC-3'

The cloned nucleic acid encoding full length *Arabidopsis* obtusifoliol C14α-demethylase is identified as SEQ ID No:8. The amplified *Arabidopsis* obtusifoliol C14α-demethylase structural gene is useful for making constructs that express *Arabidopsis* obtusifoliol C14α-demethylase in transgenic plants.

In light of the detailed description of the invention and the examples presented above, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventor does not intend to be bound by those conclusions and functions, but puts them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

What is claimed is:

1. A plant, the genome of which includes introduced DNA comprising:

DNA encoding a polypeptide having 3-hydroxy-3-methylglutaryl-Coenzyme A reductase enzyme activity, wherein said plant contains an elevated level of total accumulated sterol, compared to an otherwise identical plant, the genome of which does not comprise said introduced DNA encoding a polypeptide having 3-hydroxy-3-methylglutaryl-Coenzyme A reductase enzyme activity; and further comprising introduced DNA encoding at least one polypeptide having steroid pathway enzyme activity selected from the group consisting of squalene epoxidase enzyme activity, sterol methyl transferase I enzyme activity, sterol C4-demethylase enzyme activity, obtusifoliol C14α-demethylase enzyme activity, sterol C5-desaturase enzyme activity, and sterol methyl transferase II enzyme activity, wherein said introduced DNAs are operatively linked to regulatory signals that cause seed-specific expression of said introduced DNAs, and wherein seeds of said plant contain a reduced level of squalene, cycloartenol, 24-methylene cycloartenol, obtusifoliol, stigmasta-7-enol, or campesterol compared to the seeds of an otherwise identical plant whose genome does not contain introduced DNA encoding said at least one polypeptide having steroid pathway enzyme activity.

2. A plant, the genome of which includes an introduced DNA sequence encoding a polypeptide having 3-hydroxy-3-methylglutaryl-Coenzyme A reductase enzyme activity and an introduced DNA sequence encoding at least one polypeptide having squalene epoxidase enzyme activity, sterol methyl transferase I enzyme activity, sterol C4-demethylase enzyme activity, obtusifoliol C14α-demethylase enzyme activity, sterol C5-desaturase enzyme activity, or sterol methyl transferase II enzyme activity, wherein said introduced DNA is operably linked to regulatory signals that cause seed-specific expression of said introduced DNA, and wherein said plant produces seed having an elevated level of a steroid pathway product, compared to a corresponding transgenic or non-transgenic plant that does not contain said introduced DNA.

3. A plant comprising introduced DNA encoding (i) a polypeptide having 3-hydroxy-3-methylglutaryl-Coenzyme A reductase enzyme activity and (ii) at least one additional polypeptide having squalene epoxidase enzyme activity, sterol methyl transferase I enzyme activity, sterol C4-demethylase enzyme activity, obtusifoliol C14α-demethylase enzyme activity, sterol C5-desaturase enzyme activity, or sterol methyl transferase II enzyme activity, wherein said plant produces a storage organ having an elevated level of a sterol pathway product compared to a corresponding transgenic or non-transgenic plant that does not contain said introduced DNA.

4. The plant of claim 3, wherein said storage organ contains a reduced level of squalene, cycloartenol, 24-methylene cycloartenol, obtusifoliol, stigmasta-7-enol, campesterol, or mixtures thereof, compared to a corresponding transgenic plant that comprises introduced DNA encoding a polypeptide having 3-hydroxy-3-methylglutaryl-Coenzyme A reductase enzyme activity but that does not contain introduced DNA encoding at least one polypeptide having squalene epoxidase enzyme activity, sterol methyl transferase I enzyme activity, sterol C4-demethylase enzyme activity, obtusifoliol C14α-demethylase enzyme activity, sterol C5-desaturase enzyme activity or sterol methyl transferase II enzyme activity.

5. The plant of claim 1, wherein said regulatory signals cause seed-specific expression of said introduced DNAs.

6. A seed of a plant according to claim 1.

7. Progeny of a plant according to claim 1.

8. A plant cell or transformed plant cell of a plant according to claim 1.

9. A cell culture, comprising cells according to claim 8.

10. A plant according to claim 1, wherein said plant is an apomictic plant.

11. A uniform population of plants according to claim 1.

12. A part, other than a seed, of a plant according to claim 1.

* * * * *

SEQUENCE LISTING

<160> NUMBER OF SEQ ID NOS: 33

<210> SEQ ID NO 1
<211> LENGTH: 585
<212> TYPE: PRT
<213> ORGANISM: Arabidopsis thaliana

<400> SEQUENCE: 1

```
Met Lys Pro Phe Val Ile Arg Asn Leu Pro Arg Phe Gln Ser Thr Leu
1               5                  10                  15

Arg Ser Ser Leu Leu Tyr Thr Asn His Arg Pro Ser Ser Arg Phe Ser
            20                  25                  30

Leu Ser Thr Arg Arg Phe Thr Thr Gly Ala Thr Tyr Ile Arg Arg Trp
        35                  40                  45

Lys Ala Thr Ala Ala Gln Thr Leu Lys Leu Ser Ala Val Asn Ser Thr
    50                  55                  60

Val Met Met Lys Pro Ala Lys Ile Ala Leu Asp Gln Phe Ile Ala Ser
65                  70                  75                  80

Leu Phe Thr Phe Leu Leu Leu Tyr Ile Leu Arg Arg Ser Ser Asn Lys
                85                  90                  95

Asn Lys Lys Asn Arg Gly Leu Val Val Ser Gln Asn Asp Thr Val Ser
            100                 105                 110

Lys Asn Leu Glu Thr Glu Val Asp Ser Gly Thr Asp Val Ile Ile Val
        115                 120                 125

Gly Ala Gly Val Ala Gly Ser Ala Leu Ala His Thr Leu Gly Lys Glu
    130                 135                 140
```

```
Gly Arg Arg Val His Val Ile Glu Arg Asp Phe Ser Glu Gln Asp Arg
145                 150                 155                 160

Ile Val Gly Glu Leu Leu Gln Pro Gly Gly Tyr Leu Lys Leu Ile Glu
                165                 170                 175

Leu Gly Leu Glu Asp Cys Val Lys Lys Ile Asp Ala Gln Arg Val Leu
            180                 185                 190

Gly Tyr Val Leu Phe Lys Asp Gly Lys His Thr Lys Leu Ala Tyr Pro
        195                 200                 205

Leu Glu Thr Phe Asp Ser Asp Val Ala Gly Arg Ser Phe His Asn Gly
210                 215                 220

Arg Phe Val Gln Arg Met Arg Glu Lys Ala Leu Thr Leu Ser Asn Val
225                 230                 235                 240

Arg Leu Glu Gln Gly Thr Val Thr Ser Leu Leu Glu Glu His Gly Thr
                245                 250                 255

Ile Lys Gly Val Arg Tyr Arg Thr Lys Glu Gly Asn Glu Phe Arg Ser
            260                 265                 270

Phe Ala Pro Leu Thr Ile Val Cys Asp Gly Cys Phe Ser Asn Leu Arg
        275                 280                 285

Arg Ser Leu Cys Lys Pro Lys Val Asp Val Pro Ser Thr Phe Val Gly
290                 295                 300

Leu Val Leu Glu Asn Cys Glu Leu Pro Phe Ala Asn His Gly His Val
305                 310                 315                 320

Val Leu Gly Asp Pro Ser Pro Ile Leu Met Tyr Pro Ile Ser Ser Ser
                325                 330                 335

Glu Val Arg Cys Leu Val Asp Val Pro Gly Gln Lys Leu Pro Pro Ile
            340                 345                 350

Ala Asn Gly Glu Met Ala Lys Tyr Leu Lys Thr Arg Val Ala Pro Gln
        355                 360                 365

Val Pro Thr Lys Val Arg Glu Ala Phe Ile Thr Ala Val Glu Lys Gly
370                 375                 380

Asn Ile Arg Thr Met Pro Asn Arg Ser Met Pro Ala Asp Pro Ile Pro
385                 390                 395                 400

Thr Pro Gly Ala Leu Leu Gly Asp Ala Phe Asn Met Arg His Pro
                405                 410                 415

Leu Thr Gly Gly Gly Met Thr Val Ala Leu Ala Asp Ile Val Val Leu
                420                 425                 430

Arg Asp Leu Leu Arg Pro Ile Arg Asn Leu Asn Asp Lys Glu Ala Leu
            435                 440                 445

Ser Lys Tyr Ile Glu Ser Phe Tyr Thr Leu Arg Lys Pro Val Ala Ser
        450                 455                 460

Thr Ile Asn Thr Leu Ala Asp Ala Leu Tyr Lys Val Phe Leu Ala Ser
465                 470                 475                 480

Ser Asp Glu Ala Arg Thr Glu Met Arg Glu Ala Cys Phe Asp Tyr Leu
                485                 490                 495

Ser Leu Gly Gly Val Phe Ser Ser Gly Pro Val Ala Leu Leu Ser Gly
            500                 505                 510

Leu Asn Pro Arg Pro Leu Ser Leu Val Leu His Phe Phe Ala Val Ala
        515                 520                 525

Ile Tyr Ala Val Cys Arg Leu Met Leu Pro Phe Pro Ser Ile Glu Ser
530                 535                 540

Phe Trp Leu Gly Ala Arg Ile Ile Ser Ala Ser Ser Ile Ile Phe
545                 550                 555                 560

Pro Ile Ile Lys Ala Glu Gly Val Arg Gln Met Phe Phe Pro Arg Thr
```

```
                    565                 570                 575
Ile Pro Ala Ile Tyr Arg Ala Pro Pro
            580                 585

<210> SEQ ID NO 2
<211> LENGTH: 418
<212> TYPE: DNA
<213> ORGANISM: Arabidopsis thaliana
<220> FEATURE:
<221> NAME/KEY: misc_feature
<222> LOCATION: (1)..(418)
<223> OTHER INFORMATION: n=a, c, g or t

<400> SEQUENCE: 2
cttacgcgtg gttatngacg cttctcgcct tgttctgac atggatgatt tttcacctca      60
tcaagatgaa gaaggcggca accggagatt tagaggccga ggcagaagca agaagagatg     120
gtgcaacgga tgtcatcatt gtnggggcgg gtgttgcagg cgcttctctt gcttatgcnt     180
tagctaagga tngacgacga gtacatgtga tagagangga cttaaaagag ccacaaagat     240
tcatgggaga nctgatgcaa ncggaggtc gctttcatgt taagcccagc ttggcctcga      300
agattgttnt ggaggacatn gacgcacaag aatncgaaan cctttggcat atnccaagnn     360
tggaaacacg cgaaatggcc tttccanatg aaaagaattt cctcatgag ccagtagg       418

<210> SEQ ID NO 3
<211> LENGTH: 354
<212> TYPE: DNA
<213> ORGANISM: Arabidopsis thaliana
<220> FEATURE:
<221> NAME/KEY: misc_feature
<222> LOCATION: (1)..(354)
<223> OTHER INFORMATION: n=a, c, g or t

<400> SEQUENCE: 3
gcaatgactt acgcgtggtt atggacgctt ctngcctttn tnctgacatg gatggttttt      60
cacctcanca agatgaagaa ggcggcaacc ggagatttag aggccgaggc agaagcaaga     120
agagatggtg caacggatgt natcattgtt gggcgggtn ttgcaggcgc ttctnttgct     180
tatnctttag ctaaggatgg acgacgagta catgtgatag agagggactt aaaagagcca     240
caaagattca tggagaganct gatgcaagcg gggaggtcgc ttcatgttag cccagnttgg   300
cctcgaagat tttttttgna gggcataaga cgnaccaana agcggaatnc cttt           354

<210> SEQ ID NO 4
<211> LENGTH: 1829
<212> TYPE: DNA
<213> ORGANISM: Arabidopsis thaliana

<400> SEQUENCE: 4
gaattcccgg gtcgacccac gcgtccgctt atagataagg atatggcctt tacgaacgtt      60
tgcctatgga cgctactcgc cttcatgctg acttggacag tgttctacgt cacaaacagg     120
gggaagaagg cgacgcagtt ggcggatgcg gtggttgaag agcgagaaga cggtgctact     180
gacgttatca tcgttggggc tggagtaggc ggctcggctc tcgcatatgc tcttgctaag     240
gacgggcgtc gagtccatgt aatagagagg gacctgagag aaccagagag aatcatgggt     300
gagtttatgc aaccaggagg acgactcatg ctctctaagc ttggtcttga agattgtttg     360
gagggaatag atgcccaaaa agccacgggc atgacagttt ataaggacgg aaaagaagca     420
gtcgcatctt ttcccgtgga caacaacaat tttccttttg atccttcggc tcgatctttt     480
cacaatggcc gattcgtcca acgattgcgg caaaaggctt cttctcttcc caatgtgcgc     540
```

```
ctggaagaag gaacggtgaa gtctttgata gaagaaaaag gagtgatcaa aggagtgaca    600
tacaaaaata gcgcaggcga agaaacaaca gccttggcac ctctcactgt agtatgcgac    660
ggttgctact caaaccttcg ccggtctctt aatgacaaca atgcggaggt tctgtcatac    720
caagttggtt ttatctcaaa gaactgtcag cttgaagaac ccgaaaagtt aaagttgata    780
atgtctaaac cctccttcac catgttgtat caaatcagca gcaccgacgt tcgttgtgtt    840
tttgaagttc tccccaacaa cattccttct atttcaaatg gtgaaatggc tactttcgtg    900
aagaacacta ttgctcctca ggtaccttta aaactccgca aaatattttt gaagggatt    960
gatgaaggag aacatataaa agccatgcca acaaagaaga tgacagctac tttgagcgag   1020
aagaaaggag tgattttatt gggagatgca ttcaacatgc gtcatccagc aatcgcatct   1080
ggaatgatgg ttttattatc tgacattctc attttacgcc gtcttctcca gccattaagc   1140
aaccttggca atgcgcaaaa aatctcacaa gttatcaagt cctttttatga tatccgcaag   1200
ccaatgtcag cgacagttaa cacgttagga atgcattct ctcaagtgct agttgcatcg   1260
acggacgaag caaagaggc aatgagacaa ggttgctatg attacctctc tagtggtggg   1320
tttcgcacgt cagggatgat ggctttgcta ggcggcatga cccctcgtcc gatctctctc   1380
atctatcatc tatgtgctat cactctatcc tccattggcc atctactctc tccatttccc   1440
tctccccttg gcatttggca tagccttcga cttttgggtt tggctatgaa atgttggtt   1500
ccccatctca aggctgaagg agttagccaa atgttgtttc cagtcaacgc cgccgcgtat   1560
agcaaaagct atatggctgc aacggctctt taaaacactg gtgctttaaa ctgcaaaata   1620
taacacatat ataaatcccg aatctttgtg attctgcata tattgtgttc tacaattatt   1680
ctcatataaa tgaaaattgt tctacgtaaa agtaaaaaga aggaattgta atactaataa   1740
aacgagtttt taattctgtt gaatgcttgt gtatattggt gaaaaaaaaa aaaaaaaaaa   1800
aaaaaaaaa aaaaaaaaag ggcggccgc                                      1829

<210> SEQ ID NO 5
<211> LENGTH: 530
<212> TYPE: PRT
<213> ORGANISM: Arabidopsis thaliana

<400> SEQUENCE: 5

Glu Phe Pro Gly Arg Pro Thr Arg Pro Leu Ile Asp Lys Asp Met Ala
1               5                   10                  15

Phe Thr Asn Val Cys Leu Trp Thr Leu Leu Ala Phe Met Leu Thr Trp
            20                  25                  30

Thr Val Phe Tyr Val Thr Asn Arg Gly Lys Lys Ala Thr Gln Leu Ala
        35                  40                  45

Asp Ala Val Glu Glu Arg Glu Asp Gly Ala Thr Asp Val Ile Ile
    50                  55                  60

Val Gly Ala Gly Val Gly Gly Ser Ala Leu Ala Tyr Ala Leu Ala Lys
65                  70                  75                  80

Asp Gly Arg Arg Val His Val Ile Glu Arg Asp Leu Arg Glu Pro Glu
                85                  90                  95

Arg Ile Met Gly Glu Phe Met Gln Pro Gly Gly Arg Leu Met Leu Ser
            100                 105                 110

Lys Leu Gly Leu Glu Asp Cys Leu Glu Gly Ile Asp Ala Gln Lys Ala
        115                 120                 125

Thr Gly Met Thr Val Tyr Lys Asp Gly Lys Glu Ala Val Ala Ser Phe
    130                 135                 140
```

```
Pro Val Asp Asn Asn Asn Phe Pro Phe Asp Pro Ser Ala Arg Ser Phe
145                 150                 155                 160

His Asn Gly Arg Phe Val Gln Arg Leu Arg Gln Lys Ala Ser Ser Leu
            165                 170                 175

Pro Asn Val Arg Leu Glu Glu Gly Thr Val Lys Ser Leu Ile Glu Glu
        180                 185                 190

Lys Gly Val Ile Lys Gly Val Thr Tyr Lys Asn Ser Ala Gly Glu Glu
    195                 200                 205

Thr Thr Ala Leu Ala Pro Leu Thr Val Val Cys Asp Gly Cys Tyr Ser
210                 215                 220

Asn Leu Arg Arg Ser Leu Asn Asp Asn Asn Ala Glu Val Leu Ser Tyr
225                 230                 235                 240

Gln Val Gly Phe Ile Ser Lys Asn Cys Gln Leu Glu Glu Pro Glu Lys
                245                 250                 255

Leu Lys Leu Ile Met Ser Lys Pro Ser Phe Thr Met Leu Tyr Gln Ile
            260                 265                 270

Ser Ser Thr Asp Val Arg Cys Val Phe Glu Val Leu Pro Asn Asn Ile
        275                 280                 285

Pro Ser Ile Ser Asn Gly Glu Met Ala Thr Phe Val Lys Asn Thr Ile
290                 295                 300

Ala Pro Gln Val Pro Leu Lys Leu Arg Lys Ile Phe Leu Lys Gly Ile
305                 310                 315                 320

Asp Glu Gly Glu His Ile Lys Ala Met Pro Thr Lys Lys Met Thr Ala
                325                 330                 335

Thr Leu Ser Glu Lys Lys Gly Val Ile Leu Leu Gly Asp Ala Phe Asn
            340                 345                 350

Met Arg His Pro Ala Ile Ala Ser Gly Met Met Val Leu Leu Ser Asp
        355                 360                 365

Ile Leu Ile Leu Arg Arg Leu Leu Gln Pro Leu Ser Asn Leu Gly Asn
370                 375                 380

Ala Gln Lys Ile Ser Gln Val Ile Lys Ser Phe Tyr Asp Ile Arg Lys
385                 390                 395                 400

Pro Met Ser Ala Thr Val Asn Thr Leu Gly Asn Ala Phe Ser Gln Val
                405                 410                 415

Leu Val Ala Ser Thr Asp Glu Ala Lys Glu Ala Met Arg Gln Gly Cys
            420                 425                 430

Tyr Asp Tyr Leu Ser Ser Gly Phe Arg Thr Ser Gly Met Met Ala
        435                 440                 445

Leu Leu Gly Gly Met Asn Pro Arg Pro Ile Ser Leu Ile Tyr His Leu
450                 455                 460

Cys Ala Ile Thr Leu Ser Ser Ile Gly His Leu Leu Ser Pro Phe Pro
465                 470                 475                 480

Ser Pro Leu Gly Ile Trp His Ser Leu Arg Leu Phe Gly Leu Ala Met
                485                 490                 495

Lys Met Leu Val Pro His Leu Lys Ala Glu Gly Val Ser Gln Met Leu
            500                 505                 510

Phe Pro Val Asn Ala Ala Ala Tyr Ser Lys Ser Tyr Met Ala Ala Thr
        515                 520                 525

Ala Leu
    530

<210> SEQ ID NO 6
<211> LENGTH: 2038
<212> TYPE: DNA
<213> ORGANISM: Arabidopsis thaliana
```

<400> SEQUENCE: 6

```
gaattcccgg gtcgacccac gcgtccgcgg acgcgtggga ttgagaacaa atagatttgg      60
ttatatatgg cttttacgca cgtttgttta tggacgttag tcgccttcgt gctgacgtgg     120
acggtgttct accttaccaa catgaagaag aaggcgacgg atttggctga tacggtggct     180
gaggatcaaa aagacggtgc tgctgacgtc attatcgtcg gggctggtgt aggtggttcg     240
gctctcgcat atgctcttgc taaggatggg cgtcgagtac atgtgatcga gagggacatg     300
agagaaccag aaagaatgat gggtgagttt atgcaacctg cggacgact  catgctttct     360
aaacttggcc ttcaagattg cttggaagac atagatgcac agaaagccac gggtttggca     420
gtttataaag atgaaaaga agcagacgca ccttttccag tggataacaa caattttct      480
tatgaacctt ctgctcgatc ttttcacaat ggccgattcg tccaacaact gcgtcgaaag     540
gcttttctc tttccaatgt gcgcctggaa gaggaacgg tgaagtcttt actagaagaa      600
aaaggagtgg tcaaaggagt gacatacaag aataaagaag gcgaagaaac aacagccttg     660
gcacctctca ctgtggtatg cgacggttgc tactcaaacc ttcgtcggtc tcttaatgat     720
gacaacaatg ctgagattat gtcgtacata gttggttaca tctcaaagaa ttgtcggctt     780
gaagaacccg aaaagctaca cttgatattg tctaaaccat ctttcaccat ggtataccaa     840
ataagcagca ctgacgttcg ttgtggtttt gaggttctcc ccgaaaattt tccttctatt     900
gcaaatggtg aaatgtctac tttcatgaag aatactatag ttcctcaggt acctccaaaa     960
ctccgcaaaa tattttttgaa aggtatagat gagggagcac acataaaagt ggtgccggca    1020
aagcgcatga catctacttt aagcaagaag aaaggtgtga ttgtattggg agatgcattc    1080
aatatgcgtc atccagttgt tgcatctgga atgatggttt tactgtcgga cattctcatt    1140
ctacgccgtc ttcttcagcc attaagcaac ctcggcgatg caaacaaagt ctcagaagtt    1200
atcaattcct tttatgatat ccgcaagcca atgtcggcga cggttaacac attgggaaat    1260
gcatttttctc aagtactaat tggatcaacg gatgaagcaa agaggcaat  gagacagggt    1320
gtctatgatt accttttgtag tggcgggttt cgtacgtcag ggatgatggc tctgctcggc    1380
ggcatgaatc ctcgtcctct ctctctcgtc tatcatcttt gtgccatcac tctatcctcc    1440
attggccaac tgctctctcc atttccctct cccttcgca tttggcatag cctcaagctt     1500
tttggtttgg ccatgaaaat gttggttccc aatctcaaag ctgaaggagt tagccaaatg    1560
ttgttccag caaatgcagc cgcgtatcac aaaagctata tggctgcaac cactctctaa    1620
actttgatgc tctcaatcgc aatatatatg gagcacgaat ctatgtgatt gtgcatttgg    1680
taaacgtgta ttgcagtgct tataattatt agtatgtaac ggggaaaagt tctaaacaca    1740
aaaaaataaa cttttgaatg ttatatgtgt gaattatttt tgttgttaca agtaatgctc    1800
tttttttta gcttcacaca tgtattattg gagctaattt tttgtttctc tgttcttta      1860
ttttttgttt cttactgtat ttactttgaa aagtttcgtt ttatacatat tggacatttt    1920
ttaaaaaaaa aaaaaaaaaa aaaaaaaaaa aaaaaaaaaa aaaaaaaaa aaaaaaaaaa    1980
aaaaaaaaaa aaaaaaaaaa aaaaaaaaaa aaaaaaaaaa aaaaaaaagg gcggccgc      2038
```

<210> SEQ ID NO 7
<211> LENGTH: 517
<212> TYPE: PRT
<213> ORGANISM: Arabidopsis thaliana

<400> SEQUENCE: 7

Met Ala Phe Thr His Val Cys Leu Trp Thr Leu Val Ala Phe Val Leu

```
1               5               10              15
Thr Trp Thr Val Phe Tyr Leu Thr Asn Met Lys Lys Lys Ala Thr Asp
                20              25              30

Leu Ala Asp Thr Val Ala Glu Asp Gln Lys Asp Gly Ala Ala Asp Val
                35              40              45

Ile Ile Val Gly Ala Gly Val Gly Gly Ser Ala Leu Ala Tyr Ala Leu
                50              55              60

Ala Lys Asp Gly Arg Arg Val His Val Ile Glu Arg Asp Met Arg Glu
65              70              75              80

Pro Glu Arg Met Met Gly Glu Phe Met Gln Pro Gly Gly Arg Leu Met
                85              90              95

Leu Ser Lys Leu Gly Leu Gln Asp Cys Leu Glu Asp Ile Asp Ala Gln
                100             105             110

Lys Ala Thr Gly Leu Ala Val Tyr Lys Asp Gly Lys Glu Ala Asp Ala
                115             120             125

Pro Phe Pro Val Asp Asn Asn Phe Ser Tyr Glu Pro Ser Ala Arg
                130             135             140

Ser Phe His Asn Gly Arg Phe Val Gln Gln Leu Arg Arg Lys Ala Phe
145             150             155             160

Ser Leu Ser Asn Val Arg Leu Glu Glu Gly Thr Val Lys Ser Leu Leu
                165             170             175

Glu Glu Lys Gly Val Val Lys Gly Val Thr Tyr Lys Asn Lys Glu Gly
                180             185             190

Glu Glu Thr Thr Ala Leu Ala Pro Leu Thr Val Val Cys Asp Gly Cys
                195             200             205

Tyr Ser Asn Leu Arg Arg Ser Leu Asn Asp Asp Asn Asn Ala Glu Ile
                210             215             220

Met Ser Tyr Ile Val Gly Tyr Ile Ser Lys Asn Cys Arg Leu Glu Glu
225             230             235             240

Pro Glu Lys Leu His Leu Ile Leu Ser Lys Pro Ser Phe Thr Met Val
                245             250             255

Tyr Gln Ile Ser Ser Thr Asp Val Arg Cys Gly Phe Glu Val Leu Pro
                260             265             270

Glu Asn Phe Pro Ser Ile Ala Asn Gly Glu Met Ser Thr Phe Met Lys
                275             280             285

Asn Thr Ile Val Pro Gln Val Pro Pro Lys Leu Arg Lys Ile Phe Leu
                290             295             300

Lys Gly Ile Asp Glu Gly Ala His Ile Lys Val Val Pro Ala Lys Arg
305             310             315             320

Met Thr Ser Thr Leu Ser Lys Lys Lys Gly Val Ile Val Leu Gly Asp
                325             330             335

Ala Phe Asn Met Arg His Pro Val Val Ala Ser Gly Met Met Val Leu
                340             345             350

Leu Ser Asp Ile Leu Ile Leu Arg Arg Leu Leu Gln Pro Leu Ser Asn
                355             360             365

Leu Gly Asp Ala Asn Lys Val Ser Glu Val Ile Asn Ser Phe Tyr Asp
                370             375             380

Ile Arg Lys Pro Met Ser Ala Thr Val Asn Thr Leu Gly Asn Ala Phe
385             390             395             400

Ser Gln Val Leu Ile Gly Ser Thr Asp Glu Ala Lys Glu Ala Met Arg
                405             410             415

Gln Gly Val Tyr Asp Tyr Leu Cys Ser Gly Phe Arg Thr Ser Gly
                420             425             430
```

```
Met Met Ala Leu Leu Gly Gly Met Asn Pro Arg Pro Leu Ser Leu Val
        435                 440                 445
Tyr His Leu Cys Ala Ile Thr Leu Ser Ser Ile Gly Gln Leu Leu Ser
        450                 455                 460
Pro Phe Pro Ser Pro Leu Arg Ile Trp His Ser Leu Lys Leu Phe Gly
465                 470                 475                 480
Leu Ala Met Lys Met Leu Val Pro Asn Leu Lys Ala Glu Gly Val Ser
                485                 490                 495
Gln Met Leu Phe Pro Ala Asn Ala Ala Tyr His Lys Ser Tyr Met
                500                 505                 510
Ala Ala Thr Thr Leu
        515

<210> SEQ ID NO 8
<211> LENGTH: 392
<212> TYPE: DNA
<213> ORGANISM: Arabidopsis thaliana

<400> SEQUENCE: 8
aaatcatatt gagaacaaat agatttggtt atatatggct tttacgcacg tttgtttatg    60
gacgttagtc gccttcgtgc tgacgtggac ggtgttctac cttaccaaca tgaagaagaa   120
ggcgacggat ttggctgata cggtggctga ggatcaaaaa gacggtgctg ctgacgtcat   180
tatcgtcggg gctggtgtag gtggttcggc tctcgcatat gctctgctaa gtgtgcgcct   240
ggaagaagga acggtgaagt ctttactaga agaaaaagga gtggtcaaag gagtgacata   300
caagaataaa gaatgcgaac aaacaacagc cttggcacct ctcactgtgg tatgcgacgg   360
ttgctaatca aaccttcgtc ggtctcttaa tg                                 392

<210> SEQ ID NO 9
<211> LENGTH: 110
<212> TYPE: PRT
<213> ORGANISM: Arabidopsis thaliana

<400> SEQUENCE: 9

Met Ala Phe Thr His Val Cys Leu Trp Thr Leu Val Ala Phe Val Leu
1               5                   10                  15
Thr Trp Thr Val Phe Tyr Leu Thr Asn Met Lys Lys Lys Ala Thr Asp
                20                  25                  30
Leu Ala Asp Thr Val Ala Glu Asp Gln Lys Asp Gly Ala Ala Asp Val
        35                  40                  45
Ile Ile Val Gly Ala Gly Val Gly Gly Ser Ala Leu Ala Tyr Ala Leu
    50                  55                  60
Leu Ser Val Arg Leu Glu Glu Gly Thr Val Lys Ser Leu Leu Glu Glu
65                  70                  75                  80
Lys Gly Val Val Lys Gly Val Thr Tyr Lys Asn Lys Glu Cys Glu Gln
                85                  90                  95
Thr Thr Ala Leu Ala Pro Leu Thr Val Val Cys Asp Gly Cys
            100                 105                 110

<210> SEQ ID NO 10
<211> LENGTH: 457
<212> TYPE: DNA
<213> ORGANISM: Arabidopsis thaliana
<220> FEATURE:
<221> NAME/KEY: misc_feature
<222> LOCATION: (1)..(457)
<223> OTHER INFORMATION: n=a, c, g or t

<400> SEQUENCE: 10
```

```
cacaaagcaa aaaaatctct gtaaaagcag aacgataatg gagtcacaat tatggaattg      60
gatcttacct cttttgatct cttctctcct catctccttc gtcgctttct atggattctt     120
cgtcaaaccg aagcggaacg gtctccgtca cgatcggaaa actgttctta ccgtcacctc     180
cgacgtcgga tctgttaata ttaccggaga tactgtcgct gatgtcattg ttgttggagc     240
tggtgttgct ggttctgctc ttgcttatac tcttggaaag gggaaattta acgccgagt     300 tcatgtgatt gaaagagatt tatcggagcc tgatcgtatt gttggggagt tgttacagcc     360
tgngggttac ctcaagttac tggagtgtgg aattggagat tgtgtggaag aaatagatgc     420
tcagcntgtg tatggttatg cacttttaa aaatggg                                457
```

<210> SEQ ID NO 11
<211> LENGTH: 152
<212> TYPE: PRT
<213> ORGANISM: Arabidopsis thaliana
<220> FEATURE:
<221> NAME/KEY: misc_feature
<222> LOCATION: (1)..(152)
<223> OTHER INFORMATION: X=any amino acid

<400> SEQUENCE: 11

```
Thr Lys Gln Lys Asn Leu Cys Lys Ser Arg Thr Ile Met Glu Ser Gln
1               5                  10                  15

Leu Trp Asn Trp Ile Leu Pro Leu Leu Ile Ser Ser Leu Leu Ile Ser
            20                  25                  30

Phe Val Ala Phe Tyr Gly Phe Phe Val Lys Pro Lys Arg Asn Gly Leu
        35                  40                  45

Arg His Asp Arg Lys Thr Val Ser Thr Val Thr Ser Asp Val Gly Ser
    50                  55                  60

Val Asn Ile Thr Gly Asp Thr Val Ala Asp Val Ile Val Val Gly Ala
65                  70                  75                  80

Gly Val Ala Gly Ser Ala Leu Ala Tyr Thr Leu Gly Lys Gly Lys Phe
                85                  90                  95

Lys Arg Arg Val His Val Ile Glu Arg Asp Leu Ser Glu Pro Asp Arg
            100                 105                 110

Ile Val Gly Glu Leu Leu Gln Pro Xaa Gly Tyr Leu Lys Leu Leu Glu
        115                 120                 125

Cys Gly Ile Gly Asp Cys Val Glu Glu Ile Asp Ala Gln Xaa Val Tyr
    130                 135                 140

Gly Tyr Ala Leu Phe Lys Asn Gly
145                 150
```

<210> SEQ ID NO 12
<211> LENGTH: 1486
<212> TYPE: DNA
<213> ORGANISM: Arabidopsis thaliana

<400> SEQUENCE: 12

```
cgtgttttac aaatttcctt tgttggtttt ccacagattt aaagaaccct aacgagagaa      60
aaaaatggac tgggattact atacgctgtt gaagacgagt gtggctatta ttatagtgtt     120
tgttgtggcc aaactcataa cctcctccaa atccaagaag aaaacaagtg tcgtcccact     180
ccctccagtt cttcaagcgt ggcctccatt tatcggatcc ctaatccgct tcatgaaagg     240
tccaatagtg ctacttagag aggaatatcc taagcttgga agtgttttca cagtgaagct     300
tcttcacaaa acatcacttt ttctcatcgg tcccgaagtc tcgtcccact ttttcaacgc     360
ttatgaatct gaactcagcc agaaagaaat ttacaaattt aatgtgccta cttttggccc     420
```

-continued

```
cggagttgtg tttgatgttg actatcccgt tcggatggag cagttccgat tcttctccag    480
cgctctcaag gattacttct caaaatgggg agaaagtggg gaagtggatc taaaggccga    540
gttagagcgt ctaatcacct tgactgctag tagatgtcta ttgggtcgag aagtccgtga    600 ccaactttt  gatgatgttg ctccattgtt ccatgacctt gataaaggca tgcaacccat    660
aagtgtcatc ttcccaaagc tccccattcc agctcacaat tgtcgtgacc gtgctcgcgg    720
aaagattgca aaaatctttt caaacatcat agcaacaaga aaacgctctg gtgacaaatc    780
agagaacgac atgctacaat gtttcatcga ctcaaagtac aaagacggta gagagacaac    840
tgaatctgaa gtaactggtt tgctcattgc tggtttgttt gcaggacaac atacaagctc    900
tatcactgcc acatggaccg tgcttatct  aattcaaaac aaacactggt ggtccgcggc    960
tttggacgag cagaagaaac tgattggaaa acatggggac aagatcgact acgatgtttt   1020
gtctgagatg gattttctgt ttcgcagtgc aaaagaagct ttaaggcttc accctccaaa   1080
gatcttactg ctgagaacag tacacagtga tttcaccgtg acaactcgag aaggaaagca   1140
atatgagata ccaaagggtc atatcgttgc aacttctcct gcattcgcca accgcttacc   1200
tcatgtctac aaagatccgg aaaattttga tccggataga ttttcaaagg aaagagaaga   1260
ggataaagca gctggttcgt gttcatacat ctctttggga gctggtaggc acgagtgtcc   1320
tggtggatca tttgcgttct tgcagatcaa agccgtatgg tgtcacttat tgagaaactt   1380
tgagcttgag ttagtgtcac cttttccctga aatcaactgg aatgctttgg tcgttggtgc   1440
taaaggaaat gtcatggttc gttacaagcg tcgtcccttt tcttaa                  1486
```

<210> SEQ ID NO 13
<211> LENGTH: 473
<212> TYPE: PRT
<213> ORGANISM: Arabidopsis thaliana

<400> SEQUENCE: 13

```
Met Asp Trp Asp Tyr Tyr Thr Leu Leu Lys Thr Ser Val Ala Ile Ile
1               5                   10                  15

Ile Val Phe Val Val Ala Lys Leu Ile Thr Ser Ser Lys Ser Lys Lys
            20                  25                  30

Lys Thr Ser Val Val Pro Leu Pro Pro Val Leu Gln Ala Trp Pro Pro
        35                  40                  45

Phe Ile Gly Ser Leu Ile Arg Phe Met Lys Gly Pro Ile Val Leu Leu
    50                  55                  60

Arg Glu Glu Tyr Pro Lys Leu Gly Ser Val Phe Thr Val Lys Leu Leu
65                  70                  75                  80

His Lys Asn Ile Thr Phe Leu Ile Gly Pro Glu Val Ser Ser His Phe
                85                  90                  95

Phe Asn Ala Tyr Glu Ser Glu Leu Ser Gln Lys Glu Ile Tyr Lys Phe
            100                 105                 110

Asn Val Pro Thr Phe Gly Pro Gly Val Val Phe Asp Val Asp Tyr Pro
        115                 120                 125

Val Arg Met Glu Gln Phe Arg Phe Phe Ser Ser Ala Leu Lys Asp Tyr
    130                 135                 140

Phe Ser Lys Trp Gly Glu Ser Gly Glu Val Asp Leu Lys Ala Glu Leu
145                 150                 155                 160

Glu Arg Leu Ile Thr Leu Thr Ala Ser Arg Cys Leu Leu Gly Arg Glu
                165                 170                 175

Val Arg Asp Gln Leu Phe Asp Asp Val Ala Pro Leu Phe His Asp Leu
            180                 185                 190
```

```
Asp Lys Gly Met Gln Pro Ile Ser Val Ile Phe Pro Lys Leu Pro Ile
            195                 200                 205

Pro Ala His Asn Cys Arg Asp Arg Ala Arg Gly Lys Ile Ala Lys Ile
        210                 215                 220

Phe Ser Asn Ile Ile Ala Thr Arg Lys Arg Ser Gly Asp Lys Ser Glu
225                 230                 235                 240

Asn Asp Met Leu Gln Cys Phe Ile Asp Ser Lys Tyr Lys Asp Gly Arg
            245                 250                 255

Glu Thr Thr Glu Ser Glu Val Thr Gly Leu Leu Ile Ala Gly Leu Phe
        260                 265                 270

Ala Gly Gln His Thr Ser Ser Ile Thr Ala Thr Trp Thr Gly Ala Tyr
        275                 280                 285

Leu Ile Gln Asn Lys His Trp Trp Ser Ala Ala Leu Asp Glu Gln Lys
        290                 295                 300

Lys Leu Ile Gly Lys His Gly Asp Lys Ile Asp Tyr Asp Val Leu Ser
305                 310                 315                 320

Glu Met Asp Phe Leu Phe Arg Ser Ala Lys Glu Ala Leu Arg Leu His
            325                 330                 335

Pro Pro Lys Ile Leu Leu Leu Arg Thr Val His Ser Asp Phe Thr Val
            340                 345                 350

Thr Thr Arg Glu Gly Lys Gln Tyr Glu Ile Pro Lys Gly His Ile Val
        355                 360                 365

Ala Thr Ser Pro Ala Phe Ala Asn Arg Leu Pro His Val Tyr Lys Asp
        370                 375                 380

Pro Glu Asn Phe Asp Pro Asp Arg Phe Ser Lys Glu Arg Glu Glu Asp
385                 390                 395                 400

Lys Ala Ala Gly Ser Cys Ser Tyr Ile Ser Leu Gly Ala Gly Arg His
            405                 410                 415

Glu Cys Pro Gly Gly Ser Phe Ala Phe Leu Gln Ile Lys Ala Val Trp
            420                 425                 430

Cys His Leu Leu Arg Asn Phe Glu Leu Glu Leu Val Ser Pro Phe Pro
            435                 440                 445

Glu Ile Asn Trp Asn Ala Leu Val Val Gly Ala Lys Gly Asn Val Met
        450                 455                 460

Val Arg Tyr Lys Arg Arg Pro Phe Ser
465                 470

<210> SEQ ID NO 14
<211> LENGTH: 523
<212> TYPE: DNA
<213> ORGANISM: Arabidopsis thaliana

<400> SEQUENCE: 14
gacactatag aagagctatg acgtcgcatg cacgcgtacg taagctcgga attcggctcg      60
agcttgttca caaaaagatt acttttctta ttggtcctga agtctctgct catttttca     120 aagcttctga atctgatctt agtcagcagg aagtgtatca gttcaatgtc cctacttttg     180
gtcctggagt tgttttcgat gttgattatt ctgtttcgtc aggagcagtt cggttcttca     240
ctgaggcact tagagttaac aagttgaagg ttatgtgga tatgatggtt actgaagctg      300
aggattactt ctctaaatgg ggagagagtg gtgaagttga tattaaggtt gagctagaga     360
ggctcatcat cttgactgca agtgatgttt actgggtcga gaagttcgtg atcagctttt     420
tgatgatgtc tctgctttgt tccatgacct tgacaatgga atgcttccca tcagtgcttc     480
ccatcagtgt tctcttccca tatctcccaa ttccagctca ccg                       523
```

<210> SEQ ID NO 15
<211> LENGTH: 87
<212> TYPE: PRT
<213> ORGANISM: Arabidopsis thaliana

<400> SEQUENCE: 15

His Tyr Arg Arg Ala Met Thr Ser His Ala Arg Val Arg Lys Leu Gly
1               5                   10                  15

Ile Arg Leu Glu Leu Val His Lys Lys Ile Thr Phe Leu Ile Gly Pro
            20                  25                  30

Glu Val Ser Ala His Phe Phe Lys Ala Ser Gly Ser Asp Leu Ser Gln
        35                  40                  45

Gln Glu Val Tyr Gln Phe Asn Val Pro Thr Phe Gly Pro Gly Val Val
    50                  55                  60

Phe Asp Val Asp Tyr Ser Val Arg Gln Glu Gln Phe Gly Ser Ser Leu
65                  70                  75                  80

Arg His Leu Glu Leu Thr Ser
                85

<210> SEQ ID NO 16
<211> LENGTH: 1852
<212> TYPE: DNA
<213> ORGANISM: Arabidopsis thaliana

<400> SEQUENCE: 16
tcgaccccgc gtccgcggac gcgtgggatc agcttcaagc ttaagagagc ttcgaaagcg     60
aaagcgacga tttcttctcc atcgtgagag caaatctcca gagccgtttt ctcttcttct    120
tcttcctcct cgcgccgtct ctgaaactcc atcatcgtat caatcaaatt gcttcctcct    180
ccaaattgaa aaacaatgga attggattcg agaacaaat tgttgaagac gggtttggtt     240
atagtggcga cacttgttat agccaaactc atcttctctt tcttcacttc tgattctaag    300
aagaagcgtc ttcctcctac tcttaaagct tggcctccat tggttggaag tcttatcaaa    360
ttcttgaaag gacctattat tatgcttaga gaggaatacc ctaagcttgg aagtgtgttt    420
actgttaatc ttgttcacaa aaagattact tttcttattg gtcctgaagt ctctgctcat    480
tttttcaaag cttctgaatc tgatcttagt cagcaggaag tgtatcagtt caatgtccct    540
acttttggtc ctggagttgt tttcgatgtt gattattctg ttcgtcagga gcagtttcgg    600
ttcttcactg aggcacttag agttaacaag ttgaagggtt atgtggatat gatggttact    660
gaagctgagg attacttctc taaatgggga gagagtggtg aagttgatat taaggttgag    720
ctagagaggc tcatcatctt gactgcaagt agatgtttac tgggtcgaga agttcgtgat    780 cagcttttg atgatgtctc tgctttgttc catgaccttg acaatggaat gcttcccatc    840
agtgttctct tcccatatct cccaattcca gctcaccgcc gtcgtgaccg tgcccgagaa    900
aagctttcgg agattttcgc aaaaatcatt gggtcgagaa acgctctgg aaaaacagag    960 aacgacatgc tgcagtgttt catcgaatca aagtacaaag atggtagaca gacaaccgaa   1020
tctgaagtca ctggttttgct cattgctgct ctgtttgcag acaacacac gagctctatc   1080 acttccacct ggaccggtgc ttatctgatg cgatacaaag agtacttctc agctgctctt   1140
gatgagcaga agaacctgat tgcgaaacat ggagacaaga tcgatcatga tatcttatcc   1200
gagatggatg ttctctaccg ctgcattaag gaagcgttga ggcttcaccc tccactcatc   1260
atgttaatga gagcctcgca cagtgatttc agcgtgacag ctcgggatgg aaaaacttac   1320
gatatcccaa agggtcacat cgttgcaacc tcccctgcat tgccaaccg cttaccgcac   1380

```
atcttcaaag accccgacac ctacgaccca gaaagattct ccctggaag agaagaggac    1440 aaagccgcag gggcattctc gtacattgca ttcggagggg gaaggcacgg gtgccttgga    1500
gagccgtttg cttacctgca gatcaaagcc atatggagtc atttgttgag gaacttcgag    1560
cttgagctag tttcaccgtt ccctgagatt gactggaacg ctatggtggt tggagttaaa    1620
ggcaatgtga tggtgcgtta caagaggcgc cagctttctt aaagacaagt ttaaggttat    1680
tgcagctttg gattttctc tctggtttct gctttgcttt tgtccctctc tggttttagt    1740
tttgttgttg aataattctt ctgttttttat aaactgttgt tactctttaa ttgacattta    1800 ttttaagct tcctaagttt gtggttcaaa aaaaaaaaaa ggcggcgtta ct    1852
```

<210> SEQ ID NO 17
<211> LENGTH: 488
<212> TYPE: PRT
<213> ORGANISM: Arabidopsis thaliana

<400> SEQUENCE: 17

```
Met Glu Leu Asp Ser Glu Asn Lys Leu Leu Lys Thr Gly Leu Val Ile
1               5                   10                  15

Val Ala Thr Leu Val Ile Ala Lys Leu Ile Phe Ser Phe Phe Thr Ser
            20                  25                  30

Asp Ser Lys Lys Lys Arg Leu Pro Pro Thr Leu Lys Ala Trp Pro Pro
        35                  40                  45

Leu Val Gly Ser Leu Ile Lys Phe Leu Lys Gly Pro Ile Ile Met Leu
    50                  55                  60

Arg Glu Glu Tyr Pro Lys Leu Gly Ser Val Phe Thr Val Asn Leu Val
65                  70                  75                  80

His Lys Lys Ile Thr Phe Leu Ile Gly Pro Glu Val Ser Ala His Phe
                85                  90                  95

Phe Lys Ala Ser Glu Ser Asp Leu Ser Gln Gln Glu Val Tyr Gln Phe
            100                 105                 110

Asn Val Pro Thr Phe Gly Pro Gly Val Val Phe Asp Val Asp Tyr Ser
        115                 120                 125

Val Arg Gln Glu Gln Phe Arg Phe Phe Thr Glu Ala Leu Arg Val Asn
    130                 135                 140

Lys Leu Lys Gly Tyr Val Asp Met Met Val Thr Glu Ala Glu Asp Tyr
145                 150                 155                 160

Phe Ser Lys Trp Gly Glu Ser Gly Glu Val Asp Ile Lys Val Glu Leu
                165                 170                 175

Glu Arg Leu Ile Ile Leu Thr Ala Ser Arg Cys Leu Leu Gly Arg Glu
            180                 185                 190

Val Arg Asp Gln Leu Phe Asp Asp Val Ser Ala Leu Phe His Asp Leu
        195                 200                 205

Asp Asn Gly Met Leu Pro Ile Ser Val Leu Phe Pro Tyr Leu Pro Ile
    210                 215                 220

Pro Ala His Arg Arg Arg Asp Arg Ala Arg Glu Lys Leu Ser Glu Ile
225                 230                 235                 240

Phe Ala Lys Ile Ile Gly Ser Arg Lys Arg Ser Gly Lys Thr Glu Asn
                245                 250                 255

Asp Met Leu Gln Cys Phe Ile Glu Ser Lys Tyr Lys Asp Gly Arg Gln
            260                 265                 270

Thr Thr Glu Ser Glu Val Thr Gly Leu Leu Ile Ala Ala Leu Phe Ala
        275                 280                 285

Gly Gln His Thr Ser Ser Ile Thr Ser Thr Trp Thr Gly Ala Tyr Leu
```

```
                290                  295                  300
Met Arg Tyr Lys Glu Tyr Phe Ser Ala Ala Leu Asp Glu Gln Lys Asn
305                 310                 315                 320

Leu Ile Ala Lys His Gly Asp Lys Ile Asp His Asp Ile Leu Ser Glu
                325                 330                 335

Met Asp Val Leu Tyr Arg Cys Ile Lys Glu Ala Leu Arg Leu His Pro
                340                 345                 350

Pro Leu Ile Met Leu Met Arg Ala Ser His Ser Asp Phe Ser Val Thr
                355                 360                 365

Ala Arg Asp Gly Lys Thr Tyr Asp Ile Pro Lys Gly His Ile Val Ala
            370                 375                 380

Thr Ser Pro Ala Phe Ala Asn Arg Leu Pro His Ile Phe Lys Asp Pro
385                 390                 395                 400

Asp Thr Tyr Asp Pro Glu Arg Phe Ser Pro Gly Arg Glu Glu Asp Lys
                405                 410                 415

Ala Ala Gly Ala Phe Ser Tyr Ile Ala Phe Gly Gly Arg His Gly
            420                 425                 430

Cys Leu Gly Glu Pro Phe Ala Tyr Leu Gln Ile Lys Ala Ile Trp Ser
            435                 440                 445

His Leu Leu Arg Asn Phe Glu Leu Glu Leu Val Ser Pro Phe Pro Glu
450                 455                 460

Ile Asp Trp Asn Ala Met Val Val Gly Val Lys Gly Asn Val Met Val
465                 470                 475                 480

Arg Tyr Lys Arg Arg Gln Leu Ser
            485

<210> SEQ ID NO 18
<211> LENGTH: 1852
<212> TYPE: DNA
<213> ORGANISM: Arabidopsis thaliana

<400> SEQUENCE: 18
tcgaccccgc gtccgcggac gcgtgggatc agcttcaagc ttaagagagc ttcgaaagcg      60
aaagcgacga tttcttctcc atcgtgagag caaatctcca gagccgtttt ctcttcttct     120
tcttcctcct cgcgccgtct ctgaaactcc atcatcgtat caatcaaatt gcttcctcct     180
ccaaattgaa aaacaatgga attggattcg gagaacaaat tgttgaagac gggtttggtt     240
atagtggcga cacttgttat agccaaactc atcttctctt tcttcacttc tgattctaag     300
aagaagcgtc ttcctcctac tcttaaagct tggcctccat ggttggaagt cttatcaaa     360
ttcttgaaag gacctattat tatgcttaga gaggaatacc ctaagcttgg aagtgtgttt     420
actgttaatc ttgttcacaa aaagattact tttcttattg gtcctgaagt ctctgctcat     480
tttttcaaag cttctgaatc tgatcttagt cagcaggaag tgtatcagtt caatgtccct     540
acttttggtc ctggagttgt tttcgatgtt gattattctg ttcgtcagga gcagtttcgg     600
ttcttcactg aggcacttag agttaacaag ttgaagggtt atgtggatat gatggttact     660
gaagctgagg attacttctc taaatgggga gagagtggtg aagttgatat taaggttgag     720
ctagagaggc tcatcatctt gactgcaagt agatgtttac tgggtcgaga agttcgtgat     780
cagcttttg atgatgtctc tgctttgttc catgaccttg acaatggaat gcttcccatc     840
agtgttctct tcccatatct cccaattcca gctcaccgcc gtcgtgaccg tgcccgagaa     900
aagctttcgg agattttcgc aaaaatcatt gggtcgagaa aacgctctgg aaaaacagag     960
aacgacatgc tgcagtgttt catcgaatca agtacaaag atggtagaca gacaaccgaa    1020
```

```
tctgaagtca ctggtttgct cattgctgct ctgtttgcag gacaacacac gagctctatc    1080
acttccacct ggaccggtgc ttatctgatg cgatacaaag agtacttctc agctgctctt    1140
gatgagcaga agaacctgat tgcgaaacat ggagacaaga tcgatcatga tatcttatcc    1200
gagatggatg ttctctaccg ctgcattaag gaagcgttga ggcttcaccc tccactcatc    1260
atgttaatga gagcctcgca cagtgatttc agcgtgacag ctcgggatgg aaaaacttac    1320
gatatcccaa agggtcacat cgttgcaacc tcccctgcat tgccaaccg cttaccgcac    1380 atcttcaaag accccgacac ctacgaccca gaaagattct cccctggaag agaagaggac    1440
aaagccgcag gggcattctc gtacattgca ttcggagggg gaaggcacgg gtgccttgga    1500
gagccgtttg cttacctgca gatcaaagcc atatggagtc atttgttgag gaacttcgag    1560
cttgagctag tttcaccgtt ccctgagatt gactggaacg ctatggtggt tggagttaaa    1620
ggcaatgtga tggtgcgtta caagaggcgc cagcttttct taaagacaagt ttaaggttat    1680 tgcagctttg gattttctc tctggtttct gctttgcttt tgtccctctc tggttttagt    1740
tttgttgttg aataattctt ctgtttttat aaactgttgt tactctttaa ttgacattta    1800
tttttaagct tcctaagttt gtggttcaaa aaaaaaaaaa ggcggcgtta ct            1852

<210> SEQ ID NO 19
<211> LENGTH: 488
<212> TYPE: PRT
<213> ORGANISM: Arabidopsis thaliana

<400> SEQUENCE: 19

Met Glu Leu Asp Ser Glu Asn Lys Leu Leu Lys Thr Gly Leu Val Ile
1               5                   10                  15

Val Ala Thr Leu Val Ile Ala Lys Leu Ile Phe Ser Phe Phe Thr Ser
            20                  25                  30

Asp Ser Lys Lys Lys Arg Leu Pro Pro Thr Leu Lys Ala Trp Pro Pro
        35                  40                  45

Leu Val Gly Ser Leu Ile Lys Phe Leu Lys Gly Pro Ile Ile Met Leu
    50                  55                  60

Arg Glu Glu Tyr Pro Lys Leu Gly Ser Val Phe Thr Val Asn Leu Val
65                  70                  75                  80

His Lys Lys Ile Thr Phe Leu Ile Gly Pro Glu Val Ser Ala His Phe
                85                  90                  95

Phe Lys Ala Ser Glu Ser Asp Leu Ser Gln Gln Glu Val Tyr Gln Phe
            100                 105                 110

Asn Val Pro Thr Phe Gly Pro Gly Val Val Phe Asp Val Asp Tyr Ser
        115                 120                 125

Val Arg Gln Glu Gln Phe Arg Phe Phe Thr Glu Ala Leu Arg Val Asn
    130                 135                 140

Lys Leu Lys Gly Tyr Val Asp Met Met Val Thr Glu Ala Glu Asp Tyr
145                 150                 155                 160

Phe Ser Lys Trp Gly Glu Ser Gly Glu Val Asp Ile Lys Val Glu Leu
                165                 170                 175

Glu Arg Leu Ile Ile Leu Thr Ala Ser Arg Cys Leu Leu Gly Arg Glu
            180                 185                 190

Val Arg Asp Gln Leu Phe Asp Asp Val Ser Ala Leu Phe His Asp Leu
        195                 200                 205

Asp Asn Gly Met Leu Pro Ile Ser Val Leu Phe Pro Tyr Leu Pro Ile
    210                 215                 220

Pro Ala His Arg Arg Asp Arg Ala Arg Glu Lys Leu Ser Glu Ile
225                 230                 235                 240
```

Phe Ala Lys Ile Ile Gly Ser Arg Lys Arg Ser Gly Lys Thr Glu Asn
                245                 250                 255

Asp Met Leu Gln Cys Phe Ile Glu Ser Lys Tyr Lys Asp Gly Arg Gln
            260                 265                 270

Thr Thr Glu Ser Glu Val Thr Gly Leu Leu Ile Ala Ala Leu Phe Ala
        275                 280                 285

Gly Gln His Thr Ser Ser Ile Thr Ser Thr Trp Thr Gly Ala Tyr Leu
    290                 295                 300

Met Arg Tyr Lys Glu Tyr Phe Ser Ala Ala Leu Asp Glu Gln Lys Asn
305                 310                 315                 320

Leu Ile Ala Lys His Gly Asp Lys Ile Asp His Ile Leu Ser Glu
                325                 330                 335

Met Asp Val Leu Tyr Arg Cys Ile Lys Glu Ala Leu Arg Leu His Pro
            340                 345                 350

Pro Leu Ile Met Leu Met Arg Ala Ser His Ser Asp Phe Ser Val Thr
        355                 360                 365

Ala Arg Asp Gly Lys Thr Tyr Asp Ile Pro Lys Gly His Ile Val Ala
    370                 375                 380

Thr Ser Pro Ala Phe Ala Asn Arg Leu Pro His Ile Phe Lys Asp Pro
385                 390                 395                 400

Asp Thr Tyr Asp Pro Glu Arg Phe Ser Pro Gly Arg Glu Glu Asp Lys
                405                 410                 415

Ala Ala Gly Ala Phe Ser Tyr Ile Ala Phe Gly Gly Arg His Gly
            420                 425                 430

Cys Leu Gly Glu Pro Phe Ala Tyr Leu Gln Ile Lys Ala Ile Trp Ser
        435                 440                 445

His Leu Leu Arg Asn Phe Glu Leu Glu Leu Val Ser Pro Phe Pro Glu
    450                 455                 460

Ile Asp Trp Asn Ala Met Val Val Gly Val Lys Gly Asn Val Met Val
465                 470                 475                 480

Arg Tyr Lys Arg Arg Gln Leu Ser
                485

<210> SEQ ID NO 20
<211> LENGTH: 1249
<212> TYPE: DNA
<213> ORGANISM: Arabidopsis thaliana

<400> SEQUENCE: 20
ctttctccct gtgaaaaaat ggactcggtg ctctctact gcaccgctgg tctcattgcc      60
ggcgccgtct actggttcat atgcgtccta ggtccagcag aacgaaaagg caaacgagcc    120
tctgatctct ccggcggctc aatctccgca gaaaaagtca agacaacta taaccaatac    180 tggtctttct ccgcaaacc aaaagagatc gaatcagccg agaaagtacc tgacttcgtc    240
gacacgttct acaatcttgt cactgatacc tacgagtggg gatggggaca atctttccat    300
ttctctcctc atgtccctgg aaatccgac aaagacgcca caagaatcca cgaagaaatg    360
gccgtcgatc tcatcaaagt gaaaccggga caaaagattc ttgacgctgg ttgcggcgtg    420
ggtgggccga tgagagccat cgcggcccat tccaaggccc aagtcactgg aatcactatc    480
aacgagtacc aagtgcaacg agccaagctt cacaacaaga agctggact tgattctctc    540 tgcaacgtcg tttgtggtaa ctttttaaag atgccgttcg atgaaaacac gtttgacgga    600
gcttactcga tcgaagctac gtgtcacgct cctaagctcg aagaagtata tcggagatc    660 ttcagagtga tgaaaccagg atctttgttc gtgtcctacg aatgggtcac cactgaaaaa    720

```
tacagagacg atgacgaaga acacaaggac gtgattcaag ggatcgagag aggagacgca    780
cttcctggac taagaagcta cgctgatata gccgtgacgg cgaagaaagt tgggtttgag    840
gtagtgaagg agaaagattt ggctaaacca ccgtctaaac cgtggtggaa ccggttaaag    900
atgggaagga ttgcttattg gagaaaccat gttgtggttg tgattctttc tgctattggg    960
gttgctccta aggaactgt tgatgttcat aagatgttgt ttaagactgc tgattatttg    1020
accagaggtg gtgagactgg aatcttctct ccgatgcata tgattctctg tagaaaacca    1080
gagaaagctt ctgaatgaat gattgagaat acttcttcct tgttctcgtt ttcttcttct    1140
ttctttctaa gttcatgttt ttccccttaa gaatctcttt gtccgtcgta ttaatgttat    1200
cactttgttg tttattgtat tttttttttt caatttgcta aattactcc                1249
```

```
<210> SEQ ID NO 21
<211> LENGTH: 1444
<212> TYPE: DNA
<213> ORGANISM: Nicotiana tabacum

<400> SEQUENCE: 21
gcacgagtac tctttcccat ttctctcttg aaaggtgaaa ggttctctcc aagaatacag     60
agatcctttc tctacataga ttttgtgtat atcttgtgat ttgggaaaga aatgtcaaaa    120
caagggcctt ttgatctggc atctgggggtt ggtggcaaaa ttaacaagga ggaagttctc   180
tctgctgttg acaagtatga aagtaccat ggttattatg gaggtgaaga agaagagaga    240
aagaataact atactgacat ggttaacaaa tactatgatc tttgcactag cttctacgaa    300
tacggctggg gagagtcatt ccattttgca cccaggtgga aaggagaatc actccaagag    360
agcattaaaa ggcatgagca ctttcttgcc ttgcaactgg gattgaaacc aggacaaaag    420
gtcttggacg taggatgtgg aattggtggg ccgttaagag aaattgctcg attcagctct    480
acatcagtta caggcctcaa caataatgaa tatcagatat ctaggggaca ggtgttgaac    540
cgcaaagtag gattggatca gacttgcaac tttgtaaagg gtgatttcat gaaaatgcca    600
ttccctgaca atagctttga tgcagtgtac gcaatagaag ctacctgcca tgcaccagat    660
ccattgggat gctataaaga gatttaccgg gtgctgaagc ctggtcaatg tttcgctgtg    720
tatgagtggt gcatgaccga ttcttacaac cccaataacg aagagcacaa caggatcaag    780
gccgaaattg agctcggaaa tggcctccct gaggttagat tgacaacaca gtgcctcgaa    840
gcagccaaac aagctggttt tgaagttgta tgggacaagg atctggctga tgactcacct    900
gttccatggt acttgccttt ggatacgagt cacttctcgc tcagtagctt ccgcctaaca    960
gcagttggca acttttcac cagaaatctg gtttcggcgc ttgaatacgt gggacttgct    1020
cctaaaggta gtcaaagggt tcaagctttc ttagagaaag ctgcagaagg tcttgtcggt    1080
ggtgccaaga aagggatttt cacaccaatg tacttcttcg tggttcgcaa gcccatttca    1140
gactctcagt aatatggagt ttagtcactt agctttttgc tttagctagc aaatctgtaa    1200
gattcttcgc acagaacttt acacattgaa tatgaccgcc taattaagg tgactacagt     1260 ttttggaggg cgttgtgggt ggagggtttc ttttctgtg ttgcttgtct ggcacaattt    1320
gatttcatgt cttgctattt ttgccattga tgtccttgtt ctaagatata tacctattga    1380
caagctcata aaggtgggca tttgctaata tatggtgttt caggtaaaaa aaaaaaaaaa    1440
aaaa                                                                 1444
```

```
<210> SEQ ID NO 22
<211> LENGTH: 1421
```

```
<212> TYPE: DNA
<213> ORGANISM: Arabidopsis thaliana

<400> SEQUENCE: 22
ctctctctct ctctctcttg gtcttcctca ctcttaacga aaatggactc tttaacactc      60
ttcttcaccg gtgcactcgt cgccgtcggt atctactggt tcctctgcgt tctcggtcca     120
gcagagcgta aaggcaaacg agccgtagat ctctctggtg gctcaatctc cgccgagaaa     180
gtccaagaca actacaaaca gtactggtct ttcttccgcc gtccaaaaga aatcgaaacc     240
gccgagaaag ttccagactt cgtcgacaca ttctacaatc tcgtcaccga catatacgag     300
tggggatggg gacaatcctt ccacttctca ccatcaatcc ccggaaaatc tcacaaagac     360
gccacgcgcc tccacgaaga gatggcggta gatctgatcc aagtcaaacc tggtcaaaag     420
atcctagacg tcggatgcgg tgtcggcggt ccgatgcgag cgattgcatc tcactcgcga     480
gctaacgtag tcgggattac aataaacgag tatcaggtga acagagctcg tctccacaat     540
aagaaagctg gtctcgacgc gctttgcgag gtcgtgtgtg gtaacttcct ccagatgccg     600
ttcgatgaca acagtttcga cggagcttat tccatcgaag ccacgtgtca cgcgccgaag     660
ctggaagaag tgtacgcaga gatctacagg gtgtttgaaac ccggatctat gtatgtgtcg     720
tacgagtggg ttacgacgga gaaatttaag gcggaggatg acgaacacgt ggaggtaatc     780
caagggattg agagaggcga tgcgttacca gggcttaggg cttacgtgga tatagctgag     840
acggctaaaa aggttgggtt tgagatagtg aaggagaagg atctggcgag tccaccggct     900
gagccgtggt ggactaggct taagatgggt aggcttgctt attggaggaa tcacattgtg     960
gttcagattt tgtcagcggt tggagttgct cctaaaggaa ctgttgatgt tcatgagatg    1020
ttgtttaaga ctgctgattg tttgaccaga ggaggtgaaa ccggaatatt ctctccgatg    1080
catatgattc tctgcagaaa accggagtca ccggaggaga gttcttgaga aaggtagaaa    1140
ggaaacatca ccggaaaaag tatggagaat tttctcaatt tgtttttatt tttaagttaa    1200
atcaacttgg ttattgtact attttttgtgt tttaatttgg tttgtgtttc aagaattatt    1260
agttttttt  tgttttgttg catatgagaa tcttactctt gatttctccg ccgtagagcc    1320
ggcgagacat aggggattat tagtattttt aagtgtgttt aagattgatt aacaagttag    1380
taaaataaaa tgtacttagg tgtcgaaaaa aaaaggaatt c                        1421

<210> SEQ ID NO 23
<211> LENGTH: 1175
<212> TYPE: DNA
<213> ORGANISM: Arabidopsis thaliana

<400> SEQUENCE: 23
cagtgtgagt aatttagcat tactactgtt gacttgttca ataaaggtaa agtaagatca      60
atccggcgca atcttctttc gttttccggc accgatctcg gtggatctcc gattcacatg     120
gcggcggata atgcttatct gatgcagttt gttgacgaaa cctctttta  caaccgaatc     180
gttctgagtc atcttttgcc ggcgaatcta tgggaaccct tacctcattt tctccagaca     240
tggctccgaa attacctcgc cggaacccta ctatacatca tctccggttt cctctggtgc     300
ttctacatct attaccgtaa aatcaacgtt taccttccca agatgcaatt tcctacaata     360
aaggctatgc gtttgcaaat gtttgtggca atgaaggcta tgccatgta  cactcttctt     420
ccaactgtct ccgagagtat gattgaacgt ggttggacca aatgttttgc tagcataggc     480
gaattcggtt ggattctgta ttttgtttac atcgccatct atcttgtttt cgttgagttt     540
ggtatttatt ggatgcacag agagcttcat gacattaagc ctctctataa gtatctccat     600
```

```
gccacccatc atatctacaa caagcagaat acactctctc catttgccgg gcttgcattt      660
cacccagtag acgggatact tcaggctgta ccgcatgtga tagcgctgtt tatagtgcca      720
attcatttca caactcatat aggtcttttg ttcatggaag cgatatgggc ggcgaacatc      780
catgactgca tccatggcaa catctggcca gtaatgggtg caggatacca tacgatacac      840
cacacgacat acaagcataa ctatggtcat tataccatat ggatggattg gatgtttggc      900
tctcttaggg atcctctctt agaagaagat gacaacaaag acagcttcaa gaaagcagag      960
tgaggatgcc cacttggggg ttgttcttct gtgttgtctt gtgttgttgt tgtccaaagt     1020
ttcagccttt cttgttcttt ttcttcttct tcttattcat gtgtctctct caacctttcc     1080
aattatattg ttacaaacat ttgctgtcta gtttaaaaca tgtaaatgtt tgatgatctt     1140
tccccaaaaa aaaaaaaact aaattactca cactg                                1175

<210> SEQ ID NO 24
<211> LENGTH: 1431
<212> TYPE: DNA
<213> ORGANISM: Hevea brasiliensis

<400> SEQUENCE: 24
atggcacgcg cctcccatga cgtgtgggac ctcgaagata cggatcccaa ctacctcatc       60
gatgaagatc accgtctcgt tacttgccct cccgctaata tatctactaa gactaccatt      120
attgccgcac ctaccaaatt gcctacctcg gaacccttaa ttgcacccct agtctcggag      180
gaagacgaaa tgatcgtcaa ctccgtcgtg gatgggaaga taccctccta ttctctggag      240
tcgaagctcg gggactgcaa acgagcggct gcgattcgac gcgaggcttt gcagaggatg      300
acaaggaggt cgctggaagg cttgccagta gaagggttcg attacgagtc gattttagga      360
caatgctgtg aaatgccagt gggatacgtg cagattccgg tggggattgc ggggccgttg      420
ttgctgaacg gcgggagta ctctgttcca atggcgacca cggagggttg tttggtggcg      480
agcactaata gagggtgtaa ggcgatttac ttgtcaggtg gggccaccag cgtcttgttg      540
aaggatggca tgacaagagc gcctgttgta agattcgcgt cggcgactag agccgcggag      600
ttgaagttct tcttggagga tcctgacaat tttgataccct tggccgtagt ttttaacaag      660
tccagtagat ttgcgaggct ccaaggcatt aaatgctcaa ttgctggtaa gaatctttat      720
ataagattca gctgcagcac tggcgatgca atggggatga acatggtttc taaagggggtt      780 caaaacgttc ttgaatttct tcaaagtgat ttttctgata tggatgtcat tggaatctca      840
ggaaattttt gttcggataa gaagcctgct gctgtaaatt ggattgaagg acgtggcaaa      900
tcagttgttt gtgaggcaat tatcaaggaa gaggtggtga agaaggtgtt gaaaaccaat      960
gtggcctccc tagtggagct taacatgctc aagaatcttg ctggttctgc tgttgctggt     1020
gctttgggtg gatttaatgc ccatgcaggc aacatcgtat ctgcaatctt tattgccact     1080
ggccaggatc cagcacagaa tgttgagagt tctcattgca ttaccatgat ggaagctgtc     1140
aatgatggaa aggatctcca tatctctgtg accatgccct ccattgaggt gggtacagtc     1200
ggaggtggaa ctcaacttgc atctcagtct gcttgtctca atttgcttgg ggtgaagggt     1260
gcaaacaaag agtcgccagg atcaaactca aggctccttg ctgccatcgt agctggttca     1320
gttttggctg gtgagctctc cttgatgtct gccattgcag ctgggcagct tgtcaagagt     1380
cacatgaagt acaacagagc cagcaaagat atgtctaaag ctgcatctta g              1431

<210> SEQ ID NO 25
<211> LENGTH: 476
```

<212> TYPE: PRT
<213> ORGANISM: Hevea brasiliensis

<400> SEQUENCE: 25

```
Met Ala Arg Ala Ser His Asp Val Trp Asp Leu Glu Asp Thr Asp Pro
1               5                   10                  15

Asn Tyr Leu Ile Asp Glu Asp His Arg Leu Val Thr Cys Pro Pro Ala
            20                  25                  30

Asn Ile Ser Thr Lys Thr Thr Ile Ala Ala Pro Thr Lys Leu Pro
        35                  40                  45

Thr Ser Glu Pro Leu Ile Ala Pro Leu Val Ser Glu Glu Asp Glu Met
    50                  55                  60

Ile Val Asn Ser Val Val Asp Gly Lys Ile Pro Ser Tyr Ser Leu Glu
65                  70                  75                  80

Ser Lys Leu Gly Asp Cys Lys Arg Ala Ala Ile Arg Arg Glu Ala
                85                  90                  95

Leu Gln Arg Met Thr Arg Arg Ser Leu Glu Gly Leu Pro Val Glu Gly
                100                 105                 110

Phe Asp Tyr Glu Ser Ile Leu Gly Gln Cys Cys Glu Met Pro Val Gly
            115                 120                 125

Tyr Val Gln Ile Pro Val Gly Ile Ala Gly Pro Leu Leu Leu Asn Gly
130                 135                 140

Arg Glu Tyr Ser Val Pro Met Ala Thr Thr Glu Gly Cys Leu Val Ala
145                 150                 155                 160

Ser Thr Asn Arg Gly Cys Lys Ala Ile Tyr Leu Ser Gly Gly Ala Thr
                165                 170                 175

Ser Val Leu Leu Lys Asp Gly Met Thr Arg Ala Pro Val Val Arg Phe
            180                 185                 190

Ala Ser Ala Thr Arg Ala Ala Glu Leu Lys Phe Phe Leu Glu Asp Pro
        195                 200                 205

Asp Asn Phe Asp Thr Leu Ala Val Val Phe Asn Lys Ser Ser Arg Phe
210                 215                 220

Ala Arg Leu Gln Gly Ile Lys Cys Ser Ile Ala Gly Lys Asn Leu Tyr
225                 230                 235                 240

Ile Arg Phe Ser Cys Ser Thr Gly Asp Ala Met Gly Met Asn Met Val
                245                 250                 255

Ser Lys Gly Val Gln Asn Val Leu Glu Phe Leu Gln Ser Asp Phe Ser
            260                 265                 270

Asp Met Asp Val Ile Gly Ile Ser Gly Asn Phe Cys Ser Asp Lys Lys
        275                 280                 285

Pro Ala Ala Val Asn Trp Ile Glu Gly Arg Gly Lys Ser Val Val Cys
290                 295                 300

Glu Ala Ile Ile Lys Glu Glu Val Val Lys Lys Val Leu Lys Thr Asn
305                 310                 315                 320

Val Ala Ser Leu Val Glu Leu Asn Met Leu Lys Asn Leu Ala Gly Ser
                325                 330                 335

Ala Val Ala Gly Ala Leu Gly Gly Phe Asn Ala His Ala Gly Asn Ile
            340                 345                 350

Val Ser Ala Ile Phe Ile Ala Thr Gly Gln Asp Pro Ala Gln Asn Val
        355                 360                 365

Glu Ser Ser His Cys Ile Thr Met Met Glu Ala Val Asn Asp Gly Lys
    370                 375                 380

Asp Leu His Ile Ser Val Thr Met Pro Ser Ile Glu Val Gly Thr Val
385                 390                 395                 400
```

```
Gly Gly Gly Thr Gln Leu Ala Ser Gln Ser Ala Cys Leu Asn Leu Leu
            405                 410                 415

Gly Val Lys Gly Ala Asn Lys Glu Ser Pro Gly Ser Asn Ser Arg Leu
            420                 425                 430

Leu Ala Ala Ile Val Ala Gly Ser Val Leu Ala Gly Glu Leu Ser Leu
            435                 440                 445

Met Ser Ala Ile Ala Ala Gly Gln Leu Val Lys Ser His Met Lys Tyr
        450                 455                 460

Asn Arg Ala Ser Lys Asp Met Ser Lys Ala Ala Ser
465                 470                 475
```

<210> SEQ ID NO 26
<211> LENGTH: 1431
<212> TYPE: DNA
<213> ORGANISM: Hevea brasiliensis

<400> SEQUENCE: 26

```
atggcacgcg cctcccatga cgtgtgggac ctcgaagata cggatcccaa ctacctcatc     60
gatgaagatc accgtctcgt tacttgccct cccgctaata tatctactaa gactaccatt    120
attgccgcac ctaccaaatt gcctacctcg aacccttaa ttgcacccctt agtctcggag    180
gaagacgaaa tgatcgtcaa ctccgtcgtg gatgggaaga taccctccta ttctctggag    240
tcgaagctcg gggactgcaa acgagcggct gcgattcgac gcgaggcttt gcagaggatg    300
acaaggaggt cgctggaagg cttgccagta aaggggttcg attacgagtc gattttagga    360
caatgctgtg aaatgccagt gggatacgtg cagattccgg tggggattgc ggggccgttg    420
ttgctgaacg gcgggagta ctctgttcca atggcgacca cggagggttg tttggtggcg    480
agcactaata gagggtgtaa ggcgatttac ttgtcaggtg gggccaccag cgtcttgttg    540
aaggatggca tgacaagagc gcctgttgta agattcgcgt cggcgactag agccgcggag    600
ttgaagttct tcttggagga tcctgacaat tttgatacct tggccgtagt ttttaacaag    660
tccagtagat ttgcgaggct ccaaggcatt aaatgctcaa ttgctggtaa gaatctttat    720
ataagattca gctgcagcac tggcgatgca atggggatga acatggtttc taaaggggtt    780
caaaacgttc ttgaatttct tcaaagtgat ttttctgata tggatgtcat ggaatctca    840
ggaaattttt gttcggataa gaagcctgct gctgtaaatt ggattgaagg acgtggcaaa    900
tcagttgttt gtgaggcaat tatcaaggaa gaggtggtga agaaggtgtt gaaaaccaat    960
gtggcctccc tagtggagct taacatgctc aagaatcttg ctggttctgc tgttgctggt   1020
gctttgggtg gatttaatgc ccatgcaggc aacatcgtat ctgcaatctt tattgccact   1080
ggccaggatc cagcacagaa tgttgagagt tctcattgca ttaccatgat ggaagctgtc   1140
aatgatggaa aggatctcca tatctctgtg accatgccct ccattgaggt gggtacagtc   1200
ggaggtggaa ctcaacttgc atctcagtct gcttgtctca atttgcttgg ggtgaagggt   1260
gcaaacaaag agtcgccagg atcaaactca aggctccttg ctgccatcgt agctggttca   1320
gttttggctg gtgagctctc cttgatgtct gccattgcag ctgggcagct tgtcaagagt   1380
cacatgaagt acaacagatc cgccaaagat atgtctaaag ctgcatctta g            1431
```

<210> SEQ ID NO 27
<211> LENGTH: 476
<212> TYPE: PRT
<213> ORGANISM: Hevea brasiliensis

<400> SEQUENCE: 27

Met Ala Arg Ala Ser His Asp Val Trp Asp Leu Glu Asp Thr Asp Pro

-continued

```
1               5                   10                  15
Asn Tyr Leu Ile Asp Glu Asp His Arg Leu Val Thr Cys Pro Pro Ala
                20                  25                  30

Asn Ile Ser Thr Lys Thr Thr Ile Ile Ala Ala Pro Thr Lys Leu Pro
                35                  40                  45

Thr Ser Glu Pro Leu Ile Ala Pro Leu Val Ser Glu Glu Asp Glu Met
            50                  55                  60

Ile Val Asn Ser Val Val Asp Gly Lys Ile Pro Ser Tyr Ser Leu Glu
65                  70                  75                  80

Ser Lys Leu Gly Asp Cys Lys Arg Ala Ala Ile Arg Arg Glu Ala
                85                  90                  95

Leu Gln Arg Met Thr Arg Arg Ser Leu Glu Gly Leu Pro Val Glu Gly
                100                 105                 110

Phe Asp Tyr Glu Ser Ile Leu Gly Gln Cys Cys Glu Met Pro Val Gly
            115                 120                 125

Tyr Val Gln Ile Pro Val Gly Ile Ala Gly Pro Leu Leu Leu Asn Gly
        130                 135                 140

Arg Glu Tyr Ser Val Pro Met Ala Thr Thr Glu Gly Cys Leu Val Ala
145                 150                 155                 160

Ser Thr Asn Arg Gly Cys Lys Ala Ile Tyr Leu Ser Gly Gly Ala Thr
                165                 170                 175

Ser Val Leu Leu Lys Asp Gly Met Thr Arg Ala Pro Val Val Arg Phe
            180                 185                 190

Ala Ser Ala Thr Arg Ala Ala Glu Leu Lys Phe Phe Leu Glu Asp Pro
            195                 200                 205

Asp Asn Phe Asp Thr Leu Ala Val Val Phe Asn Lys Ser Ser Arg Phe
        210                 215                 220

Ala Arg Leu Gln Gly Ile Lys Cys Ser Ile Ala Gly Lys Asn Leu Tyr
225                 230                 235                 240

Ile Arg Phe Ser Cys Ser Thr Gly Asp Ala Met Gly Met Asn Met Val
                245                 250                 255

Ser Lys Gly Val Gln Asn Val Leu Glu Phe Leu Gln Ser Asp Phe Ser
            260                 265                 270

Asp Met Asp Val Ile Gly Ile Ser Gly Asn Phe Cys Ser Asp Lys Lys
        275                 280                 285

Pro Ala Ala Val Asn Trp Ile Glu Gly Arg Gly Lys Ser Val Val Cys
        290                 295                 300

Glu Ala Ile Ile Lys Glu Val Val Lys Val Leu Lys Thr Asn
305                 310                 315                 320

Val Ala Ser Leu Val Glu Leu Asn Met Leu Lys Asn Leu Ala Gly Ser
            325                 330                 335

Ala Val Ala Gly Ala Leu Gly Gly Phe Asn Ala His Ala Gly Asn Ile
            340                 345                 350

Val Ser Ala Ile Phe Ile Ala Thr Gly Gln Asp Pro Ala Gln Asn Val
        355                 360                 365

Glu Ser Ser His Cys Ile Thr Met Met Glu Ala Val Asn Asp Gly Lys
        370                 375                 380

Asp Leu His Ile Ser Val Thr Met Pro Ser Ile Glu Val Gly Thr Val
385                 390                 395                 400

Gly Gly Gly Thr Gln Leu Ala Ser Gln Ser Ala Cys Leu Asn Leu Leu
                405                 410                 415

Gly Val Lys Gly Ala Asn Lys Glu Ser Pro Gly Ser Asn Ser Arg Leu
            420                 425                 430
```

```
Leu Ala Ala Ile Val Ala Gly Ser Val Leu Ala Gly Glu Leu Ser Leu
        435                 440                 445

Met Ser Ala Ile Ala Ala Gly Gln Leu Val Lys Ser His Met Lys Tyr
    450                 455                 460

Asn Arg Ser Ala Lys Asp Met Ser Lys Ala Ala Ser
465                 470                 475

<210> SEQ ID NO 28
<211> LENGTH: 22
<212> TYPE: DNA
<213> ORGANISM: Artificial sequence
<220> FEATURE:
<223> OTHER INFORMATION: Description of Artificial Sequence:  Synthetic
      Primer

<400> SEQUENCE: 28
gagatctgaa ccctaacgag ag                                            22

<210> SEQ ID NO 29
<211> LENGTH: 26
<212> TYPE: DNA
<213> ORGANISM: Artificial sequence
<220> FEATURE:
<223> OTHER INFORMATION: Description of Artificial Sequence:  Synthetic
      Primer

<400> SEQUENCE: 29
ggagctctta agaaaaggga cgacgc                                        26

<210> SEQ ID NO 30
<211> LENGTH: 26
<212> TYPE: DNA
<213> ORGANISM: Artificial sequence
<220> FEATURE:
<223> OTHER INFORMATION: Description of Artificial Sequence:  Synthetic
      Primer

<400> SEQUENCE: 30
gtctctgaat cagaaatcct tctatc                                        26

<210> SEQ ID NO 31
<211> LENGTH: 25
<212> TYPE: DNA
<213> ORGANISM: Artificial sequence
<220> FEATURE:
<223> OTHER INFORMATION: Description of Artificial Sequence:  Synthetic
      Primer

<400> SEQUENCE: 31
catgtcaaat ttcactgctt catcc                                         25

<210> SEQ ID NO 32
<211> LENGTH: 31
<212> TYPE: DNA
<213> ORGANISM: Artificial sequence
<220> FEATURE:
<223> OTHER INFORMATION: Description of Artificial Sequence:  Synthetic
      Primer

<400> SEQUENCE: 32
gagatctcca cagatttaaa gaaccctaac g                                  31

<210> SEQ ID NO 33
<211> LENGTH: 31
<212> TYPE: DNA
<213> ORGANISM: Artificial sequence
<220> FEATURE:
```

```
<223> OTHER INFORMATION: Description of Artificial Sequence:  Synthetic
      Primer

<400> SEQUENCE: 33
ggagctcggt ttttaagaaa agggacgacg c                                        31
```